(12) United States Patent  (10) Patent No.: US 9,309,224 B2
Flynn et al.  (45) Date of Patent: Apr. 12, 2016

(54) N-ACYL-N'-(PYRIDIN-2-YL) UREAS AND ANALOGS EXHIBITING ANTI-CANCER AND ANTI-PROLIFERATIVE ACTIVITIES

(71) Applicant: Deciphera Pharmaceuticals, LLC, Lawrence, KS (US)

(72) Inventors: Daniel L. Flynn, Lawrence, KS (US); Timothy Malcolm Caldwell, Fishers, IN (US); Thiwanka Samarakoon, Quincy, MA (US); Lakshminarayana Vogeti, Arlington, MA (US); Michael D. Kaufman, Lawrence, KS (US); William C. Patt, Lawrence, KS (US); YuMi Ahn, Lawrence, KS (US)

(73) Assignee: Deciphera Pharmaceuticals, LLC., Lawrence, KS (US)

( * ) Notice: Subject to any disclaimer, the term of this patent is extended or adjusted under 35 U.S.C. 154(b) by 0 days.

(21) Appl. No.: 14/214,179

(22) Filed: Mar. 14, 2014

(65) Prior Publication Data

US 2014/0275016 A1   Sep. 18, 2014

Related U.S. Application Data

(60) Provisional application No. 61/791,890, filed on Mar. 15, 2013.

(51) Int. Cl.
| | |
|---|---|
| *C07D 213/65* | (2006.01) |
| *C07D 401/14* | (2006.01) |
| *C07D 401/12* | (2006.01) |
| *C07D 405/14* | (2006.01) |
| *C07D 493/08* | (2006.01) |

(52) U.S. Cl.
CPC ............ *C07D 401/12* (2013.01); *C07D 401/14* (2013.01); *C07D 405/14* (2013.01); *C07D 493/08* (2013.01)

(58) Field of Classification Search
CPC ............................ C07D 213/65; C07D 401/14
USPC ............................................ 546/261; 514/335
See application file for complete search history.

(56) References Cited

U.S. PATENT DOCUMENTS

| | | | | |
|---|---|---|---|---|
| 8,278,331 | B2 * | 10/2012 | Flynn et al. ............ | 514/333 |
| 2008/0214544 | A1 | 9/2008 | Bellon et al. | |
| 2008/0255155 | A1 | 10/2008 | Raeppel et al. | |
| 2010/0120806 | A1 | 5/2010 | Flynn et al. | |

OTHER PUBLICATIONS

Dorwald , Side Reactions in Organic Synthesis, 2005, Wiley: VCH Weinheim Preface, pp. 1-15 & Chapter 8, pp. 279-308.*
International Search Report from corresponding PCT International Application No. PCT/US2014/029666, dated Nov. 6, 2014.

* cited by examiner

*Primary Examiner* — Patricia L Morris
(74) *Attorney, Agent, or Firm* — Cooley LLP

(57) ABSTRACT

Described are compounds of Formula 1

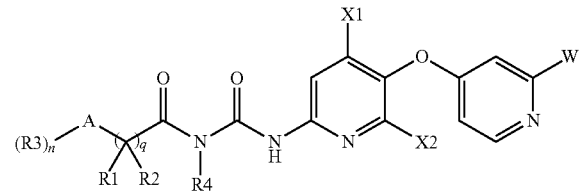

which find utility in the treatment of cancer, autoimmune diseases and metabolic bone disorders through inhibition of c-FMS (CSF-1R), c-KIT, and/or PDGFR kinases. These compounds also find utility in the treatment of other mammalian diseases mediated by c-FMS, c-KIT, or PDGFR kinases.

40 Claims, No Drawings

SEQUENCE LISTING

```
<160> NUMBER OF SEQ ID NOS: 3

<210> SEQ ID NO 1
<211> LENGTH: 435
<212> TYPE: PRT
<213> ORGANISM: Homo sapiens

<400> SEQUENCE: 1

Tyr Lys Tyr Lys Gln Lys Pro Lys Tyr Gln Val Arg Trp Lys Ile Ile
1               5                   10                  15

Glu Ser Tyr Glu Gly Asn Ser Tyr Thr Phe Ile Asp Pro Thr Gln Leu
            20                  25                  30

Pro Tyr Asn Glu Lys Trp Glu Phe Pro Arg Asn Asn Leu Gln Phe Gly
        35                  40                  45

Lys Thr Leu Gly Ala Gly Ala Phe Gly Lys Val Val Glu Ala Thr Ala
    50                  55                  60

Phe Gly Leu Gly Lys Glu Asp Ala Val Leu Lys Val Ala Val Lys Met
65                  70                  75                  80

Leu Lys Ser Thr Ala His Ala Asp Glu Lys Glu Ala Leu Met Ser Glu
```

```
            85                  90                  95
Leu Lys Ile Met Ser His Leu Gly Gln His Glu Asn Ile Val Asn Leu
            100                 105                 110

Leu Gly Ala Cys Thr His Gly Gly Pro Val Leu Val Ile Thr Glu Tyr
            115                 120                 125

Cys Cys Tyr Gly Asp Leu Leu Asn Phe Leu Arg Arg Lys Ala Glu Ala
        130                 135                 140

Met Leu Gly Pro Ser Leu Ser Pro Gly Gln Asp Pro Glu Gly Gly Val
145                 150                 155                 160

Asp Tyr Lys Asn Ile His Leu Glu Lys Lys Tyr Val Arg Arg Asp Ser
                165                 170                 175

Gly Phe Ser Ser Gln Gly Val Asp Thr Tyr Val Glu Met Arg Pro Val
            180                 185                 190

Ser Thr Ser Ser Asn Asp Ser Phe Ser Glu Gln Asp Leu Asp Lys Glu
            195                 200                 205

Asp Gly Arg Pro Leu Glu Leu Arg Asp Leu Leu His Phe Ser Ser Gln
        210                 215                 220

Val Ala Gln Gly Met Ala Phe Leu Ala Ser Lys Asn Cys Ile His Arg
225                 230                 235                 240

Asp Val Ala Ala Arg Asn Val Leu Leu Thr Asn Gly His Val Ala Lys
                245                 250                 255

Ile Gly Asp Phe Gly Leu Ala Arg Asp Ile Met Asn Asp Ser Asn Tyr
            260                 265                 270

Ile Val Lys Gly Asn Ala Arg Leu Pro Val Lys Trp Met Ala Pro Glu
            275                 280                 285

Ser Ile Phe Asp Cys Val Tyr Thr Val Gln Ser Asp Val Trp Ser Tyr
        290                 295                 300

Gly Ile Leu Leu Trp Glu Ile Phe Ser Leu Gly Leu Asn Pro Tyr Pro
305                 310                 315                 320

Gly Ile Leu Val Asn Ser Lys Phe Tyr Lys Leu Val Lys Asp Gly Tyr
                325                 330                 335

Gln Met Ala Gln Pro Ala Phe Ala Pro Lys Asn Ile Tyr Ser Ile Met
            340                 345                 350

Gln Ala Cys Trp Ala Leu Glu Pro Thr His Arg Pro Thr Phe Gln Gln
        355                 360                 365

Ile Cys Ser Phe Leu Gln Glu Gln Ala Gln Glu Asp Arg Arg Glu Arg
        370                 375                 380

Asp Tyr Thr Asn Leu Pro Ser Ser Ser Arg Ser Gly Gly Ser Gly Ser
385                 390                 395                 400

Ser Ser Ser Glu Leu Glu Glu Glu Ser Ser Ser Glu His Leu Thr Cys
                405                 410                 415

Cys Glu Gln Gly Asp Ile Ala Gly Pro Leu Leu Gln Pro Asn Asn Tyr
            420                 425                 430

Gln Phe Cys
        435

<210> SEQ ID NO 2
<211> LENGTH: 676
<212> TYPE: PRT
<213> ORGANISM: Artificial Sequence
<220> FEATURE:
<223> OTHER INFORMATION: uKit with N-terminal GST fusion

<400> SEQUENCE: 2

Leu Gly Tyr Trp Lys Ile Lys Gly Leu Val Gln Pro Thr Arg Leu Leu
```

```
  1               5                   10                  15
Leu Glu Tyr Leu Glu Glu Lys Tyr Glu Glu His Leu Tyr Glu Arg Asp
                20                  25                  30

Glu Gly Asp Lys Trp Arg Asn Lys Lys Phe Glu Leu Gly Leu Glu Phe
                35                  40                  45

Pro Asn Leu Pro Tyr Tyr Ile Asp Gly Asp Val Lys Leu Thr Gln Ser
            50                  55                  60

Met Ala Ile Ile Arg Tyr Ile Ala Asp Lys His Asn Met Leu Gly Gly
65                  70                  75                  80

Cys Pro Lys Glu Arg Ala Glu Ile Ser Met Leu Glu Gly Ala Val Asp
                85                  90                  95

Ile Arg Tyr Gly Val Ser Arg Ile Ala Tyr Ser Lys Asp Phe Glu Thr
                100                 105                 110

Leu Lys Val Asp Phe Leu Ser Lys Leu Pro Glu Met Leu Lys Met Phe
            115                 120                 125

Glu Asp Arg Leu Cys His Lys Thr Tyr Leu Asn Gly Asp His Val Thr
            130                 135                 140

His Pro Asp Phe Met Leu Tyr Asp Ala Leu Asp Val Val Leu Tyr Met
145                 150                 155                 160

Asp Pro Met Cys Leu Asp Ala Phe Pro Lys Leu Val Cys Phe Lys Lys
                165                 170                 175

Arg Ile Glu Ala Ile Pro Gln Ile Asp Lys Tyr Leu Lys Ser Ser Lys
                180                 185                 190

Tyr Ile Trp Pro Leu Gln Gly Trp Gln Ala Thr Phe Gly Gly Gly Asp
            195                 200                 205

His Pro Pro Lys Ser Asp Leu Val Pro Arg His Asn Gln Thr Ser Leu
210                 215                 220

Tyr Lys Lys Ala Gly Ser Ala Ala Ala Val Leu Glu Glu Asn Leu Tyr
225                 230                 235                 240

Phe Gln Gly Thr Tyr Lys Tyr Leu Gln Lys Pro Met Tyr Glu Val Gln
                245                 250                 255

Trp Lys Val Val Glu Glu Ile Asn Gly Asn Asn Tyr Val Tyr Ile Asp
            260                 265                 270

Pro Thr Gln Leu Pro Tyr Asp His Lys Trp Glu Phe Pro Arg Asn Arg
        275                 280                 285

Leu Ser Phe Gly Lys Thr Leu Gly Ala Gly Ala Phe Gly Lys Val Val
        290                 295                 300

Glu Ala Thr Ala Tyr Gly Leu Ile Lys Ser Asp Ala Ala Met Thr Val
305                 310                 315                 320

Ala Val Lys Met Leu Lys Pro Ser Ala His Leu Thr Glu Arg Glu Ala
                325                 330                 335

Leu Met Ser Glu Leu Lys Val Leu Ser Tyr Leu Gly Asn His Met Asn
                340                 345                 350

Ile Val Asn Leu Leu Gly Ala Cys Thr Ile Gly Gly Pro Thr Leu Val
            355                 360                 365

Ile Thr Glu Tyr Cys Cys Tyr Gly Asp Leu Leu Asn Phe Leu Arg Arg
        370                 375                 380

Lys Arg Asp Ser Phe Ile Cys Ser Lys Gln Glu Asp His Ala Glu Ala
385                 390                 395                 400

Ala Leu Tyr Lys Asn Leu Leu His Ser Lys Glu Ser Ser Cys Ser Asp
                405                 410                 415

Ser Thr Asn Glu Tyr Met Asp Met Lys Pro Gly Val Ser Tyr Val Val
            420                 425                 430
```

```
Pro Thr Lys Ala Asp Lys Arg Arg Ser Val Arg Ile Gly Ser Tyr Ile
            435                 440                 445

Glu Arg Asp Val Thr Pro Ala Ile Met Glu Asp Glu Leu Ala Leu
    450                 455                 460

Asp Leu Glu Asp Leu Leu Ser Phe Ser Tyr Gln Val Ala Lys Gly Met
465                 470                 475                 480

Ala Phe Leu Ala Ser Lys Asn Cys Ile His Arg Asp Leu Ala Ala Arg
                485                 490                 495

Asn Ile Leu Leu Thr His Gly Arg Ile Thr Lys Ile Cys Asp Phe Gly
            500                 505                 510

Leu Ala Arg Asp Ile Lys Asn Asp Ser Asn Tyr Val Val Lys Gly Asn
        515                 520                 525

Ala Arg Leu Pro Val Lys Trp Met Ala Pro Glu Ser Ile Phe Asn Cys
    530                 535                 540

Val Tyr Thr Phe Glu Ser Asp Val Trp Ser Tyr Gly Ile Phe Leu Trp
545                 550                 555                 560

Glu Leu Phe Ser Leu Gly Ser Ser Pro Tyr Pro Gly Met Pro Val Asp
                565                 570                 575

Ser Lys Phe Tyr Lys Met Ile Lys Glu Gly Phe Arg Met Leu Ser Pro
            580                 585                 590

Glu His Ala Pro Ala Glu Met Tyr Asp Ile Met Lys Thr Cys Trp Asp
        595                 600                 605

Ala Asp Pro Leu Lys Arg Pro Thr Phe Lys Gln Ile Val Gln Leu Ile
610                 615                 620

Glu Lys Gln Ile Ser Glu Ser Thr Asn His Ile Tyr Ser Asn Leu Ala
625                 630                 635                 640

Asn Cys Ser Pro Asn Arg Gln Lys Pro Val Val Asp His Ser Val Arg
                645                 650                 655

Ile Asn Ser Val Gly Ser Thr Ala Ser Ser Ser Gln Pro Leu Leu Val
            660                 665                 670

His Asp Asp Val
        675

<210> SEQ ID NO 3
<211> LENGTH: 549
<212> TYPE: PRT
<213> ORGANISM: Homo sapiens

<400> SEQUENCE: 3

Gln Lys Lys Pro Arg Tyr Glu Ile Arg Trp Lys Val Ile Glu Ser Val
1               5                   10                  15

Ser Ser Asp Gly His Glu Tyr Ile Tyr Val Asp Pro Met Gln Leu Pro
            20                  25                  30

Tyr Asp Ser Thr Trp Glu Leu Pro Arg Asp Gln Leu Val Leu Gly Arg
        35                  40                  45

Thr Leu Gly Ser Gly Ala Phe Gly Gln Val Val Glu Ala Thr Ala His
    50                  55                  60

Gly Leu Ser His Ser Gln Ala Thr Met Lys Val Ala Val Lys Met Leu
65                  70                  75                  80

Lys Ser Thr Ala Arg Ser Ser Glu Lys Gln Ala Leu Met Ser Glu Leu
                85                  90                  95

Lys Ile Met Ser His Leu Gly Pro His Leu Asn Val Val Asn Leu Leu
            100                 105                 110

Gly Ala Cys Thr Lys Gly Gly Pro Ile Tyr Ile Ile Thr Glu Tyr Cys
```

```
                115                 120                 125
    Arg Tyr Gly Asp Leu Val Asp Tyr Leu His Arg Asn Lys His Thr Phe
    130                 135                 140

Leu Gln His His Ser Asp Lys Arg Arg Pro Pro Ser Ala Glu Leu Tyr
    145                 150                 155                 160

Ser Asn Ala Leu Pro Val Gly Leu Pro Leu Pro Ser His Val Ser Leu
                    165                 170                 175

Thr Gly Glu Ser Asp Gly Gly Tyr Met Asp Met Ser Lys Asp Glu Ser
                    180                 185                 190

Val Asp Tyr Val Pro Met Leu Asp Met Lys Gly Asp Val Lys Tyr Ala
                195                 200                 205

Asp Ile Glu Ser Ser Asn Tyr Met Ala Pro Tyr Asp Asn Tyr Val Pro
                210                 215                 220

Ser Ala Pro Glu Arg Thr Cys Arg Ala Thr Leu Ile Asn Glu Ser Pro
    225                 230                 235                 240

Val Leu Ser Tyr Met Asp Leu Val Gly Phe Ser Tyr Gln Val Ala Asn
                    245                 250                 255

Gly Met Glu Phe Leu Ala Ser Lys Asn Cys Val His Arg Asp Leu Ala
                    260                 265                 270

Ala Arg Asn Val Leu Ile Cys Glu Gly Lys Leu Val Lys Ile Cys Asp
                275                 280                 285

Phe Gly Leu Ala Arg Asp Ile Met Arg Asp Ser Asn Tyr Ile Ser Lys
    290                 295                 300

Gly Ser Thr Phe Leu Pro Leu Lys Trp Met Ala Pro Glu Ser Ile Phe
    305                 310                 315                 320

Asn Ser Leu Tyr Thr Thr Leu Ser Asp Val Trp Ser Phe Gly Ile Leu
                    325                 330                 335

Leu Trp Glu Ile Phe Thr Leu Gly Gly Thr Pro Tyr Pro Glu Leu Pro
                    340                 345                 350

Met Asn Glu Gln Phe Tyr Asn Ala Ile Lys Arg Gly Tyr Arg Met Ala
                    355                 360                 365

Gln Pro Ala His Ala Ser Asp Glu Ile Tyr Glu Ile Met Gln Lys Cys
                370                 375                 380

Trp Glu Glu Lys Phe Glu Ile Arg Pro Pro Phe Ser Gln Leu Val Leu
    385                 390                 395                 400

Leu Leu Glu Arg Leu Leu Gly Glu Gly Tyr Lys Lys Lys Tyr Gln Gln
                    405                 410                 415

Val Asp Glu Glu Phe Leu Arg Ser Asp His Pro Ala Ile Leu Arg Ser
                420                 425                 430

Gln Ala Arg Leu Pro Gly Phe His Gly Leu Arg Ser Pro Leu Asp Thr
                435                 440                 445

Ser Ser Val Leu Tyr Thr Ala Val Gln Pro Asn Glu Gly Asp Asn Asp
    450                 455                 460

Tyr Ile Ile Pro Leu Pro Asp Pro Lys Pro Glu Val Ala Asp Glu Gly
    465                 470                 475                 480

Pro Leu Glu Gly Ser Pro Ser Leu Ala Ser Ser Thr Leu Asn Glu Val
                    485                 490                 495

Asn Thr Ser Ser Thr Ile Ser Cys Asp Ser Pro Leu Glu Pro Gln Asp
                    500                 505                 510

Glu Pro Glu Pro Glu Pro Gln Leu Glu Leu Gln Val Glu Pro Glu Pro
                515                 520                 525

Glu Leu Glu Gln Leu Pro Asp Ser Gly Cys Pro Ala Pro Arg Ala Glu
                530                 535                 540
```

```
Ala Glu Asp Ser Phe
545
```

N-ACYL-N'-(PYRIDIN-2-YL) UREAS AND ANALOGS EXHIBITING ANTI-CANCER AND ANTI-PROLIFERATIVE ACTIVITIES

PRIORITY

This application claims the benefit of U.S. Provisional Application No. 61/791,890, filed Mar. 15, 2013. The entire disclosure of this application is relied on and incorporated into this application by reference.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: DECP_064_01US_SeqList_ST25.txt, date recorded: Mar. 15, 2014, file size 18 kilobytes).

FIELD OF THE INVENTION

Disclosed are compounds which find utility in the treatment of cancer, autoimmune diseases and metabolic bone disorders through inhibition of c-FMS (CSF-1R), c-KIT, and/or PDGFR kinases. These compounds also find utility in the treatment of other mammalian diseases mediated by c-FMS, c-KIT, or PDGFR kinases.

BACKGROUND OF THE INVENTION

Autoimmune diseases, including autoimmune arthritis, represent significant human diseases of high morbidity and prevalence. Rheumatoid arthritis affects ~0.6% of the world population (Firestein, G. S., Nature (2003) 423: 356). While the adaptive immune response, involving generation of autoantibodies which react with tissue antigen, is involved in the etiology and initial propagation of these diseases (Edwards, J. C. et al, New England Journal of Medicine (2004) 350: 2572; Genovese, M. C. et al, New England Journal of Medicine (2005) 353: 1114), the chronic manifestations of tissue and joint damage are mediated in large part by cellular events mediated by the innate immune response (Firestein, G. S., Nature (2003) 423: 356; Paniagua, R. T. et al, Arthritis Research & Therapy (2010) 12: R32). Contributing cell types from the innate immune response which mediate chronic tissue damage include fibroblast-like synoviocytes, macrophages, mast cells, and osteoclasts.

Kinases represent a protein family that play critical roles in mammalian cell function, including cell proliferation, survival, motility, response to growth factors, and secretion of cytokines and other proinflammatory, proangiogenic, and immunomodulatory substances. Thus, elucidation of kinases which mediate these events in fibroblast-like synoviocytes, macrophages, mast cells, and osteoclasts represents a rational approach to new therapies for the treatment of autoimmune diseases.

Imatinib is a marketed kinase inhibitor for the treatment of the cancer chronic myelogenous leukemia (CML, Druker, B. J. et al, New England Journal of Medicine (2001) 344: 1031) and for the treatment of gastrointestinal stromal tumors (GIST, Demetri, G. D., et al, New England Journal of Medicine (2002) 347: 472). Imatinib has also shown benefit in cancer patients co-presenting with autoimmune diseases such as rheumatoid arthritis (Ihara, M. K. et al, Clinical Rheumatology (2003) 22: 362; Eklund, K. K. and Joensuu, H., Ann Medicine (2003) 35: 362; Ames, P. R. et al, Journal of Rheumatology (2008) 35: 1682). The kinases inhibited by imatinib which confer its efficacy in the treatment of CML and GIST are BCR-ABL kinase and c-KIT kinase, respectively. Beyond these two kinases, other kinases inhibited by imatinib include c-FMS, PDGFR-alpha, and PDGFR-beta (Dewer, A. L. et al, Blood (2005) 105: 3127; Fabian, M. A. et al, Nature Biotechnology (2005) 23: 329.

Recent research disclosures have identified c-FMS kinase to be associated with activation of synovial macrophages, PDGFR kinase to be associated with activation of fibroblast-like synoviocytes, and c-KIT kinase to be associated with activation of mast cells (Paniagua, R. T., et al Journal of Clinical Investigation (2006) 116: 2633). c-FMS kinase has also been associated with the proliferation and differentiation of monocytes into macrophages and osteoclasts, which are recruited to mediate joint damage in rheumatoid arthritis (Paniagua, R. T. et al, Arthritis Research & Therapy (2010) 12: R32; Yao, Z. et al, Journal of Biological Chemistry (2006) 281: 11846; Patel, S, and Player, M. R. Current Topics in Medicinal Chemistry (2009) 9: 599; Pixley, F. J. et al, Trends in Cell Biology (2004) 14: 628).

In recent years, the importance of the tumor microenvironment in cancer motility, invasion, and metastasis has become more clearly defined. Specifically, the role of tumor-associated macrophages (TAMs) in tumor progression has been studied. These host (stromal) macrophages are recruited to tumor sites or to pre-metastatic niches to modify the tumor environment and render that environment more conducive to tumor motility, invasion and metastasis. These TAMs are known to express c-FMS receptor tyrosine kinase (also known as CSF-1R) on their surfaces and to rely on signaling through this kinase by binding to the activating ligands CSF-1 (also known as macrophage colony stimulating factor, or MCSF) and interleukin-34 (IL-34). Activation of this c-FMS/MCSF (CSF1-R/CSF-1) signaling axis stimulates monocyte proliferation, differentiation into tumor associated macrophages, and promotion of macrophage cell survival. By stimulating the TAM component of the tumor microenvironment, c-FMS kinase activation is associated with tumor cell migration, invasion, and metastasis (J. Condeelis and J. W. Pollard, Cell (2006) 124: 263; S. Patel and M. R. Player, Current Topics in Medicinal Chemistry (2009) 9: 599). Ablation of CSF-1, the ligand for c-FMS kinase, in mice reduced tumor progression and significantly reduced metastasis in a murine model of breast cancer; whereas overexpression of CSF-1 accelerated metastasis in this model (E. Y. Lin et al, Journal of Experimental Medicine (2001) 193: 727). Furthermore, an interaction between tumor cells and macrophages has been described, wherein macrophage secretion of the tumor growth factor EGF and tumor cell secretion of CSF-1 establish a paracrine loop that promotes tumor migration and invasiveness. This paracrine loop was blocked by administration of an antibody to the c-FMS kinase (J. Wyckoff et al, Cancer Research (2004) 64: 7022). Correlative clinical data have also shown that overexpression of CSF-1 in tumors is a predictor of poor prognosis (R. D. Leek and A. L. Harris, Journal of Mammary Gland Biology Neoplasia (2002) 7: 177; E. Y. Lin et al, Journal of Mammary Gland Biology Neoplasia (2002) 7: 147). c-FMS kinase activation is also required for osteoclast differentiation and activation. Its involvement in mediating bone metastases of various cancers, including breast and prostate cancers, has been reported (S. Patel and M. R. Player, Current Topics in Medicinal Chemistry (2009) 9: 599). High plasma concentrations of CSF-1 have been reported in bone metastatic prostate cancer, implicating activation of osteoclast c-FMS kinase in prostate cancer bone metastases (H. Ide, et al, Human Cell (2008) 21:1). c-FMS inhibitors have been reported to reduce radiographic bone lesions when evaluated in models of metastatic bone disease (C. L. Manthey, et al, Molecular Cancer Therapy (2009) 8: 3151; H. Ohno et al, Mol. Cancer. Therapy (2006) 5: 2634). MCSF-mediated activation of both LYVE-1+ and LYVE1− macrophages also mediates pathological angiogenesis and lymphangiogenesis in murine models of cancer, and blockade of c-FMS signaling resulted in suppression of tumor angiogenesis/lymphangiogenesis (Y. Kubota et al., Journal of Experimental Medicine (2009) 206: 1089). Administration of a CSF-1R inhibitor blocked the recruitment of bone marrow derived TAMs and also bone marrow derived monocytic myeloid-derived suppressor cells (MDSCs) to tumor sites; this blockade led to a significant decrease in tumor angiogenesis and when combined with anti-VEGFR-2 therapy synergistically suppressed tumor growth (S. J. Priceman, et al. Blood (2010) 115: 1461). Irradiation of glioblastoma tumors in mice was shown to cause a temporary decrease in tumor size only to be followed by a rebound tumor vasculogenesis mediated by the recruitment of bone marrow derived monocytes expressing CD11b and F4/80 surface antigens (M. Kioi et al, Journal of Clinical Investigation (2010) 120: 694). CD11b+ and F4/80+ monocytes are also known to express functional c-FMS receptors. Hence, blockade of tumor infiltrating c-FMS+ bone marrow derived monocytes by the use of c-FMS kinase inhibitors offers the potential to prevent tumor rebound vasculogenesis and glioblastoma tumor progression. CSF-1R blockade has also been shown to reverse immunotolerance mechanisms in an immunocompetent murine breast cancer model and promote the appearance of anti-tumor immune programs by upregulating CD8+ T-cell-mediated tumor suppression. Restoration of an anti-tumor immune program was mechanistically linked to c-FMS inhibitor blockade of TAM-mediated Programmed Death Ligand-1 (PDL-1) immunotolerance (D. G. DeNardo, et al. Cancer Discovery (2011) 1: OF52).

Hence, small molecule inhibitors of c-FMS kinase, c-KIT kinase, or PDGFR kinases provide a rational approach to new therapies for the treatment of autoimmune diseases, and to particularly block the chronic tissue destruction mediated by the innate immune system. Inhibition of c-FMS kinase also provides a rational approach to new therapies for the treatment of cancers, especially for the treatment of cancer invasiveness, cancer angiogenesis or vasculogenesis, cancer metastasis, cancer immunotolerance, and for the treatment of cancers prone to bone metastases.

There is a need to provide kinase inhibitors which selectively inhibit kinases causative of the chronic tissue destruction in autoimmune disease (c-FMS, c-KIT, PDGFR), without inhibiting other kinases targeted by marketed cancer therapeutics (ABL, BCR-ABL, KDR, SRC, LCK, LYN, FGFR and other kinases). The present invention discloses novel inhibitors that inhibit c-FMS, c-KIT, and/or PDGFR kinases for the treatment of autoimmune diseases which also exhibit selectivity by not potently inhibiting other kinases including ABL, BCR-ABL, KDR, SRC, LCK, LYN, FGFR, MET and other kinases. The inhibitors of the present invention also find utility in the treatment of other mammalian diseases, including human diseases, mediated by c-FMS, c-KIT, or PDGFR kinases. Such diseases include, without limitation, cancers, autoimmune diseases, and bone resorptive diseases.

SUMMARY OF THE INVENTION

In one aspect, compounds of the Formula I are described

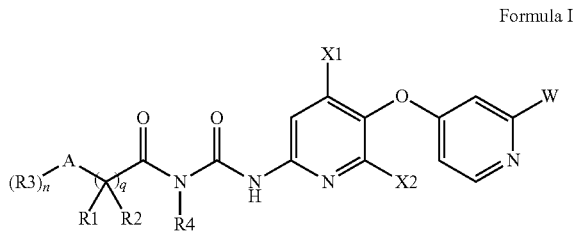

Formula I and pharmaceutically acceptable salts, enantiomers, stereoisomers, and tautomers thereof, wherein A is taken from the group consisting of C1-C6 alkyl, deutero-C1-C6 alkyl wherein the alkyl chain is partially or completely deuterated, branched C3-C8alkyl, fluoroC1-C6alkyl wherein the alkyl is fully or partially fluorinated, C3-C8-carbocyclyl, or a 4-8 membered heterocyclic ring, and wherein each A moiety may be further substituted with one, two, or three R3 moieties;

W is —NHC(O)R5, —NHC(O)R6, —NHC(O)N(R7)R8 or —C(O)N(R7)R8;

X1 and X2 are individually and independently hydrogen, C1-C6 alkyl, fluoro-C1-C6 alkyl wherein the alkyl chain is partially or completely fluorinated;

each R1 and R2 is individually and independently H, C1-C6 alkyl, fluoroC1-C6alkyl wherein the alkyl is fully or partially fluorinated, hydroxyl, C1-C6 alkoxy, fluoroC1-C6alkoxy wherein the alkyl group is fully or partially fluorinated, or cyano;

each R3 is individually and independently H, halogen, C1-C6 alkyl, fluoro-C1-C6 alkyl wherein the alkyl chain is partially or completely fluorinated, branched C3-C8 alkyl, C3-C8 cycloalkyl, C1-C6 alkoxy, fluoro-C1-C6 alkoxy wherein the alkyl chain is partially or completely fluorinated, branched C3-C6 alkoxy, hydroxyl, or cyano;

each R4 is individually and independently hydrogen, C1-C6 alkyl, or branched C3-C8 alkyl;

each R5 is individually and independently hydrogen, C1-C6 alkyl, branched C3-C8 alkyl, C3-C8 cycloalkyl, —(CH$_2$)$_m$—CN, —(CH$_2$)$_m$—OR7, —(CH$_2$)$_m$—NR7(R8), or —(CH$_2$)$_m$—R6, wherein each alkyene of R5 may be further substituted with one or more C1-C6alkyl;

each R6 is independently and individually selected from the group consisting of

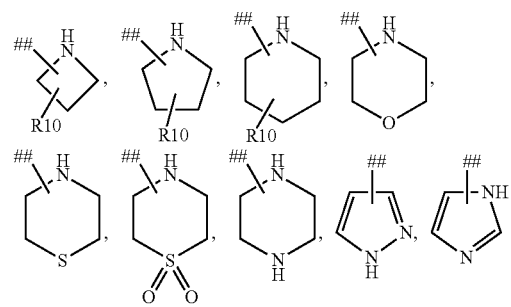

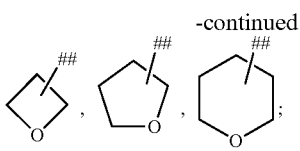

and wherein the symbol (##) is the point of attachment to respective R5 or W moieties containing a R6 moiety; each R6 is optionally substituted with —(R9)$_p$; each R7 and R8 is individually and independently H, C1-C6 alkyl, fluoro-C1-C6 alkyl wherein the alkyl chain is partially or completely fluorinated, branched C3-C8 alkyl, —(CH$_2$)$_m$—CN, —(CH$_2$)$_m$—OR7, —(CH$_2$)$_m$—NR7(R8), or —(CH$_2$)$_m$—R6, each R9 is individually and independently C1-C6 alkyl, —(CH$_2$)$_m$—CN, —(CH$_2$)$_m$—OR3, —(CH$_2$)$_m$—NR7(R8), or —(CH$_2$)$_m$—C(O)—R5, wherein each alkyl or alkylene is optionally substituted with one or two C1-C6 alkyl;

each R10 is H, 4-(C1-C4alkyl)-piperazin-1-yl, morpholinyl, piperidinyl, pyrrolidinyl or azetidinyl;

each m is individually and independently 0, 1, 2, or 3;
each n is individually and independently 0, 1, 2, or 3;
each p is 0, 1, 2, or 3;
each q is 0, 1, 2, or 3.

In one embodiment of Formula I, A is C1-C6alkyl.
In one embodiment of Formula I, A is branched C3-C8alkyl.
In one embodiment of Formula I, A is fluoroC1-C6alkyl wherein the alkyl is fully or partially fluorinated.
In one embodiment of Formula I, A is C3-C8-carbocyclyl.
In one embodiment of Formula I, A is a 4-8 membered heterocyclic ring.
In one embodiment of Formula I, W is —NHC(O)R5.
In one embodiment of Formula I, In one embodiment of Formula I, W is —NHC(O)R6.
In one embodiment of Formula I, In one embodiment of Formula I, W is —NHC(O)N(R7)R8.
In one embodiment of Formula I, In one embodiment of Formula I, W is —C(O)N(R7)R8.
In one embodiment of Formula I, X1 and X2 are individually and independently hydrogen, C1-C6 alkyl, or fluoro-C1-C6 alkyl wherein the alkyl chain is partially or completely fluorinated.
In one embodiment of Formula I, X1 and X2 are individually and independently hydrogen or C1-C6 alkyl.
In one embodiment of Formula I, X1 and X2 are hydrogen.
In one embodiment of Formula I, one of X1 and X2 is hydrogen and the other is C1-C6alkyl.
In one embodiment of Formula I, each R1 and R2 is individually and independently H or C1-C6 alkyl.
In one embodiment of Formula I, each R1 and R2 is H.
In one embodiment of Formula I, each R3 is individually and independently C1-C6alkyl, hydrogen, C1-C6alkoxy, or fluoro-C1-C6 alkyl wherein the alkyl chain is partially or completely fluorinated.
In one embodiment of Formula I, each R3 is individually and independently C1-C6alkyl.
In one embodiment of Formula I, each R3 is individually and independently hydrogen.
In one embodiment of Formula I, each R3 is individually and independently C1-C6alkoxy.
In one embodiment of Formula I, each R3 is individually and independently fluoro-C1-C6 alkyl wherein the alkyl chain is partially or completely fluorinated.
In one embodiment of Formula I, R4 is hydrogen.
In one embodiment of Formula I, R4 is C1-C6 alkyl or branched C3-C8 alkyl.

In one embodiment of Formula I, q is 0, 1, 2, or 3.
In one embodiment of Formula I, q is 0, 1, or 2.
In one embodiment of Formula I, q is 0 or 1.
In one embodiment of Formula I, q is 0.
In one embodiment of Formula I, q is 1.
In one embodiment of Formula I, n is 0, 1, 2, or 3.
In one embodiment of Formula I, n is 0, 1, or 2.
In one embodiment of Formula I, n is 0 or 1.
In one embodiment of Formula I, n is 0.
In one embodiment of Formula I, n is 1.
In one embodiment, the compound of Formula I is a compound of Formula Ia

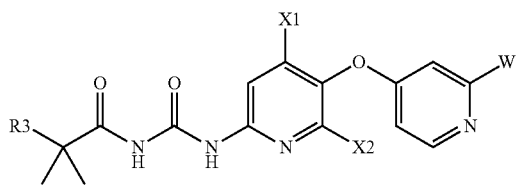

Formula Ia wherein R3, X1, X2 and W are as defined above.

In one embodiment of Formula Ia, R3 is C1-C6alkyl, hydrogen or C1-C6alkoxy.
In one embodiment of Formula Ia, R3 is C1-C6alkyl.
In one embodiment of Formula Ia, R3 is methyl.
In one embodiment of Formula Ia, R3 is hydrogen.
In one embodiment of Formula Ia, R3 is C1-C6alkoxy.
In one embodiment of Formula Ia, R3 is methoxy.
In one embodiment of Formula Ia, R3 is ethoxy.
In one embodiment of Formula Ia, W is —NHC(O)R5, —NHC(O)R6 or —NHC(O)N(R7)R8.
In one embodiment of Formula Ia, W is —NHC(O)R5.
In one embodiment of Formula Ia, W is —NHC(O)R6.
In one embodiment of Formula Ia, W is —NHC(O)N(R7)R8.
In one embodiment of Formula Ia, W is —C(O)N(R7)R8.
In one embodiment of Formula Ia, X1 and X2 are individually and independently hydrogen, C1-C6 alkyl, or fluoro-C1-C6 alkyl wherein the alkyl chain is partially or completely fluorinated.
In one embodiment of Formula Ia, X1 and X2 are individually and independently hydrogen or C1-C6 alkyl.
In one embodiment of Formula Ia, X1 and X2 are hydrogen.
In one embodiment of Formula Ia, one of X1 and X2 is hydrogen and the other is C1-C6alkyl.
In one embodiment of Formula Ia, X1 is hydrogen and X2 is C1-C6alkyl.
In one embodiment of Formula Ia, X1 is hydrogen and X2 is methyl.
In one embodiment of Formula Ia, X1 is C1-C6alkyl and X2 is hydrogen.
In one embodiment of Formula Ia, X1 is methyl and X2 is hydrogen.
In one embodiment of Formula Ia, R3 is methyl, hydrogen or methoxy and X1 and X2 are individually and independently hydrogen or methyl.
In one embodiment of Formula Ia, R3 is methyl, hydrogen or methoxy and X1 and X2 are individually and independently hydrogen or methyl, and W is —NHC(O)R5.
In one embodiment of Formula Ia, R3 is methyl, hydrogen or methoxy and X1 and X2 are individually and independently hydrogen or methyl, W is —NHC(O)R5, and R5 is C1-C6 alkyl, branched C3-C8 alkyl, or C3-C8 cycloalkyl.

In one embodiment of Formula Ia, R3 is methyl, hydrogen or methoxy and X1 and X2 are individually and independently hydrogen or methyl, and W is —NHC(O)R6.

In one embodiment of Formula Ia, R3 is methyl, hydrogen or methoxy and X1 and X2 are individually and independently hydrogen or methyl, W is —NHC(O)R6, and R6 is taken from

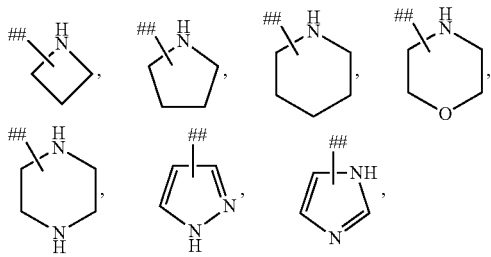

and wherein the symbol (##) is the point of attachment to the W moiety; and wherein each R6 is optionally substituted with —(R9)$_p$.

In one embodiment of Formula Ia, R3 is methyl, hydrogen or methoxy and X1 and X2 are individually and independently hydrogen or methyl, W is —NHC(O)R6, and R6 is taken from

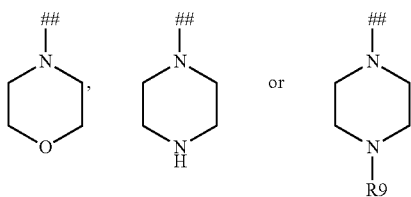

and wherein the symbol (##) is the point of attachment to the W moiety.

In one embodiment of Formula Ia, R3 is methyl, hydrogen or methoxy and X1 and X2 are individually and independently hydrogen or methyl, and W is —NHC(O)N(R7)R8.

In one embodiment of Formula Ia, R3 is methyl, hydrogen or methoxy and X1 and X2 are individually and independently hydrogen or methyl, W is —NHC(O)N(R7)R8, and each R7 and R8 is individually and independently H, or C1-C6 alkyl.

In one embodiment of Formula Ia, R3 is methyl, hydrogen or methoxy and X1 and X2 are individually and independently hydrogen or methyl, W is —NHC(O)N(R7)R8, and R7 and R8 are methyl.

In one embodiment of Formula Ia, R3 is methyl, hydrogen or methoxy and X1 and X2 are individually and independently hydrogen or methyl, and W is —C(O)N(R7)R8.

In one embodiment of Formula Ia, R3 is methyl, hydrogen or methoxy and X1 and X2 are individually and independently hydrogen or methyl, W is —C(O)N(R7)R8, R7 is H, and R8 is C1-C6 alkyl.

In one embodiment, the compound of Formula I is a compound of Formula Ib

Formula Ib

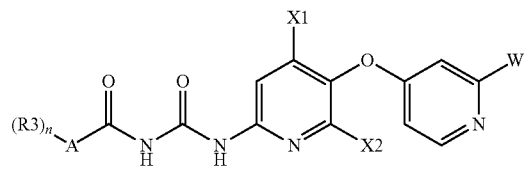

wherein A is C3-C8 carbocyclyl and R3, X1, X2, W and n are as defined above.

In one embodiment of Formula Ib, A is cyclopropyl.
In one embodiment of Formula Ib, A is cyclobutyl.
In one embodiment of Formula Ib, A is cyclopentyl.
In one embodiment of Formula Ib, A is cyclohexyl.
In one embodiment of Formula Ib, each R3 is individually and independently C1-C6alkyl, hydrogen, C1-C6alkoxy, or fluoro-C1-C6 alkyl wherein the alkyl chain is partially or completely fluorinated.
In one embodiment of Formula Ib, each R3 is individually and independently C1-C6alkyl.
In one embodiment of Formula Ib, n is 0, 1, or 2.
In one embodiment of Formula Ib, n is 0 or 1.
In one embodiment of Formula Ib, n is 0.
In one embodiment of Formula Ib, n is 1.
In one embodiment of Formula Ib, n is 1 and R3 is methyl.
In one embodiment of Formula Ib, n is 1 and R3 is hydrogen.
In one embodiment of Formula Ib, n is 1 and R3 is C1-C6alkoxy.
In one embodiment of Formula Ib, n is 1 and R3 is methoxy.
In one embodiment of Formula Ib, n is 1 and R3 is ethoxy.
In one embodiment of Formula Ib, n is 1 and R3 is fluoro-C1-C6 alkyl wherein the alkyl chain is partially or completely fluorinated.
In one embodiment of Formula Ib, n is 1 and R3 is trifluoromethyl.
In one embodiment of Formula Ib, W is —NHC(O)R5, —NHC(O)R6 or —NHC(O)N(R7)R8.
In one embodiment of Formula Ib, W is —NHC(O)R5.
In one embodiment of Formula Ib, W is —NHC(O)R6.
In one embodiment of Formula Ib, W is —NHC(O)N(R7)R8.
In one embodiment of Formula Ib, W is —C(O)N(R7)R8.
In one embodiment of Formula Ib, X1 and X2 are individually and independently hydrogen, C1-C6 alkyl, or fluoro-C1-C6 alkyl wherein the alkyl chain is partially or completely fluorinated.
In one embodiment of Formula Ib, X1 and X2 are individually and independently hydrogen or C1-C6 alkyl.
In one embodiment of Formula Ib, X1 and X2 are hydrogen.
In one embodiment of Formula Ib, one of X1 and X2 is hydrogen and the other is C1-C6alkyl.
In one embodiment of Formula Ib, X1 is hydrogen and X2 is C1-C6alkyl.
In one embodiment of Formula Ib, X1 is hydrogen and X2 is methyl.
In one embodiment of Formula Ib, X1 is C1-C6alkyl and X2 is hydrogen.
In one embodiment of Formula Ib, X1 is methyl and X2 is hydrogen.
In one embodiment, the compound of Formula I is a compound of Formula Ic Formula Ic (R3)n-A-C(O)-NH-C(O)-NH-[pyridine with X1, X2]-O-[pyridine with W]

wherein A is a 4-8 membered heterocyclic ring and R3, X1, X2, W and n are as defined above.

In one embodiment of Formula Ic, A is tetrahydrofuranyl.
In one embodiment of Formula Ic, A is tetrahydropyranyl.
In one embodiment of Formula Ic, A is oxetanyl.
In one embodiment of Formula Ic, each R3 is individually and independently C1-C6alkyl, hydrogen, C1-C6alkoxy, or fluoro-C1-C6 alkyl wherein the alkyl chain is partially or completely fluorinated.
In one embodiment of Formula Ic, each R3 is individually and independently C1-C6alkyl.
In one embodiment of Formula Ic, n is 0, 1, or 2.
In one embodiment of Formula Ic, n is 0 or 1.
In one embodiment of Formula Ic, n is 0.
In one embodiment of Formula Ic, n is 1.
In one embodiment of Formula Ic, n is 1 and R3 is methyl.
In one embodiment of Formula Ic, n is 1 and R3 is hydrogen.
In one embodiment of Formula Ic, n is 1 and R3 is C1-C6alkoxy.
In one embodiment of Formula Ic, n is 1 and R3 is methoxy.
In one embodiment of Formula Ic, n is 1 and R3 is ethoxy.
In one embodiment of Formula Ic, n is 1 and R3 is fluoro-C1-C6 alkyl wherein the alkyl chain is partially or completely fluorinated.
In one embodiment of Formula Ic, n is 1 and R3 is trifluoromethyl.
In one embodiment of Formula Ic, W is —NHC(O)R5, —NHC(O)R6 or —NHC(O)N(R7)R8.
In one embodiment of Formula Ic, W is —NHC(O)R5.
In one embodiment of Formula Ic, W is —NHC(O)R6.
In one embodiment of Formula Ic, W is —NHC(O)N(R7)R8.
In one embodiment of Formula Ic, W is —C(O)N(R7)R8.
In one embodiment of Formula Ic, X1 and X2 are individually and independently hydrogen, C1-C6 alkyl, or fluoro-C1-C6 alkyl wherein the alkyl chain is partially or completely fluorinated.
In one embodiment of Formula Ic, X1 and X2 are individually and independently hydrogen or C1-C6 alkyl.
In one embodiment of Formula Ic, X1 and X2 are hydrogen.
In one embodiment of Formula Ic, one of X1 and X2 is hydrogen and the other is C1-C6 alkyl.
In one embodiment of Formula Ic, X1 is hydrogen and X2 is C1-C6alkyl.
In one embodiment of Formula Ic, X1 is hydrogen and X2 is methyl.
In one embodiment of Formula Ic, X1 is C1-C6alkyl and X2 is hydrogen.
In one embodiment of Formula Ic, X1 is methyl and X2 is hydrogen.

In some embodiments, the invention comprises a compound selected from the group consisting of N-((5-((2-acetamidopyridin-4-yl)oxy)pyridin-2-yl)carbamoyl)cyclohexanecarboxamide, N-((5-((2-acetamidopyridin-4-yl)oxy) pyridin-2-yl)carbamoyl)cyclopentanecarboxamide, N-((5-((2-acetamidopyridin-4-yl)oxy)pyridin-2-yl)carbamoyl) pivalamide, N-((5-((2-acetamidopyridin-4-yl)oxy)pyridin-2-yl)carbamoyl)-2-cyclohexylacetamide, N-((5-((2-acetamidopyridin-4-yl)oxy)pyridin-2-yl)carbamoyl) tetrahydro-2H-pyran-4-carboxamide, N-((5-((2-acetamidopyridin-4-yl)oxy)pyridin-2-yl)carbamoyl)-2-(tetrahydro-2H-pyran-4-yl)acetamide, N-((5-((2-acetamidopyridin-4-yl)oxy)-6-methylpyridin-2-yl) carbamoyl)tetrahydro-2H-pyran-4-carboxamide, N-((5-((2-acetamidopyridin-4-yl)oxy)-6-methylpyridin-2-yl) carbamoyl)cyclopentanecarboxamide, N-((5-((2-acetamidopyridin-4-yl)oxy)-6-methylpyridin-2-yl) carbamoyl)pivalamide, N-((5-((2-acetamidopyridin-4-yl) oxy)-6-methylpyridin-2-yl)carbamoyl)isobutyramide, N-(4-((2-methyl-6-(3-pivaloylureido)pyridin-3-yl)oxy)pyridin-2-yl)cyclopropanecarboxamide, N-((6-methyl-5-((2-propionamidopyridin-4-yl)oxy)pyridin-2-yl)carbamoyl) pivalamide, N-((5-((2-isobutyramidopyridin-4-yl)oxy)-6-methylpyridin-2-yl)carbamoyl)pivalamide, N-((5-((2-acetamidopyridin-4-yl)oxy)-6-methylpyridin-2-yl) carbamoyl)tetrahydrofuran-3-carboxamide, N-((5-((2-acetamidopyridin-4-yl)oxy)pyridin-2-yl)carbamoyl) isobutyramide, N-((5-((2-acetamidopyridin-4-yl)oxy) pyridin-2-yl)carbamoyl)propionamide, N-((5-((2-isobutyramidopyridin-4-yl)oxy)pyridin-2-yl)carbamoyl) pivalamide, N-(4-((6-(3-pivaloylureido)pyridin-3-yl)oxy) pyridin-2-yl)cyclopropanecarboxamide, N-((5-((2-acetamidopyridin-4-yl)oxy)pyridin-2-yl)carbamoyl)-1-methylcyclopropanecarboxamide, N-((5-((2-acetamidopyridin-4-yl)oxy)-6-methylpyridin-2-yl) carbamoyl)-2-methoxy-2-methylpropanamide, 1-methyl-N-(4-((6-(3-pivaloylureido)pyridin-3-yl)oxy)pyridin-2-yl) piperidine-4-carboxamide, N-((5-((2-acetamidopyridin-4-yl)oxy)pyridin-2-yl)carbamoyl)tetrahydrofuran-3-carboxamide, N-((5-((2-(3,3-dimethylureido)pyridin-4-yl) oxy)pyridin-2-yl)carbamoyl)pivalamide, N-((5-((2-propionamidopyridin-4-yl)oxy)pyridin-2-yl)carbamoyl) pivalamide, N-((5-((2-acetamidopyridin-4-yl)oxy)pyridin-2-yl)carbamoyl)-1-(trifluoromethyl)cyclobutanecarboxamide, N-((5-((2-acetamidopyridin-4-yl)oxy)pyridin-2-yl)carbamoyl)-2-methoxy-2-methylpropanamide, N-((5-((2-acetamidopyridin-4-yl)oxy)pyridin-2-yl)carbamoyl)-1-methoxycyclopropanecarboxamide, N-((5-((2-acetamidopyridin-4-yl) oxy)pyridin-2-yl)carbamoyl)-7-oxabicyclo[2.2.1]heptane-2-carboxamide, N-((5-((2-acetamidopyridin-4-yl)oxy)-6-methylpyridin-2-yl)carbamoyl)-7-oxabicyclo[2.2.1] heptane-2-carboxamide, N-((5-((2-(cyclopropanecarboxamido)pyridin-4-yl)oxy)pyridin-2-yl) carbamoyl)-1-methylcyclopropanecarboxamide, N-(4-((6-(3-(2-methoxy-2-methylpropanoyl)ureido)pyridin-3-yl) oxy)pyridin-2-yl)cyclopropanecarboxamide, N-((5-((2-propionamidopyridin-4-yl)oxy)pyridin-2-yl)carbamoyl) tetrahydro-2H-pyran-4-carboxamide, 1-methyl-N-(4-((6-(3-(1-methylcyclopropanecarbonyl)ureido)pyridin-3-yl)oxy) pyridin-2-yl)piperidine-4-carboxamide, N-methyl-4-((6-(3-pivaloylureido)pyridin-3-yl)oxy)picolinamide, N-((5-((cyclopropanecarboxamido)pyridin-4-yl)oxy)pyridin-2-yl) carbamoyl)tetrahydro-2H-pyran-4-carboxamide, 1-methyl-N-(5-((2-propionamidopyridin-4-yl)oxy)pyridin-2-yl) carbamoyl)cyclopropanecarboxamide, 2-methoxy-2-methyl-N-((5-((2-propionamidopyridin-4-yl)oxy)pyridin-2-yl)carbamoyl)propanamide, N-((5-((2-acetamidopyridin-4-yl)oxy)-4-methylpyridin-2-yl)carbamoyl)-2-methoxy-2-methylpropanamide, 1-methoxy-N-((5-((2-propionamidopyridin-4-yl)oxy)pyridin-2-yl)carbamoyl) cyclopropanecarboxamide, N-(4-((6-(3-(2-methoxy-2- methylpropanoyl)ureido)pyridin-3-yl)oxy)pyridin-2-yl)-1-methylpiperidine-4-carboxamide, N-((5-((cyclopropanecarboxamido)pyridin-4-yl)oxy)pyridin-2-yl)carbamoyl)-1-methoxycyclopropanecarboxamide, N-((5-((2-acetamidopyridin-4-yl)oxy)-4-methylpyridin-2-yl)carbamoyl)pivalamide, N-((5-((2-acetamidopyridin-4-yl)oxy)-6-methylpyridin-2-yl)carbamoyl)-1-methylcyclobutanecarboxamide, N—N-((5-((2-acetamidopyridin-4-yl)oxy)pyridin-2-yl)carbamoyl)-1-methylcyclobutanecarboxamide, 4-methyl-N-(4-((6-(3-pivaloylureido)pyridin-3-yl)oxy)pyridin-2-yl)piperazine-1-carboxamide, N-(4-((6-(3-pivaloylureido)pyridin-3-yl)oxy)pyridin-2-yl)morpholine-4-carboxamide, (S)-3-(dimethylamino)-N-(4-((6-(3-pivaloylureido)pyridin-3-yl)oxy)pyridin-2-yl)pyrrolidine-1-carboxamide, N-(4-((6-(3-pivaloylureido)pyridin-3-yl)oxy)pyridin-2-yl)azetidine-1-carboxamide, N-(4-((6-(3-(1-methoxycyclopropanecarbonyl)ureido)pyridin-3-yl)oxy)pyridin-2-yl)-1-methylpiperidine-4-carboxamide, N-((5-((2-(3,3-dimethylureido)pyridin-4-yl)oxy)pyridin-2-yl)carbamoyl)-1-methylcyclopropanecarboxamide, N-((5-((2-(3,3-dimethylureido)pyridin-4-yl)oxy)pyridin-2-yl)carbamoyl)tetrahydro-2H-pyran-4-carboxamide, 1-methyl-N-(4-((6-(3-pivaloylureido)pyridin-3-yl)oxy)pyridin-2-yl)-1H-pyrazole-4-carboxamide, N-((5-((2-(2-(pyrrolidin-1-yl)acetamido)pyridin-4-yl)oxy)pyridin-2-yl)carbamoyl)pivalamide, N-((5-((2-(dimethylamino)acetamido)pyridin-4-yl)oxy)pyridin-2-yl)carbamoyl)pivalamide, 1-methyl-N-(4-((6-(3-pivaloylureido)pyridin-3-yl)oxy)pyridin-2-yl)pyrrolidine-3-carboxamide, N-((5-((2-(2-cyanoacetamido)pyridin-4-yl)oxy)pyridin-2-yl)carbamoyl)pivalamide, N-(4-((6-(3-isobutyrylureido)pyridin-3-yl)oxy)pyridin-2-yl)-1-methylpiperidine-4-carboxamide, 4-((6-(3-(2-methoxy-2-methylpropanoyl)ureido)pyridin-3-yl)oxy)-N-methylpicolinamide, 1-methyl-N-(4-((6-(3-pivaloylureido)pyridin-3-yl)oxy)pyridin-2-yl)-1H-imidazole-4-carboxamide, (1s,3s)-3-(dimethylamino)-N-(4-((6-(3-pivaloylureido)pyridin-3-yl)oxy)pyridin-2-yl)cyclobutanecarboxamide, (1r,3r)-3-(dimethylamino)-N-(4-((6-(3-pivaloylureido)pyridin-3-yl)oxy)pyridin-2-yl)cyclobutanecarboxamide, N-((5-((2-(3,3-dimethylureido)pyridin-4-yl)oxy)-6-methylpyridin-2-yl)carbamoyl)pivalamide, N-(4-((2-methyl-6-(3-pivaloylureido)pyridin-3-yl)oxy)pyridin-2-yl)morpholine-4-carboxamide, 4-((6-(3-(1-methoxycyclopentanecarbonyl)ureido)pyridin-3-yl)oxy)-N-methylpicolinamide, N-((5-((2-(3,3-dimethylureido)pyridin-4-yl)oxy)pyridin-2-yl)carbamoyl)-4-methyltetrahydro-2H-pyran-4-carboxamide, N-(4-((6-(3-isobutyrylureido)pyridin-3-yl)oxy)pyridin-2-yl)-4-methylpiperazine-1-carboxamide, N-((5-((2-acetamidopyridin-4-yl)oxy)pyridin-2-yl)carbamoyl)-1-methoxycyclopentanecarboxamide, (R)-3-(dimethylamino)-N-(4-((6-(3-pivaloylureido)pyridin-3-yl)oxy)pyridin-2-yl)pyrrolidine-1-carboxamide, 4-methyl-N-(4-((2-methyl-6-(3-pivaloylureido)pyridin-3-yl)oxy)pyridin-2-yl)piperazine-1-carboxamide, N-methyl-4-((6-(3-(4-methyltetrahydro-2H-pyran-4-carbonyl)ureido)pyridin-3-yl)oxy)picolinamide, N-(4-((2-methyl-6-(3-pivaloylureido)pyridin-3-yl)oxy)pyridin-2-yl)pyrrolidine-1-carboxamide, N-methyl-4-((6-(3-(1-(trifluoromethyl)cyclobutanecarbonyl)ureido)pyridin-3-yl)oxy)picolinamide, N-isopropyl-4-((6-(3-pivaloylureido)pyridin-3-yl)oxy)picolinamide, N-cyclopropyl-4-((6-(3-pivaloylureido)pyridin-3-yl)oxy)picolinamide, N-(1-methylpiperidin-4-yl)-4-((6-(3-pivaloylureido)pyridin-3-yl)oxy)picolinamide, 4-(dimethylamino)-N-(4-((6-(3-pivaloylureido)pyridin-3-yl)oxy)pyridin-2-yl)piperidine-1-carboxamide, 3-(dimethylamino)-N-(4-((6-(3-pivaloylureido)pyridin-3-yl)oxy)pyridin-2-yl)azetidine-1-carboxamide, N-(4-((6-(3-pivaloylureido)pyridin-3-yl)oxy)pyridin-2-yl)pyrrolidine-1-carboxamide, N-((5-((2-(3-methylureido)pyridin-4-yl)oxy)pyridin-2-yl)carbamoyl)pivalamide, 4-ethyl-N-(4-((6-(3-pivaloylureido)pyridin-3-yl)oxy)pyridin-2-yl)piperazine-1-carboxamide, 4-(4-methylpiperazin-1-yl)-N-(4-((6-(3-pivaloylureido)pyridin-3-yl)oxy)pyridin-2-yl)piperidine-1-carboxamide, N-((5-((2-(3-(2-methoxyethyl)ureido)pyridin-4-yl)oxy)pyridin-2-yl)carbamoyl)pivalamide, and N-(4-((6-(3-pivaloylureido)pyridin-3-yl)oxy)pyridin-2-yl)piperazine-1-carboxamide, or a pharmaceutically acceptable salt, enantiomer, stereoisomer, or tautomer thereof.

In certain embodiments, the invention comprises a method of treating mammalian disease wherein the disease etiology or progression is at least partially mediated by the kinase activity of c-FMS, PDGFR-b, or c-KIT kinases, wherein the kinase is a wildtype form, a mutant oncogenic form, an aberrant fusion protein form or a polymorph thereof, the method comprising administering to a mammal in need thereof an effective amount of a compound of formula I.

In other embodiments, the present invention comprises a pharmaceutical composition, comprising a compound of formula I and a pharmaceutically acceptable carrier.

In certain embodiments, the composition comprises an additive selected from adjuvants, excipients, diluents, or stabilizers.

In some embodiments, the invention includes a method of treating cancer, gastrointestinal stromal tumors, hyperproliferative diseases, metabolic diseases, neurodegenerative diseases, solid tumors, melanomas, glioblastomas, ovarian cancer, pancreatic cancer, prostate cancer, lung cancers, breast cancers, renal cancers, hepatic cancers, osteosarcomas, multiple myelomas, cervical carcinomas, metastasis of primary tumor sites, cancers that are metastatic to bone, papillary thyroid carcinoma, non-small cell lung cancer, colonic cancers, rheumatoid arthritis, osteoarthritis, multiple sclerosis, autoimmune nephritis, lupus, Crohn's disease, asthma, chronic obstructive pulmonary disease, osteoporosis, mastocytosis, or mast cell leukemia, the method comprising administering to a patient in need thereof an effective amount of a compound of formula I.

In some embodiments, the invention includes a method of treating glioblastomas, breast cancers, pancreatic cancers, metastasis of primary tumor sites, or cancers that are metastatic to bone, the method comprising administering to a patient in need thereof an effective amount of a compound of formula I.

In certain embodiments of the present methods, the compound is administered orally, parenterally, by inhalation, or subcutaneously.

In some embodiments, the invention provides the use of a compound of Formula I, or a pharmaceutically acceptable salt thereof, in the treatment of cancer, gastrointestinal stromal tumors, hyperproliferative diseases, metabolic diseases, neurodegenerative diseases, solid tumors, melanomas, glioblastomas, ovarian cancer, pancreatic cancer, prostate cancer, lung cancers, breast cancers, renal cancers, hepatic cancers, osteosarcomas, multiple myelomas, cervical carcinomas, metastasis of primary tumor sites, cancers that are metastatic to bone, papillary thyroid carcinoma, non-small cell lung cancer, colonic cancers, rheumatoid arthritis, osteoarthritis, multiple sclerosis, autoimmune nephritis, lupus, Crohn's disease, asthma, chronic obstructive pulmonary disease, osteoporosis, mastocytosis, or mast cell leukemia, the method comprising administering to a patient in need thereof an effective amount of a compound of formula I.

In some embodiments, the invention provides the use of a compound of Formula I, or a pharmaceutically acceptable salt thereof, in the treatment of glioblastomas, breast cancers, pancreatic cancers, metastasis of primary tumor sites, or cancers that are metastatic to bone, the method comprising administering to a patient in need thereof an effective amount of a compound of formula I.

In some embodiments, the invention provides for the use of a compound of Formula I, or a pharmaceutically acceptable salt thereof, for the manufacture of a medicament for the treatment of cancer, gastrointestinal stromal tumors, hyperproliferative diseases, metabolic diseases, neurodegenerative diseases, solid tumors, melanomas, glioblastomas, ovarian cancer, pancreatic cancer, prostate cancer, lung cancers, breast cancers, renal cancers, hepatic cancers, osteosarcomas, multiple myelomas, cervical carcinomas, metastasis of primary tumor sites, cancers that are metastatic to bone, papillary thyroid carcinoma, non-small cell lung cancer, colonic cancers, rheumatoid arthritis, osteoarthritis, multiple sclerosis, autoimmune nephritis, lupus, Crohn's disease, asthma, chronic obstructive pulmonary disease, osteoporosis, mastocytosis, or mast cell leukemia.

In certain embodiments, the invention provides for the use of a compound of Formula I, or a pharmaceutically acceptable salt thereof, for the manufacture of a medicament for the treatment of glioblastomas, breast cancers, pancreatic cancers, metastasis of primary tumor sites, or cancers that are metastatic to bone.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs. The initial definition provided for a group or term provided in this disclosure applies to that group or term throughout the present disclosure individually or as part of another group, unless otherwise indicated.

The compounds of this disclosure include any and all possible isomers, stereoisomers, enantiomers, diastereomers, tautomers, and pharmaceutically acceptable salts. Thus, the terms "compound", "compounds", "test compound" or "test compounds" as used in this disclosure refer to the compounds of this disclosure and any and all possible isomers, stereoisomers, enantiomers, diastereomers, tautomers, and pharmaceutically acceptable salts thereof.

DEFINITIONS

The term "alkyl" as used herein refers to a straight chain alkyl, wherein alkyl chain length is indicated by a range of numbers. In exemplary embodiments, "alkyl" refers to an alkyl chain as defined above containing 1, 2, 3, 4, 5, or 6 carbons (i.e., C1-C6 alkyl). Examples of an alkyl group include, but are not limited to, methyl, ethyl, propyl, butyl, pentyl, and hexyl.

The term "branched alkyl" as used herein refers to an alkyl chain wherein a branching point in the chain exists, and the total number of carbons in the chain is indicated by a range of numbers. In exemplary embodiments, "branched alkyl" refers to an alkyl chain as defined above containing from 3, 4, 5, 6, 7, or 8 carbons (i.e., branched C3-C8 alkyl). Examples of a branched alkyl group include, but are not limited to, iso-propyl, iso-butyl, secondary-butyl, and tertiary-butyl, 2-pentyl, 3-pentyl, 2-hexyl, and 3-hexyl.

The term "alkoxy" as used herein refers to —O-(alkyl), wherein "alkyl" is as defined above.

The term "branched alkoxy" as used herein refers to —O—(branched alkyl), wherein "branched alkyl" is as defined above.

The term "alkylene" as used herein refers to an alkyl moiety interposed between two other atoms. In exemplary embodiments, "alkylene" refers to an alkyl moiety as defined above containing 1, 2, or 3 carbons. Examples of an alkylene group include, but are not limited to —CH2-, —CH2CH2-, and —CH2CH2CH2-. In exemplary embodiments, alkylene groups are branched.

The term "alkynyl" as used herein refers to a carbon chain containing one carbon-carbon triple bond. In exemplary embodiments, "alkynyl" refers to a carbon chain as described above containing 2 or 3 carbons (i.e., C2-C3 alkynyl). Examples of an alkynyl group include, but are not limited to, ethyne and propyne.

The term "aryl" as used herein refers to a cyclic hydrocarbon, where the ring is characterized by delocalized π electrons (aromaticity) shared among the ring members, and wherein the number of ring atoms is indicated by a range of numbers. In exemplary embodiments, "aryl" refers to a cyclic hydrocarbon as described above containing 6, 7, 8, 9, or ring atoms (i.e., C6-C10 aryl). Examples of an aryl group include, but are not limited to, benzene, naphthalene, tetralin, indene, and indane.

The term "cycloalkyl" as used herein refers to a monocyclic saturated carbon ring, wherein the number of ring atoms is indicated by a range of numbers. In exemplary embodiments, "cycloalkyl" refers to a carbon ring as defined above containing 3, 4, 5, 6, 7, or 8 ring atoms (i.e., C3-C8 cycloalkyl). Examples of a cycloalkyl group include, but are not limited to, cyclopropyl, cyclobutyl, cyclopentyl, cyclohexyl, cycloheptyl, and cyclooctyl.

The term "halogen" or "halo" as used herein refers to fluorine, chlorine, bromine, and iodine.

The term "heterocycle" or "heterocyclyl" as used herein refers to a cyclic hydrocarbon, wherein at least one of the ring atoms is an O, N, or S, wherein the number of ring atoms is indicated by a range of numbers. Heterocyclyl moieties as defined herein have C or N bonding hands through which the heterocyclyl ring is connected to an adjacent moiety. For example, in some embodiments, a ring N atom from the heterocyclyl is the bonding atom of the heterocylic moiety. In exemplary embodiments, "heterocyclyl" refers to a mono- or bi-cyclic hydrocarbon containing 4, 5, 6, 7 or 8 ring atoms (i.e., C4-C8 heterocyclyl). Examples of a heterocycle group include, but are not limited to, aziridine, oxirane, thiirane, azetidine, oxetane, thietane, pyrrolidine, tetrahydrofuran, pyran, thiopyran, thiomorpholine, thiomorpholine S-oxide, thiomorpholine S-dioxide, oxazoline, tetrahydrothiophene, piperidine, tetrahydropyran, thiane, imidazolidine, oxazolidine, thiazolidine, dioxolane, dithiolane, piperazine, oxazine, dithiane, dioxane, and 7-oxabicyclo[2.2.1]heptane.

The term "heteroaryl" as used herein refers to a cyclic hydrocarbon, where at least one of the ring atoms is an O, N, or S, the ring is characterized by delocalized π electrons (aromaticity) shared among the ring members, and wherein the number of ring atoms is indicated by a range of numbers. Heteroaryl moieties as defined herein have C or N bonding hands through which the heteroaryl ring is connected to an adjacent moiety. For example, in some embodiments, a ring N atom from the heteroaryl is the bonding atom of the heteroaryl moiety. In exemplary embodiments, "heteroaryl" refers to a cyclic hydrocarbon as described above containing 5 or 6 ring atoms (i.e., C5-C6 heteroaryl). Examples of a heteroaryl group include, but are not limited to, pyrrole, furan, thiene, oxazole, thiazole, isoxazole, isothiazole, imidazole, pyrazole, oxadiazole, thiadiazole, triazole, tetrazole, pyridine, pyrimidine, pyrazine, pyridazine, and triazine.

The term "substituted" in connection with a moiety as used herein refers to a further substituent which is attached to the moiety at any acceptable location on the moiety. Unless otherwise indicated, moieties can bond through a carbon, nitrogen, oxygen, sulfur, or any other acceptable atom.

The term "salts" as used herein embraces pharmaceutically acceptable salts commonly used to form alkali metal salts of free acids and to form addition salts of free bases. The nature of the salt is not critical, provided that it is pharmaceutically acceptable. Suitable pharmaceutically acceptable acid addition salts may be prepared from an inorganic acid or from an organic acid. Exemplary pharmaceutical salts are disclosed in Stahl, P. H., Wermuth, C. G., Eds. *Handbook of Pharmaceutical Salts: Properties, Selection and Use*; Verlag Helvetica Chimica Acta/Wiley-VCH: Zurich, 2002, the contents of which are hereby incorporated by reference in their entirety. Specific non-limiting examples of inorganic acids are hydrochloric, hydrobromic, hydroiodic, nitric, carbonic, sulfuric and phosphoric acid. Appropriate organic acids include, without limitation, aliphatic, cycloaliphatic, aromatic, arylaliphatic, and heterocyclyl containing carboxylic acids and sulfonic acids, for example formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, 3-hydroxybutyric, galactaric or galacturonic acid. Suitable pharmaceutically acceptable salts of free acid-containing compounds disclosed herein include, without limitation, metallic salts and organic salts. Exemplary metallic salts include, but are not limited to, appropriate alkali metal (group Ia) salts, alkaline earth metal (group IIa) salts, and other physiological acceptable metals. Such salts can be made from aluminum, calcium, lithium, magnesium, potassium, sodium and zinc. Exemplary organic salts can be made from primary amines, secondary amines, tertiary amines and quaternary ammonium salts, for example, tromethamine, diethylamine, tetra-N-methylammonium, N,N'-dibenzylethylenediamine, chloroprocaine, choline, diethanolamine, ethylenediamine, meglumine (N-methylglucamine) and procaine.

The terms "administer," "administering, or "administration" as used herein refer to either directly administering a compound or pharmaceutically acceptable salt of the compound or a composition to a subject.

The term "carrier" as used herein encompasses carriers, excipients, and diluents, meaning a material, composition or vehicle, such as a liquid or solid filler, diluent, excipient, solvent or encapsulating material involved in carrying or transporting a pharmaceutical agent from one organ, or portion of the body, to another organ or portion of the body.

The term "disorder" is used in this disclosure to mean, and is used interchangeably with, the terms disease, condition, or illness, unless otherwise indicated.

The terms "effective amount" and "therapeutically effective amount" are used interchangeably in this disclosure and refer to an amount of a compound that, when administered to a subject, is capable of reducing a symptom of a disorder in a subject. The actual amount which comprises the "effective amount" or "therapeutically effective amount" will vary depending on a number of conditions including, but not limited to, the particular disorder being treated, the severity of the disorder, the size and health of the patient, and the route of administration. A skilled medical practitioner can readily determine the appropriate amount using methods known in the medical arts.

The terms "isolated" and "purified" as used herein refer to a component separated from other components of a reaction mixture or a natural source. In certain embodiments, the isolate contains at least about 50%, at least about 55%, at least about 60%, at least about 65%, at least about 70%, at least about 75%, at least about 80%, at least about 85%, at least about 90%, at least about 95%, or at least about 98% of the compound or pharmaceutically acceptable salt of the compound by weight of the isolate.

The phrase "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used in this disclosure, the terms "patient" or "subject" include, without limitation, a human or an animal. Exemplary animals include, but are not limited to, mammals such as mouse, rat, guinea pig, dog, feline, horse, cow, pig, monkey, chimpanzee, baboon, or rhesus monkey.

The terms "treatment," "treat," and "treating," are meant to include the full spectrum of intervention for the cancer from which the patient is suffering, such as administration of the active compound to alleviate, slow or reverse one or more of the symptoms and to delay progression of the cancer even if the cancer is not actually eliminated. Treating can be curing, improving, or at least partially ameliorating the disorder.

Structural, chemical and stereochemical definitions are broadly taken from IUPAC recommendations, and more specifically from Glossary of Terms used in Physical Organic Chemistry (IUPAC Recommendations 1994) as summarized by Müller, P. *Pure Appl. Chem.* 1994, 66, pp. 1077-1184 and Basic Terminology of Stereochemistry (IUPAC Recommendations 1996) as summarized by Moss, G. P. *Pure Appl. Chem.* 1996, 68, pp. 2193-2222.

Atropisomers are defined as a subclass of conformers which can be isolated as separate chemical species and which arise from restricted rotation about a single bond.

Regioisomers or structural isomers are defined as isomers involving the same atoms in different arrangements.

Enantiomers are defined as one of a pair of molecular entities which are mirror images of each other and non-superimposable.

Diastereomers or diastereoisomers are defined as stereoisomers other than enantiomers. Diastereomers or diastereoisomers are stereoisomers not related as mirror images. Diastereoisomers are characterized by differences in physical properties, and by some differences in chemical behavior towards achiral as well as chiral reagents.

The term "tautomer" as used herein refers to compounds produced by the phenomenon wherein a proton of one atom of a molecule shifts to another atom. See March, Advanced Organic Chemistry: Reactions, Mechanisms and Structures, 4th Ed., John Wiley & Sons, pp. 69-74 (1992). Tautomerism is defined as isomerism of the general form

where the isomers (called tautomers) are readily interconvertible; the atoms connecting the groups X, Y and Z are typically any of C, H, O, or S, and G is a group which becomes an electrofuge or nucleofuge during isomerization. The most common case, when the electrofuge is H$^+$, is also known as "prototropy." Tautomers are defined as isomers that arise from tautomerism, independent of whether the isomers are isolable.

The exemplified compounds of the present invention are preferably formulated as a pharmaceutical composition using a pharmaceutically acceptable carrier and administered by a variety of routes. Preferably, such compositions are for oral administration. Such pharmaceutical compositions and processes for preparing them are well known in the art. See, e.g., REMINGTON: THE SCIENCE AND PRACTICE OF PHARMACY (A. Gennaro, et al., eds., 19th ed., Mack Publishing Co., 1995).

The compounds of Formula I, or a pharmaceutically acceptable salt thereof, may be prepared by a variety of procedures known in the art, as well as those described below. The specific synthetic steps may be combined in different ways to prepare the Formula I compounds, or a pharmaceutically acceptable salt thereof.

The compounds employed as initial starting materials in the synthesis of the compounds of Formula Ia are well known and, to the extent not commercially available, are readily synthesized using specific references provided, by standard procedures commonly employed by those of ordinary skill in the art, or are found in general reference texts.

Examples of known procedures and methods include those described in general reference texts such as Comprehensive Organic Transformations, VCH Publishers Inc, 1989; Compendium of Organic Synthetic Methods, Volumes 1-10, 1974-2002, Wiley Interscience; Advanced Organic Chemistry, Reactions Mechanisms, and Structure, 5th Edition, Michael B. Smith and Jerry March, Wiley Interscience, 2001; Advanced Organic Chemistry, 4th Edition, Part B, Reactions and Synthesis, Francis A. Carey and Richard J. Sundberg, Kluwer Academic/Plenum Publishers, 2000, etc., and references cited therein.

ChemDraw version 10 or 12 (CambridgeSoft Corporation, Cambridge, Mass.) was used to name the structures of intermediates and exemplified compounds.

The following abbreviations are used in this disclosure and have the following definitions: "ADP" is adenosine diphosphate, "ATP" is adenosine triphosphate, "conc." is concentrated, "CDI" is 1,1'-carbonyldiimidazole, "DBU" is 1,8-diazabicyclo[5.4.0]undec-7-ene, "DCE" is 1,2-dichloroethane, "DCM" is dichloromethane, "DIEA" is N,N-diisopropylethylamine, "DMA" is N,N-dimethylacetamide, "DMAP" is 4-(dimethylamino)pyridine, "DMEM" is Dulbecco's Modified Eagle Media, "DMF" is N,N-dimethylformamide, "DMSO" is dimethylsulfoxide, "DPPF" is 1,1'-bis(diphenylphosphino)ferrocene, "EDC" is N-(3-dimethylaminopropyl)-N'-ethylcarbodiimide hydrochloride, "ESI" is electrospray ionization, "Et$_2$O" is diethylether, "EtOAc" is ethyl acetate, "EtOH" is ethanol, "GST" is glutathione S-transferase, "h" is hour or hours, "Hex" is hexane, "HOBT" is 1-hydroxybenzotriazole, "IC$_{50}$" is half maximal inhibitory concentration, "IPA" refers to isopropyl alcohol, "KF/Al$_2$O$_3$" is potassium fluoride on alumina, "LiHMDS" is lithium bis(trimethylsilyl)amide, "mCPBA" is 3-chloroperbenzoic acid, "MeCN" is acetonitrile, "MeOH" is methanol, "MHz" is megahertz, "min" is minute or minutes, "MS" is mass spectrometry, "MTBE" is methyl tert-butyl ether, "NADH" is nicotinamide adenine dinucleotide, "NMR" is nuclear magnetic resonance, "PBS" is phosphate buffered saline, "Pd/C" is palladium on carbon, "Pd(OAc)$_2$" is palladium(II) acetate, "Pd$_2$(dba)$_3$" is tris(dibenzylideneacetone)dipalladium(0), "pet ether" is petroleum ether, "prep-HPLC" is preparative high performance liquid chromatography, "prep-TLC" is preparative thin layer chromatography, "RT" is room temperature which is also known as "ambient temp," which will be understood to consist of a range of normal laboratory temperatures ranging from 15-25° C., "satd." is saturated, "TBTU" is O-benzotriazole-1-yl-N,N,N',N'-tetramethyluronium tetrafluoroborate, "TEA" is triethylamine, "TFA" is trifluoroacetic acid, "THF" is tetrahydrofuran, "Tris" is tris(hydroxymethyl)aminomethane, "Xantphos" is 4,5-bis(diphenylphosphino)-9,9-dimethylxanthene, and "X-Phos" is 2-dicyclohexylphosphino-2',4',6'-triisopropylbiphenyl.

General Chemistry

The compounds of Formula I (1) are prepared by the general synthetic methods illustrated in the schemes below and the accompanying examples. Suitable reaction conditions for the steps of these schemes are well known in the art and appropriate substitutions of solvents and co-reagents are within the skill of the art. Those skilled in the art will understand that synthetic intermediates may be isolated and/or purified by well known techniques as needed or desired, and that it will be possible to use various intermediates directly in subsequent synthetic steps with little or no purification. Furthermore, those skilled in the art will appreciate that in some instances, the order in which moieties are introduced is not critical. The particular order of steps required to produce the compounds of Formula I is dependent upon the particular compound being synthesized, the starting compound, and the relative lability of the substituted moieties, as is well appreciated by the ordinary skilled chemist. All substituents, unless otherwise indicated, are as defined above.

The compounds of Formula I (1) may contain —NH or —OH moieties in the W, R1, R2, R3, R5, R6, and R9 positions. It will be understood by those skilled in the art that in some instances it may be advantageous to use an amine protecting group during synthesis to temporarily mask one or more —NH or —OH moieties. Said protecting group can be removed from any subsequent intermediate leading to the synthesis of compound 1, using standard conditions that effect removal of said protecting group, said conditions of which will be familiar to those skilled in the art. When not specified in a scheme, it will be understood by those skilled in the art that the W, R1, R2, and R3 moieties represented in the schemes below may optionally contain standard amino or hydroxyl protecting groups that can be removed at any opportune time in the synthetic sequence.

Compounds 1 of the invention can be prepared as illustrated in Scheme 1. In one embodiment, N-acylisocyantes of formula 3 are reacted with amine 5, typically in the presence of a base such as triethylamine or pyridine, to provide compound 1 (R4=H). Isocyanate 3 is prepared from acid chloride 2 by reaction with silver cyanate, or alternately from amide 6 (R4=H) by reaction with oxalyl chloride. If not commercially available, 2 and 6 can readily be prepared from acid 4 by standard methods. In another embodiment, compound 1 (R4=H) can be prepared by reaction of N-acyl carbamate 7 with amine 5 in the presence of a base, for example N-methylpyrrolidine, typically at elevated temperature, for example 50-80° C. Carbamate 7 is prepared from amide 6 (R4=H) by treatment with a strong base, for example lithium bis(trimethylsilyl)amide, and quenching of the resultant anion with isopropenyl chloroformate to provide 7. In another embodiment, compound 1 (R4≠H) is prepared by reaction of carbonyl chloride 8 (R4≠H) with general amine 5. Intermediate 8 is prepared from amide 6 (R4≠H) by reaction with phosgene or the like. Those skilled in the art will appreciate that intermediates of scheme 1 may be isolated or may be generated and used in situ.

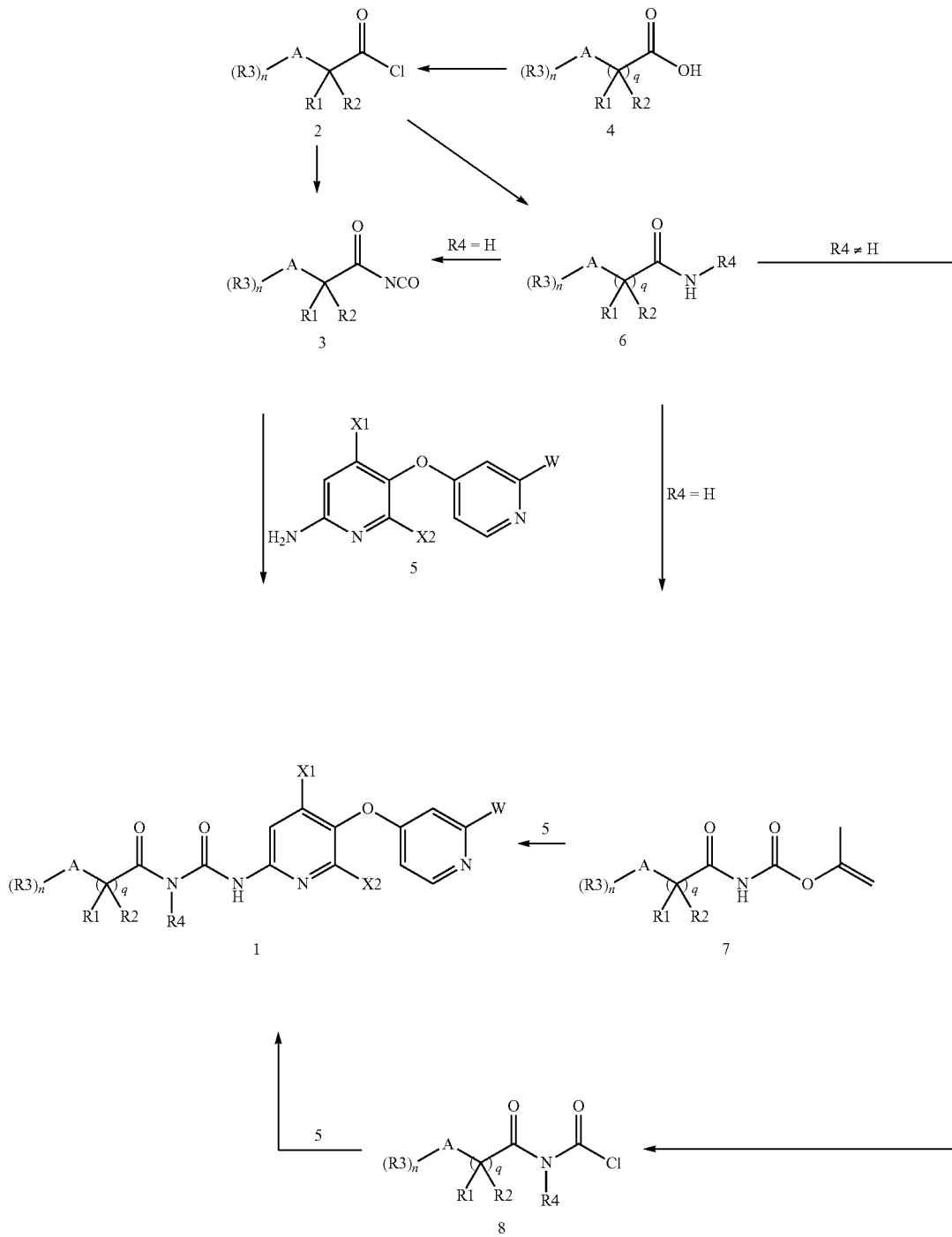

Scheme 1

General amines 5 wherein W is —NHC(O)R5, —NHC(O)R6, or —NHC(O)N(R7)R8 can be synthesized according to methods commonly known to those skilled in the art as illustrated in Scheme 2. In one embodiment, halonitropyridine 9 (Y is halo) is reacted with 2-chloro-4-hydroxypyridine (10) to provide ether 11. Suitable conditions include combining 9 and 10 with a base, for example cesium carbonate or potassium carbonate, and heating said mixture at a temp of 80-120° C. in a solvent such as dimethylformamide to effect ether formation. Further conversion of 11 to 13 is effected by reaction of 11 with reagent H—W (12) in the presence of a palladium catalyst, typically tris(dibenzylideneacetone)dipalladium [Pd$_2$(dba)$_3$], and a suitable ligand, for example 4,5-bis(diphenylphosphino)-9,9-dimethylxanthene [Xantphos], 2-dicyclohexylphosphino-2',4',6'-triisopropylbiphenyl [X-phos], or 1,1'-bis(diphenylphosphino)ferrocene [dppf], and a base such as cesium carbonate. Additional conditions include heating in a solvent such as dioxane at a temperature of 80-120° C. under inert atmosphere. Further reduction of the nitro group of 13 provides general amine 5.

Scheme 2

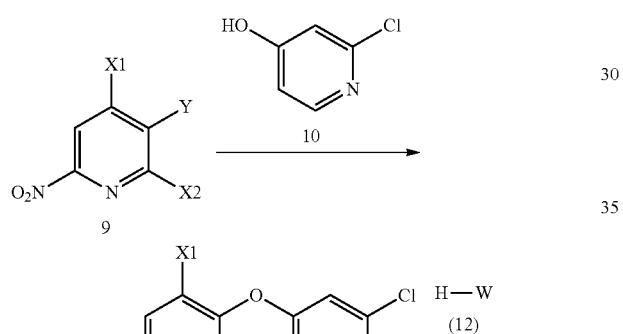

General amines 5 wherein W is —C(O)N(R7)R8 are prepared as illustrated in Scheme 3. Thus, treatment of 4-chloropyridine-2-carbonyl chloride (14) with amine 15 provides 16. Further reaction of chloropyridine 16 with hydroxypyridine 17 in the presence of a base, for example potassium tert-butoxide in a polar aprotic solvent, such as dimethylacetamide, provides 18, an example of general amine 5 wherein W is —C(O)N(R7)R8.

Scheme 3

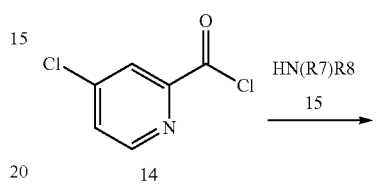

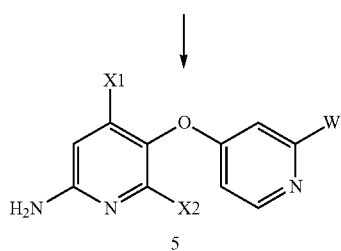

In addition to the methods above, an alternative synthesis of compounds I wherein the W moiety is ureido [—NHC(O)N(R7)R8 and —NHC(O)R6) (wherein R6 is an nitrogen containing heterocycle with an N-bonding hand)] is illustrated in Scheme 4. Using the methods of Scheme 1, amine 19, prepared according to scheme 2 employing tert-butylcarbamate as reagent 12, is converted to 20. Removal of the carbamate protecting group, for example by exposure to trifluoracetic acid, provides aminopyridine 21. Further reaction of 21 with isopropenyl chloroformate in the presence of a base provides intermediate 22. Treatment of 22 with amine 15 or heterocyclic amine 24 provides compounds 23 or 25, respectively.

Scheme 4

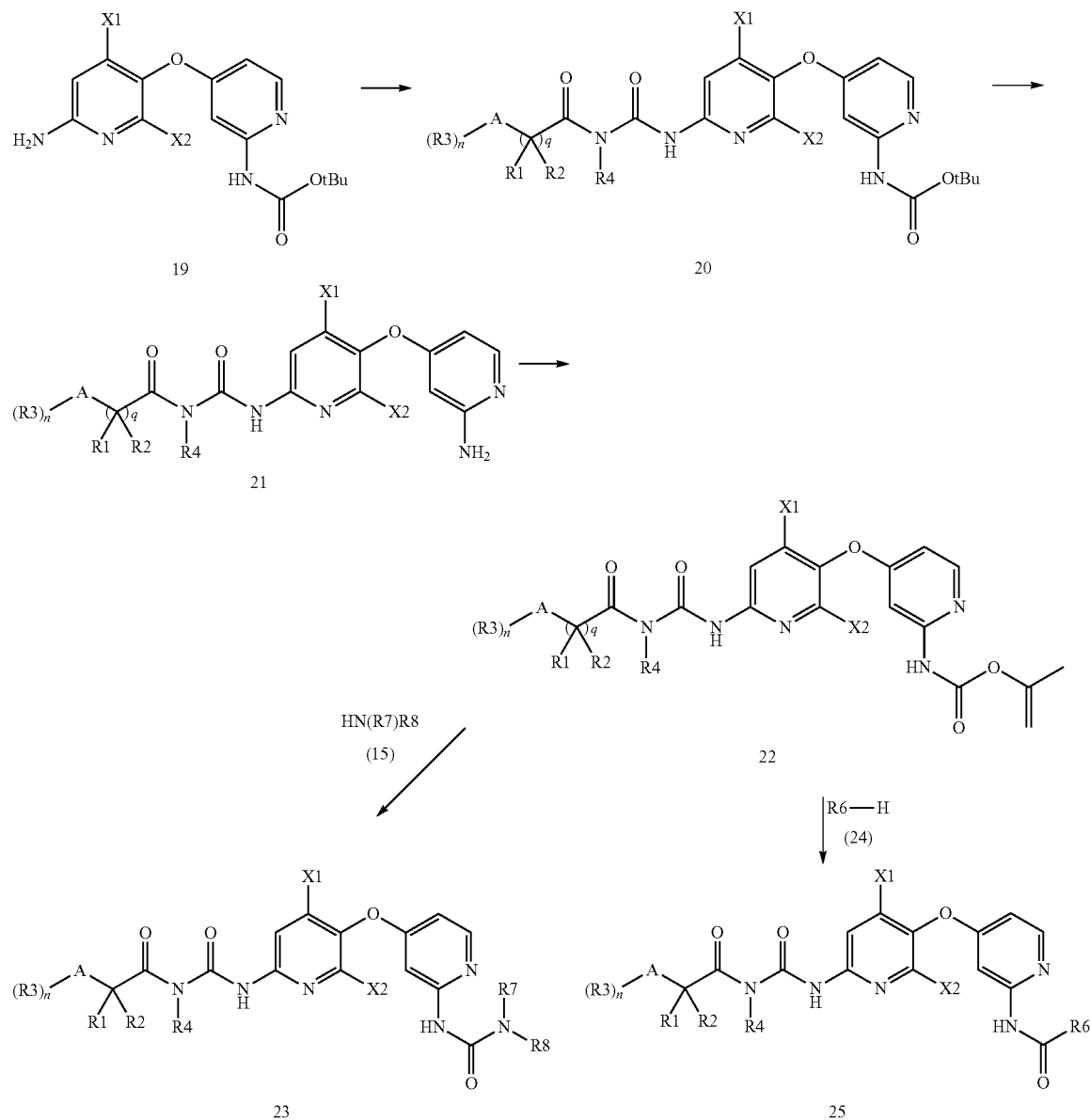

Using the synthetic procedures and methods described herein and methods known to those skilled in the art, the following compounds were made: N-((5-((2-acetamidopyridin-4-yl)oxy)pyridin-2-yl)carbamoyl)cyclohexanecarboxamide, N-((5-((2-acetamidopyridin-4-yl)oxy)pyridin-2-yl)carbamoyl)cyclopentanecarboxamide, N-((5-((2-acetamidopyridin-4-yl)oxy)pyridin-2-yl)carbamoyl)pivalamide, N-((5-((2-acetamidopyridin-4-yl)oxy)pyridin-2-yl)carbamoyl)-2-cyclohexylacetamide, N-((5-((2-acetamidopyridin-4-yl)oxy)pyridin-2-yl)carbamoyl)tetrahydro-2H-pyran-4-carboxamide, N-((5-((2-acetamidopyridin-4-yl)oxy)pyridin-2-yl)carbamoyl)-2-(tetrahydro-2H-pyran-4-yl)acetamide, N-((5-((2-acetamidopyridin-4-yl)oxy)-6-methylpyridin-2-yl)carbamoyl)tetrahydro-2H-pyran-4-carboxamide, N-((5-((2-acetamidopyridin-4-yl)oxy)-6-methylpyridin-2-yl)carbamoyl)cyclopentanecarboxamide, N-((5-((2-acetamidopyridin-4-yl)oxy)-6-methylpyridin-2-yl)carbamoyl)pivalamide, N-((5-((2-acetamidopyridin-4-yl)oxy)-6-methylpyridin-2-yl)carbamoyl)isobutyramide, N-(4-((2-methyl-6-(3-pivaloylureido)pyridin-3-yl)oxy)pyridin-2-yl)cyclopropanecarboxamide, N-((6-methyl-5-((2-propionamidopyridin-4-yl)oxy)pyridin-2-yl)carbamoyl)pivalamide, N-((5-((2-isobutyramidopyridin-4-yl)oxy)-6-methylpyridin-2-yl)carbamoyl)pivalamide, N-((5-((2-acetamidopyridin-4-yl)oxy)-6-methylpyridin-2-yl)carbamoyl)tetrahydrofuran-3-carboxamide, N-((5-((2-acetamidopyridin-4-yl)oxy)pyridin-2-yl)carbamoyl)isobutyramide, N-((5-((2-acetamidopyridin-4-yl)oxy)pyridin-2-yl)carbamoyl)propionamide, N-((5-((2-isobutyramidopyridin-4-yl)oxy)pyridin-2-yl)carbamoyl)pivalamide, N-(4-((6-(3-pivaloylureido)pyridin-3-yl)oxy)pyridin-2-yl)cyclopropanecarboxamide, N-((5-((2-acetamidopyridin-4-yl)oxy)pyridin-2-yl)carbamoyl)-1- methylcyclopropanecarboxamide, N-((5-((2-acetamidopyridin-4-yl)oxy)-6-methylpyridin-2-yl)carbamoyl)-2-methoxy-2-methylpropanamide, 1-methyl-N-(4-((6-(3-pivaloylureido)pyridin-3-yl)oxy)pyridin-2-yl)piperidine-4-carboxamide, N-((5-((2-acetamidopyridin-4-yl)oxy)pyridin-2-yl)carbamoyl)tetrahydrofuran-3-carboxamide, N-((5-((2-(3,3-dimethylureido)pyridin-4-yl)oxy)pyridin-2-yl)carbamoyl)pivalamide, N-((5-((2-propionamidopyridin-4-yl)oxy)pyridin-2-yl)carbamoyl)pivalamide, N-((5-((2-acetamidopyridin-4-yl)oxy)pyridin-2-yl)carbamoyl)-1-(trifluoromethyl)cyclobutanecarboxamide, N-((5-((2-acetamidopyridin-4-yl)oxy)pyridin-2-yl)carbamoyl)-2-methoxy-2-methylpropanamide, N-((5-((2-acetamidopyridin-4-yl)oxy)pyridin-2-yl)carbamoyl)-1-methoxycyclopropanecarboxamide, N-((5-((2-acetamidopyridin-4-yl)oxy)pyridin-2-yl)carbamoyl)-7-oxabicyclo[2.2.1]heptane-2-carboxamide, N-((5-((2-acetamidopyridin-4-yl)oxy)-6-methylpyridin-2-yl)carbamoyl)-7-oxabicyclo[2.2.1]heptane-2-carboxamide, N-((5-((2-(cyclopropanecarboxamido)pyridin-4-yl)oxy)pyridin-2-yl)carbamoyl)-1-methylcyclopropanecarboxamide, N-(4-((6-(3-(2-methoxy-2-methylpropanoyl)ureido)pyridin-3-yl)oxy)pyridin-2-yl)cyclopropanecarboxamide, N-((5-((2-propionamidopyridin-4-yl)oxy)pyridin-2-yl)carbamoyl)tetrahydro-2H-pyran-4-carboxamide, 1-methyl-N-(4-((6-(3-(1-methylcyclopropanecarbonyl)ureido)pyridin-3-yl)oxy)pyridin-2-yl)piperidine-4-carboxamide, N-methyl-4-((6-(3-pivaloylureido)pyridin-3-yl)oxy)picolinamide, N-((5-((2-(cyclopropanecarboxamido)pyridin-4-yl)oxy)pyridin-2-yl)carbamoyl)tetrahydro-2H-pyran-4-carboxamide, 1-methyl-N-((5-((2-propionamidopyridin-4-yl)oxy)pyridin-2-yl)carbamoyl)cyclopropanecarboxamide, 2-methoxy-2-methyl-N-((5-((2-propionamidopyridin-4-yl)oxy)pyridin-2-yl)carbamoyl)propanamide, N-((5-((2-acetamidopyridin-4-yl)oxy)-4-methylpyridin-2-yl)carbamoyl)-2-methoxy-2-methylpropanamide, 1-methoxy-N-((5-((2-propionamidopyridin-4-yl)oxy)pyridin-2-yl)carbamoyl)cyclopropanecarboxamide, N-(4-((6-(3-(2-methoxy-2-methylpropanoyl)ureido)pyridin-3-yl)oxy)pyridin-2-yl)-1-methylpiperidine-4-carboxamide, N-((5-((2-(cyclopropanecarboxamido)pyridin-4-yl)oxy)pyridin-2-yl)carbamoyl)-1-methoxycyclopropanecarboxamide, N-((5-((2-acetamidopyridin-4-yl)oxy)-4-methylpyridin-2-yl)carbamoyl)pivalamide, N-((5-((2-acetamidopyridin-4-yl)oxy)-6-methylpyridin-2-yl)carbamoyl)-1-methylcyclobutanecarboxamide, N-((5-((2-acetamidopyridin-4-yl)oxy)pyridin-2-yl)carbamoyl)-1-methylcyclobutanecarboxamide, 4-methyl-N-(4-((6-(3-pivaloylureido)pyridin-3-yl)oxy)pyridin-2-yl)piperazine-1-carboxamide, N-(4-((6-(3-pivaloylureido)pyridin-3-yl)oxy)pyridin-2-yl)morpholine-4-carboxamide, (S)-3-(dimethylamino)-N-(4-((6-(3-pivaloylureido)pyridin-3-yl)oxy)pyridin-2-yl)pyrrolidine-1-carboxamide, N-(4-((6-(3-pivaloylureido)pyridin-3-yl)oxy)pyridin-2-yl)azetidine-1-carboxamide, N-(4-((6-(3-(1-methoxycyclopropanecarbonyl)ureido)pyridin-3-yl)oxy)pyridin-2-yl)-1-methylpiperidine-4-carboxamide, N-((5-((2-(3,3-dimethylureido)pyridin-4-yl)oxy)pyridin-2-yl)carbamoyl)-1-methylcyclopropanecarboxamide, N-((5-((2-(3,3-dimethylureido)pyridin-4-yl)oxy)pyridin-2-yl)carbamoyl)tetrahydro-2H-pyran-4-carboxamide, 1-methyl-N-(4-((6-(3-pivaloylureido)pyridin-3-yl)oxy)pyridin-2-yl)-1H-pyrazole-4-carboxamide, N-((5-((2-(2-(pyrrolidin-1-yl)acetamido)pyridin-4-yl)oxy)pyridin-2-yl)carbamoyl)pivalamide, N-((5-((2-(2-(dimethylamino)acetamido)pyridin-4-yl)oxy)pyridin-2-yl)carbamoyl)pivalamide, 1-methyl-N-(4-((6-(3-pivaloylureido)pyridin-3-yl)oxy)pyridin-2-yl)pyrrolidine-3-carboxamide, N-((5-((2-cyanoacetamido)pyridin-4-yl)oxy)pyridin-2-yl)carbamoyl)pivalamide, N-(4-((6-(3-isobutyrylureido)pyridin-3-yl)oxy)pyridin-2-yl)-1-methylpiperidine-4-carboxamide, 4-((6-(3-(2-methoxy-2-methylpropanoyl)ureido)pyridin-3-yl)oxy)-N-methylpicolinamide, 1-methyl-N-(4-((6-(3-pivaloylureido)pyridin-3-yl)oxy)pyridin-2-yl)-1H-imidazole-4-carboxamide, (1s,3s)-3-(dimethylamino)-N-(4-((6-(3-pivaloylureido)pyridin-3-yl)oxy)pyridin-2-yl)cyclobutanecarboxamide, (1r,3r)-3-(dimethylamino)-N-(4-((6-(3-pivaloylureido)pyridin-3-yl)oxy)pyridin-2-yl)cyclobutanecarboxamide, N-((5-((2-(3,3-dimethylureido)pyridin-4-yl)oxy)-6-methylpyridin-2-yl)carbamoyl)pivalamide, N-(4-((2-methyl-6-(3-pivaloylureido)pyridin-3-yl)oxy)pyridin-2-yl)morpholine-4-carboxamide, 4-((6-(3-(1-methoxycyclopentanecarbonyl)ureido)pyridin-3-yl)oxy)-N-methylpicolinamide, N—N-((5-((2-(3,3-dimethylureido)pyridin-4-yl)oxy)pyridin-2-yl)carbamoyl)-4-methyltetrahydro-2H-pyran-4-carboxamide, N-(4-((6-(3-isobutyrylureido)pyridin-3-yl)oxy)pyridin-2-yl)-4-methylpiperazine-1-carboxamide, N-((5-((2-acetamidopyridin-4-yl)oxy)pyridin-2-yl)carbamoyl)-1-methoxycyclopentanecarboxamide, (R)-3-(dimethylamino)-N-(4-((6-(3-pivaloylureido)pyridin-3-yl)oxy)pyridin-2-yl)pyrrolidine-1-carboxamide, 4-methyl-N-(4-((2-methyl-6-(3-pivaloylureido)pyridin-3-yl)oxy)pyridin-2-yl)piperazine-1-carboxamide, N-methyl-4-((6-(3-(4-methyltetrahydro-2H-pyran-4-carbonyl)ureido)pyridin-3-yl)oxy)picolinamide, N-(4-((2-methyl-6-(3-pivaloylureido)pyridin-3-yl)oxy)pyridin-2-yl)pyrrolidine-1-carboxamide, N-methyl-4-((6-(3-(1-(trifluoromethyl)cyclobutanecarbonyl)ureido)pyridin-3-yl)oxy)picolinamide, N-isopropyl-4-((6-(3-pivaloylureido)pyridin-3-yl)oxy)picolinamide, N-cyclopropyl-4-((6-(3-pivaloylureido)pyridin-3-yl)oxy)picolinamide, N-(1-methylpiperidin-4-yl)-4-((6-(3-pivaloylureido)pyridin-3-yl)oxy)picolinamide, 4-(dimethylamino)-N-(4-((6-(3-pivaloylureido)pyridin-3-yl)oxy)pyridin-2-yl)piperidine-1-carboxamide, 3-(dimethylamino)-N-(4-((6-(3-pivaloylureido)pyridin-3-yl)oxy)pyridin-2-yl)azetidine-1-carboxamide, N-(4-((6-(3-pivaloylureido)pyridin-3-yl)oxy)pyridin-2-yl)pyrrolidine-1-carboxamide, N-((5-((2-(3-methylureido)pyridin-4-yl)oxy)pyridin-2-yl)carbamoyl)pivalamide, 4-ethyl-N-(4-((6-(3-pivaloylureido)pyridin-3-yl)oxy)pyridin-2-yl)piperazine-1-carboxamide, 4-(4-methylpiperazin-1-yl)-N-(4-((6-(3-pivaloylureido)pyridin-3-yl)oxy)pyridin-2-yl)piperidine-1-carboxamide, N-((5-((2-(3-(2-methoxyethyl)ureido)pyridin-4-yl)oxy)pyridin-2-yl)carbamoyl)pivalamide, and N-(4-((6-(3-pivaloylureido)pyridin-3-yl)oxy)pyridin-2-yl)piperazine-1-carboxamide.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

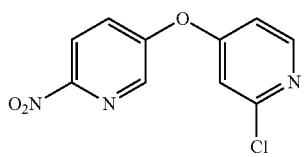 [SMILES: O=[N+]([O-])c1ccc(Oc2ccnc(Cl)c2)cn1]

Example A1

A solution of 5-bromo-2-nitropyridine (15 g, 73.9 mmol) in DMF (300 mL) was sparged with Ar, treated with $Cs_2CO_3$ (48.2 g, 148 mmol) and 2-chloro-4-hydroxypyridine (10.53 g, 81 mmol), sparged again with Ar and heated at 85° C. overnight. The mixture was cooled to RT, filtered through a bed of silica gel, washed thoroughly with EtOAc, and the filtrate treated with 5% LiCl and stirred overnight. The layers were separated, the aqueous layer extracted with additional EtOAc (4×) and the combined organics were dried over $Na_2SO_4$ and concentrated to dryness. The residue was dissolved in EtOAc, treated with 5% LiCl, stirred for 1 h, the layers separated and the aqueous layer extracted with EtOAc (3×). The combined organics were dried over $Na_2SO_4$, concentrated to dryness and purified via silica gel chromatography (EtOAc/Hex). The material was suspended in MTBE, sonicated and the resulting solid collected via filtration to afford 2-chloro-4-((6-nitropyridin-3-yl)oxy)pyridine (6.06 g, 33%). $^1$H NMR (400 MHz, DMSO-$d_6$): δ 8.62 (d, J=2.4, 1H), 8.43-8.39 (m, 2H), 8.06 (dd, J=8.8, 2.8 Hz, 1H), 7.36 (d, J=2.0 Hz, 1H), 7.23 (dd, J=5.6, 2.0 Hz, 1H); MS (ESI) m/z: 252.0 (M+H$^+$).

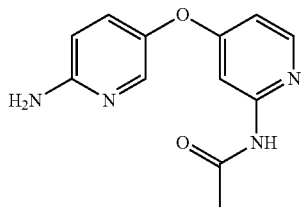 [SMILES: CC(=O)Nc1cc(Oc2ccc(N)nc2)ccn1]

Example A2

A degassed solution of Example A1 (2.0 g, 7.95 mmol) in dioxane (30 mL) added treated with acetamide (1.878 g, 31.8 mmol), $Cs_2CO_3$ (2.59 g, 7.95 mmol), X-Phos (0.189 g, 0.397 mmol), and $Pd_2(dba)_3$ (0.364 g, 0.397 mmol) and heated at 80° C. for 16 h. The mixture was cooled to RT, treated with EtOAc, the solids removed via filtration through diatomaceous earth and rinsed well with EtOAc. The filtrate was washed with water, then brine, dried over $Na_2SO_4$, concentrated to dryness and purified via silica gel chromatography (EtOAc/Hex) to afford N-(4-((6-nitropyridin-3-yl)oxy)pyridin-2-yl)acetamide (1.48 g, 68%). MS (ESI) m/z: 275.1 (M+H$^+$).

A solution of N-(4-((6-nitropyridin-3-yl)oxy)pyridin-2-yl)acetamide (1.48 g, 5.40 mmol) and $NH_4Cl$ (7.22 g, 135 mmol) in MeOH (25 mL) was treated with zinc (2.82 g, 43.2 mmol) and stirred at RT for 1 h. The solids were removed via filtration through diatomaceous earth, washed with MeOH and the filtrate concentrated to near-dryness. The residue was treated with water, extracted with EtOAc (2×) and the combined organics were washed with brined, dried over $Na_2SO_4$ and concentrated to dryness. The material was treated with 60% EtOAc/Hex, the solid collected via filtration, washed with 60% EtOAc/Hex and dried to afford N-(4-((6-aminopyridin-3-yl)oxy)pyridin-2-yl)acetamide (750 mg, 57%) as an off-white solid. $^1$H NMR (400 MHz, DMSO-$d_6$): δ 10.47 (s, 1H), 8.11 (d, J=5.7 Hz, 1H), 7.76 (d, J=2.9 Hz, 1H), 7.59 (d, J=2.4 Hz, 1H), 7.24 (dd, J=8.9, 3.0 Hz, 1H), 6.59 (dd, J=5.7, 2.4 Hz, 1H), 6.49 (d, J=8.9 Hz, 1H), 6.00 (s, 2H), 2.01 (s, 3H); MS (ESI) m/z: 245.1 (M+H$^+$).

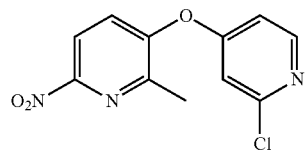 [SMILES: Cc1nc([N+](=O)[O-])ccc1Oc1ccnc(Cl)c1]

Example A3

A 0° C. solution of sulfuric acid (125 mL) was treated drop-wise with $H_2O_2$ (30%, 63.1 mL, 2058 mmol), stirred for 15 min, treated drop-wise with a cold solution of 6-amino-3-bromo-2-picoline (35 g, 187 mmol) in sulfuric acid (125 mL), allowed to warm to RT and stirred for 4 h. The mixture was poured onto ice (1.2 kg) and the resulting solid collected via filtration, dissolved in DCM, washed with brine, dried over $Na_2SO_4$ and concentrated to dryness. The aqueous filtrate and washes were combined, extracted with DCM (2×) and the combined organics were dried over $Na_2SO_4$, concentrated to dryness, purified via silica gel chromatography (EtOAc/Hex) and combined with the above-isolated solid to afford 3-bromo-2-methyl-6-nitropyridine (25.59 g, 63%). MS (ESI) m/z: 218.9 (M+H$^+$).

A solution of 3-bromo-2-methyl-6-nitropyridine (25.59 g, 118 mmol), $K_2CO_3$ (48.9 g, 354 mmol) and 2-chloro-4-hydroxy-pyridine (30.6 g, 236 mmol) in DMF (160 mL) was sparged with Ar, heated at 100° C. overnight, then cooled to RT. The mixture was treated with water and EtOAc, the solids removed via filtration through diatomaceous earth and washed with water, EtOAc, then DCM. The aqueous filtrate was extracted with EtOAc (2×) and the organic extracts were combined with the organic filtrates, washed with water, then brine, dried over $Na_2SO_4$ and concentrated to dryness. The residue was treated with MTBE, sonicated and the resulting solid collected via filtration to afford 3-((2-chloropyridin-4-yl)oxy)-2-methyl-6-nitropyridine (17.16 g, 55%). $^1$H NMR (400 MHz, DMSO-$d_6$): δ 8.38 (d, J=5.7 Hz, 1H), 8.25 (d, J=8.7 Hz, 1H), 7.95 (d, J=8.7 Hz, 1H), 7.29 (d, J=2.3 Hz, 1H), 7.16 (dd, J=5.7, 2.3 Hz, 1H), 2.46 (s, 3H); MS (ESI) m/z: 266.0 (M+H$^+$).

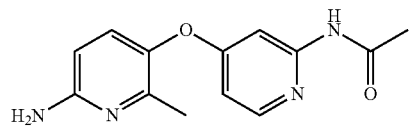 [SMILES: CC(=O)Nc1cc(Oc2ccc(N)nc2C)ccn1]

Example A4

A solution of Example A3 (1.7 g, 6.40 mmol) in dioxane (30 mL) was sparged with Ar, treated with acetamide (1.512 g, 25.6 mmol), $Cs_2CO_3$ (2.085 g, 6.40 mmol), X-Phos (0.153 g, 0.320 mmol) and $Pd_2(dba)_3$ (0.293 g, 0.320 mmol) and heated at 80° C. for 20 h. The mixture was cooled to RT, treated with EtOAc, the solids removed via filtration through diatomaceous earth and rinsed well with EtOAc. The filtrate was washed with water, then brine, dried over Na₂SO₄, concentrated to dryness and purified via silica gel chromatography (EtOAc/DCM) to afford N-(4-((2-methyl-6-nitropyridin-3-yl)oxy)pyridin-2-yl)acetamide (450 mg, 24%) as a light yellow solid. MS (ESI) m/z: 289.1 (M+H⁺).

A solution of N-(4-((2-methyl-6-nitropyridin-3-yl)oxy)pyridin-2-yl)acetamide (0.44 g, 1.526 mmol) in MeOH (30 mL) was treated with palladium on carbon (50% wet, 0.162 g, 0.153 mmol) and hydrogenated (1 atm) at RT for 24 h. The solids were removed via filtration through diatomaceous earth, washed well with MeOH and the filtrate concentrated to afford N-(4-(((6-amino-2-methylpyridin-3-yl)oxy)pyridin-2-yl)acetamide (370 mg, 94%) as a white solid. ¹H NMR (400 MHz, DMSO-d₆): δ 10.46 (s, 1H), 8.10 (d, J=5.7 Hz, 1H), 7.53 (d, J=2.3 Hz, 1H), 7.13 (d, J=8.7 Hz, 1H), 6.53 (dd, J=5.7, 2.4 Hz, 1H), 6.32 (d, J=8.7 Hz, 1H), 5.91 (s, 2H), 2.02 (s, 3H), 2.01 (s, 3H); MS (ESI) m/z: 259.2 (M+H⁺).

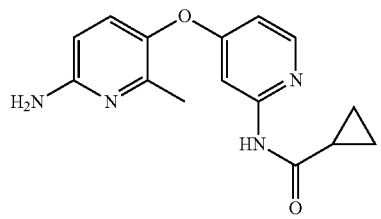 [SMILES: Cc1nc(N)ccc1Oc1ccnc(NC(=O)C2CC2)c1]

Example A5

A mixture of Example A3 (0.50 g, 1.882 mmol), cyclopropanecarboxamide (0.641 g, 7.53 mmol), Cs₂CO₃ (0.920 g, 2.82 mmol), and X-phos (0.045 g, 0.094 mmol) in dioxane (10 mL) was sparged with Ar, treated with Pd₂(dba)₃ (0.086 g, 0.094 mmol), sparged again with Ar and heated at 90° C. overnight. The mixture was cooled to RT, treated with EtOAc and the solids removed via filtration. The filtrate was washed with brine, dried over Na₂SO₄, concentrated to dryness and purified via silica gel chromatography (EtOAc/DCM) to afford N-(4-((2-methyl-6-nitropyridin-3-yl)oxy)pyridin-2-yl)cyclopropanecarboxamide (500 mg, 85%). MS (ESI) m/z: 315.1 (M+H⁺).

A solution of N-(4-((2-methyl-6-nitropyridin-3-yl)oxy)pyridin-2-yl)cyclopropanecarboxamide (0.50 g, 1.591 mmol) in 2:1 EtOAc/MeOH (30 mL) was treated with palladium on carbon (50% wet, 0.188 g, 0.159 mmol) and hydrogenated (1 atm) for 2 days. The solids were removed via filtration through diatomaceous earth, washed well with MeOH and the filtrate was concentrated to dryness to afford N-(4-((6-amino-2-methylpyridin-3-yl)oxy)pyridin-2-yl)cyclopropanecarboxamide (400 mg, 88%). ¹H NMR (400 MHz, DMSO-d₆): δ 10.77 (s, 1H), 8.13 (d, J=5.7 Hz, 1H), 7.52 (d, J=2.4 Hz, 1H), 7.14 (d, J=8.7 Hz, 1H), 6.58 (dd, J=5.7, 2.4 Hz, 1H), 6.32 (d, J=8.7 Hz, 1H), 5.92 (s, 2H), 2.03 (s, 3H), 1.95 (m, 1H), 0.76 (s, 4H); MS (ESI) m/z: 285.1 (M+H⁺).

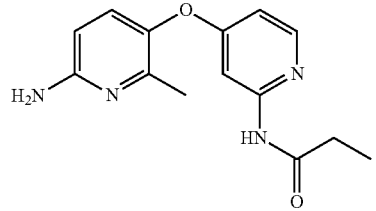 [SMILES: CCC(=O)Nc1cc(Oc2ccc(N)nc2C)ccn1]

Example A6

A mixture of Example A3 (0.50 g, 1.882 mmol), propionamide (0.550 g, 7.53 mmol), Cs₂CO₃ (0.920 g, 2.82 mmol), and X-phos (0.045 g, 0.094 mmol) in dioxane (10 mL) was sparged with Ar, treated with Pd₂(dba)₃ (0.086 g, 0.094 mmol), sparged again with Ar and heated at 90° C. for 20 h. The mixture was cooled to RT, treated with EtOAc and the solids removed via filtration. The filtrate was washed with brine, dried over Na₂SO₄, concentrated to dryness and purified via silica gel chromatography (EtOAc/DCM) to afford N-(4-((2-methyl-6-nitropyridin-3-yl)oxy)pyridin-2-yl)propionamide (420 mg, 74%). MS (ESI) m/z: 303.1 (M+H⁺).

A solution of N-(4-((2-methyl-6-nitropyridin-3-yl)oxy)pyridin-2-yl)propionamide (0.42 g, 1.389 mmol) in 2:1 EtOAc/MeOH (30 mL) was treated with palladium on carbon (50% wet, 0.165 g, 0.139 mmol) and hydrogenated (1 atm) for 2 days. The solids were removed via filtration through diatomaceous earth, washed well with MeOH and the filtrate was concentrated to dryness to afford N-(4-((6-amino-2-methylpyridin-3-yl)oxy)pyridin-2-yl)propionamide (320 mg, 85%). ¹H NMR (400 MHz, DMSO-d₆): δ 10.41 (s, 1H), 8.12 (d, J=5.7 Hz, 1H), 7.56 (d, J=2.4 Hz, 1H), 7.15 (d, J=8.7 Hz, 1H), 6.56 (dd, J=5.7, 2.4 Hz, 1H), 6.34 (d, J=8.7 Hz, 1H), 5.93 (s, 2H), 2.33 (q, J=7.5 Hz, 2H), 2.04 (s, 3H), 1.00 (t, J=7.5 Hz, 3H); MS (ESI) m/z: 273.2 (M+H⁺).

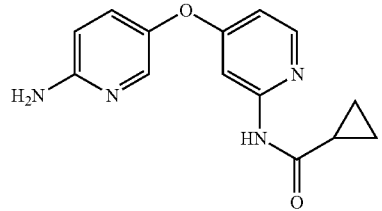 [SMILES: Nc1ccc(Oc2ccnc(NC(=O)C3CC3)c2)cn1]

Example A7

A suspension of Example A1 (2.00 g, 7.95 mmol), Cs₂CO₃ (5.00 g, 15.35 mmol), XPhos (0.200 g, 0.420 mmol), Pd₂(dba)₃ (0.200 g, 0.218 mmol) and cyclopropylcarboxamide (1.00 g, 11.75 mmol) in dioxane (20 mL) was heated at 90° C. under argon overnight. The mixture was cooled to RT and the solids removed via filtration and washed with DCM and THF. The filtrate was concentrated to dryness and purified via silica gel chromatography (EtOAc/Hex) to afford N-(4-((6-nitropyridin-3-yl)oxy)pyridin-2-yl)cyclopropanecarboxamide (1.52 g, 64%) as an off-white solid. ¹H NMR (400 MHz, DMSO-d₆): δ 11.01 (s, 1H), 8.57 (dd, J=2.8, 0.5 Hz, 1H), 8.40 (m, 1H), 8.31 (d, J=5.7 Hz, 1H), 7.98 (dd, J=8.9, 2.8 Hz, 1H), 7.85 (d, J=2.4 Hz, 1H), 6.89 (dd, J=5.7, 2.4 Hz, 1H), 1.97 (m, 1H), 0.77 (m, 4H); MS (ESI) m/z: 301.1 (M+H⁺).

A solution of N-(4-((6-nitropyridin-3-yl)oxy)pyridin-2-yl)cyclopropanecarboxamide (1.50 g, 5.00 mmol) in MeOH (30 mL) was treated with hydrazine hydrate (1.50 g, 30.0 mmol) followed by Raney nickel (0.300 g, 5.11 mmol) and stirred at RT for 3 h. The solids were removed via filtration through diatomaceous earth, rinsed with DCM, then MeOH and the filtrate concentrated to dryness to afford N-(4-((6-aminopyridin-3-yl)oxy)pyridin-2-yl)cyclopropanecarboxamide (1.17 g, 87%) as a white solid. $^1$H NMR (400 MHz, DMSO-$d_6$): δ 11.21 (s, 1H), 8.56 (d, J=5.7 Hz, 1H), 8.19 (s, 1H), 8.01 (s, 1H), 7.68 (d, J=8.9 Hz, 1H), 7.06 (m, 1H), 6.92 (d, J=8.9 Hz, 1H), 6.43 (s, 2H), 2.37 (m, 1H), 1.18 (s, 4H); MS (ESI) m/z: 271.2 (M+H$^+$).

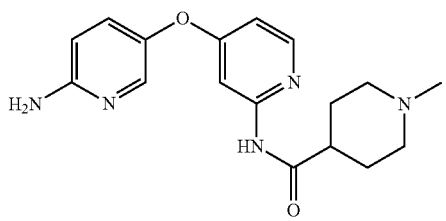 [SMILES: CN1CCC(C(=O)Nc2cc(Oc3ccc(N)nc3)ccn2)CC1]

Example A8

A mixture of Example A1 (0.25 g, 0.994 mmol), Cs$_2$CO$_3$ (0.486 g, 1.490 mmol), 1-methylpiperidine-4-carboxamide (0.155 g, 1.093 mmol), and X-phos (0.024 g, 0.050 mmol) in dioxane (5 mL) was sparged with Ar, treated with Pd$_2$(dba)$_3$ (0.045 g, 0.050 mmol) and heated at 90° C. overnight. Additional X-phos (17 mg) and Pd$_2$(dba)$_3$ (30 mg) were added and the mixture heated at 90° C. for 7 h. The mixture was cooled to RT, treated with water and extracted with EtOAc (3×). The combined organics were dried over Na$_2$SO$_4$, concentrated to dryness and purified via silica gel chromatography (MeOH/DCM) to afford 1-methyl-N-(4-((6-nitropyridin-3-yl)oxy)pyridin-2-yl)piperidine-4-carboxamide (200 mg, 56%). MS (ESI) m/z: 358.2 (M+H$^+$).

A solution of 1-methyl-N-(4-((6-nitropyridin-3-yl)oxy)pyridin-2-yl)piperidine-4-carboxamide (0.20 g, 0.560 mmol) in 2:1 EtOAc/MeOH (15 mL) was treated with Palladium on carbon (50% wet) (0.066 g, 0.056 mmol) was hydrogenated (1 atm) overnight. The solids were removed via filtration through diatomaceous earth, washed with MeOH and the filtrate concentrated to dryness to afford N-(4-((6-aminopyridin-3-yl)oxy)pyridin-2-yl)-1-methylpiperidine-4-carboxamide (130 mg, 71%). $^1$H NMR (400 MHz, DMSO-$d_6$): δ 10.43 (s, 1H), 8.13 (d, J=5.7 Hz, 1H), 7.77 (d, J=2.9 Hz, 1H), 7.60 (d, J=2.4 Hz, 1H), 7.26 (dd, J=8.9, 3.0 Hz, 1H), 6.63 (dd, J=5.7, 2.4 Hz, 1H), 6.51 (d, J=8.9 Hz, 1H), 6.01 (s, 2H), 2.77 (m, 2H), 2.39 (m, 1H), 2.14 (s, 3H), 1.83 (m, 2H), 1.67 (m, 2H), 1.57 (m, 2H); MS (ESI) m/z: 328.2 (M+H$^+$).

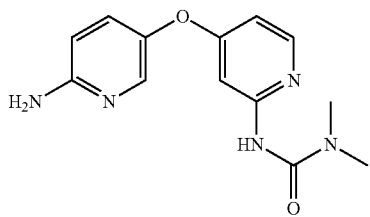 [SMILES: CN(C)C(=O)Nc1cc(Oc2ccc(N)nc2)ccn1]

Example A9

Method A

A mixture of Example A1 (1 g, 3.97 mmol) in dioxane (20 mL) was sparged with Ar, treated with N,N-dimethyl urea (0.700 g, 7.95 mmol) and Cs$_2$CO$_3$ (1.942 g, 5.96 mmol), sparged with Ar, treated with dppf [1,1'-bis(diphenylphosphino)ferrocene] (12.38 g, 22.33 mmol) and Pd$_2$(dba)$_3$ (0.182 g, 0.199 mmol), sparged once again with Ar and heated at 95° C. overnight. The mixture was cooled to RT, treated with EtOAc and the solids removed via filtration through silica gel. The filtrate was concentrated to dryness and purified twice via silica gel chromatography (MeOH/DCM) to afford 1,1-dimethyl-3-(4-((6-nitropyridin-3-yl)oxy)pyridin-2-yl)urea (616 mg, 51%). MS (ESI) m/z: 304.1 (M+H$^+$).

A solution of 1,1-dimethyl-3-(4-((6-nitropyridin-3-yl)oxy)pyridin-2-yl)urea (0.631 g, 2.081 mmol) in MeOH (20 mL) was treated with NH$_4$Cl (3.34 g, 62.4 mmol) followed by zinc dust (1.361 g, 20.81 mmol) and stirred at RT overnight. The solids were removed via filtration, washed with THF and the filtrate concentrated to dryness to afford 3-(4-((6-aminopyridin-3-yl)oxy)pyridin-2-yl)-1,1-dimethylurea (560 mg, 98%). MS (ESI) m/z: 274.1 (M+H$^+$).

Method B

A mixture of Example A1 (6 g, 23.8 mmol) in dioxane (100 mL) was sparged with Ar under sonication for 20 min, then treated with N,N-dimethyl urea (10.50 g, 119 mmol), Cs$_2$CO$_3$ (1.942 g, 5.96 mmol), and XANTPHOS (2.76 g, 4.77 mmol), and again sparged with Ar under sonication for 15 min. Pd$_2$(dba)$_3$ (2.18 g, 2.38 mmol) was added and the mixture was again sparged with Ar for 15 min under sonication. The reaction was then heated to 100° C. for 3 h. The mixture was cooled to RT, diluted with EtOAc and the solids removed via filtration through diatomaceous earth. The filtrate was concentrated to dryness and purified by silica gel chromatography (MeOH/DCM) to afford 1,1-dimethyl-3-(4-((6-nitropyridin-3-yl)oxy)pyridin-2-yl)urea (6.22 g, 81%). MS (ESI) m/z: 304.1 (M+H$^+$).

A solution of 1,1-dimethyl-3-(4-((6-nitropyridin-3-yl)oxy)pyridin-2-yl)urea (6.2 g, 20.4 mmol) in MeOH (100 mL) and THF (100 mL) was treated with NH$_4$Cl (332.8 g, 613 mmol) and cooled to 0° C. with stirring. Zinc dust (13.37 g, 204 mmol) was added portion-wise over 10 min and the mixture was stirred overnight as the cooling bath expired. The mixture was diluted with EtOAc and the solids were removed via filtration, and washed with EtOAc. The filtrate was concentrated to dryness, then suspended in EtOAc. The solids were removed by filtration and the filtrate was concentrated to dryness. The resultant brown solid was suspended in MeCN and sonicated for a few minutes. The light brown solid was collected to afford a first crop of 3-(4-((6-aminopyridin-3-yl)oxy)pyridin-2-yl)-1,1-dimethylurea. The MeCN filtrate was concentrated to dryness and again suspended in MeCN. The light brown solid was collected and dried to afford a second crop of 3-(4-((6-aminopyridin-3-yl)oxy)pyridin-2-yl)-1,1-dimethylurea (5.57 g combined, 100%). $^1$H NMR (400 MHz, DMSO-$d_6$) δ 8.81 (s, 1H), 8.05 (d, J=5.7 Hz, 1H), 7.77 (d, J=2.9 Hz, 1H), 7.33 (d, J=2.4 Hz, 1H), 7.24 (dd, J=8.9, 2.9 Hz, 1H), 6.53-6.49 (m, 2H), 6.00 (br s, 2H), 2.88 (s, 6H); MS (ESI) m/z: 274.1 (M+H$^+$).

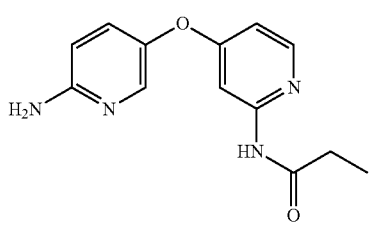 [SMILES: CCC(=O)Nc1cc(Oc2ccc(N)nc2)ccn1]

Example A10

A solution of Example A1 (1.0 g, 3.97 mmol) in dioxane (20 mL) was sparged with Ar, treated with propionamide (0.581 g, 7.95 mmol) and Cs$_2$CO$_3$ (1.942 g, 5.96 mmol), sparged with, treated with dppf (12.38 g, 22.33 mmol) and Pd$_2$(dba)$_3$ (0.182 g, 0.199 mmol), sparged once again with Ar and heated at 95° C. overnight. Pd(dppf)$_2$Cl$_2$.DCM (50 mg) was added and the mixture heated at 95° C. for 4 h. The mixture was cooled to RT, treated with EtOAc and the solids removed via filtration through silica gel. The filtrate was concentrated to dryness and purified twice via silica gel chromatography (MeOH/DCM) to afford N-(4-((6-nitropyridin-3-yl)oxy)pyridin-2-yl)propionamide (513 mg, 45%). MS (ESI) m/z: 289.1 (M+H$^+$).

A solution of N-(4-((6-nitropyridin-3-yl)oxy)pyridin-2-yl)propionamide (0.513 g, 1.780 mmol) in MeOH (10 mL) and THF (10 mL) was treated with NH$_4$Cl (3.81 g, 71.2 mmol) followed by zinc dust (1.164 g, 17.80 mmol) and stirred at RT overnight. Additional zinc dust (1 g) was added the mixture stirred at RT for 2 days. The solids were removed via filtration, washed with THF and filtrate concentrated to dryness. The material was suspended in THF, sonicated, the resulting solid removed via filtration and the filtrate concentrated to dryness to afford crude N-(4-((6-aminopyridin-3-yl)oxy)pyridin-2-yl)propionamide (1.02 g, 222%) which was carried on without further purification. MS (ESI) m/z: 259.1 (M+H$^+$).

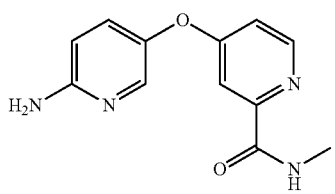 [SMILES: CNC(=O)c1cc(Oc2ccc(N)nc2)ccn1]

Example A11

DMF (25 mL) was slowly treated with SOCl$_2$ (125 mL) to maintain a temperature of 40-50° C. The mixture was then treated portion-wise with pyridine-2-carboxylic acid (25 g, 0.2 mol) over 0.5 h, then heated at reflux for 16 h, cooled to RT, diluted with toluene (80 mL) and concentrated to dryness (this process was repeated three times). The resulting residue was washed with toluene and dried under reduced pressure to yield 4-chloro-pyridine-2-carbonyl chloride (27.6 g, 79% yield), which was used in the next step without purification.

A 0° C. solution of 4-chloro-pyridine-2-carbonyl chloride (27.6 g, 0.16 mol) in THF (100 mL) at was treated drop-wise with a solution of MeNH$_2$ in EtOH, stirred at 3° C. for 4 h, then concentrated to dryness. The material was suspended in EtOAc, the solids removed via filtration and the filtrate was washed with brine (2×), dried and concentrated to yield 4-chloro-N-methylpicolinamide (16.4 g, 60%) as a yellow solid. $^1$H NMR (400 MHz, DMSO-d$_6$) δ 8.78 (br s, 1H), 8.55 (d, J=5.2 Hz, 1H), 7.97 (d, J=2.0 Hz, 1H), 7.66 (m, 1H), 2.82 (d, J=4.8 Hz, 3H); MS (ESI) m/z: 171.0 (M+H$^+$).

A solution of 2-amino-5-hydroxypyridine (0.968 g, 8.79 mmol) in DMA (15 mL) was treated with potassium tert-butoxide (0.987 g, 8.79 mmol), stirred at RT for 3 h, treated with 4-chloro-N-methylpicolinamide (1.5 g, 8.79 mmol) and stirred at RT for 2 days. The mixture was concentrated to dryness, treated with water, extracted with EtOAc (3×) and the combined organics were washed with brine, dried over Na$_2$SO$_4$, concentrated to dryness and purified via silica gel chromatography (EtOAc, MeOH/DCM) to afford 4-((6-aminopyridin-3-yl)oxy)-N-methylpicolinamide (1.3 g, 61%). $^1$H NMR (400 MHz, DMSO-d$_6$): δ 8.75 (m, 1H), 8.46 (d, J=5.6 Hz, 1H), 7.82 (d, J=2.9 Hz, 1H), 7.34 (d, J=2.6 Hz, 1H), 7.30 (dd, J=8.9, 3.0 Hz, 1H), 7.10 (dd, J=5.6, 2.7 Hz, 1H), 6.53 (d, J=8.9 Hz, 1H), 6.07 (s, 2H), 2.77 (d, J=4.8 Hz, 3H); MS (ESI) m/z: 245.1 (M+H$^+$).

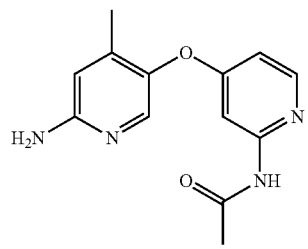 [SMILES: CC(=O)Nc1cc(Oc2cnc(N)cc2C)ccn1]

Example A12

Sulphuric acid (10 mL) was cooled to 0-5° C., treated with H$_2$O$_2$ (7.29 mL, 71.4 mmol), stirred for 10 minutes, treated with a solution of 2-amino-5-fluoro-4-methylpyridine (1.5 g, 11.89 mmol) in sulphuric acid (5 mL) at 0° C., stirred for 15 minutes, then warmed to RT and stirred for 1 h. The mixture was poured onto ice, treated with 10% sodium thiosulfate (50 mL) then solid Na$_2$CO$_3$ until solids precipitated and extracted with EtOAc (2×). The combined organics were washed with brine, dried over Na$_2$SO$_4$ and concentrated to dryness to afford 5-fluoro-4-methyl-2-nitropyridine (1.41 g, 76%) as an orange solid. MS (ESI) m/z: 157.1 (M+H$^+$).

A mixture of 5-fluoro-4-methyl-2-nitropyridine (0.8 g, 5.12 mmol), 4-hydroxy-2-chloropyridine (0.996 g, 7.69 mmol) and K$_2$CO$_3$ (0.708 g, 5.12 mmol) in DMF (10 mL) was heated at 80° C. for 4 h. The mixture was cooled to RT, poured onto water, extracted with EtOAc (2×) and the combined organics were washed with brine, dried over Na$_2$SO$_4$, concentrated to dryness and purified via silica gel chromatography (EtOAc/Hex) to afford 5-((2-chloropyridin-4-yl)oxy)-4-methyl-2-nitropyridine (850 mg, 62%) as an off-white solid. MS (ESI) m/z: 266.0 (M+H$^+$).

A solution of 5-((2-chloropyridin-4-yl)oxy)-4-methyl-2-nitropyridine (0.52 g, 1.957 mmol) in dioxane (15 mL) was sparged with Ar, treated with acetamide (0.347 g, 5.87 mmol), Cs$_2$CO$_3$ (0.638 g, 1.957 mmol), X-Phos (0.093 g, 0.196 mmol) and Pd$_2$(dba)$_3$ (0.179 g, 0.196 mmol) and heated at 90° C. overnight. The mixture was cooled to RT, diluted with EtOAc, the solids removed via filtration through diatomaceous earth, washed with EtOAc and the filtrate was washed with water, then brine, dried over Na$_2$SO$_4$, concentrated to dryness and purified via silica gel chromatography (EtOAc/DCM) to afford N-(4-((4-methyl-6-nitropyridin-3-yl)oxy)

pyridin-2-yl)acetamide (360 mg, 64%). $^1$H NMR (400 MHz, DMSO-d$_6$): δ 10.66 (s, 1H), 8.47 (s, 1H), 8.43 (s, 1H), 8.24 (d, J=5.7 Hz, 1H), 7.72 (d, J=2.4 Hz, 1H), 6.74 (dd, J=5.7, 2.4 Hz, 1H), 2.33 (s, 3H), 2.05 (s, 3H); MS (ESI) m/z: 289.1 (M+H$^+$).

A solution of N-(4-((4-methyl-6-nitropyridin-3-yl)oxy)pyridin-2-yl)acetamide (0.36 g, 1.249 mmol) in EtOAc (15 mL) was treated with 10% Pd/C (50% w/w water, 0.133 g, 0.125 mmol) and hydrogenated (1 atm) overnight. The solids were removed via filtration through diatomaceous earth, washed with EtOAc and the filtrate was concentrated to dryness to afford N-(4-((6-amino-4-methylpyridin-3-yl)oxy)pyridin-2-yl)acetamide (320 mg, 99%). $^1$H NMR (400 MHz, DMSO-d$_6$): δ 10.47 (s, 1H), 8.11 (d, J=5.7 Hz, 1H), 7.66 (s, 1H), 7.55 (d, J=2.4 Hz, 1H), 6.55 (dd, J=5.7, 2.4 Hz, 1H), 6.37 (s, 1H), 5.88 (s, 2H), 2.02 (s, 3H), 1.93 (s, 3H); MS (ESI) m/z: 259.1 (M+H$^+$).

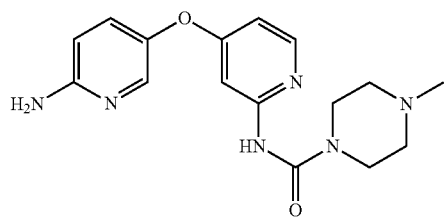 [SMILES: CN1CCN(C(=O)Nc2cc(Oc3ccc(N)nc3)ccn2)CC1]

Example A13

Method A

A suspension of Example A1 (0.800 g, 3.18 mmol), Example C3 (0.300 g, 2.095 mmol), Cs$_2$CO$_3$ (1.365 g, 4.19 mmol) and X-Phos (0.040 g, 0.084 mmol) in dioxane (20 mL) was sparged with Ar, treated with Pd$_2$(dba)$_3$ (0.038 g, 0.042 mmol) and heated at 110° C. for 13 h. The mixture was cooled to RT, the solids removed via filtration, washed with THF and the filtrate concentrated to dryness and purified via silica gel chromatography (MeOH/DCM) to afford 4-methyl-N-(4-((6-nitropyridin-3-yl)oxy)pyridin-2-yl)piperazine-1-carboxamide (584 mg, 78%). $^1$H NMR (400 MHz, DMSO-d$_6$): δ 9.40 (s, 1H), 8.55 (d, J=2.8 Hz, 1H), 8.39 (d, J=8.9 Hz, 1H), 8.24 (d, J=5.7 Hz, 1H), 7.94 (dd, J=8.9, 2.8 Hz, 1H), 7.55 (d, J=2.3 Hz, 1H), 6.78 (dd, J=5.7, 2.3 Hz, 1H), 3.41 (t, J=4.8 Hz, 4H), 2.25 (t, J=4.9 Hz, 4H), 2.15 (s, 3H); MS (ESI) m/z: 359.1 (M+H$^+$).

A solution of 4-methyl-N-(4-((6-nitropyridin-3-yl)oxy)pyridin-2-yl)piperazine-1-carboxamide (0.400 g, 1.116 mmol) in MeOH (20 mL) was treated with NH$_4$Cl (2.00 g, 37.4 mmol) and zinc powder (1.00 g, 15.29 mmol) and stirred at RT overnight. The solids were removed via filtration, washed with DCM and the filtrate concentrated to dryness. The residue was treated with DCM and a few drops of MeOH, the solids again removed via filtration and the filtrate concentrated to dryness to afford N-(4-((6-aminopyridin-3-yl)oxy)pyridin-2-yl)-4-methylpiperazine-1-carboxamide (346 mg, 94%). MS (ESI) m/z: 329.2 (M+H$^+$).

Method B

Example A1 (10.00 g, 39.7 mmol), Example C3 (10.00 g, 69.8 mmol), Cs$_2$CO$_3$ (20.0 g, 61.4 mmol) and X-Phos (0.900 g, 1.888 mmol) were combined in dioxane (140 mL) in a re-closable sealed tube (400 mL) and the mixture was purged with argon for 5 min. Pd$_2$(dba)$_3$ (1.00 g, 1.092 mmol) was added, the vessel was sealed and placed in 120° C. bath for 13 h with stirring. The reaction mixture was cooled to RT and the solids were collected by filtration and washed with DCM. The filtrate was concentrated to dryness and purified by silica gel chromatography (MeOH/DCM) to provide 4-methyl-N-(4-((6-nitropyridin-3-yl)oxy)pyridin-2-yl)piperazine-1-carboxamide (6.4 g, 45%) as light brownish solid. The solid was dissolved in DCM (150 mL) and stirred with thiol-modified silica gel (1.4 mmol thiol/g, 10 g, 14 mmol)[Pd scavenging resin] for 2 h. The resin was removed by filtration and the filtrate concentrated to provide 4-methyl-N-(4-((6-nitropyridin-3-yl)oxy)pyridin-2-yl)piperazine-1-carboxamide. MS (ESI) m/z: 359.1 (M+H$^+$).

A suspension of 4-methyl-N-(4-((6-nitropyridin-3-yl)oxy)pyridin-2-yl)piperazine-1-carboxamide, DN-01540-085-1 (6.40 g, 17.86 mmol) and Raney Nickel (1.00 g, 17.26 mmol) in MeOH (100 mL) was hydrogenated (40 psi) in a Parr shaker flask at RT for 2 h. The catalyst from the reaction mixture was removed by filtration and washed with MeOH. The filtrate was evaporated to provide N-(4-((6-aminopyridin-3-yl)oxy)pyridin-2-yl)-4-methylpiperazine-1-carboxamide (5.80 g, 99%) as light brownish solid. MS (ESI) m/z: 329.2 (M+H$^+$).

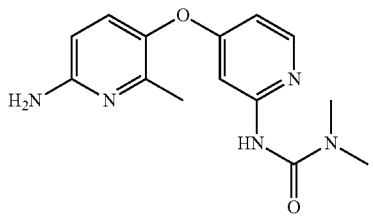

Example A14

Method A

A solution of Example A3 (0.500 g, 1.882 mmol) in dioxane (10 mL) was sparged with Ar, treated with N,N-dimethylurea (0.829 g, 9.41 mmol), XANTPHOS (218 mg, 0.376 mmol), and Cs$_2$CO$_3$ (1.226 g, 3.76 mmol), sparged with Ar, treated with Pd$_2$(dba)$_3$ (0.172 g, 0.188 mmol), sparged again with Ar and heated at 100° C. overnight. The mixture was cooled to RT and diluted with EtOAc. The solids were removed via filtration through diatomaceous earth and washed with EtOAc. The filtrates were concentrated to dryness and purified via silica gel chromatography (MeOH/EtOAc) to afford 1,1-dimethyl-3-(4-((2-methyl-6-nitropyridin-3-yl)oxy)pyridin-2-yl)urea (511 mg, 86%). $^1$H NMR (400 MHz, DMSO-d$_6$): δ 9.05 (s, 1H), 8.25-8.19 (m, 2H), 7.82 (d, J=8.7 Hz, 1H), 7.50 (d, J=2.3 Hz, 1H), 6.71 (dd, J=5.7, 2.4 Hz, 1H), 2.89 (s, 6H), 2.73 (s, 3H); MS (ESI) m/z: 318.1 (M+H$^+$).

A mixture of 1,1-dimethyl-3-(4-((2-methyl-6-nitropyridin-3-yl)oxy)pyridin-2-yl)urea (0.500 g, 1.576 mmol) and NH$_4$Cl (2.53 g, 47.3 mmol) in MeOH (10 mL) and THF (10 mL) was treated with zinc dust (1.030 g, 15.76 mmol) and stirred at RT for 0.5 h. The mixture was diluted with EtOAc, the solids removed via filtration, washed with EtOAc and the filtrate concentrated to dryness. The residue was treated with DCM, sonicated, the solids removed via filtration and the filtrate concentrated to dryness to afford 3-(4-((6-amino-2-methylpyridin-3-yl)oxy)pyridin-2-yl)-1,1-dimethylurea (510 mg, 113%). MS (ESI) m/z: 288.1 (M+H$^+$).

Method B

A solution of Example A3 (8.0 g, 30 mmol) in dioxane (150 mL) was sparged with Ar under sonication for 20 min, treated with N,N-dimethylurea (10.6 g, 120 mmol), XANTPHOS (3.48 g, 6.02 mmol), and Cs$_2$CO$_3$ (1.226 g, 3.76 mmol), sparged with Ar under sonication for 30 min, treated with Pd$_2$(dba)$_3$ (2.76 g, 3.01 mmol), sparged again with Ar under sonication for 30 min and heated at 100° C. overnight. The mixture was cooled to RT and diluted with EtOAc. The solids were removed via filtration through diatomaceous earth and washed with EtOAc. The filtrates were concentrated to dryness. The residue was partitioned into EtOAc and water. The aqueous layer was back-extracted with EtOAc (3×) and the combined organics were dried (Na$_2$SO$_4$) and concentrated. MeCN was added and the mixture was sonicated. The solids were collected by filtration to provide 1,1-dimethyl-3-(4-((2-methyl-6-nitropyridin-3-yl)oxy)pyridin-2-yl)urea, crop 1. The filtrate was concentrated to dryness. Fresh MeCN was added and the mixture was again sonicated. The solids were collected by filtration to provide 1,1-dimethyl-3-(4-((2-methyl-6-nitropyridin-3-yl)oxy)pyridin-2-yl)urea, crop 2. The filtrate was concentrated in vacuo and purified via silica gel chromatography (MeOH/EtOAc) to afford 1,1-dimethyl-3-(4-((2-methyl-6-nitropyridin-3-yl)oxy)pyridin-2-yl)urea, crop 3. Crops 1-3 of 1,1-dimethyl-3-(4-((2-methyl-6-nitropyridin-3-yl)oxy)pyridin-2-yl)urea were combined (5.2 g, 54%). MS (ESI) m/z: 288.1 (M+H$^+$).

A mixture of 1,1-dimethyl-3-(4-((2-methyl-6-nitropyridin-3-yl)oxy)pyridin-2-yl)urea (5.2 g, 16.4 mmol) in MeOH (60 mL) and THF (60 mL) was treated with NH$_4$Cl (26.3 g, 492 mmol) and stirred vigorously at RT. Zinc dust (10.72 g, 164 mmol) was added portion-wise and the mixture was stirred at RT for 2 h. Additional portions of NH$_4$Cl (5 g, 93 mmol) and zinc dust (1 g, 15 mmol) were added and stirring was continued overnight. The mixture was diluted with EtOAc and filtered. The filtered solids were washed with EtOAc. The combined filtrates were further filtered (2×) and concentrated to dryness. THF (150 mL) and thiol-modified silica gel (1.4 mmol/g loading, 22 g, 31 mmol) were added and the mixture was stirred at RT overnight. The solids were removed by filtration and washed with THF. The combined filtrates were concentrated to dryness to give 3-(4-((6-amino-2-methylpyridin-3-yl)oxy)pyridin-2-yl)-1,1-dimethylurea (4.54 g, 96%) as a foam. MS (ESI) m/z: 288.1 (M+H$^+$).

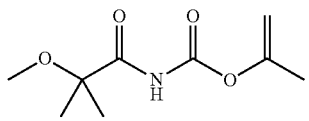

Example B1

A 0° C. solution of methyl 2-hydroxyisobutyrate (2 g, 16.93 mmol) in DMF (20 mL) was treated with NaH (60% in mineral oil, 0.813 g, 20.33 mmol), stirred for 0.5 h at 0° C., treated with iodomethane (1.269 mL, 20.29 mmol), allowed to warm to RT and stirred overnight. The mixture was diluted with EtOAc, quenched with cold satd. NH$_4$Cl, extracted with EtOAc (3×) and the combined organics were washed with satd. NaHCO$_3$, 10% LiCl, then brine, dried over Na$_2$SO$_4$ and concentrated to dryness to afford methyl 2-methoxy-2-methylpropanoate (2.08 g, 93%). $^1$H NMR (400 MHz, DMSO-d$_6$): δ 3.64 (s, 3H), 3.11 (s, 3H), 1.30 (s, 6H).

A solution of methyl 2-methoxy-2-methylpropanoate (2.08 g, 15.74 mmol) in MeOH (20 mL) was treated with a solution of KOH (1.766 g, 31.5 mmol) in water (10 mL) and stirred at RT for 4 h. The organics were removed under reduced pressure, the aqueous residue washed with 1:1 hexane/Et$_2$O, acidified with 3N HCl, extracted with DCM (3×) and the combined organics were dried over Na$_2$SO$_4$ and concentrated to dryness to afford 2-methoxy-2-methylpropanoic acid (1.24 g, 67%). $^1$H NMR (400 MHz, DMSO-d$_6$): δ 12.48 (s, 1H), 3.12 (s, 3H), 1.27 (s, 6H).

A solution of 2-methoxy-2-methylpropanoic acid (1.24 g, 10.50 mmol) and HOBt (2.090 g, 13.65 mmol) in MeCN (26.2 mL) was treated portion-wise with EDC (2.62 g, 13.65 mmol) and stirred at RT for 2 h. NH$_4$OH (~15 M, 2.04 mL, ~30.6 mmol) was added and the mixture was stirred at RT overnight. The mixture was treated with 50% satd. brine, saturated with solid NaHCO$_3$, extracted with EtOAc (3×) and the combined organics were dried over Na2SO4 and concentrated to dryness to afford 2-methoxy-2-methylpropanamide (860 mg, 70%). $^1$H NMR (400 MHz, DMSO-d$_6$): δ 7.14 (s, 1H), 7.02 (s, 1H), 3.12 (s, 3H), 1.21 (s, 6H).

A −78° C. solution of 2-methoxy-2-methylpropanamide (0.25 g, 2.134 mmol) in THF (6 mL) was treated drop-wise with lithium bis(trimethylsilyl)amide (1M in THF, 2.77 mL, 2.77 mmol) stirred for 0.5 h. A solution of isopropenyl chloroformate (0.257 mL, 2.347 mmol) in THF (1 mL) was added drop-wise and the mixture was stirred at −78° C. for 1 h. The mixture was warmed to RT, stirred for 1 h, quenched with satd. NaHCO$_3$, extracted with EtOAc (3×) and the combined organics were dried over Na$_2$SO$_4$ and concentrated to dryness to afford prop-1-en-2-yl (2-methoxy-2-methylpropanoyl)carbamate (440 mg, 102%). MS (ESI) m/z: 202.1 (M+H$^+$).

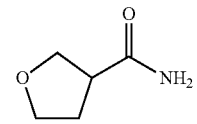

Example B2

A solution of tetrahydrofuran-3-carboxylic acid (1.000 g, 8.61 mmol) in EtOAc (20 mL) was treated with 1,1'-carbonyldiimidazole [CDI] (1.500 g, 9.25 mmol) and stirred at RT for 20 minutes. Ammonium hydroxide (~14 M, 5.00 mL, ~70.0 mmol) was added, stirred for 20 minutes, then concentrated to dryness. The material was treated with satd. NaHCO$_3$, extracted with DCM (3×) and the combined organics washed with brine, dried over Na$_2$SO$_4$ and concentrated to dryness to afford tetrahydrofuran-3-carboxamide (584 mg, 59%) as a colorless oil. MS (ESI) m/z: 138.2 (M+H$^+$).

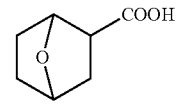

Example B3

Acrylonitrile (2.50 g, 47.1 mmol) was treated portion-wise with zinc chloride (1.926 g, 14.13 mmol), stirred at RT for 10 minutes, treated with furan (10.38 mL, 143 mmol) and stirred at RT for 14 h. The mixture was treated with water, extracted with EtOAc (3×) and the combined organics were washed with brine, dried over Na$_2$SO$_4$ and concentrated to afford an exo/endo mixture of 7-oxabicyclo[2.2.1]hept-5-ene-2-carbonitrile (4.75 g, 83%) as a pale oil.

The exo/endo-mixture of 7-oxabicyclo[2.2.1]hept-5-ene-2-carbonitrile (4.70 g, 38.8 mmol) in EtOAc (30 mL) was dissolved in EtOAc (30 mL), treated with 10% Pd/C (0.300 g, 0.282 mmol) and hydrogenated (20 psi) for 2 h. The solids were removed via filtration, washed with EtOAc and the filtrate concentrated in vacuo to afford an exo/endo-mixture of 7-oxabicyclo[2.2.1]heptane-2-carbonitrile (4.80 g, 100%) as a colorless oil.

A solution of the exo/endo-mixture of 7-oxabicyclo[2.2.1]heptane-2-carbonitrile (4.80 g, 39.0 mmol) in EtOH (30 mL) was treated with KOH (10 M, 10 mL, 100 mmol), heated at 100° C. for 90 minutes, then cooled to RT and stirred overnight. The mixture was concentrated to dryness, treated with water, acidified to pH 1 with conc. HCl, saturated with solid NaCl and extracted with MTBE (3×). The combined organics were dried over Na$_2$SO$_4$ and concentrated to dryness to afford exo-7-oxabicyclo[2.2.1]heptane-2-carboxylic acid (2.40 g, 43%) as a light brown solid. $^1$H NMR (400 MHz, DMSO-d$_6$): δ 12.13 (s, 1H), 4.64 (d, J=4.6 Hz, 1H), 4.51 (t, J=4.8 Hz, 1H), 2.57 (dd, J=9.1, 4.8 Hz, 1H), 1.88-1.83 (m, 1H), 1.63-1.38 (m, 5H).

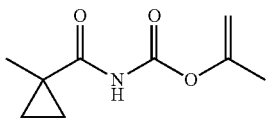

Example B4

A solution of methylcyclopropyl carboxylic acid (1.24 g, 12.39 mmol) and HOBt (2.466 g, 16.10 mmol) were in MeCN (31 mL) was treated portion-wise with EDC (3.09 g, 16.10 mmol), stirred at RT for 2 h, treated with NH$_4$OH (~15M, 2.4 mL, ~36 mmol) and stirred at RT overnight. The mixture was treated with 50% satd. brine, then solid NaHCO$_3$ until saturated and extracted with EtOAc (3×). The combined organics were dried over Na$_2$SO$_4$ and concentrated to dryness to afford 1-methylcyclopropanecarboxamide (1.35 g, 110%) which was used without further purification. $^1$H NMR (400 MHz, DMSO-d$_6$): δ 7.01 (br s, 1H), 6.81 (br s, 1H), 1.20 (s, 3H), 0.92-0.88 (m, 2H), 0.47-0.43 (m, 2H).

A −78° C. solution of 1-methylcyclopropanecarboxamide (1.35 g, 13.6 mmol) in THF (30 mL) was treated drop-wise with lithium bis(trimethylsilyl)amide (1M THF, 17.7 mL, 17.7 mmol), stirred for 0.5 h, treated drop-wise with a solution of isopropenyl chloroformate (1.94 mL, 17.7 mmol) in THF (5 mL), stirred at −78° C. for 1 h, then allowed to warm to RT and stirred for 1 h. The mixture was quenched with satd. NaHCO$_3$, extracted with EtOAc (3×) and the combined organics were dried over Na$_2$SO$_4$ and concentrated to dryness to afford crude prop-1-en-2-yl (1-methylcyclopropanecarbonyl)carbamate (2.9 g, 116%) which was used without further purification.

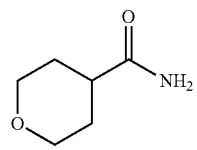

Example B5

A 0° C. solution of tetrahydro-2H-pyran-4-carboxylic acid (0.5 g, 3.84 mmol) in MeCN (15 mL) was treated with EDC (0.884 g, 4.61 mmol) and HOBT (0.706 g, 4.61 mmol) under an argon atmosphere and stirred at 0° C. for 1 h. Ammonium hydroxide (~15M, 0.512 mL, 7.68 mmol) was added slowly and the mixture was warmed to RT and stirred overnight. The mixture was treated with water, saturated with solid NaCl and the aqueous layer was extracted with THF (2×). The combined organics were washed with brine, dried over Na$_2$SO$_4$ and concentrated to afford tetrahydro-2H-pyran-4-carboxamide (0.23 g, 46%) as a white solid. $^1$H NMR (400 MHz, DMSO-d$_6$): δ 7.20 (s, 1H), 6.73 (s, 1H), 3.82-3.81 (m, 2H), 3.30-3.21 (m, 2H), 2.30-2.27 (m, 1H), 1.60-1.46 (m, 4H).

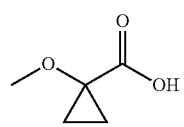

Example B6

A 0° C. solution of methyl 1-hydroxycyclopropane-1-carboxylate (1 g, 8.61 mmol) in DMF (10 mL) was treated with NaH (60% in mineral oil, 0.689 g, 17.22 mmol), stirred at 0° C. for 0.5 h, treated with iodomethane (0.646 mL, 10.33 mmol), allowed to slowly warm to RT and stirred for 2 h. The mixture was quenched with satd. NH$_4$Cl, diluted with water and extracted with Et$_2$O (3×). The combined organics were washed with water, then brine, dried and concentrated to afford methyl 1-methoxycyclopropane-1-carboxylate (1.10 g, 98%). $^1$H NMR (400 MHz, DMSO-d$_6$): δ 3.62 (s, 3H), 3.27 (s, 3H), 1.12-1.11 (m, 4H).

A solution of methyl 1-methoxycyclopropane-1-carboxylate (1.10 g, 8.45 mmol) in MeOH (10 mL) was treated drop-wise with a solution of KOH (0.948 g, 16.90 mmol) in water (5 mL) and stirred at RT overnight. The mixture was concentrated to a small volume, washed with 1:1 Hex/Et$_2$O and the aqueous layer poured onto ice and acidified with 3M HCl. The mixture was extracted with DCM (3×) and the combined organics were dried over Na$_2$SO$_4$ and concentrated to dryness to afford 1-methoxycyclopropane-1-carboxylic acid (392 mg, 40%). $^1$H NMR (400 MHz, DMSO-d$_6$): δ 12.53 (s, 1H), 3.26 (s, 3H), 1.06-1.05 (m, 4H).

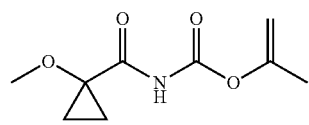

Example B7

A solution of Example B6 (0.392 g, 3.38 mmol) and HOBt (0.672 g, 4.39 mmol) in MeCN (8.44 mL) was treated portion-wise with EDC (0.841 g, 4.39 mmol), stirred at RT for 2 h, treated with NH$_4$OH (~15M, 0.657 mL, ~9.9 mmol) and stirred at RT overnight. The mixture was treated with brine, extracted with 4:1 EtOAc/THF (4×) and the combined organics were washed with satd. NaHCO$_3$, then brine, dried over Na$_2$SO$_4$ and concentrated to dryness to afford 1-methoxycyclopropane-1-carboxamide (230 mg, 59%). $^1$H NMR (400 MHz, DMSO-d$_6$): δ 7.47 (s, 1H), 7.26 (s, 1H), 3.21 (s, 3H), 0.95-0.94 (m, 4H).

A –78° C. solution of 1-methoxycyclopropane-1-carboxamide (0.23 g, 1.998 mmol) in THF (6 mL) was treated drop-wise with lithium bis(trimethylsilyl)amide (1M THF, 2.80 mL, 2.80 mmol), stirred for 0.5 h, treated drop-wise with a solution of isopropenyl chloroformate (0.262 mL, 2.397 mmol) in dry THF (1 mL), stirred for 1 h at –78° C., allowed to slowly warm to RT and stirred for 1 h. The mixture was quenched with satd. NaHCO$_3$), extracted with EtOAc (3×) and the combined organics were dried over Na$_2$SO$_4$ and concentrated to dryness to afford prop-1-en-2-yl (1-methoxycyclopropane-1-carbonyl)carbamate (0.423 g, 106%). MS(ESI) m/z: 222.1 (M+Na$^+$).

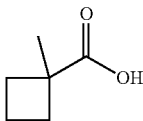

Example B8

A 0° C. solution of diisopropylamine (17 mL, 121 mmol) in THF (50 mL) was treated with n-butyl lithium (2.5M in hexane, 48 mL, 120 mmol), stirred for 10 minutes, treated with cyclobutane carboxylic acid (5.00 g, 49.9 mmol) and stirred for 0.5 h. Methyl iodide (9.00 g, 63.4 mmol) was added and the mixture was stirred at RT for 3 h, then concentrated to dryness. The mixture was treated with satd. NH$_4$Cl, extracted with DCM (2×) and the combined organics were washed with brine, dried over Na$_2$SO$_4$ and concentrated to dryness to afford crude 1-methylcyclobutanecarboxylic acid (3.54 g, 62%) as a brown oil which was used without further purification.

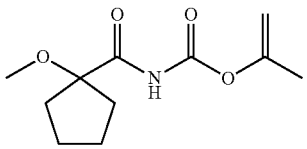 [SMILES: C=C(C)OC(=O)NC(=O)C1(OC)CCCC1]

Example B9

A solution of cyclopentanone (2.0 g, 23.78 mmol) in DCM (30 mL) was treated with zinc chloride (0.5M in THF, 4.76 mL, 2.378 mmol) followed by trimethylsilyl cyanide (3.83 mL, 28.5 mmol) and stirred at RT overnight. The mixture was treated with satd. NaHCO$_3$, extracted with DCM (1×) and the organic layer was washed with brine, dried over Na$_2$SO$_4$ and concentrated to dryness. The residue was treated with THF (5 mL) and HCl (2M, 4 mL), stirred at RT for 3 h, then the organics removed under reduced pressure. Additional HCl (12 M, 5 mL) was added, the mixture heated at 100° C. for 3 h, then cooled to RT, treated with water and extracted with EtOAc (2×). The combined organics were washed with brine, dried over Na$_2$SO$_4$ and concentrated to dryness to afford 1-hydroxycyclopentanecarboxylic acid (2.3 g, 74%). $^1$H NMR (400 MHz, DMSO-d$_6$): δ 12.28 (s, 1H), 4.92 (s, 1H), 1.93-1.83 (m, 2H), 1.74-1.57 (m, 6H).

A solution of 1-hydroxycyclopentanecarboxylic acid (1.4 g, 10.76 mmol) in MeOH (10 mL) was treated with conc. H$_2$SO$_4$ (1 drop), heated at 65° C. for 2 h, cooled to RT and concentrated to dryness. The residue was treated with satd. NaHCO$_3$, extracted with DCM (3×) and the combined organics were washed with brine, dried over Na$_2$SO$_4$ and concentrated to dryness to afford methyl 1-hydroxycyclopentanecarboxylate (1.45 g, 92%). $^1$H NMR (400 MHz, CDCl$_3$): δ 3.79 (s, 3H), 2.92 (br s, 1H), 2.11-2.00 (m, 2H), 1.91-1.83 (m, 2H), 1.82-1.72 (m, 4H).

A 0° C. suspension of NaH (60% in mineral oil, 0.644 g, 16.09 mmol) (pre-washed with hexanes, 2×) in THF (10 mL) was treated slowly with a solution of methyl 1-hydroxycyclopentanecarboxylate (1.45 g, 10.06 mmol) in THF (10 mL), stirred at 0° C. for 15 min, treated with iodomethane (1.258 mL, 20.12 mmol), warmed to RT and stirred overnight. The mixture was poured into satd. NH$_4$Cl, extracted with EtOAc (3×) and the combined organics were washed with brine, dried over Na$_2$SO$_4$ and concentrated to dryness to afford methyl 1-methoxycyclopentanecarboxylate (1.0 g, 63%). $^1$H NMR (400 MHz, CDCl$_3$): δ 3.76 (s, 3H), 3.24 (s, 3H), 1.98-1.96 (m, 4H), 1.76-1.74 (m, 4H).

A solution of methyl 1-methoxycyclopentanecarboxylate (1.00 g, 6.32 mmol) in THF (10 mL) was treated with a solution of LiOH (0.531 g, 12.64 mmol) in water (5 mL), stirred at RT overnight and concentrated to dryness. The residue was diluted with water, acidified with HCl (2M, 6 mL), extracted with EtOAc (3×) and the combined organics were washed with brine, dried over Na$_2$SO$_4$ and concentrated to dryness to afford 1-methoxycyclopentanecarboxylic acid (900 mg, 99%). $^1$H NMR (400 MHz, CDCl$_3$): δ 3.31 (s, 3H), 2.05-2.03 (m, 4H), 1.78-1.77 (m, 4H) [CO$_2$H not observed].

A solution of 1-methoxycyclopentanecarboxylic acid (0.9 g, 6.24 mmol) in EtOAc (30 mL) was treated with CDI (1.316 g, 8.12 mmol), stirred at RT for 0.5 h, treated with NH$_4$OH (~15M, 0.729 mL, ~10.9 mmol) and stirred at RT overnight. The mixture was treated with water, extracted with EtOAc (3×) and the combined organics were washed with brine, dried over Na2SO4 and concentrated to dryness to afford 1-methoxycyclopentanecarboxamide (900 mg, 101%). $^1$H NMR (400 MHz, CDCl$_3$): δ 6.45 (br s, 1H), 5.42 (br s, 1H), 3.24 (s, 3H), 2.07-2.04 (m, 2H), 1.90-1.87 (m, 2H), 1.75-1.73 (m, 4H).

A –78° C. solution of 1-methoxycyclopentanecarboxamide (0.9 g, 6.29 mmol) in THF (40 mL), under Ar, was treated with LiHMDS (1M in THF, 8.17 mL, 8.17 mmol), stirred for 0.5 h, treated with a solution of isopropenyl chloroformate (0.824 mL, 7.54 mmol) in THF (5 mL), stirred at –78° C. for 15 min, warmed to RT and stirred for 1 h. The mixture was treated with satd. NH$_4$Cl, the layers separated and the aqueous layer extracted with EtOAc (1×). The combined organics were washed with brine, dried over Na$_2$SO$_4$ and concentrated to dryness to afford crude prop-1-en-2-yl (1-methoxycyclopentanecarbonyl)carbamate (1.5 g, 105%) which was used without further purification. MS (ESI) m/z: 228.1 (M+H$^+$).

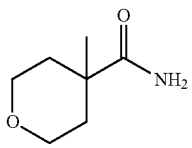

Example B10

A solution of methyl 4-methyltetrahydro-2H-pyran-4-carboxylate (5.00 g, 31.6 mmol) in 1:1:1 dioxane/water/MeOH (60 mL) was treated with lithium hydroxide hydrate (5.31 g, 126 mmol) and stirred at RT overnight. The mixture was partially concentrated, diluted with water and EtOAc and acidified to pH=1 with 6M HCl. The layers were separated, the aqueous layer extracted with additional EtOAc (50 mL) and the combined organics were washed with brine, dried over $Na_2SO_4$ and concentrated to dryness to afford 4-methyltetrahydro-2H-pyran-4-carboxylic acid (4.61 g, 100%). $^1$H NMR (400 MHz, DMSO-$d_6$): δ 12.29 (s, 1H), 3.65 (dt, J=11.8, 4.3 Hz, 2H), 3.33-3.32 (m, 2H), 1.87-1.86 (m, 2H), 1.35 (ddd, J=13.5, 9.9, 4.1 Hz, 2H), 1.13 (s, 3H).

A mixture of 4-methyltetrahydro-2H-pyran-4-carboxylic acid (2.60 g, 18.0 mmol), HOBt (2.76 g, 18.0 mmol) and EDC (4.49 g, 23.4 mmol) in MeCN (75 mL) was stirred at RT for 3 h, treated with $NH_4OH$ (~15M, 7 mL, ~105 mmol) and stirred at RT overnight. The mixture was concentrated to dryness, and the residue was partitioned between satd. Brine (40 mL) and DCM (100 mL). The aqueous was extracted with THF (50 mL) and DCM (5×30 mL). The combined organics were washed with 10% aq $K_2CO_3$ (50 mL), dried over $Na_2SO_4$ and concentrated in vacuo to afford 4-methyltetrahydro-2H-pyran-4-carboxamide (1.83 g, 70%). $^1$H NMR (400 MHz, DMSO-$d_6$): δ 7.14 (s, 1H), 6.86 (s, 1H), 3.60 (dt, J=11.7, 4.5 Hz, 2H), 3.36 (m, 2H), 1.91-1.89 (m, 2H), 1.30 (m, 2H), 1.08 (s, 3H).

Example C1

A solution of Example A1 (1.5 g, 5.96 mmol) in dioxane (50 mL) was sparged with Ar, treated with tert-butyl carbamate (1.536 g, 13.11 mmol), $Cs_2CO_3$ (3.88 g, 11.92 mmol) and DPPF (0.420 g, 0.775 mmol), sparged with Ar, treated with $Pd_2(dba)_3$ (0.382 g, 0.417 mmol), sparged again with Ar and heated at 100° C. overnight. The mixture was cooled to RT, diluted with EtOAc, the solids removed via filtration through diatomaceous earth and washed with EtOAc. The filtrate was concentrated to dryness, treated with MeCN, sonicated and the solid collected via filtration. The filtrate was concentrated to dryness, treated again with MeCN and the solid collected. The filtrate was again concentrated to dryness, purified via silica gel chromatography (EtOAc/Hex) and combined with the two above-isolated solids to afford tert-butyl (4-((6-nitropyridin-3-yl)oxy)pyridin-2-yl)carbamate (1.5 g, 76%). MS (ESI) m/z: 333.1 (M+H$^+$).

A solution of tert-butyl (4-((6-nitropyridin-3-yl)oxy)pyridin-2-yl)carbamate (1.6 g, 4.81 mmol) in MeOH (25 mL) and THF (25 mL) was treated with $NH_4Cl$ (7.73 g, 144 mmol) followed by the portion-wise addition of zinc dust (3.15 g, 48.1 mmol) and stirred at RT overnight. The solids were removed via filtration through diatomaceous earth, washed with THF and EtOAc and the filtrate concentrated to dryness. The residue was suspended in THF, sonicated, the solids removed via filtration and the filtrate concentrated to dryness. The material was suspended in DCM, washed with water, the aqueous layer back-extracted with DCM and the combined organics were dried over $Na_2SO_4$ and concentrated to dryness to afford tert-butyl (4-((6-aminopyridin-3-yl)oxy)pyridin-2-yl)carbamate (1.6 g, 110%). $^1$H NMR (400 MHz, DMSO-$d_6$): δ 9.76 (s, 1H), 8.06 (d, J=5.7 Hz, 1H), 7.78 (d, J=2.9 Hz, 1H), 7.26-7.25 (m, 2H), 6.55-6.48 (m, 2H), 6.01 (s, 2H), 1.40 (s, 9H); MS (ESI) m/z: 303.1 (M+H$^+$).

A solution of 2,2,2-trimethylacetamide (0.750 g, 7.42 mmol) in DCE (10 mL) was treated with oxalyl chloride (0.600 mL, 7.09 mmol), stirred at RT for 10 min, then heated at 80° C. for 1 h. The mixture was cooled to RT, partially concentrated, then added drop-wise to a solution of tert-butyl (4-((6-aminopyridin-3-yl)oxy)pyridin-2-yl)carbamate (1.6 g, 5.29 mmol) in pyridine (0.60 mL, 7.44 mmol) and stirred at RT for 45 min. The mixture was concentrated to dryness, treated with MeCN, sonicated and the solids collected via filtration. The filtrate was concentrated to dryness, suspended in MeCN, sonicated, the resulting solid collected via filtration and combined with the above-isolated solid to afford tert-butyl (4-((6-(3-pivaloylureido)pyridin-3-yl)oxy)pyridin-2-yl)carbamate (1.6 g, 70%). MS (ESI) m/z: 430.2 (M+H$^+$).

tert-Butyl (4-((6-(3-pivaloylureido)pyridin-3-yl)oxy)pyridin-2-yl)carbamate (1.6 g, 3.73 mmol) was suspended in TFA (20 mL), stirred at RT for 45 min, then concentrated to dryness. The residue was suspended in THF, treated with satd. $NaHCO_3$ and the layers separated. The aqueous layer was diluted with brine, extracted with THF (3×) and the combined organics were dried over $Na_2SO_4$ and concentrated to dryness to afford crude N-((5-((2-aminopyridin-4-yl)oxy)pyridin-2-yl)carbamoyl)pivalamide (100% yield assumed) which was used without further purification. MS (ESI) m/z: 330.2 (M+H$^+$).

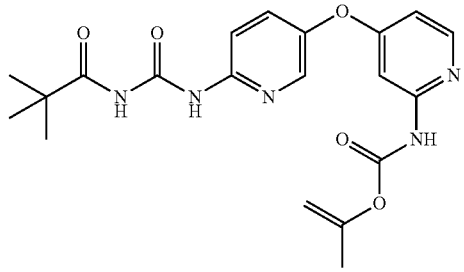 [SMILES: C=C(C)OC(=O)Nc1cc(Oc2ccc(NC(=O)NC(=O)C(C)(C)C)nc2)ccn1]

Example C2

A 0° C. suspension of Example C1 (1.2 g, 3.64 mmol) in pyridine (20 mL) was treated with isopropenyl chloroformate (0.398 mL, 3.64 mmol), stirred for 30 min, then treated with water. The resulting solid was collected via filtration and purified via silica gel chromatography (EtOAc/Hex, MeOH/DCM) to afford prop-1-en-2-yl (4-((6-(3-pivaloylureido)pyridin-3-yl)oxy)pyridin-2-yl)carbamate (820 mg, 54%). MS (ESI) m/z: 414.2 (M+H$^+$).

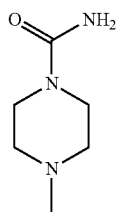

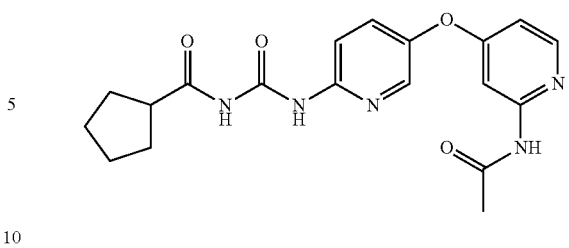

Example 2

A solution of cyclopenyl carbonylchloride (0.109 g, 0.819 mmol) in DCE (3 mL) was treated with silver cyanate (0.368 g, 2.457 mmol) and heated at 80° C. for 3 h. The mixture was cooled to RT, treated with a solution of Example A2 (0.1 g, 0.409 mmol) and TEA (0.171 mL, 1.228 mmol) in THF (3 mL) and stirred at RT for 0.5 h. The solids were removed via filtration through diatomaceous earth, washed with THF and the filtrate was concentrated to dryness and purified via reverse-phase chromatography (MeCN/H$_2$O with 0.1% TFA). The combined fractions were made basic with satd. NaHCO$_3$, extracted with EtOAc (2×) and the combined organics were washed with brine, dried over Na$_2$SO$_4$ and concentrated to dryness. The resulting material was treated with 60% EtOAc/Hex, the solids collected via filtration, rinsed with 60% EtOAc/Hex and dried to afford N-((5-((2-acetamidopyridin-4-yl)oxy)pyridin-2-yl)carbamoyl)cyclopentanecarboxamide (60 mg, 38%) as a white solid. $^1$H NMR (400 MHz, DMSO-d$_6$): δ 11.11 (s, 1H), 10.86 (s, 1H), 10.56 (s, 1H), 8.23 (d, J=2.9 Hz, 1H), 8.18 (d, J=5.7 Hz, 1H), 8.08 (d, J=9.0 Hz, 1H), 7.71 (dd, J=9.0, 2.9 Hz, 1H), 7.64 (d, J=2.4 Hz, 1H), 6.68 (dd, J=5.7, 2.4 Hz, 1H), 2.85 (m, 1H), 2.02 (s, 3H), 1.84-1.81 (m, 2H), 1.69-1.65 (m, 4H), 1.53-1.52 (m, 2H); MS (ESI) m/z: 384.2 (M+H$^+$).

Example C3

To a solution of phenyl carbamate (20.0 g, 146 mmol) in MeCN (200 mL) was added N-methylpiperazine (20.00 g, 200 mmol) followed by catalytic amount of ytterbium triflate (0.500 g, 1.061 mmol) and the resulting mixture was heated at 80° C. for 1 h. The solvent from the reaction mixture was completely evaporated and the residue was crystallized from MTBE to provide 4-methylpiperazine-1-carboxamide (14.2 g, 68% yield) as white solid $^1$H NMR (400 MHz, DMSO-d$_6$): δ 5.92 (s, 2H), 3.42 (t, J=4.9 Hz, 4H), 2.19 (t, J=4.9 Hz, 4H), 2.14 (s, 3H).

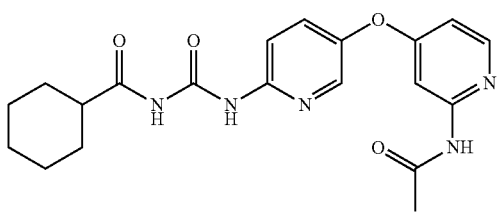 [SMILES: CC(=O)Nc1cc(Oc2ccc(NC(=O)NC(=O)C3CCCCC3)nc2)ccn1]

Example 1

A solution of cyclohexane carbonylchloride (0.108 g, 0.737 mmol) in DCE (4 mL) was treated with silver cyanate (0.331 g, 2.211 mmol) and the suspension was heated at 80° C. for 3 h. The mixture was cooled to RT, treated with a solution of Example A2 (0.09 g, 0.368 mmol) and TEA (0.154 mL, 1.105 mmol) in THF (2 mL) and stirred at RT for 0.5 h. The solids were removed via filtration through diatomaceous earth, washed with THF and the filtrate concentrated to dryness and purified via silica gel chromatography (MeOH/DCM). The material was treated with MeCN, sonicated, the solid collected via filtration and dried to afford N-((5-((2-acetamidopyridin-4-yl)oxy)pyridin-2-yl)carbamoyl)cyclohexanecarboxamide (81 mg, 55%) as a white solid. $^1$H NMR (400 MHz, DMSO-d$_6$): δ 11.11 (s, 1H), 10.80 (s, 1H), 10.56 (s, 1H), 8.23 (d, J=2.9 Hz, 1H), 8.18 (d, J=5.7 Hz, 1H), 8.07 (d, J=9.0 Hz, 1H), 7.71 (dd, J=9.0, 2.9 Hz, 1H), 7.64 (d, J=2.4 Hz, 1H), 6.68 (dd, J=5.7, 2.4 Hz, 1H), 2.43-2.40 (m, 1H), 2.02 (s, 3H), 1.81-1.54 (m, 5H), 1.39-1.11 (m, 5H); MS (ESI) m/z: 398.2 (M+H$^+$).

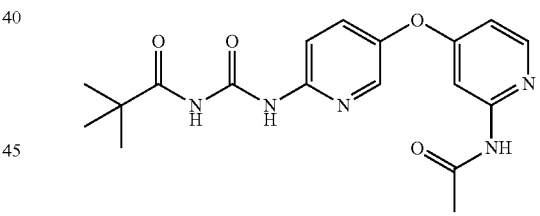

Example 3

A solution of trimethylacetyl chloride (0.089 g, 0.737 mmol) in DCE (3 mL) was treated with silver cyanate (0.331 g, 2.211 mmol) and heated at 80° C. for 3 h. The mixture was cooled to RT, treated with a solution of Example A2 (0.09 g, 0.368 mmol) and TEA (0.154 mL, 1.105 mmol) in THF (3 mL) and stirred at RT for 0.5 h. The solids were removed via filtration through diatomaceous earth, washed with THF and the filtration was concentrated to dryness and purified via silica gel chromatography (MeOH/DCM). The material was suspended in MeCN/H$_2$O, frozen and lyophilized to afford N-((5-((2-acetamidopyridin-4-yl)oxy)pyridin-2-yl)carbamoyl)pivalamide (25 mg, 18%) as a white solid. $^1$H NMR (400 MHz, DMSO-d$_6$): δ 11.21 (s, 1H), 10.56 (s, 1H), 10.43 (s, 1H), 8.24 (d, J=2.9 Hz, 1H), 8.18 (d, J=5.7 Hz, 1H), 8.08 (d, J=9.0 Hz, 1H), 7.72 (dd, J=9.0, 2.9 Hz, 1H), 7.64 (d, J=2.4 Hz, 1H), 6.68 (dd, J=5.7, 2.4 Hz, 1H), 2.02 (s, 3H), 1.20 (s, 9H); MS (ESI) m/z: 372.3 (M+H+).

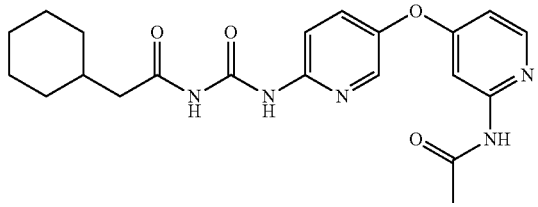 [SMILES: CC(=O)Nc1cc(Oc2ccc(NC(=O)NC(=O)CC3CCCCC3)nc2)ccn1]

Example 4

A solution 2-cyclohexylacetamide (0.104 g, 0.737 mmol) in DCE (4 mL) was treated with oxalyl chloride (0.129 mL, 1.474 mmol) and heated at 70° C. overnight. The mixture was concentrated to dryness, added to a solution of Example A2 (0.09 g, 0.368 mmol) and TEA (0.154 mL, 1.105 mmol) in THF (3 mL) and stirred at RT for 1 h. The mixture was treated with water, extracted with EtOAc (2×) and the combined organics were washed with brine, dried over Na$_2$SO$_4$ and concentrated to dryness. The resulting residue was suspended in 60% EtOAc/Hex, sonicated and the solid collected via filtration and dried to afford N-((5-((2-acetamidopyridin-4-yl)oxy)pyridin-2-yl)carbamoyl)-2-cyclohexylacetamide (77 mg, 51%) as a white solid. $^1$H NMR (400 MHz, DMSO-d$_6$): δ 11.11 (s, 1H), 10.83 (s, 1H), 10.56 (s, 1H), 8.23 (d, J=2.9 Hz, 1H), 8.18 (d, J=5.7 Hz, 1H), 8.07 (d, J=9.0 Hz, 1H), 7.71 (dd, J=9.0, 2.9 Hz, 1H), 7.64 (d, J=2.4 Hz, 1H), 6.68 (dd, J=5.7, 2.4 Hz, 1H), 2.27 (d, J=7.0 Hz, 2H), 2.02 (s, 3H), 1.73-1.56 (br m, 5H), 1.18-1.13 (m, 4H), 0.97-0.94 (m, 2H); MS (ESI) m/z: 412.2 (M+H+).

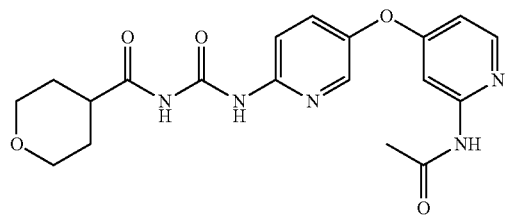 [SMILES: CC(=O)Nc1cc(Oc2ccc(NC(=O)NC(=O)C3CCOCC3)nc2)ccn1]

Example 5

A solution of Example B5 (0.095 g, 0.737 mmol) in DCE (3 mL) was treated with oxalyl chloride (0.129 mL, 1.474 mmol) and heated at 80° C. for 3 h. The mixture was cooled to RT, concentrated to dryness, treated with a solution of Example A2 (0.09 g, 0.368 mmol) and TEA (0.205 mL, 1.474 mmol) in THF (4 mL) and stirred at RT for 0.5 h. The mixture was treated with satd. NaHCO$_3$, extracted with EtOAc (2×) and the combined organics were washed with brine, dried over Na$_2$SO$_4$, concentrated to dryness and purified via silica gel chromatography (MeOH/DCM). The material was suspended in MeCN/H$_2$O, frozen and lyophilized to afford N-((5-((2-acetamidopyridin-4-yl)oxy)pyridin-2-yl)carbamoyl)tetrahydro-2H-pyran-4-carboxamide (77 mg, 52%) as a white solid. $^1$H NMR (400 MHz, DMSO-d$_6$): δ 11.05 (s, 1H), 10.88 (s, 1H), 10.56 (s, 1H), 8.24 (d, J=2.9 Hz, 1H), 8.18 (d, J=5.7 Hz, 1H), 8.07 (d, J=9.0 Hz, 1H), 7.72 (dd, J=9.0, 2.9 Hz, 1H), 7.64 (d, J=2.4 Hz, 1H), 6.68 (dd, J=5.7, 2.4 Hz, 1H), 3.87 (m, 2H), 3.29-3.25 (m, 2H), 2.72-2.64 (m, 1H), 2.02 (s, 3H), 1.71 (m, 2H), 1.66-1.54 (m, 2H); MS (ESI) m/z: 400.2 (M+H+).

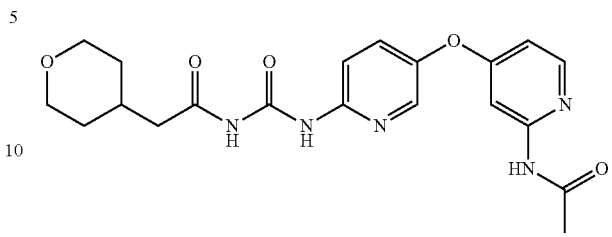

Example 6

A solution of 2-(tetrahydro-2H-pyran-4-yl)acetamide (0.117 g, 0.819 mmol) in DCE (4 mL) was treated with oxalyl chloride (0.143 mL, 1.638 mmol) and heated at 80° C. for 3 h. The suspension was concentrated to dryness, treated with a solution Example A2 (0.1 g, 0.409 mmol) and TEA (0.171 mL, 1.228 mmol) in THF (3 mL) and stirred at RT for 2 h. The mixture was treated with satd. NaHCO$_3$, extracted with EtOAc (2×) and the combined organics were washed with brine, dried over Na$_2$SO$_4$, concentrated to dryness and purified via silica gel chromatography (MeOH/DCM). The resulting material was suspended in MeCN/H$_2$O, frozen and lyophilized to afford N-((5-((2-acetamidopyridin-4-yl)oxy)pyridin-2-yl)carbamoyl)-2-(tetrahydro-2H-pyran-4-yl)acetamide (68 mg, 40%) as a white solid. $^1$H NMR (400 MHz, DMSO-d$_6$): δ 11.07 (s, 1H), 10.86 (s, 1H), 10.55 (s, 1H), 8.23 (d, J=2.9 Hz, 1H), 8.17 (d, J=5.7 Hz, 1H), 8.06 (d, J=9.0 Hz, 1H), 7.71 (dd, J=9.0, 2.9 Hz, 1H), 7.63 (d, J=2.4 Hz, 1H), 6.67 (dd, J=5.7, 2.4 Hz, 1H), 3.79 (d, J=11.5 Hz, 2H), 3.27-3.23 (m, 2H), 2.33 (d, J=7.1 Hz, 2H), 2.02 (s, 3H), 1.96 (m, 1H), 1.56 (m, 2H), 1.21-1.19 (m, 2H); MS (ESI) m/z: 414.2 (M+H+).

Example 7

A solution of Example B5 (0.090 g, 0.697 mmol) in DCE (3 mL) was treated with oxalyl chloride (0.122 mL, 1.394 mmol), heated at 80° C. for 3 h, cooled to RT and concentrated to dryness. The solid was treated with a solution of Example A4 (0.09 g, 0.348 mmol) and TEA (0.194 mL, 1.394 mmol) in THF (3 mL) and stirred at RT for 2 h. The mixture was treated with satd. NaHCO$_3$, extracted with EtOAc (2×) and the combined organics were washed with brine, dried over Na$_2$SO$_4$, concentrated to dryness and purified via silica gel chromatography (MeOH/DCM) to afford N-((5-((2-acetamidopyridin-4-yl)oxy)-6-methylpyridin-2-yl)carbamoyl)tetrahydro-2H-pyran-4-carboxamide (44 mg, 31%) as a white solid. $^1$H NMR (400 MHz, DMSO-d$_6$): δ 10.99 (s, 1H), 10.86 (s, 1H), 10.54 (s, 1H), 8.16 (d, J=5.7 Hz, 1H), 7.89 (d, J=8.8 Hz, 1H), 7.60 (d, J=8.8 Hz, 1H), 7.57 (d, J=2.3 Hz, 1H), 6.61 (dd, J=5.7, 2.5 Hz, 1H), 3.87 (m, 2H), 3.32-3.25 (m, 2H), 2.68 (m, 1H), 2.21 (s, 3H), 2.01 (s, 3H), 1.71 (m, 2H), 1.66-1.54 (m, 2H); MS (ESI) m/z: 414.2 (M+H⁺).

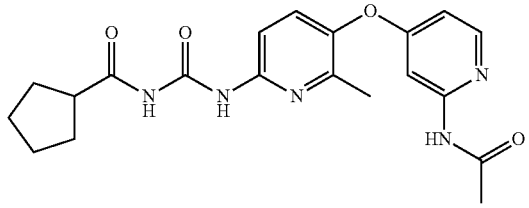 [SMILES: CC(=O)Nc1cc(Oc2ccc(NC(=O)NC(=O)C3CCCC3)nc2C)ccn1]

Example 8

A solution of cyclopentanecarboxamide (0.079 g, 0.697 mmol) in DCE (3 mL) was treated with oxalyl chloride (0.122 mL, 1.394 mmol), heated at 80° C. for 3 h, cooled to RT and concentrated to dryness. The semi-solid was treated with a solution of Example A4 (0.09 g, 0.348 mmol) and TEA (0.146 mL, 1.045 mmol) in THF (3 mL) and stirred at RT for 2 h. The mixture was treated with satd. NaHCO₃, extracted with EtOAc (2×) and the combined organics were washed with brine, dried over Na₂SO₄ and concentrated to dryness. The resulting material was suspended in EtOAc, sonicated briefly, the solid collected via filtration and dried to afford N-((5-((2-acetamidopyridin-4-yl)oxy)-6-methylpyridin-2-yl)carbamoyl)cyclopentanecarboxamide (117 mg, 84%) as a white solid. ¹H NMR (400 MHz, DMSO-d₆): δ 11.05 (s, 1H), 10.83 (s, 1H), 10.53 (s, 1H), 8.15 (d, J=5.7 Hz, 1H), 7.89 (d, J=8.8 Hz, 1H), 7.60 (d, J=8.8 Hz, 1H), 7.56 (s, 1H), 6.60 (dd, J=5.7, 2.4 Hz, 1H), 2.87-2.84 (m, 1H), 2.21 (s, 3H), 2.01 (s, 3H), 1.84-1.82 (m, 2H), 1.69-1.65 (m, 4H), 1.54-1.52 (m, 2H); MS (ESI) m/z: 398.2 (M+H⁺).

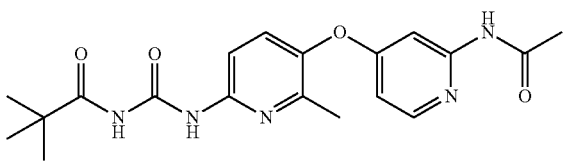 [SMILES: CC(=O)Nc1cc(Oc2ccc(NC(=O)NC(=O)C(C)(C)C)nc2C)ccn1]

Example 9

A solution of 2,2,2-trimethylacetamide (0.066 g, 0.650 mmol) in DCE (2 mL) was treated with oxalyl chloride (0.057 mL, 0.650 mmol), stirred at RT for 0.5 h, then heated to 75° C. for 1 h. The mixture was cooled to RT, treated with a solution of Example A4 (0.12 g, 0.465 mmol) and TEA (0.149 mL, 0.929 mmol) in THF (2 mL) and stirred at RT for 1 h. The solid was collected via filtration, rinsed with water and EtOAc and dried to afford N-((5-((2-acetamidopyridin-4-yl)oxy)-6-methylpyridin-2-yl)carbamoyl)pivalamide (130 mg, 73%) as a white solid. ¹H NMR (400 MHz, DMSO-d₆): δ 11.15 (s, 1H), 10.55 (s, 1H), 10.40 (s, 1H), 8.17 (d, J=5.7 Hz, 1H), 7.90 (d, J=8.8 Hz, 1H), 7.62 (d, J=8.8 Hz, 1H), 7.58 (d, J=2.3 Hz, 1H), 6.62 (dd, J=5.7, 2.4 Hz, 1H), 2.22 (s, 3H), 2.02 (s, 3H), 1.21 (s, 9H); MS (ESI) m/z: 386.2 (M+H⁺).

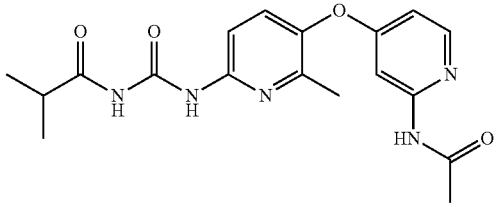 [SMILES: CC(=O)Nc1cc(Oc2ccc(NC(=O)NC(=O)C(C)C)nc2C)ccn1]

Example 10

A solution of isobutyramide (0.051 g, 0.581 mmol) in DCE (2 mL) was treated with oxalyl chloride (0.051 mL, 0.581 mmol), stirred at RT for 1 h, then heated at 75° C. for 1 h. The mixture was cooled to RT, treated with a solution of Example A4 (0.1 g, 0.387 mmol) and TEA (0.108 mL, 0.774 mmol) in THF (2 mL) and stirred at RT for 1 h. The mixture was treated with water, extracted with 10% MeOH/DCM (1×), then DCM (1×) and the combined organics were washed with brine, dried over Na₂SO₄, concentrated to dryness and purified via silica gel chromatography (MeOH/DCM) to afford N-((5-((2-acetamidopyridin-4-yl)oxy)-6-methylpyridin-2-yl)carbamoyl)isobutyramide (71 mg, 49%) as an off-white solid. ¹H NMR (400 MHz, DMSO-d₆): δ 11.05 (s, 1H), 10.83 (s, 1H), 10.55 (s, 1H), 8.17 (d, J=5.7 Hz, 1H), 7.90 (d, J=8.8 Hz, 1H), 7.61 (d, J=8.8 Hz, 1H), 7.58 (d, J=2.4 Hz, 1H), 6.61 (dd, J=5.7, 2.4 Hz, 1H), 2.68-2.65 (m, 1H), 2.22 (s, 3H), 2.02 (s, 3H), 1.09 (d, J=6.8 Hz, 6H); MS (ESI) m/z: 372.2 (M+H⁺).

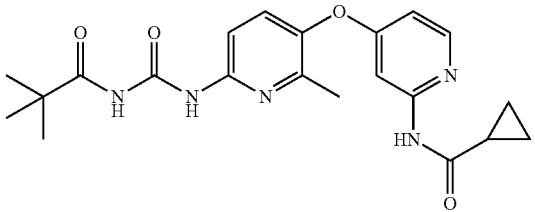 [SMILES: Cc1nc(NC(=O)NC(=O)C(C)(C)C)ccc1Oc1ccnc(NC(=O)C2CC2)c1]

Example 11

A solution of 2,2,2-trimethylacetamide (0.046 g, 0.457 mmol) in DCE (2 mL) was treated with oxalyl chloride (0.040 mL, 0.457 mmol), stirred at RT for 0.5 h, then heated at 75° C. for 1 h. The mixture was cooled to RT, treated with a solution of Example A5 (0.10 g, 0.352 mmol) and TEA (0.098 mL, 0.703 mmol) in THF (2 mL) and stirred at RT for 1 h. The mixture was concentrated to dryness, the residue treated with EtOAc, the solid collected via filtration, washed with water and EtOAc and dried to afford N-(4-((2-methyl-6-(3-pivaloylureido)pyridin-3-yl)oxy)pyridin-2-yl)cyclopropanecarboxamide (57 mg, 39%) as a white solid. ¹H NMR (400 MHz, DMSO-d₆): δ 11.16 (s, 1H), 10.86 (s, 1H), 10.41 (br s, 1H), 8.19 (d, J=5.6 Hz, 1H), 7.90 (m, 1H), 7.62 (d, J=8.9 Hz, 1H), 7.55 (m, 1H), 6.66 (m, 1H), 2.22 (s, 3H), 1.95 (m, 1H), 1.21 (s, 9H), 0.75 (d, J=5.9 Hz, 4H); MS (ESI) m/z: 412.2 (M+H⁺).

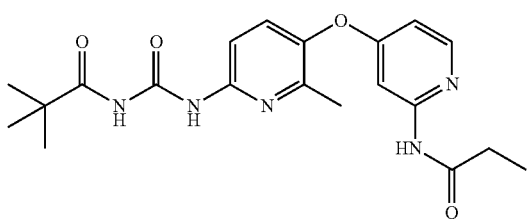 [SMILES: CCC(=O)Nc1cc(Oc2ccc(NC(=O)NC(=O)C(C)(C)C)nc2C)ccn1]

Example 12

A solution of 2,2,2-trimethylacetamide (0.048 g, 0.477 mmol) in DCE (2 mL) was treated with oxalyl chloride (0.042 mL, 0.477 mmol), stirred at RT for 0.5 h, then heated at 75° C. for 1 h. The mixture was cooled to RT, added to a solution of Example A6 (0.10 g, 0.367 mmol) and TEA (0.1 mL, 0.744 mmol) in THF (2 mL) and stirred at RT for 1 h. The mixture was concentrated to dryness, the residue treated with EtOAc, the solid collected via filtration, washed with water and EtOAc and dried to afford N-((6-methyl-5-((2-propionamidopyridin-4-yl)oxy)pyridin-2-yl)carbamoyl)pivalamide (87 mg, 59%) as a white solid. $^1$H NMR (400 MHz, DMSO-d$_6$): δ 11.17 (s, 1H), 10.49 (s, 1H), 10.41 (br s, 1H), 8.17 (d, J=5.7 Hz, 1H), 7.90 (m, 1H), 7.63 (d, J=8.8 Hz, 1H), 7.59 (d, J=2.4 Hz, 1H), 6.65 (dd, J=5.7, 2.4 Hz, 1H), 2.33 (q, J=7.5 Hz, 2H), 2.23 (s, 3H), 1.22 (s, 9H), 0.99 (t, J=7.5 Hz, 3H); MS (ESI) m/z: 400.2 (M+H$^+$).

Example 13

A mixture of Example A3 (0.50 g, 1.882 mmol), isobutyramide (0.656 g, 7.53 mmol), Cs$_2$CO$_3$ (0.920 g, 2.82 mmol), and X-phos (0.045 g, 0.094 mmol) in dioxane (10 mL) was sparged with Ar, treated with Pd$_2$(dba)$_3$ (0.086 g, 0.094 mmol), sparged again with Ar and heated at 90° C. for 20 h. The mixture was cooled to RT, treated with EtOAc and the solids removed via filtration. The filtrate was washed with brine, dried over Na$_2$SO$_4$, concentrated to dryness and purified via silica gel chromatography (EtOAc/DCM) to afford N-(4-((2-methyl-6-nitropyridin-3-yl)oxy)pyridin-2-yl) isobutyramide (550 mg, 92%). MS (ESI) m/z: 317.1 (M+H$^+$).

A solution of N-(4-((2-methyl-6-nitropyridin-3-yl)oxy) pyridin-2-yl)isobutyramide (0.55 g, 1.739 mmol) in 2:1 EtOAc/MeOH (30 mL) was treated with palladium on carbon (50% wet, 0.206 g, 0.174 mmol) and hydrogenated (1 atm) for 2 days. The solids were removed via filtration through diatomaceous earth, washed well with MeOH and the filtrate was concentrated to dryness to afford N-(4-((6-amino-2-methylpyridin-3-yl)oxy)pyridin-2-yl)isobutyramide (410 mg, 82%). $^1$H NMR (400 MHz, DMSO-d6): δ 10.41 (s, 1H), 8.12 (d, J=5.7 Hz, 1H), 7.57 (d, J=2.4 Hz, 1H), 7.16 (d, J=8.7 Hz, 1H), 6.58 (dd, J=5.7, 2.4 Hz, 1H), 6.35 (d, J=8.7 Hz, 1H), 5.95 (s, 2H), 2.69 (m, 1H), 2.04 (s, 3H), 1.02 (d, J=6.8 Hz, 6H); MS (ESI) m/z: 287.2 (M+H$^+$).

A solution of 2,2,2-trimethylacetamide (0.046 g, 0.454 mmol) in DCE (2 mL) was treated with oxalyl chloride (0.040 mL, 0.454 mmol), stirred at RT for 0.5 h, then heated at 75° C. for 1 h. The mixture was cooled to RT, added to a solution of N-(4-((6-amino-2-methylpyridin-3-yl)oxy)pyridin-2-yl) isobutyramide (0.10 g, 0.349 mmol) and TEA (0.1 mL, 0.70 mmol) in THF (2 mL) and stirred at RT for 1 h. The mixture was concentrated to dryness, the residue treated with EtOAc, washed with brine, dried over Na$_2$SO$_4$ and concentrated to dryness. The material was treated with EtOAc, allowed to stand at RT overnight and the resulting solid collected via filtration and dried to afford N-((5-((2-isobutyramidopyridin-4-yl)oxy)-6-methylpyridin-2-yl)carbamoyl)pivalamide (63 mg, 42%) as a white solid. $^1$H NMR (400 MHz, DMSO-d$_6$): δ 11.17 (s, 1H), 10.50 (s, 1H), 10.42 (br s, 1H), 8.18 (d, J=5.7 Hz, 1H), 7.92 (m, 1H), 7.63 (d, J=8.8 Hz, 1H), 7.60 (d, J=2.4 Hz, 1H), 6.66 (dd, J=5.7, 2.4 Hz, 1H), 2.69 (m, 1H), 2.24 (s, 3H), 1.22 (s, 9H), 1.02 (d, J=6.8 Hz, 6H); MS (ESI) m/z: 414.2 (M+H$^+$).

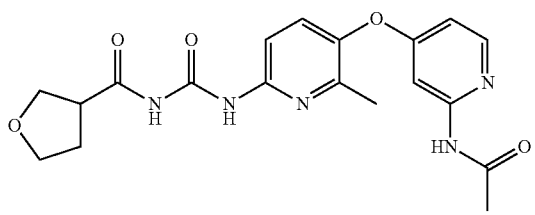 [SMILES: CC(=O)Nc1cc(Oc2ccc(NC(=O)NC(=O)C3CCOC3)nc2C)ccn1]

Example 14

A solution of Example B2 (0.080 g, 0.697 mmol) in DCE (3 mL) was treated with oxalyl chloride (0.061 mL, 0.697 mmol), stirred at RT for 1 h, then heated at 75° C. for 1 h. The mixture was cooled to RT, treated with a solution of Example A4 (0.09 g, 0.348 mmol) and TEA (0.146 mL, 1.045 mmol) in THF (3 mL) and stirred at RT for 1 h. The mixture was treated with water, extracted with 10% MeOH/DCM (1×), then DCM (1×) and the combined organics were washed with brine, dried over Na$_2$SO$_4$ and concentrated to dryness. The residue was treated with MeCN, sonicated and the resulting solid collected via filtration and dried to afford N-((5-((2-acetamidopyridin-4-yl)oxy)-6-methylpyridin-2-yl)carbamoyl)tetrahydrofuran-3-carboxamide (66 mg, 47%) as an off-white solid. $^1$H NMR (400 MHz, DMSO-d$_6$): δ 10.96 (s, 1H), 10.93 (s, 1H), 10.54 (s, 1H), 8.17 (d, J=5.7 Hz, 1H), 7.90 (d, J=8.8 Hz, 1H), 7.62 (d, J=8.8 Hz, 1H), 7.57 (d, J=2.4 Hz, 1H), 6.62 (dd, J=5.7, 2.4 Hz, 1H), 3.87 (t, J=8.3 Hz, 1H), 3.76-3.75 (m, 2H), 3.67-3.66 (m, 1H), 3.25-3.22 (m, 1H), 2.22 (s, 3H), 2.07 (q, J=7.1 Hz, 2H), 2.02 (s, 3H); MS (ESI) m/z: 400.2 (M+H$^+$).

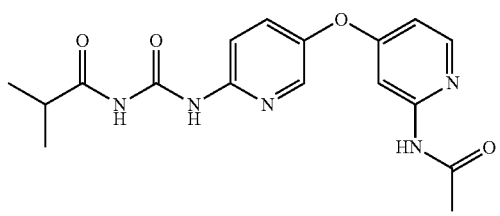 [SMILES: CC(=O)Nc1cc(Oc2ccc(NC(=O)NC(=O)C(C)C)nc2)ccn1]

Example 15

A solution of isobutyramide (0.071 g, 0.819 mmol) in DCE (3 mL) was treated with oxalyl chloride (0.104 g, 0.819 mmol), stirred at RT for 1 h, then heated at 75° C. for 1 h. The mixture was cooled to RT, treated with a solution of Example A2 (0.1 g, 0.409 mmol) and TEA (0.124 g, 1.228 mmol) in THF (3 mL) and stirred at RT for 1 h. The mixture was treated with water, extracted with 10% MeOH/DCM (1×), then DCM (1×) and the combined organics were washed with brine, dried over Na$_2$SO$_4$ and concentrated to dryness. The residue was treated with EtOAc, sonicated and the resulting solid collected via filtration. The solid was re-suspended in EtOAc, sonicated and again collected via filtration and dried to afford N-((5-((2-acetamidopyridin-4-yl)oxy)pyridin-2-yl)carbamoyl)isobutyramide (45 mg, 31%). $^1$H NMR (400 MHz, DMSO-d$_6$): δ 11.11 (s, 1H), 10.85 (s, 1H), 10.56 (s, 1H), 8.24 (d, J=2.9 Hz, 1H), 8.18 (d, J=5.7 Hz, 1H), 8.08 (d, J=9.0 Hz, 1H), 7.72 (dd, J=9.0, 2.9 Hz, 1H), 7.64 (d, J=2.4 Hz, 1H), 6.68 (dd, J=5.7, 2.4 Hz, 1H), 2.68-2.66 (m, 1H), 2.03 (s, 3H), 1.09 (d, J=6.8 Hz, 6H); MS (ESI) m/z: 358.2 (M+H$^+$).

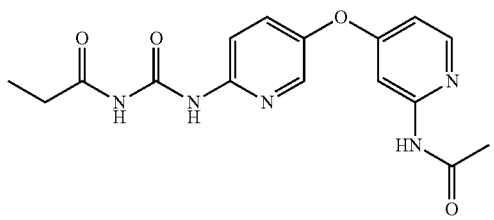 [SMILES: CCC(=O)NC(=O)Nc1ccc(Oc2ccnc(NC(C)=O)c2)cn1]

Example 16

A solution of propionyl chloride (0.250 g, 2.70 mmol), in DCM (10 mL) was treated with silver cyanate (0.450 g, 3.00 mmol) and stirred at RT for 4 h. Example A2 (0.250 g, 1.024 mmol) was added and the mixture was stirred at RT overnight. The solids were removed via filtration through diatomaceous earth and washed with DCM and THF. The filtrate was concentrated to dryness, the residue treated with MeCN and the solid collected via filtration. The solid was then suspended in water, heated to 80° C. for 10 minutes and collected via filtration to afford N-((5-((2-acetamidopyridin-4-yl)oxy)pyridin-2-yl)carbamoyl)propionamide (138 mg, 39%) as an off-white solid. $^1$H NMR (400 MHz, DMSO-d$_6$): δ 11.06 (s, 1H), 10.82 (s, 1H), 10.56 (s, 1H), 8.24 (d, J=2.9 Hz, 1H), 8.18 (d, J=5.7 Hz, 1H), 8.08 (d, J=9.0 Hz, 1H), 7.72 (dd, J=9.0, 2.9 Hz, 1H), 7.65 (d, J=2.4 Hz, 1H), 6.68 (dd, J=5.7, 2.4 Hz, 1H), 2.41 (d, J=7.5 Hz, 2H), 2.03 (s, 3H), 1.05 (t, J=7.5 Hz, 3H); MS (ESI) m/z: 344.2 (M+H$^+$).

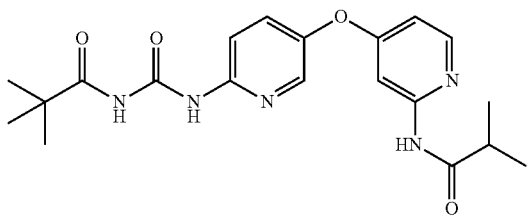 [SMILES: CC(C)C(=O)Nc1cc(Oc2ccc(NC(=O)NC(=O)C(C)(C)C)nc2)ccn1]

Example 17

A suspension of Example A1 (2.00 g, 7.95 mmol), Cs$_2$CO$_3$ (5.00 g, 15.35 mmol), X-Phos (0.200 g, 0.420 mmol), Pd$_2$(dba)$_3$ (0.200 g, 0.218 mmol) and isobutyramide (1.00 g, 11.48 mmol) in dioxane (20 mL), under Ar, was heated at 90° C. overnight. The mixture was cooled to RT, the solids removed via filtration, washed with DCM and THF and the filtrate concentrated to dryness and purified via silica gel chromatography (EtOAc/Hex) to afford N-(4-((6-nitropyridin-3-yl)oxy)pyridin-2-yl)isobutyramide (1.08 g, 45%) as an off-white solid. $^1$H NMR (400 MHz, DMSO-d$_6$): δ 10.65 (s, 1H), 8.58 (m, 1H), 8.41 (dd, J=8.9, 0.5 Hz, 1H), 8.31 (d, J=5.7 Hz, 1H), 7.99 (dd, J=8.9, 2.8 Hz, 1H), 7.85 (d, J=2.4 Hz, 1H), 6.89 (dd, J=5.7, 2.4 Hz, 1H), 2.72 (m, 1H), 1.03 (d, J=6.8 Hz, 6H); MS (ESI) m/z: 303.1 (M+H$^+$).

A solution of N-(4-((6-nitropyridin-3-yl)oxy)pyridin-2-yl)isobutyramide (1.08 g, 3.57 mmol) in MeOH (30 mL) was treated with hydrazine hydrate (1.00 g, 19.98 mmol) followed by Raney Nickel (0.300 g, 5.11 mmol) and stirred at RT for 3 h. The solids were removed via filtration through diatomaceous earth, washed with DCM and MeOH and the filtrate concentrated to dryness to afford N-(4-((6-aminopyridin-3-yl)oxy)pyridin-2-yl)isobutyramide (900 mg, 93%) as an off-white solid. MS (ESI) m/z: 273.2 (M+H$^+$).

A solution of trimethylacetylchloride (0.250 g, 2.073 mmol) in DCM (10 mL) was treated with silver cyanate (0.330 g, 2.202 mmol), stirred at RT for 4 h, treated with N-(4-((6-aminopyridin-3-yl)oxy)pyridin-2-yl)isobutyramide (0.396 mmol, 43.1% yield) and stirred at RT overnight. The solids were removed via filtration through diatomaceous earth, washed with DCM and THF and the filtrate concentrated to dryness. The residue was treated with MTBE and the solid collected via filtration to afford N-((5-((2-isobutyramidopyridin-4-yl)oxy)pyridin-2-yl)carbamoyl)pivalamide (170 mg, 46%) as a white solid. $^1$H NMR (400 MHz, DMSO-d$_6$): δ 11.23 (s, 1H), 10.49 (s, 1H), 10.44 (s, 1H), 8.25 (m, 1H), 8.19 (d, J=5.7 Hz, 1H), 8.09 (d, J=9.1 Hz, 1H), 7.74 (m, 1H), 7.66 (m, 1H), 6.73 (m, 1H), 2.69 (m, 1H), 1.21 (s, 9H), 1.01 (d, J=6.8 Hz, 6H); MS (ESI) m/z: 400.2 (M+H$^+$).

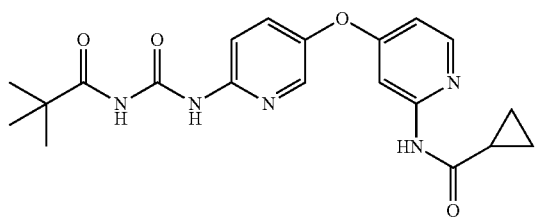 [SMILES: CC(C)(C)C(=O)NC(=O)Nc1ccc(Oc2ccnc(NC(=O)C3CC3)c2)cn1]

Example 18

A solution of trimethylacetylchloride (0.250 g, 2.073 mmol) in DCM (10 mL) was treated with silver cyanate (0.330 g, 2.202 mmol), stirred at RT for 4 h, treated with Example A7 (0.250 g, 0.925 mmol) and stirred at RT overnight. The solids were removed via filtration through diatomaceous earth, washed with DCM and THF and the filtrate concentrated to dryness. The residue was treated with MeCN and MTBE and the resulting solid collected via filtration and dried to afford N-(4-((6-(3-pivaloylureido)pyridin-3-yl)oxy)pyridin-2-yl)cyclopropanecarboxamide (177 mg, 48%) as a white solid. $^1$H NMR (400 MHz, DMSO-d$_6$): δ 11.22 (s, 1H), 10.86 (s, 1H), 10.43 (s, 1H), 8.24 (d, J=2.9 Hz, 1H), 8.19 (d, J=5.7 Hz, 1H), 8.08 (d, J=9.0 Hz, 1H), 7.72 (dd, J=9.0, 2.9 Hz, 1H), 7.63 (d, J=2.4 Hz, 1H), 6.72 (dd, J=5.7, 2.4 Hz, 1H), 1.95 (m, 1H), 1.21 (s, 9H), 0.75 (d, J=6.2 Hz, 4H); MS (ESI) m/z: 398.2 (M+H$^+$).

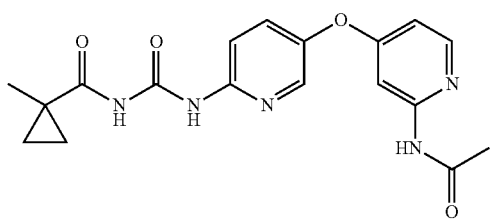 [SMILES: CC(=O)Nc1cc(Oc2ccc(NC(=O)NC(=O)C3(C)CC3)nc2)ccn1]

Example 19

A solution of 1-methylcyclopropanecarboxylic acid (0.200 g, 1.998 mmol) in DCM (10 mL) was treated with oxalyl chloride (0.200 g, 1.576 mmol) followed DMF (5.99 mg, 0.082 mmol) and stirred at RT for 2 h. The mixture was concentrated to dryness, the residue dissolved in DCM (10 mL), treated with silver cyanate (0.250 g, 1.668 mmol), stirred at RT for 1 h, treated with Example A2 (0.200 g, 0.819 mmol) and stirred at RT overnight. The solids were removed via filtration through diatomaceous earth, washed with DCM and THF and the filtrate concentrated to dryness and purified via silica gel chromatography (EtOAc/Hex) to afford N-((5-((2-acetamidopyridin-4-yl)oxy)pyridin-2-yl)carbamoyl)-1-methylcyclopropanecarboxamide (63 mg, 20%) as a white solid. $^1$H NMR (400 MHz, DMSO-d$_6$): δ 11.24 (s, 1H), 10.56 (s, 1H), 10.13 (br s, 1H), 8.23 (d, J=2.9 Hz, 1H), 8.18 (d, J=5.7 Hz, 1H), 8.06 (d, J=8.8 Hz, 1H), 7.72 (dd, J=9.0, 2.9 Hz, 1H), 7.65 (d, J=2.4 Hz, 1H), 6.68 (dd, J=5.7, 2.4 Hz, 1H), 2.03 (s, 3H), 1.35 (s, 3H), 1.21 (m, 2H), 0.75 (m, 2H); MS (ESI) m/z: 370.2 (M+H$^+$).

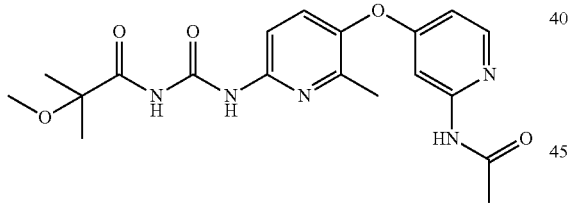

Example 20

A mixture of Example B1 (0.117 g, 0.581 mmol), Example A4 (0.1 g, 0.387 mmol) and 1-methylpyrrolidine (3.30 mg, 0.039 mmol) in THF (3 mL) was heated at 55° C. for 16 h. The mixture was concentrated to dryness and purified via silica gel chromatography (MeOH/DCM) to afford N-((5-((2-acetamidopyridin-4-yl)oxy)-6-methylpyridin-2-yl)carbamoyl)-2-methoxy-2-methylpropanamide (85 mg, 55%) as a white solid. $^1$H NMR (400 MHz, DMSO-d$_6$): δ 10.76 (s, 1H), 10.19 (s, 1H), 8.34 (d, J=5.7 Hz, 1H), 8.25 (s, 1H), 8.14 (s, 1H), 7.96 (d, J=0.7 Hz, 1H), 7.16 (d, J=2.4 Hz, 1H), 6.60 (dd, J=5.7, 2.5 Hz, 1H), 3.20 (s, 3H), 2.24 (s, 3H), 2.02 (s, 3H), 1.35 (s, 6H); MS (ESI) m/z: 402.2 (M+H$^+$).

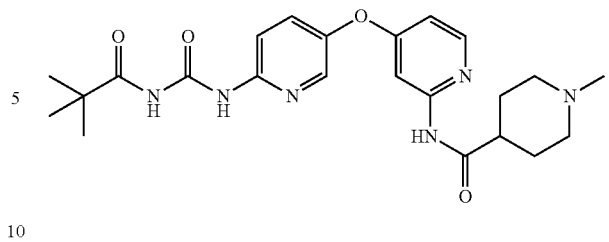

Example 21

A solution of 2,2,2-trimethylacetamide (0.042 g, 0.412 mmol) in DCE (2 mL) was treated with oxalyl chloride (0.036 mL, 0.412 mmol), stirred at RT for 0.5 h, then heated at 75° C. for 1 h. The mixture was cooled to RT, added to a mixture of Example A8 (0.09 g, 0.275 mmol) and TEA (0.1 mL) in THF (2 mL) and stirred at RT for 1.5 h. The mixture was treated with water, extracted with EtOAc (3×) and the combined organics were dried over Na$_2$SO$_4$ and concentrated to dryness. The material was layered with EtOAc, allowed to stand overnight and the resulting solid collected via filtration to afford 1-methyl-N-(4-((6-(3-pivaloylureido)pyridin-3-yl)oxy)pyridin-2-yl)piperidine-4-carboxamide (35 mg, 27%) as a peach-colored solid. $^1$H NMR (400 MHz, DMSO-d$_6$): δ 11.24 (s, 1H), 10.52 (s, 1H), 10.50 (s, 1H), 8.25 (d, J=2.9 Hz, 1H), 8.20 (d, J=5.7 Hz, 1H), 8.10 (d, J=9.0 Hz, 1H), 7.74 (dd, J=9.0, 2.9 Hz, 1H), 7.65 (d, J=2.4 Hz, 1H), 6.73 (dd, J=5.7, 2.4 Hz, 1H), 2.77 (m, 2H), 2.38 (m, 1H), 2.13 (s, 3H), 1.82 (m, 2H), 1.66 (m, 2H), 1.55 (m, 2H), 1.22 (s, 9H); MS (ESI) m/z: 455.3 (M+H$^+$).

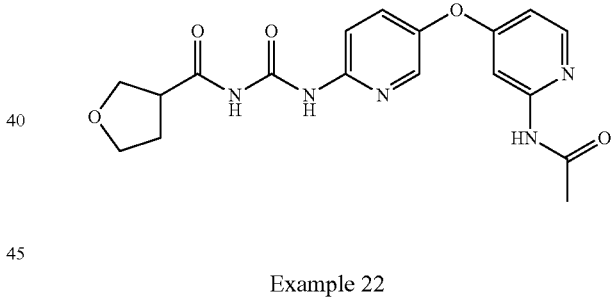

Example 22

A solution of Example B2 (0.104 g, 0.901 mmol) in DCE (3 mL) was treated with oxalyl chloride (0.079 mL, 0.901 mmol), stirred at RT for 1 h, then heated at 75° C. for 1 h. The mixture was cooled to RT, treated with a solution of Example A2 (0.11 g, 0.450 mmol) and TEA (0.188 mL, 1.351 mmol) in THF (4 mL) and stirred at RT for 1 h. The mixture was treated with water, extracted with 10% MeOH/DCM (1×), then DCM (1×) and the combined organics were washed with brine, dried over Na$_2$SO$_4$, concentrated to dryness and purified via silica gel chromatography (MeOH/DCM) to afford N-((5-((2-acetamidopyridin-4-yl)oxy)pyridin-2-yl)carbamoyl)tetrahydrofuran-3-carboxamide (42 mg, 24%) as a white solid. $^1$H NMR (400 MHz, DMSO-d$_6$): δ 10.98 (s, 2H), 10.56 (s, 1H), 8.24 (d, J=2.9 Hz, 1H), 8.18 (d, J=5.7 Hz, 1H), 8.08 (d, J=9.0 Hz, 1H), 7.72 (dd, J=9.0, 2.9 Hz, 1H), 7.64 (d, J=2.4 Hz, 1H), 6.69 (dd, J=5.7, 2.4 Hz, 1H), 3.87 (t, J=8.3 Hz, 1H), 3.76-3.75 (m, 2H), 3.67-3.66 (m, 1H), 3.28-3.26 (m, 1H), 2.08-2.06 (m, 2H), 2.03 (s, 3H); MS (ESI) m/z: 386.2 (M+H$^+$).

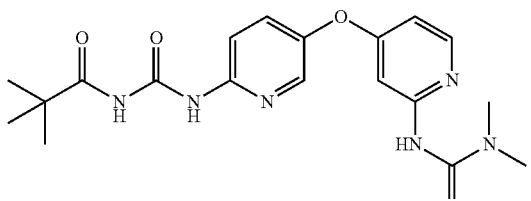

Example 23

A solution of 2,2,2-trimethylacetamide (0.311 g, 3.07 mmol) in DCE (5 mL) was treated with oxalyl chloride (0.250 mL, 2.91 mmol) and heated at 100° C. for 1 h. The mixture was cooled to RT, added to a solution of Example A9 (0.560 g, 2.049 mmol) and pyridine (0.250 mL, 3.10 mmol) in DCM (10 mL) and stirred at RT for 0.5 h. The mixture was treated with satd. NaHCO$_3$, extracted with DCM (3×) and the combined organics were dried over Na$_2$SO$_4$, concentrated to dryness and purified via silica gel chromatography (MeOH/DCM). The material was re-purified via silica gel chromatography (MeOH/EtOAc) to afford N-((5-((2-(3,3-dimethylureido)pyridin-4-yl)oxy)pyridin-2-yl)carbamoyl)pivalamide (441 mg, 54%) as a white solid. $^1$H NMR (400 MHz, Acetone-d$_6$): δ 11.29 (s, 1H), 9.12 (s, 1H), 8.20-8.17 (m, 2H), 8.08 (d, J=5.7 Hz, 1H), 7.85 (s, 1H), 7.68 (d, J=2.4 Hz, 1H), 7.64 (dd, J=9.0, 2.9 Hz, 1H), 6.56 (dd, J=5.7, 2.4 Hz, 1H), 3.02 (s, 6H), 1.35 (s, 9H); MS (ESI) m/z: 401.2 (M+H$^+$).

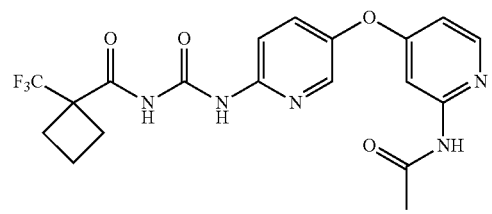

Example 25

A solution of 1-(trifluoromethyl)cyclobutanecarboxylic acid (0.250 g, 1.487 mmol) in DCM (10 mL) was treated with oxalyl chloride (0.180 g, 1.418 mmol) followed by a catalytic amount of DMF and stirred at RT for 1 h. The mixture was treated with silver cyanate (0.250 g, 1.668 mmol), stirred at RT for 2 h, treated with Example A2 (0.200 g, 0.819 mmol) and stirred at RT overnight. The solids were removed via filtration through diatomaceous earth, rinsed well with DCM, then THF and the filtrate concentrated to dryness and purified via silica gel chromatography (EtOAc/Hex) to afford N-((5-((2-acetamidopyridin-4-yl)oxy)pyridin-2-yl)carbamoyl)-1-(trifluoromethyl)cyclobutanecarboxamide (140 mg, 37%) as a white solid. $^1$H NMR (400 MHz, DMSO-d$_6$): δ 11.14 (br s, 1H), 10.84 (s, 1H), 10.56 (s, 1H), 8.26 (d, J=2.9 Hz, 1H), 8.19 (d, J=5.7 Hz, 1H), 8.05 (d, J=9.0 Hz, 1H), 7.75 (dd, J=9.0, 2.9 Hz, 1H), 7.65 (d, J=2.4 Hz, 1H), 6.69 (dd, J=5.7, 2.4 Hz, 1H), 2.70 (m, 2H), 2.42 (m, 2H), 2.03 (s, 3H), 1.90 (m, 2H); MS (ESI) m/z: 438.1 (M+H$^+$).

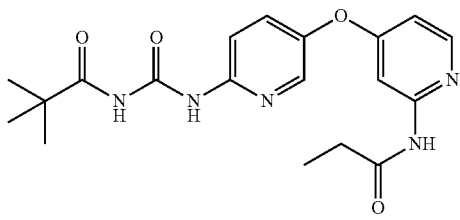 [SMILES: CCC(=O)Nc1cc(Oc2ccc(NC(=O)NC(=O)C(C)(C)C)nc2)ccn1]

Example 24

A solution of 2,2,2-trimethylacetamide (0.599 g, 5.92 mmol) in DCE (10 mL) was treated with oxalyl chloride (0.50 mL, 5.82 mmol) and heated at 100° C. for 1 h. The mixture was cooled to RT, added to a solution of Example A10 (1.02 g, 3.95 mmol) and pyridine (0.5 mL, 6.19 mmol) in DCM (10 mL) and stirred at RT for 0.5 h. The mixture was treated with satd. NaHCO$_3$, extracted with DCM (3×) and the combined organics were dried over Na$_2$SO$_4$, concentrated to dryness and purified via silica gel chromatography (MeOH/DCM). The material was re-purified via silica gel chromatography (EtOAc/Hex), suspended in MeCN, sonicated and the resulting solid collected via filtration to afford N-((5-((2-propionamidopyridin-4-yl)oxy)pyridin-2-yl)carbamoyl)pivalamide (57 mg, 3.7%) as a white solid. $^1$H NMR (400 MHz, DMSO-d$_6$): δ 11.22 (s, 1H), 10.50 (s, 1H), 10.43 (s, 1H), 8.24 (d, J=2.9 Hz, 1H), 8.18 (d, J=5.7 Hz, 1H), 8.08 (d, J=9.0 Hz, 1H), 7.73 (dd, J=9.0, 2.9 Hz, 1H), 7.65 (d, J=2.4 Hz, 1H), 6.70 (dd, J=5.7, 2.4 Hz, 1H), 2.33 (q, J=7.5 Hz, 2H), 1.20 (s, 9H), 0.99 (t, J=7.5 Hz, 3H); MS (ESI) m/z: 386.2 (M+H$^+$).

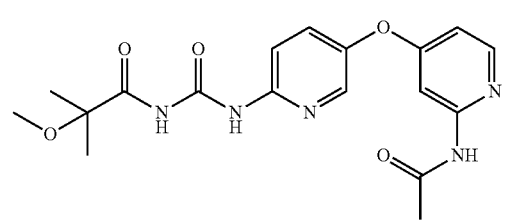 [SMILES: COC(C)(C)C(=O)NC(=O)Nc1ccc(Oc2ccnc(NC(C)=O)c2)cn1]

Example 26

A mixture of Example B1 (0.124 g, 0.614 mmol), Example A2 (0.1 g, 0.409 mmol) and 1-methylpyrrolidine (10.46 mg, 0.123 mmol) in THF (3 mL) was heated at 55° C. overnight. The mixture was concentrated to dryness and purified via silica gel chromatography (MeOH/DCM). The material was re-purified via reverse-phase chromatography (MeCN/H$_2$O with 0.1% TFA); combined fractions were neutralized with satd. NaHCO$_3$, extracted with EtOAc (2×) and the combined organics were washed with brine, dried over Na$_2$SO$_4$ and concentrated to dryness to afford N-((5-((2-acetamidopyridin-4-yl)oxy)pyridin-2-yl)carbamoyl)-2-methoxy-2-methylpropanamide (45 mg, 28%) as a white amorphous solid. $^1$H NMR (400 MHz, DMSO-d$_6$): δ 10.81 (s, 1H), 10.55 (s, 1H), 10.24 (br s, 1H), 8.24 (d, J=3.0 Hz, 1H), 8.18 (d, J=5.7 Hz, 1H), 8.01 (br s, 1H), 7.73 (dd, J=9.0, 2.9 Hz, 1H), 7.64 (d, J=2.4 Hz, 1H), 6.68 (dd, J=5.7, 2.4 Hz, 1H), 3.20 (s, 3H), 2.02 (s, 3H), 1.35 (s, 6H); MS (ESI) m/z: 388.2 (M+H$^+$).

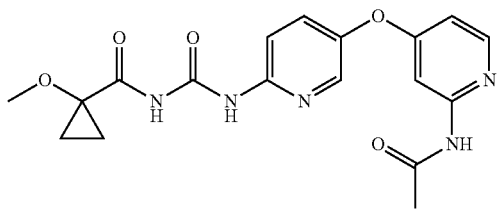 [SMILES: COC1(C(=O)NC(=O)Nc2ccc(Oc3ccnc(NC(C)=O)c3)cn2)CC1]

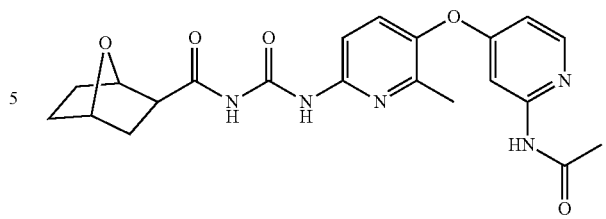

Example 27

Example 29

A solution of Example B6 (0.250 g, 2.153 mmol) in DCM (10 mL) was treated with oxalyl chloride (0.250 g, 1.970 mmol) followed catalytic DMF and stirred at RT for 1 h. The mixture was treated with silver cyanate (0.250 g, 1.668 mmol), stirred at RT for 2 h, treated with Example A2 (0.200 g, 0.819 mmol) and stirred at RT for 3 days. The solids were removed via filtration through diatomaceous earth, washed with DCM and THF, the filtrate concentrated to dryness and purified via prep-TLC (EtOAc/THF) to afford N-((5-((2-acetamidopyridin-4-yl)oxy)pyridin-2-yl)carbamoyl)-1-methoxycyclopropanecarboxamide (18 mg, 5.4%) as a white solid. $^1$H NMR (400 MHz, DMSO-$d_6$): δ 10.86 (s, 1H), 10.61-10.28 (m, 2H), 8.24 (d, J=2.9 Hz, 1H), 8.18 (d, J=5.7 Hz, 1H), 8.01 (br s, 1H), 7.73 (dd, J=9.0, 2.9 Hz, 1H), 7.65 (d, J=2.4 Hz, 1H), 6.68 (m, 1H), 2.03 (s, 3H), 1.34 (s, 3H), 1.24 (s, 4H); MS (ESI) m/z: 386.2 (M+H$^+$).

A solution of Example B3 (0.300 g, 2.110 mmol) in DCM (10 mL) was treated with oxalyl chloride (0.260 g, 2.048 mmol) followed by catalytic DMF, stirred at RT for 2 h, treated with silver cyanate (0.400 g, 2.67 mmol) and stirred for 1 h. The mixture was treated with Example A4 (0.120 g, 0.465 mmol) and pyridine (0.037 g, 0.465 mmol), stirred at RT for 2 h and the solids removed via filtration. The filtrate was concentrated to dryness and purified via silica gel chromatography (EtOAc/Hex) to afford N-((5-((2-acetamidopyridin-4-yl)oxy)-6-methylpyridin-2-yl)carbamoyl)-7-oxabicyclo[2.2.1]heptane-2-carboxamide (75 mg, 36%) as a white solid. $^1$H NMR (400 MHz, DMSO-$d_6$): δ 10.90 (s, 1H), 10.85 (s, 1H), 10.54 (s, 1H), 8.16 (d, J=5.7 Hz, 1H), 7.90 (d, J=8.8 Hz, 1H), 7.59 (m, 2H), 6.61 (dd, J=5.7, 2.4 Hz, 1H), 4.65 (t, J=4.6 Hz, 1H), 4.58 (t, J=4.6 Hz, 1H), 2.80 (dd, J=8.8, 5.0 Hz, 1H), 2.22 (s, 3H), 2.02 (s, 3H), 2.00 (m, 1H), 1.55 (m, 5H); MS (ESI) m/z: 426.2 (M+H$^+$).

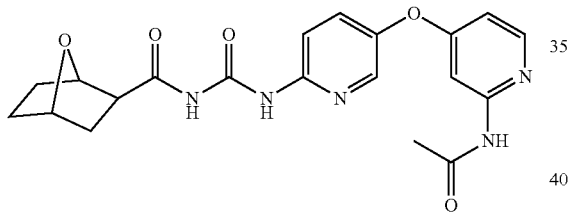

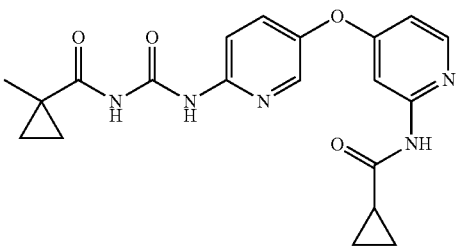 [SMILES: CC1(C(=O)NC(=O)Nc2ccc(Oc3ccnc(NC(=O)C4CC4)c3)cn2)CC1]

Example 28

Example 30

A solution of Example B3 (0.300 g, 2.110 mmol) in DCM (10 mL) was treated with oxalyl chloride (0.260 g, 2.048 mmol) followed by catalytic DMF and stirred at RT for 2 h. The mixture was treated with silver cyanate (0.500 g, 3.34 mmol), stirred for 1 h, treated with Example A2 (0.200 g, 0.819 mmol) and pyridine (0.065 g, 0.819 mmol) and stirred at RT overnight. The solids were removed via filtration, washed with DCM and the filtrate concentrated to dryness and purified via silica gel chromatography (EtOAc/Hex) to afford N-((5-((2-acetamidopyridin-4-yl)oxy)pyridin-2-yl)carbamoyl)-7-oxabicyclo[2.2.1]heptane-2-carboxamide (145 mg, 43%) as an off-white solid. $^1$H NMR (400 MHz, DMSO-$d_6$): δ 10.97 (s, 1H), 10.87 (s, 1H), 10.56 (s, 1H), 8.24 (d, J=2.9 Hz, 1H), 8.18 (d, J=5.7 Hz, 1H), 8.08 (d, J=9.0 Hz, 1H), 7.72 (dd, J=9.0, 2.9 Hz, 1H), 7.65 (d, J=2.4 Hz, 1H), 6.68 (dd, J=5.7, 2.4 Hz, 1H), 4.65 (m, 1H), 4.58 (m, 1H), 2.80 (m, 1H), 2.05-1.70 (m, 4H), 1.64-1.49 (m, 4H), 1.47-1.41 (m, 1H); MS (ESI) m/z: 412.2 (M+H$^+$).

A solution of Example B4 (0.163 g, 0.888 mmol) and Example A7 (0.120 g, 0.444 mmol) in dioxane (5 mL) was treated with 1-methylpyrrolidine (0.011 g, 0.133 mmol) and heated at 65° C. for 16 h. The mixture was cooled to RT, concentrated to dryness and purified via reverse-phase chromatography (MeCN/H$_2$O with 0.1% TFA). Combined fractions were neutralized with satd. NaHCO$_3$, extracted with EtOAc (2×) and the combined organics were washed with brine, dried over Na$_2$SO$_4$ and concentrated to dryness to afford N-((5-((2-(cyclopropanecarboxamido)pyridin-4-yl)oxy)pyridin-2-yl)carbamoyl)-1-methylcyclopropanecarboxamide (58 mg, 33%) as a white solid. $^1$H NMR (400 MHz, DMSO-$d_6$): δ 11.24 (s, 1H), 10.86 (s, 1H), 10.15 (br s, 1H), 8.23 (d, J=2.9 Hz, 1H), 8.19 (d, J=5.7 Hz, 1H), 8.06 (d, J=9.0 Hz, 1H), 7.72 (dd, J=9.0, 2.9 Hz, 1H), 7.62 (d, J=2.4 Hz, 1H), 6.71 (dd, J=5.7, 2.4 Hz, 1H), 1.95-1.93 (m, 1H), 1.35 (s, 3H), 1.20-1.19 (m, 2H), 0.75-0.74 (m, 6H); MS (ESI) m/z: 396.2 (M+H$^+$).

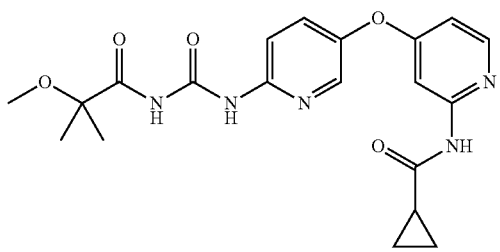 [SMILES: COC(C)(C)C(=O)NC(=O)Nc1ccc(Oc2ccnc(NC(=O)C3CC3)c2)cn1]
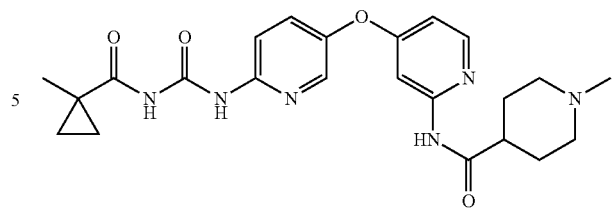

Example 31

A mixture of Example B1 (0.164 g, 0.814 mmol), Example A7 (0.11 g, 0.407 mmol) and 1-methylpyrrolidine (0.017 g, 0.203 mmol) in dioxane (4 mL) was heated at 65° C. for 16 h, then cooled to RT, concentrated to dryness and purified via reverse-phase chromatography (MeCN/H$_2$O with 0.1% TFA). Combined fractions were neutralized with satd. NaHCO$_3$, extracted with EtOAc (2×) and the combined organics were washed with brine, dried over Na$_2$SO$_4$ and concentrated to dryness to afford N-(4-((6-(3-(2-methoxy-2-methylpropanoyl)ureido)pyridin-3-yl)oxy)pyridin-2-yl)cyclopropanecarboxamide (83 mg, 49%) as a white solid. $^1$H NMR (400 MHz, DMSO-d$_6$): δ 10.87 (s, 1H), 10.81 (s, 1H), 8.24 (d, J=2.9 Hz, 1H), 8.20 (d, J=5.7 Hz, 1H), 8.01 (br s, 1H), 7.73 (dd, J=9.0, 2.9 Hz, 1H), 7.62 (d, J=2.4 Hz, 1H), 6.72 (dd, J=5.7, 2.4 Hz, 1H), 3.20 (s, 3H), 1.96-1.94 (m, 1H), 1.35 (s, 6H), 0.75 (d, J=6.3 Hz, 4H); MS (ESI) m/z: 414.2 (M+H$^+$).

Example 33

A solution of 1-methylcyclopropane carboxylic acid (0.150 g, 1.498 mmol) in DCM (10 mL) was treated with oxalyl chloride (0.180 g, 1.418 mmol) followed by catalytic DMF and stirred at RT for 1 h. The mixture was treated with silver cyanate (0.400 g, 2.67 mmol), stirred at RT for 1 h, treated with Example A8 (0.150 g, 0.458 mmol) and stirred at RT for 2 h. The solids were removed via filtration, washed with DCM and THF and the filtrate concentrated to dryness and purified via silica gel chromatography (MeOH/DCM) to afford 1-methyl-N-(4-((6-(3-(1-methylcyclopropanecarbonyl)ureido)pyridin-3-yl)oxy)pyridin-2-yl)piperidine-4-carboxamide (68 mg, 32%). $^1$H NMR (400 MHz, DMSO-d$_6$): δ 11.25 (s, 1H), 10.51 (s, 1H), 10.10 (br s, 1H), 8.23 (d, J=2.9 Hz, 1H), 8.18 (d, J=5.7 Hz, 1H), 8.07 (d, J=9.0 Hz, 1H), 7.73 (dd, J=9.0, 2.9 Hz, 1H), 7.65 (d, J=2.4 Hz, 1H), 6.72 (dd, J=5.7, 2.4 Hz, 1H) 2.76 (d, J=11.0 Hz, 2H), 2.37 (m, 1H), 2.12 (s, 3H), 1.81 (m, 2H), 1.67 (m, 2H), 1.55 (m, 2H), 1.35 (s, 3H), 1.21 (m, 2H), 0.75 (m, 2H); MS (ESI) m/z: 453.3 (M+H$^+$).

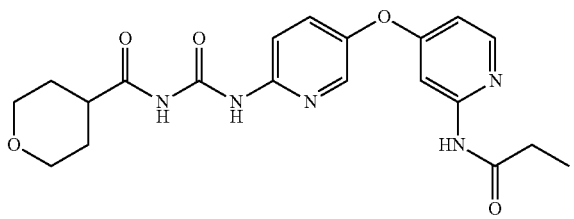 [SMILES: CCC(=O)Nc1cc(Oc2ccc(NC(=O)NC(=O)C3CCOCC3)nc2)ccn1]
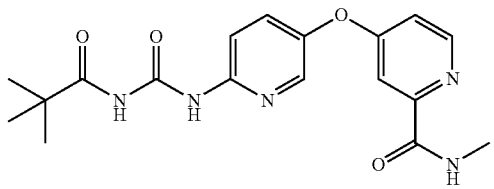 [SMILES: CNC(=O)c1cc(Oc2ccc(NC(=O)NC(=O)C(C)(C)C)nc2)ccn1]

Example 32

A solution of Example B5 (113 mg, 0.871 mmol) in DCE (3 mL) was treated with oxalyl chloride (111 mg, 0.871 mmol), heated at 80° C. for 45 min, cooled to RT, treated with a solution of DIEA (323 mg, 2.497 mmol) and Example A10 (150 mg, 0.581 mmol) in dioxane (4.50 mL) and stirred at RT for 3 h. The mixture was treated with EtOAc, washed successively with satd. NaHCO$_3$, 1N NaOH, then brine, dried over Na$_2$SO$_4$, concentrated to dryness and purified via reverse-phase chromatography (MeCN/H$_2$O with 0.1% TFA). The organics were removed under reduced pressure and the aqueous residue was treated with satd. NaHCO$_3$, extracted with EtOAc (3×) and the combined organics were washed with brine, dried over Na$_2$SO$_4$ and concentrated to dryness to afford N-((5-((2-propionamidopyridin-4-yl)oxy)pyridin-2-yl)carbamoyl)tetrahydro-2H-pyran-4-carboxamide (35 mg, 13%). $^1$H NMR (400 MHz, DMSO-d$_6$): δ 11.06 (s, 1H), 10.88 (s, 1H), 10.50 (s, 1H), 8.25 (d, J=2.9 Hz, 1H), 8.18 (d, J=5.7 Hz, 1H), 8.08 (d, J=9.0 Hz, 1H), 7.73 (dd, J=9.0, 2.9 Hz, 1H), 7.65 (d, J=2.4 Hz, 1H), 6.70 (dd, J=5.7, 2.4 Hz, 1H), 3.88 (d, J=11.3 Hz, 2H), 2.69-2.66 (m, 1H), 2.49 (m, 2H), 2.33 (q, J=7.5 Hz, 2H), 1.72 (d, J=13.1 Hz, 2H), 1.62-1.60 (m, 2H), 0.99 (t, J=7.5 Hz, 3H); MS (ESI) m/z: 414.2 (M+H$^+$).

Example 34

A solution of 2,2,2-trimethylacetamide (0.106 g, 1.044 mmol) in DCE (5 mL) was treated with oxalyl chloride (0.091 mL, 1.044 mmol), stirred at RT for 30 min, heated at 75° C. for 1.5 h and cooled to RT. The mixture was added to a solution of Example A11 (0.15 g, 0.614 mmol) and TEA (0.25 mL) in THF (5 mL) and stirred at RT for 3.5 h. The mixture was treated with satd. NaHCO$_3$, extracted with DCM (2×) and the combined organics were dried over Na$_2$SO$_4$, concentrated to dryness and purified via silica gel chromatography (EtOAc/Hex) to afford N-methyl-4-((6-(3-pivaloylureido)pyridin-3-yl)oxy)picolinamide (130 mg, 56%). $^1$H NMR (400 MHz, DMSO-d$_6$): δ 11.24 (s, 1H), 10.44 (s, 1H), 8.78 (q, J=4.8 Hz, 1H), 8.53 (d, J=5.6 Hz, 1H), 8.31 (d, J=2.9 Hz, 1H), 8.12 (d, J=9.0 Hz, 1H), 7.79 (dd, J=9.0, 2.9 Hz, 1H), 7.42 (d, J=2.6 Hz, 1H), 7.19 (dd, J=5.6, 2.7 Hz, 1H), 2.78 (d, J=4.8 Hz, 3H), 1.22 (s, 9H); MS (ESI) m/z: 372.2 (M+H$^+$).

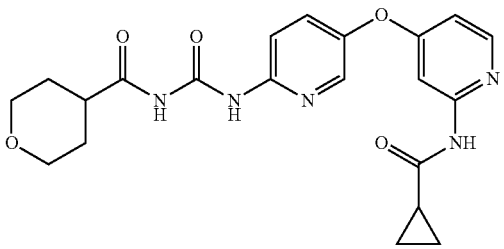 [SMILES: O=C(NC(=O)C1CCOCC1)Nc1ccc(Oc2ccnc(NC(=O)C3CC3)c2)cn1]

Example 35

A solution of Example B5 (0.096 g, 0.740 mmol) in DCE (3 mL) was treated with oxalyl chloride (0.081 mL, 0.925 mmol), stirred at RT for 0.5 h, then heated at 75° C. for 3 h. The mixture was cooled to RT, treated with a solution of Example A7 (0.1 g, 0.370 mmol) and TEA (0.155 mL, 1.110 mmol) in THF (5 mL) and stirred at RT for 1 h. The mixture was treated with water, extracted with EtOAc (2×) and the combined organics were washed with brine, dried over $Na_2SO_4$, concentrated to dryness and purified via silica gel chromatography (MeOH/EtOAc). The material was suspended in 30% MeCN/water (4 mL), sonicated and the resulting solid collected via filtration and dried to afford N-((5-((2-(cyclopropanecarboxamido)pyridin-4-yl)oxy)pyridin-2-yl)carbamoyl)tetrahydro-2H-pyran-4-carboxamide (61 mg, 39%). $^1$H NMR (400 MHz, DMSO-$d_6$): δ 11.05 (s, 1H), 10.88 (s, 1H), 10.86 (s, 1H), 8.24 (d, J=2.9 Hz, 1H), 8.19 (d, J=5.7 Hz, 1H), 8.07 (d, J=9.0 Hz, 1H), 7.72 (dd, J=9.0, 2.9 Hz, 1H), 7.62 (d, J=2.4 Hz, 1H), 6.72 (dd, J=5.7, 2.4 Hz, 1H), 3.88 (m, 2H), 3.31-3.29 (m, 2H), 2.68-2.66 (m, 1H), 1.96-1.95 (m, 1H), 1.73-1.72 (m, 2H), 1.62-1.60 (m, 2H), 0.75 (d, J=6.2 Hz, 4H); MS (ESI) m/z: 426.2 (M+H$^+$).

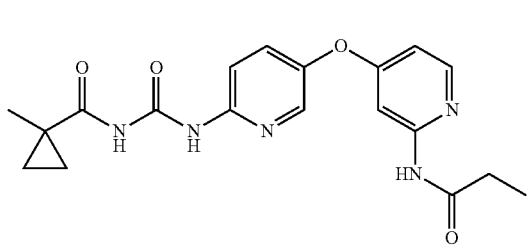 [SMILES: CCC(=O)Nc1cc(Oc2ccc(NC(=O)NC(=O)C3(C)CC3)nc2)ccn1]

Example 36

A solution of 1-methylcyclopropanecarboxylic acid (174 mg, 1.742 mmol) in DCM (3 mL) was treated with oxalyl chloride (221 mg, 1.742 mmol) and catalytic DMF, stirred at RT for 1 h, treated with silver cyanate (522 mg, 3.48 mmol), stirred at RT for 1 h, treated with Example A10 (150 mg, 0.581 mmol) and stirred at RT for 17 h. The mixture was diluted with DCM, the solids removed via filtration through diatomaceous earth and the filtrate concentrated to dryness and purified via silica gel chromatography (EtOAc/Hex) to afford 1-methyl-N-((5-((2-propionamidopyridin-4-yl)oxy)pyridin-2-yl)carbamoyl)cyclopropanecarboxamide (85 mg, 38%). $^1$H NMR (400 MHz, DMSO-$d_6$): δ 11.24 (s, 1H), 10.49 (s, 1H), 10.14-10.12 (m, 1H), 8.23 (d, J=2.9 Hz, 1H), 8.18 (d, J=5.7 Hz, 1H), 8.08-8.05 (m, 1H), 7.73 (dd, J=9.0, 2.9 Hz, 1H), 7.66 (d, J=2.4 Hz, 1H), 6.70 (dd, J=5.7, 2.4 Hz, 1H), 2.33 (q, J=7.5 Hz, 2H), 1.35 (s, 3H), 1.21-1.20 (m, 2H), 0.99 (t, J=7.5 Hz, 3H), 0.75-0.74 (m, 2H); MS (ESI) m/z: 384.2 (M+H$^+$).

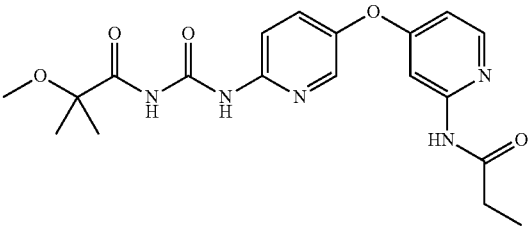 [SMILES: CCC(=O)Nc1cc(Oc2ccc(NC(=O)NC(=O)C(C)(C)OC)nc2)ccn1]

Example 37

A mixture of Example A10 (100 mg, 0.387 mmol), N-methylpyrrolidine (33 mg, 0.387 mmol) and Example B1 (0.171 g, 0.852 mmol) in dioxane (2 mL) was heated at 80° C. overnight. The mixture was cooled to RT, diluted with EtOAc, washed with satd. $NaHCO_3$, then brine, dried over $Na_2SO_4$, concentrated to dryness and purified via silica gel chromatography (EtOAc/Hex) to afford 2-methoxy-2-methyl-N-((5-((2-propionamidopyridin-4-yl)oxy)pyridin-2-yl)carbamoyl)propanamide (86 mg, 54%). $^1$H NMR (400 MHz, DMSO-$d_6$): δ 10.82 (s, 1H), 10.49 (s, 1H), 10.23 (br s, 1H), 8.25 (s, 1H), 8.18 (d, J=5.7 Hz, 1H), 8.02 (br s, 1H), 7.73 (d, J=9.1 Hz, 1H), 7.66 (s, 1H), 6.70 (d, J=5.6 Hz, 1H), 3.21 (s, 3H), 2.33 (q, J=7.5 Hz, 2H), 1.35 (s, 6H), 0.99 (t, J=7.5 Hz, 3H); MS (ESI) m/z: 402.2 (M+H$^+$).

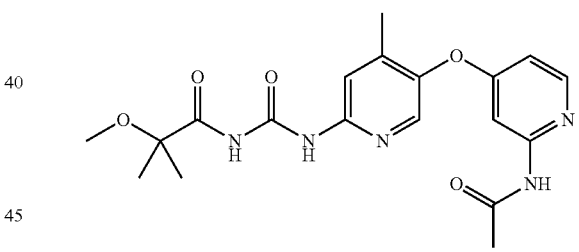

Example 38

A mixture of Example B1 (0.156 g, 0.774 mmol), Example A12 (0.1 g, 0.387 mmol) and DBU (5.84 µL, 0.039 mmol) in dioxane (3 mL) was heated at 60° C. overnight. The mixture was cooled to RT, concentrated to dryness and purified via reverse-phase chromatography (MeCN/$H_2O$ with 0.1% TFA). Combined fractions were treated with satd. $NaHCO_3$, extracted with EtOAc (2×) and the combined organics were washed with brine, dried over $Na_2SO_4$ and concentrated to dryness to afford N-((5-((2-acetamidopyridin-4-yl)oxy)-4-methylpyridin-2-yl)carbamoyl)-2-methoxy-2-methylpropanamide (109 mg, 70%). $^1$H NMR (400 MHz, DMSO-$d_6$): δ 10.75 (s, 1H), 10.54 (s, 1H), 10.18 (br s, 1H), 8.16 (d, J=5.7 Hz, 1H), 8.12 (s, 1H), 7.94 (br, s, 1H), 7.58 (d, J=2.4 Hz, 1H), 6.62 (dd, J=5.7, 2.4 Hz, 1H), 3.21 (s, 3H), 2.13 (s, 3H), 2.02 (s, 3H), 1.35 (s, 6H); MS (ESI) m/z: 402.2 (M+H$^+$).

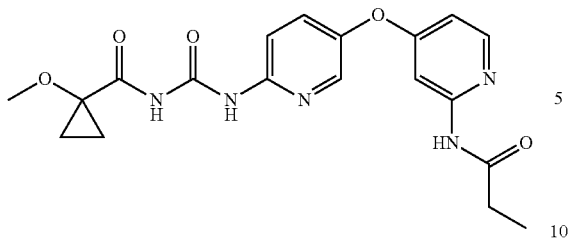

Example 39

A mixture of Example A10 (100 mg, 0.387 mmol), N-methylpyrrolidine (33 mg, 0.387 mmol) and Example B7 (170 mg, 0.852 mmol) in dioxane (2 mL) was heated at 80° C. overnight. The mixture was cooled to RT, treated with EtOAc, washed with satd. NaHCO$_3$, then brine, dried over Na$_2$SO$_4$, concentrated to dryness and purified via silica gel chromatography (EtOAc/Hex) to afford 1-methoxy-N-((5-((2-propionamidopyridin-4-yl)oxy)pyridin-2-yl)carbamoyl)cyclopropanecarboxamide (60 mg, 39%). $^1$H NMR (400 MHz, DMSO-d$_6$): δ 10.89-10.86 (br s, 1H), 10.51 (s, 1H), 8.26 (s, 1H), 8.19 (s, 1H), 8.08-8.07 (br m, 1H), 7.76 (d, J=4.4 Hz, 1H), 7.68 (s, 1H), 7.32 (br m, 1H), 6.72 (d, J=2.8 Hz, 1H), 3.30 (s, 3H), 2.36 (q, J=3.8 Hz, 2H), 1.24 (m, 4H), 1.01 (t, 3H); MS (ESI) m/z: 400.2 (M+H$^+$).

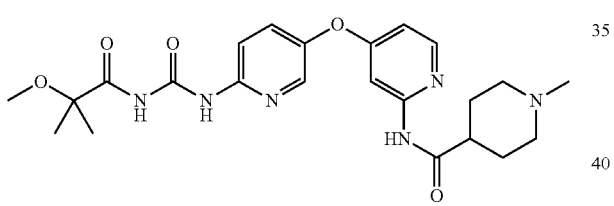

Example 40

A solution of 2-methoxy-2-methylpropanoic acid (0.400 g, 3.39 mmol) in DCM (10 mL) was treated with oxalyl chloride (0.400 g, 3.15 mmol) followed by catalytic DMF, stirred at RT for 1 h, treated with silver cyanate (0.800 g, 5.34 mmol), stirred for 1 h, treated with Example A8 (0.200 g, 0.611 mmol) and stirred at RT overnight. The solids were removed via filtration, washed with DCM and THF and the filtrate concentrated to dryness and purified via silica gel chromatography (MeOH/DCM) to afford N-(4-((6-(3-(2-methoxy-2-methylpropanoyl)ureido)pyridin-3-yl)oxy)pyridin-2-yl)-1-methylpiperidine-4-carboxamide (79 mg, 27%). NMR (400 MHz, DMSO-d$_6$): δ 10.83 (s, 1H), 10.51 (s, 1H), 10.25 (br s, 1H), 8.25 (d, J=2.9 Hz, 1H), 8.19 (d, J=5.7 Hz, 1H), 8.03 (br s, 1H), 7.73 (dd, J=9.0, 2.9 Hz, 1H), 7.65 (d, J=2.4 Hz, 1H), 6.72 (dd, J=5.7, 2.4 Hz, 1H), 3.20 (s, 3H), 2.74 (d, J=11.0 Hz, 2H), 2.38 (s, 2H), 2.10 (s, 3H), 1.78 (dd, J=12.6, 10.3 Hz, 2H), 1.66 (d, J=12.5 Hz, 2H), 1.55 (td, J=12.3, 3.7 Hz, 2H), 1.35 (s, 6H); MS (ESI) m/z: 471.3 (M+H$^+$).

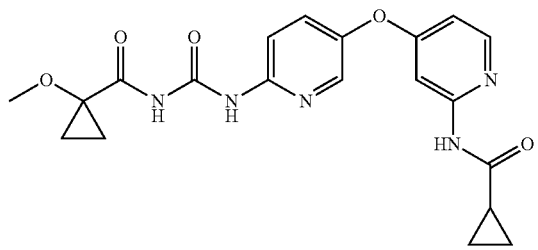 [SMILES: COC1(C(=O)NC(=O)Nc2ccc(Oc3ccnc(NC(=O)C4CC4)c3)cn2)CC1]

Example 41

A mixture of Example B7 (0.150 g, 0.555 mmol) Example A7 (0.150 g, 0.555 mmol) and N-methylpyrrolidine (0.100 g, 1.174 mmol) in dioxane (10 mL) was heated at 80° C. for 3 h. The mixture was concentrated to dryness and purified via silica gel chromatography (EtOAc/DCM) to afford N-((5-((cyclopropanecarboxamido)pyridin-4-yl)oxy)pyridin-2-yl)carbamoyl)-1-methoxycyclopropanecarboxamide (70 mg, 30%). $^1$H NMR (400 MHz, DMSO-d$_6$): δ 10.87 (br s, 2H), 10.44 (br s, 1H), 8.24 (d, J=2.9 Hz, 1H), 8.19 (d, J=5.7 Hz, 1H), 8.01 (br s, 1H), 7.73 (dd, J=9.0, 2.9 Hz, 1H), 7.62 (d, J=2.4 Hz, 1H), 6.72 (dd, J=5.7, 2.4 Hz, 1H), 4.01 (s, 3H), 1.96 (m, 1H), 1.23 (s, 4H), 0.75 (m, 4H); MS (ESI) m/z: 412.2 (M+H$^+$).

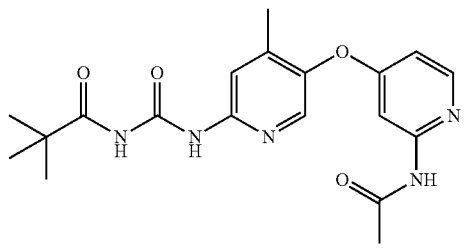 [SMILES: CC(=O)Nc1cc(Oc2cnc(NC(=O)NC(=O)C(C)(C)C)cc2C)ccn1]

Example 42

A solution of 2,2,2-trimethylacetamide (0.059 g, 0.581 mmol) in DCE (3 mL) was treated with oxalyl chloride (0.068 mL, 0.774 mmol), stirred at RT for 1 h, then heated at 80° C. for 2 h. The mixture was cooled to RT, treated with a solution of Example A12 (0.1 g, 0.387 mmol) and TEA (0.162 mL, 1.162 mmol) in THF (3 mL) and stirred at RT for 1 h. The mixture was treated with water, extracted with DCM (2×) and the combined organics were washed with brine, dried over Na$_2$SO$_4$, concentrated to dryness and purified via silica gel chromatography (MeOH/EtOAc) to afford N-((5-((2-acetamidopyridin-4-yl)oxy)-4-methylpyridin-2-yl)carbamoyl) pivalamide (81 mg, 54%). $^1$H NMR (400 MHz, DMSO-d$_6$): δ 11.17 (s, 1H), 10.55 (s, 1H), 10.42 (s, 1H), 8.16 (d, J=5.8 Hz, 1H), 8.12 (s, 2H), 8.00 (s, 1H), 7.58 (d, J=2.4 Hz, 1H), 6.62 (dd, J=5.7, 2.4 Hz, 1H), 2.14 (s, 3H), 2.02 (s, 3H), 1.21 (s, 9H); MS (ESI) m/z: 386.2 (M+H$^+$).

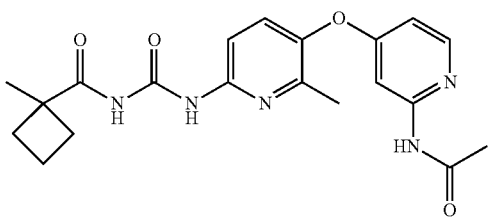 [SMILES: CC(=O)Nc1cc(Oc2ccc(NC(=O)NC(=O)C3(C)CCC3)nc2C)ccn1]

Example 43

A solution of Example B8 (0.600 g, 5.26 mmol) in DCM (25 mL) was treated with oxalyl chloride (0.600 g, 4.73 mmol) followed by catalytic DMF and stirred at RT for 1 h. The mixture was treated with silver cyanate (1.20 g, 8.01 mmol), stirred at RT for 2 h, treated with Example A4 (0.250 g, 0.968 mmol) and catalytic pyridine (1 drop) and stirred at RT overnight. The solids were removed via filtration, washed with DCM and THF and the filtrate concentrated to dryness and purified via silica gel chromatography (EtOAc/DCM) to afford N-((5-((2-acetamidopyridin-4-yl)oxy)-6-methylpyridin-2-yl)carbamoyl)-1-methylcyclobutanecarboxamide (72 mg, 17%). $^1$H NMR (400 MHz, DMSO-$d_6$): δ 11.10 (s, 1H), 10.55 (m, 2H), 8.17 (d, J=5.7 Hz, 1H), 7.90 (d, J=8.8 Hz, 1H), 7.63-7.56 (m, 2H), 6.62 (dd, J=5.7, 2.4 Hz, 1H), 2.40 (m, 2H), 2.23 (s, 3H), 2.02 (s, 3H), 1.85 (m, 3H), 1.69 (m, 1H), 1.43 (s, 3H); MS (ESI) m/z: 398.2 (M+H$^+$).

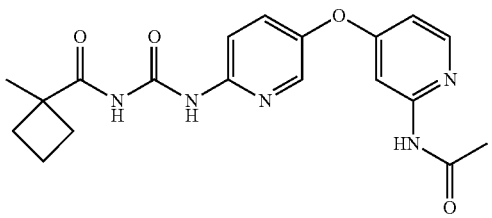 [SMILES: CC(=O)Nc1cc(Oc2ccc(NC(=O)NC(=O)C3(C)CCC3)nc2)ccn1]

Example 44

A solution of Example B8 (0.600 g, 5.26 mmol) in DCM (25 mL) was treated with oxalyl chloride (0.600 g, 4.73 mmol) followed by catalytic DMF and stirred at RT for 1 h. The mixture was treated with silver cyanate (1.200 g, 8.01 mmol), stirred at RT for 2 h, treated with Example A2 (0.200 g, 0.819 mmol) and catalytic pyridine (1 drop) and stirred at RT overnight. The solids were removed via filtration, washed with DCM and THF and the filtrate concentrated to dryness and purified via silica gel chromatography (EtOAc/DCM) to afford N—N-((5-((2-acetamidopyridin-4-yl)oxy)pyridin-2-yl)carbamoyl)-1-methylcyclobutanecarboxamide (70 mg, 21%). $^1$H NMR (400 MHz, DMSO-$d_6$): δ 11.18 (s, 1H), 10.56 (m, 2H), 8.24 (d, J=2.9 Hz, 1H), 8.18 (d, J=5.7 Hz, 1H), 8.08 (d, J=9.0 Hz, 1H), 7.72 (dd, J=9.0, 2.9 Hz, 1H), 7.65 (d, J=2.4 Hz, 1H), 6.69 (dd, J=5.7, 2.4 Hz, 1H), 2.41 (m, 2H), 2.03 (s, 3H), 1.89 (m, 3H), 1.67 (m, 1H), 1.43 (s, 3H); MS (ESI) m/z: 384.2 (M+H$^+$).

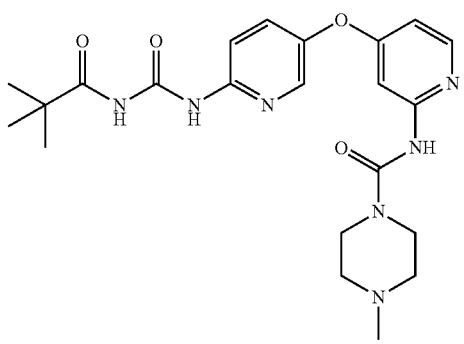 [SMILES: CN1CCN(C(=O)Nc2cc(Oc3ccc(NC(=O)NC(=O)C(C)(C)C)nc3)ccn2)CC1]

Example 45

Method A

A mixture of Example C2 (0.145 g, 0.351 mmol) 1-methylpiperizine (0.105 g, 1.052 mmol) and N-methylpyrrolidine (2.99 mg, 0.035 mmol) in dioxane (3 mL) was heated at 80° C. overnight, cooled to RT, concentrated to dryness and purified via silica gel chromatography (MeOH/DCM) to afford 4-methyl-N-(4-((6-(3-pivaloylureido)pyridin-3-yl)oxy)pyridin-2-yl)piperazine-1-carboxamide (60 mg, 38%). $^1$H NMR (400 MHz, DMSO-$d_6$): δ 11.22 (s, 1H), 10.44 (s, 1H), 9.25 (s, 1H), 8.23 (d, J=2.9 Hz, 1H), 8.12 (d, J=5.7 Hz, 1H), 8.08 (d, J=9.0 Hz, 1H), 7.71 (dd, J=9.0, 2.9 Hz, 1H), 7.36 (d, J=2.4 Hz, 1H), 6.61 (dd, J=5.7, 2.4 Hz, 1H), 3.39 (m, 4H), 2.24 (m, 4H), 2.14 (s, 3H), 1.21 (s, 9H); MS (ESI) m/z: 456.2 (M+H$^+$).

Method B

A suspension of trimethylacetamide (3.50 g, 34.6 mmol) in DCE (30 mL) was treated with oxalyl chloride (4.40 g, 34.7 mmol) and stirred at RT for 1 hour and then at 90° C. for 1 h. The mixture was cooled to RT and added to a solution of Example A13 (9.20 g, 28.0 mmol) in DCM (100 mL) and the resultant mixture was stirred at RT overnight. The solvent was evaporated and the residue was purified by silica gel chromatography (MeOH/DCM) to provide 4-methyl-N-(4-((6-(3-pivaloylureido)pyridin-3-yl)oxy)pyridin-2-yl)piperazine-1-carboxamide (8.70 g, 67%) as off-white solid. MS (ESI) m/z: 456.2 (M+H$^+$).

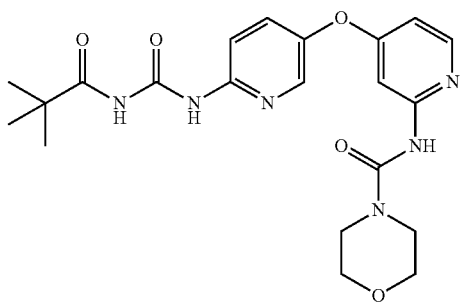 [SMILES: CC(C)(C)C(=O)NC(=O)Nc1ccc(Oc2ccnc(NC(=O)N3CCOCC3)c2)cn1]

Example 46

A mixture of Example C2 (0.145 g, 0.351 mmol), morpholine (0.092 g, 1.052 mmol) and N-methylpyrrolidine (2.99 mg, 0.035 mmol) in dioxane (3 mL) was heated at 80° C.

overnight, cooled to RT, concentrated to dryness and purified via silica gel chromatography (MeOH/DCM) to afford N-(4-((6-(3-pivaloylureido)pyridin-3-yl)oxy)pyridin-2-yl)morpholine-4-carboxamide (80 mg, 52%). $^1$H NMR (400 MHz, DMSO-d$_6$): δ 11.22 (s, 1H), 10.43 (s, 1H), 9.29 (s, 1H), 8.23 (d, J=2.9 Hz, 1H), 8.13 (d, J=5.7 Hz, 1H), 8.08 (d, J=9.0 Hz, 1H), 7.71 (dd, J=9.0, 2.9 Hz, 1H), 7.37 (d, J=2.4 Hz, 1H), 6.62 (dd, J=5.7, 2.4 Hz, 1H), 3.53 (m, 4H), 3.39 (m, 4H), 1.21 (s, 9H); MS (ESI) m/z: 443.2 (M+H$^+$).

removed under reduced pressure and the aqueous residue was treated with satd. NaHCO$_3$, extracted with EtOAc (4×) and the combined organics were dried over Na$_2$SO$_4$ and concentrated to dryness to afford N-(4-((6-(3-pivaloylureido)pyridin-3-yl)oxy)pyridin-2-yl)azetidine-1-carboxamide (70 mg, 25%). $^1$H NMR (400 MHz, DMSO-d$_6$): δ 11.21 (s, 1H), 10.43 (s, 1H), 9.09 (s, 1H), 8.23 (d, J=2.9 Hz, 1H), 8.11-8.06 (m, 2H), 7.71 (dd, J=9.0, 2.9 Hz, 1H), 7.48 (d, J=2.4 Hz, 1H), 6.59 (dd, J=5.7, 2.4 Hz, 1H), 3.92 (t, J=7.5 Hz, 4H), 2.12-2.10 (m, 2H), 1.21 (s, 9H); MS (ESI) m/z: 413.2 (M+H$^+$).

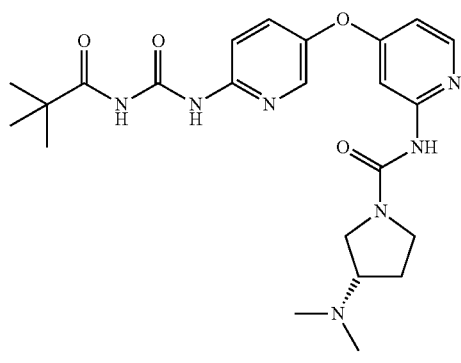

Example 47

A mixture of Example C2 (0.265 g, 0.641 mmol), (3S)—N,N-dimethylaminopyrrolidine (0.220 g, 1.923 mmol) and 1-methylpyrrolidine (5.46 mg, 0.064 mmol) in dioxane (6 mL) was heated at 80° C. overnight, cooled to RT and concentrated to dryness. The residue was treated with MeCN, sonicated and the resulting solid collected via filtration and dried to afford (S)-3-(dimethylamino)-N-(4-((6-(3-pivaloylureido)pyridin-3-yl)oxy)pyridin-2-yl)pyrrolidine-1-carboxamide (110 mg, 37%). $^1$H NMR (400 MHz, DMSO-d$_6$): δ 11.22 (s, 1H), 10.24 (br s, 1H), 8.77 (s, 1H), 8.23 (d, J=2.9 Hz, 1H), 8.11 (d, J=5.7 Hz, 1H), 8.08 (d, J=8.9 Hz, 1H), 7.71 (dd, J=9.0, 2.9 Hz, 1H), 7.47 (d, J=2.4 Hz, 1H), 6.61 (dd, J=5.7, 2.4 Hz, 1H), 3.61 (m, 1H), 3.53 (m, 1H), 3.28 (m, 1H), 3.06 (m, 1H), 2.59 (m, 1H), 2.12 (s, 6H), 1.99 (m, 1H), 1.63 (m, 1H), 1.21 (s, 9H); MS (ESI) m/z: 470.3 (M+H$^+$).

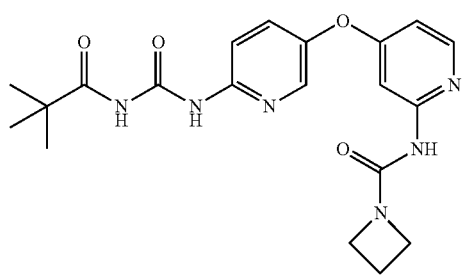 [SMILES: CC(C)(C)C(=O)NC(=O)Nc1ccc(Oc2ccnc(NC(=O)N3CCC3)c2)cn1]

Example 48

A mixture of Example C2 (0.265 g, 0.641 mmol), azetidine hydrochloride (0.120 g, 1.282 mmol) and N-methylpyrrolidine (0.065 g, 0.769 mmol) in dioxane (6 mL) was heated at 80° C. overnight, cooled to RT, concentrated to dryness and purified via silica gel chromatography (MeOH/DCM). The material was further purified via reverse-phase chromatography (MeCN/H$_2$O with 0.1% TFA); the organics were

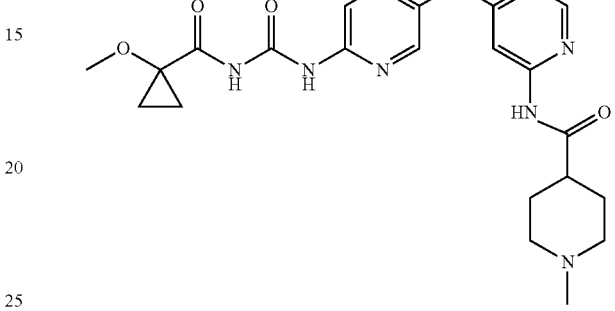

Example 49

A solution of Example B6 (0.450 g, 3.88 mmol) in DCM (10 mL) was treated with oxalyl chloride (0.450 g, 3.55 mmol) followed by catalytic DMF and stirred at RT for 1 h. The mixture was treated with silver cyanate (1.000 g, 6.67 mmol), stirred at RT for 1 h, treated with Example A8 (0.120 g, 0.367 mmol) followed by catalytic pyridine and stirred at RT for 2 h. The solids were removed via filtration through diatomaceous earth, washed with DCM and THF and the filtrate concentrated to dryness and purified via silica gel chromatography (MeOH/DCM/TEA) to afford N-(4-((6-(3-(1-methoxycyclopropanecarbonyl)ureido)pyridin-3-yl)oxy)pyridin-2-yl)-1-methylpiperidine-4-carboxamide (28 mg, 16%). $^1$H NMR (400 MHz, DMSO-d$_6$): δ 11.00 (br s, 1H), 10.59-10.30 (m, 2H), 8.24 (d, J=3.0 Hz, 1H), 8.19 (d, J=5.7 Hz, 1H), 8.14-7.90 (br m, 1H), 7.74 (dd, J=9.0, 2.9 Hz, 1H), 7.65 (d, J=2.4 Hz, 1H), 6.72 (dd, J=5.7, 2.4 Hz, 1H), 3.31 (s, 3H), 2.75 (d, J=11.0 Hz, 2H), 2.39 (m, 1H), 2.11 (s, 3H), 1.79 (t, J=11.6 Hz, 2H), 1.66 (d, J=12.5 Hz, 2H), 1.55 (m, 2H), 1.23 (s, 4H); MS (ESI) m/z: 469.2 (M+H$^+$).

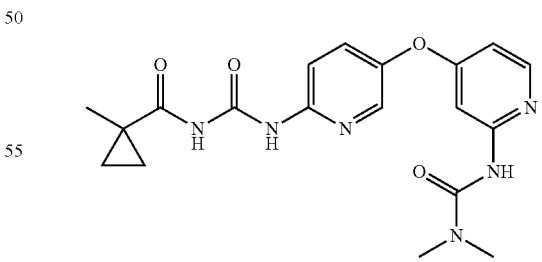

Example 50

A mixture of Example A9 (0.200 g, 0.732 mmol), Example B4 (0.268 g, 1.464 mmol) and DBU (0.011 mL, 0.073 mmol) in dioxane (6 mL) was heated at 50° C. for 1 h, then 65° C. overnight. The mixture was cooled to RT, concentrated to dryness, purified via silica gel chromatography (MeOH/DCM), and further purified via reverse-phase chromatography (MeCN/H₂O with 0.1% TFA). The organics were removed under reduced pressure and the aqueous residue was treated with satd. NaHCO₃, extracted with EtOAc (4×) and the combined organics were dried over Na₂SO₄ and concentrated to dryness to afford N-((5-((2-(3,3-dimethylureido)pyridin-4-yl)oxy)pyridin-2-yl)carbamoyl)-1-methylcyclopropanecarboxamide (37 mg, 13%). ¹H NMR (400 MHz, DMSO-d₆): δ 11.24 (s, 1H), 10.13 (br s, 1H), 8.91 (s, 1H), 8.22 (d, J=2.9 Hz, 1H), 8.11 (d, J=5.8 Hz, 1H), 8.06 (br d, J=9.0 Hz, 1H), 7.71 (dd, J=9.0, 2.9 Hz, 1H), 7.39 (d, J=2.4 Hz, 1H), 6.60 (dd, J=5.7, 2.4 Hz, 1H), 2.87 (s, 6H), 1.35 (s, 3H), 1.21-1.20 (m, 2H), 0.75-0.74 (m, 2H); MS (ESI) m/z: 399.2 (M+H⁺).

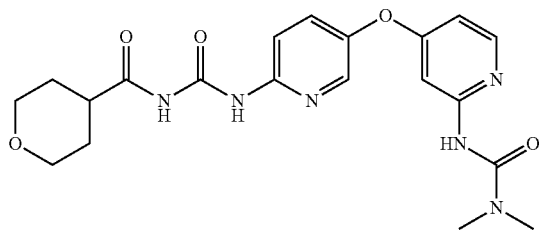 [SMILES: CN(C)C(=O)Nc1cc(Oc2ccc(NC(=O)NC(=O)C3CCOCC3)nc2)ccn1]

Example 51

A suspension of Example B5 (0.596 g, 4.61 mmol) in dioxane (15 mL) was treated with oxalyl chloride (0.820 mL, 9.69 mmol), stirred at RT for 10 min, then heated at 80° C. for 4 h. The mixture was concentrated to dryness, treated with Example A9 (0.200 g, 0.732 mmol), pyridine (0.125 mL, 1.481 mmol) and THF (5 mL) and stirred at RT overnight. The mixture was concentrated to dryness and purified via reverse-phase chromatography (MeCN/H₂O with 0.1% TFA). The organics were removed under reduced pressure and the aqueous residue was treated with satd. NaHCO₃, extracted with EtOAc (4×) and the combined organics were dried over Na₂SO₄ and concentrated to dryness to afford N-((5-((2-(3,3-dimethylureido)pyridin-4-yl)oxy)pyridin-2-yl)carbamoyl)tetrahydro-2H-pyran-4-carboxamide (45 mg, 14%). ¹H NMR (400 MHz, DMSO-d₆): δ 11.05 (s, 1H), 10.88 (br s, 1H), 8.91 (s, 1H), 8.23 (d, J=2.9 Hz, 1H), 8.11 (d, J=5.7 Hz, 1H), 8.07 (d, J=9.0 Hz, 1H), 7.71 (dd, J=9.0, 2.9 Hz, 1H), 7.38 (d, J=2.4 Hz, 1H), 6.60 (dd, J=5.7, 2.4 Hz, 1H), 3.90-3.85 (m, 2H), 3.30-3.25 (m, 2H), 2.87 (s, 6H), 2.69-2.64 (m, 1H), 1.74-1.68 (m, 2H), 1.66-1.55 (m, 2H); MS (ESI) m/z: 429.2 (M+H⁺).

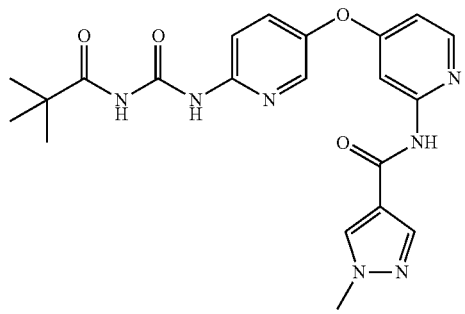 [SMILES: Cn1cc(C(=O)Nc2cc(Oc3ccc(NC(=O)NC(=O)C(C)(C)C)nc3)ccn2)cn1]

Example 52

A suspension of 1-methylpyrazolecarboxylic acid (0.069 g, 0.547 mmol) in thionyl chloride (1.50 mL, 20.66 mmol) was heated at 60° C. for 0.5 h, concentrated to dryness, treated with toluene and concentrated to dryness (3×). The residue was treated with a solution of Example C1 (0.150 g, 0.455 mmol) in pyridine (5 mL) and stirred at RT overnight. The mixture was treated with water, stirred for 0.5 h and the resulting solid collected via filtration. The material was suspended in MTBE, sonicated collected via filtration and purified via silica gel chromatography (MeOH/DCM) to afford 1-methyl-N-(4-((6-(3-pivaloylureido)pyridin-3-yl)oxy)pyridin-2-yl)-1H-pyrazole-4-carboxamide (128 mg, 64%). ¹H NMR (400 MHz, DMSO-d₆): δ 11.23 (s, 1H), 10.58 (s, 1H), 10.44 (s, 1H), 8.39 (s, 1H), 8.27 (d, J=2.9 Hz, 1H), 8.24 (d, J=5.7 Hz, 1H), 8.11-8.09 (m, 1H), 8.08 (d, J=0.7 Hz, 1H), 7.76-7.75 (m, 2H), 6.74 (dd, J=5.7, 2.4 Hz, 1H), 3.84 (s, 3H), 1.21 (s, 9H); MS (ESI) m/z: 438.2 (M+H⁺).

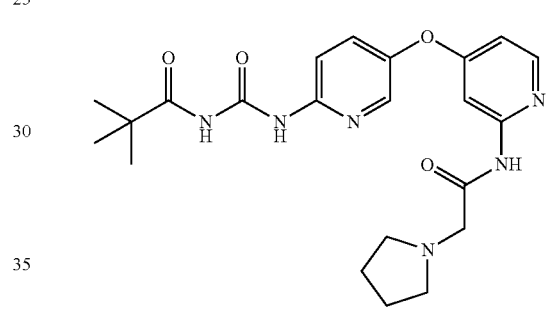

Example 53

A solution of 1-pyrrolidinylacetic acid (0.082 g, 0.638 mmol) in thionyl chloride (3 mL, 41.1 mmol) and DCM (3 mL) was stirred at RT for 3 h, concentrated to dryness, suspended in THF (5 mL), added to a 0° C. solution of Example C1 (0.15 g, 0.455 mmol) and DIEA (0.239 mL, 1.366 mmol) in THF (5 mL), allowed to warm to RT and stirred overnight. The mixture was treated with 10% K₂CO₃, extracted with DCM (4×) and the combined organics were washed with brine, dried over Na₂SO₄, concentrated to dryness and purified via silica gel chromatography (MeOH/EtOAc). The material was further purified via preparative TLC (MeOH/DCM/TEA) to afford N-((5-((2-(2-(pyrrolidin-1-yl)acetamido)pyridin-4-yl)oxy)pyridin-2-yl)carbamoyl)pivalamide (31 mg, 15%). ¹H NMR (400 MHz, DMSO-d₆): δ 11.23 (s, 1H), 10.44 (s, 1H), 9.98 (s, 1H), 8.26 (d, J=2.9 Hz, 1H), 8.20 (d, J=5.8 Hz, 1H), 8.09 (d, J=9.0 Hz, 1H), 7.74 (dd, J=9.0, 2.9 Hz, 1H), 7.64 (d, J=2.4 Hz, 1H), 6.74 (dd, J=5.8, 2.4 Hz, 1H), 3.27 (s, 2H), 2.58 (s, 4H), 1.73-1.71 (m, 4H), 1.21 (s, 9H); MS (ESI) m/z: 441.2 (M+H⁺).

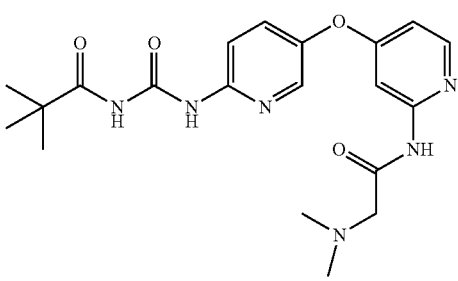 [SMILES: CN(C)CC(=O)Nc1cc(Oc2ccc(NC(=O)NC(=O)C(C)(C)C)nc2)ccn1]

Example 54

A suspension of 2-(dimethylamino)acetyl chloride hydrochloride (0.101 g, 0.638 mmol) in THF (5 mL) was added to a 0° C. solution of Example C1 (0.15 g, 0.455 mmol) and DIEA (0.239 mL, 1.366 mmol) in THF (5 mL), allowed to warm to RT and stirred overnight. Additional 2-(dimethylamino)acetyl chloride hydrochloride (0.200 g), DIEA (0.239 mL, 1.366 mmol) and DCM (5 mL) were added and the mixture stirred at RT overnight. The mixture was treated with 10% $K_2CO_3$, extracted with DCM (4×) and the combined organics were washed with brine, dried over $Na_2SO_4$, concentrated to dryness and purified via preparative TLC (MeOH/DCM/TEA) to afford N-((5-((2-(2-(dimethylamino)acetamido)pyridin-4-yl)oxy)pyridin-2-yl)carbamoyl)pivalamide (86 mg, 46%). $^1$H NMR (400 MHz, DMSO-$d_6$): δ 11.23 (s, 1H), 10.44 (s, 1H), 9.95 (s, 1H), 8.26 (d, J=2.9 Hz, 1H), 8.20 (d, J=5.8 Hz, 1H), 8.09 (d, J=9.0 Hz, 1H), 7.75 (dd, J=9.0, 2.9 Hz, 1H), 7.65 (d, J=2.4 Hz, 1H), 6.73 (dd, J=5.8, 2.4 Hz, 1H), 3.07 (s, 2H), 2.25 (s, 6H), 1.21 (s, 9H); MS (ESI) m/z: 415.2 (M+H$^+$).

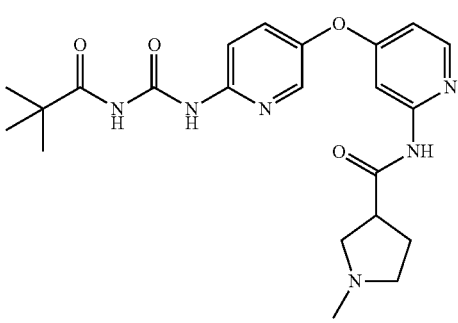 [SMILES: CN1CCC(C(=O)Nc2cc(Oc3ccc(NC(=O)NC(=O)C(C)(C)C)nc3)ccn2)C1]

Example 55

A solution of 1-methyl-pyrrolidine-3-carboxylic acid (0.082 g, 0.638 mmol) in thionyl chloride (3 mL, 41.1 mmol) and DCM (3 mL) was stirred at RT for 3 h, concentrated to dryness, suspended in THF (5 mL), added to a 0° C. solution of Example C1 (0.15 g, 0.455 mmol) and DIEA (0.239 mL, 1.366 mmol) in THF (5 mL), allowed to warm to RT and stirred overnight. The mixture was treated with 10% $K_2CO_3$, extracted with DCM (4×) and the combined organics were washed with brine, dried over $Na_2SO_4$, concentrated to dryness and purified via preparative TLC (MeOH/DCM/TEA) to afford 1-methyl-N-(4-((6-(3-pivaloylureido)pyridin-3-yl)oxy)pyridin-2-yl)pyrrolidine-3-carboxamide (113 mg, 56%). $^1$H NMR (400 MHz, DMSO-$d_6$): δ 11.23 (s, 1H), 10.54 (s, 1H), 10.44 (s, 1H), 8.25 (d, J=2.9 Hz, 1H), 8.19 (d, J=5.7 Hz, 1H), 8.09 (d, J=9.0 Hz, 1H), 7.74 (dd, J=9.0, 2.9 Hz, 1H), 7.64 (d, J=2.4 Hz, 1H), 6.72 (dd, J=5.7, 2.4 Hz, 1H), 3.11 (m, 1H), 2.71 (t, J=8.5 Hz, 1H), 2.45-2.32 (m, 3H), 2.21 (s, 3H), 1.96-1.84 (m, 2H), 1.21 (s, 9H); MS (ESI) m/z: 441.2 (M+H$^+$).

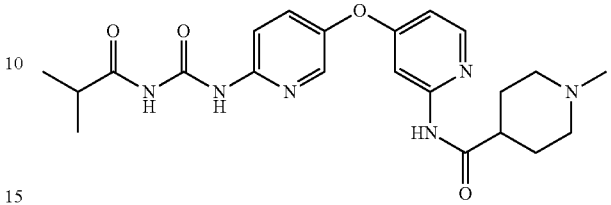

Example 56

A mixture of Example C1 (0.15 g, 0.455 mmol), cyanoacetic acid (0.080 mL, 1.206 mmol), TBTU (0.258 g, 0.804 mmol) and DIEA (0.35 mL, 2.009 mmol) in DMF (5 mL) was stirred at RT overnight, treated with 10% $K_2CO_3$, extracted with DCM (4×) and the combined organics were washed with brine, dried over $Na_2SO_4$, concentrated to dryness and purified via preparative TLC (MeOH/DCM/TEA) to afford N-((5-((2-(2-cyanoacetamido)pyridin-4-yl)oxy)pyridin-2-yl)carbamoyl)pivalamide (126 mg, 79%). $^1$H NMR (400 MHz, DMSO-$d_6$): δ 11.24 (s, 1H), 10.92 (s, 1H), 10.44 (s, 1H), 8.26 (d, J=2.9 Hz, 1H), 8.22 (d, J=5.8 Hz, 1H), 8.10 (d, J=9.0 Hz, 1H), 7.75 (dd, J=9.0, 2.9 Hz, 1H), 7.56 (s, 1H), 6.76 (dd, J=5.7, 2.4 Hz, 1H), 3.93 (s, 2H), 1.21 (s, 9H); MS (ESI) m/z: 397.2 (M+H$^+$).

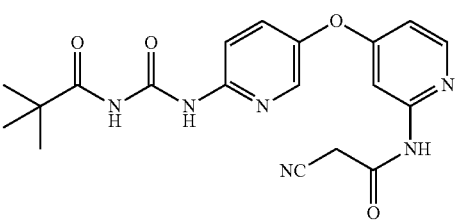 [SMILES: CC(C)(C)C(=O)NC(=O)Nc1ccc(Oc2ccnc(NC(=O)CC#N)c2)cn1]

Example 57

A solution of isobutyrylchloride (0.400 g, 3.75 mmol) in DCM (10 mL) was treated with silver cyanate (0.800 g, 5.34 mmol), stirred at RT for 1 h, treated with Example A8 (0.200 g, 0.611 mmol) and catalytic pyridine and stirred at RT for 1 h. The solids were removed via filtration, washed with DCM and the filtrate concentrated to dryness and purified via silica gel chromatography (MeOH/DCM) to afford N-(4-((6-(3-isobutyrylureido)pyridin-3-yl)oxy)pyridin-2-yl)-1-methylpiperidine-4-carboxamide (111 mg, 41%). $^1$H NMR (400 MHz, DMSO-$d_6$): δ 11.12 (s, 1H), 10.86 (s, 1H), 10.51 (s, 1H), 8.24 (d, J=2.9 Hz, 1H), 8.18 (d, J=5.7 Hz, 1H), 8.09 (d, J=9.0 Hz, 1H), 7.72 (dd, J=9.0, 2.9 Hz, 1H), 7.65 (d, J=2.4 Hz, 1H), 6.72 (dd, J=5.7, 2.4 Hz, 1H), 2.73 (m, 3H), 2.43-2.33 (m, 1H), 2.11 (s, 3H), 1.78 (m, 2H), 1.66 (m, 2H), 1.55 (m, 2H), 1.09 (d, J=6.8 Hz, 6H); MS (ESI) m/z: 441.2 (M+H$^+$).

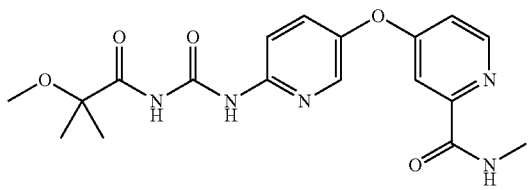

Example 58

A mixture of Example A11 (0.10 g, 0.409 mmol), Example B1 (0.165 g, 0.819 mmol) and 1-methylpyrrolidine (0.1 mL) in dioxane (5 mL) was heated at 60° C. overnight. The mixture was cooled to RT, treated with satd. NaHCO$_3$, extracted with EtOAc (3×) and the combined organics were dried over Na$_2$SO$_4$, concentrated to dryness and purified via silica gel chromatography (EtOAc/Hex) to afford 4-((6-(3-(2-methoxy-2-methylpropanoyl)ureido)pyridin-3-yl)oxy)-N-methylpicolinamide (51 mg, 31%). $^1$H NMR (400 MHz, DMSO-d$_6$): δ 10.84 (s, 1H), 10.26 (br s, 1H), 8.79 (d, J=5.4 Hz, 1H), 8.53 (d, J=5.6 Hz, 1H), 8.31 (d, J=2.9 Hz, 1H), 8.05 (br s, 1H), 7.80 (dd, J=9.0, 2.9 Hz, 1H), 7.41 (d, J=2.6 Hz, 1H), 7.19 (dd, J=5.6, 2.7 Hz, 1H), 3.21 (s, 3H), 2.78 (d, J=4.8 Hz, 3H), 1.36 (s, 6H); MS (ESI) m/z: 388.2 (M+H$^+$).

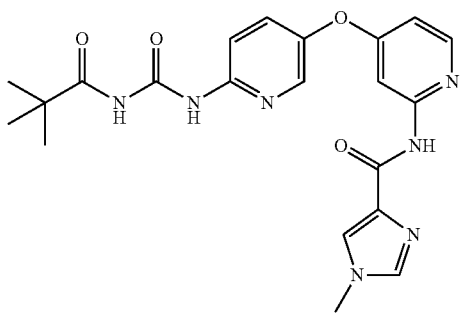 [SMILES: Cn1cnc(C(=O)Nc2cc(Oc3ccc(NC(=O)NC(=O)C(C)(C)C)nc3)ccn2)c1]

Example 59

A mixture of Example C1 (0.15 g, 0.455 mmol), 1-methyl-1H-imidazole-4-carboxylic acid (0.172 g, 1.366 mmol), TBTU (0.439 g, 1.366 mmol) and DIEA (0.476 mL, 2.73 mmol) in DMF (5 mL) was stirred at RT for 2 h, then heated at 60° C. overnight. Additional 1-methyl-1H-imidazole-4-carboxylic acid (0.172 g, 1.366 mmol) and TBTU (0.439 g, 1.366 mmol) were added and the mixture heated at 60° C. overnight. The mixture was cooled to RT, treated with 10% K$_2$CO$_3$, extracted with DCM (4×) and the combined organics were washed with brine, dried over Na$_2$SO$_4$, concentrated to dryness and purified via silica gel chromatography (MeOH/DCM). The material was further purified via preparative TLC (MeOH/DCM) to afford 1-methyl-N-(4-((6-(3-pivaloylureido)pyridin-3-yl)oxy)pyridin-2-yl)-1H-imidazole-4-carboxamide (52 mg, 26%). $^1$H NMR (400 MHz, DMSO-d$_6$): δ 11.23 (s, 1H), 10.44 (s, 1H), 9.47 (s, 1H), 8.29 (d, J=2.9 Hz, 1H), 8.22 (d, J=5.8 Hz, 1H), 8.10 (d, J=9.0 Hz, 1H), 7.85 (d, J=1.2 Hz, 1H), 7.78-7.77 (m, 2H), 7.75 (d, J=2.4 Hz, 1H), 6.75 (dd, J=5.8, 2.4 Hz, 1H), 3.71 (s, 3H), 1.22 (s, 9H); MS (ESI) m/z: 438.2 (M+H$^+$).

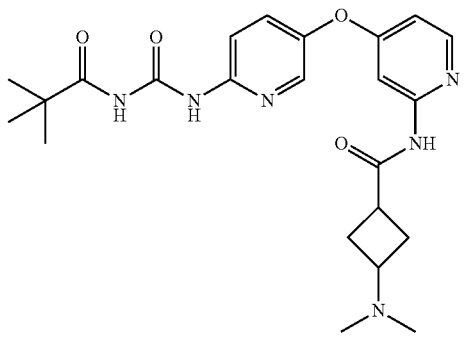 [SMILES: CN(C)C1CC(C(=O)Nc2cc(Oc3ccc(NC(=O)NC(=O)C(C)(C)C)nc3)ccn2)C1]

Example 60, 61

A solution of methyl 3-oxocyclobutanecarboxylate (0.5 g, 3.90 mmol) in EtOAc (10 mL) was treated with dimethylamine (1M in THF, 11.71 mL, 11.71 mmol), stirred at RT for 1 h, treated portion-wise with sodium triacetoxyborohydride (1.158 g, 5.46 mmol) and stirred at RT overnight. The mixture was treated with 1N NaOH, extracted with EtOAc (3×) and the combined organics were washed with brine, dried over Na$_2$SO$_4$ and concentrated to dryness to afford methyl 3-(dimethylamino)cyclobutanecarboxylate (596 mg, 97%). $^1$H NMR (400 MHz, DMSO-d$_6$): δ 3.57 (s, 3H), 3.33-3.26 (m, 1H), 2.75-2.74 (m, 1H), 2.19-2.18 (m, 2H), 1.97 (s, 6H), 1.88-1.85 (m, 2H).

A solution of methyl 3-(dimethylamino)cyclobutanecarboxylate (0.596 g, 3.79 mmol) in dioxane (5 mL) was treated with HCl (6N, 10 mL, 60 mmol) and heated at 70° C. overnight. The organics were removed under reduced pressure and the aqueous residue was treated with MeCN, frozen and lyophilized to afford 3-(dimethylamino)cyclobutanecarboxylic acid hydrochloride (686 mg, 101%). $^1$H NMR (400 MHz, DMSO-d$_6$): δ 10.86 (br s, 1H), 3.56-3.48 (m, 1H), 2.83-2.73 (m, 1H), 2.58 (d, J=4.9 Hz, 6H), 2.41-2.33 (m, 4H).

A solution of 3-(dimethylamino)cyclobutanecarboxylic acid hydrochloride (0.245 g, 1.366 mmol) in thionyl chloride (3 mL, 41.1 mmol) and DCM (3 mL) was heated at 40° C. for 3 h, concentrate to dryness, suspended in DCM (5 mL), added to a 0° C. solution of Example C1 (0.15 g, 0.455 mmol) and pyridine (3 mL) in DCM (5 mL), allowed to warm to RT and stirred overnight. The mixture was treated with 10% K$_2$CO$_3$, extracted with DCM (4×) and the combined organics were washed with brine, dried over Na$_2$SO$_4$, concentrated to dryness and purified via preparative TLC (MeOH/DCM/TEA) to afford:

Example 60 (cis isomer): (1s,3s)-3-(dimethylamino)-N-(4-((6-(3-pivaloylureido)pyridin-3-yl)oxy)pyridin-2-yl)cyclobutanecarboxamide (104 mg, 50%). $^1$H NMR (400 MHz, DMSO-d$_6$): δ 11.23 (s, 1H), 10.48 (s, 1H), 10.42 (s, 1H), 8.25 (d, J=2.9 Hz, 1H), 8.18 (d, J=5.7 Hz, 1H), 8.09 (d, J=9.0 Hz, 1H), 7.73 (dd, J=9.0, 2.9 Hz, 1H), 7.67 (d, J=2.4 Hz, 1H), 6.70 (dd, J=5.7, 2.4 Hz, 1H), 2.93-2.85 (m, 1H), 2.53-2.51 (m, 1H), 2.16-2.08 (m, 2H), 1.99 (s, 6H), 1.94-1.84 (m, 2H), 1.22 (s, 9H); MS (ESI) m/z: 455.3 (M+H$^+$).

Example 61 (trans isomer): (1r,3r)-3-(dimethylamino)-N-(4-((6-(3-pivaloylureido)pyridin-3-yl)oxy)pyridin-2-yl)cyclobutanecarboxamide (22 mg, 11%). $^1$H NMR (400 MHz, DMSO-d$_6$): δ 11.24 (s, 1H), 10.50-10.47 (m, 1H), 10.44-10.43 (m, 1H), 8.26 (d, J=2.9 Hz, 1H), 8.19 (d, J=5.7 Hz, 1H), 8.10 (d, J=9.0 Hz, 1H), 7.75 (dd, J=9.0, 3.0 Hz, 1H), 7.68 (d, J=2.4 Hz, 1H), 6.74 (dd, J=5.8, 2.4 Hz, 1H), 3.14-3.11 (m, 1H), 2.38-2.29 (m, 1H), 2.11-1.97 (m, 10H), 1.21 (s, 9H); MS (ESI) m/z: 455.2 (M+H⁺).

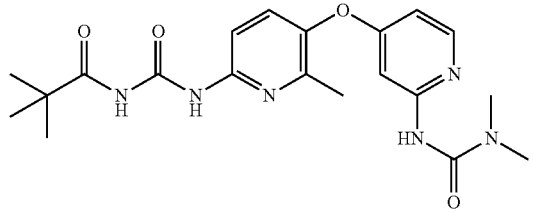 [SMILES: Cc1nc(NC(=O)NC(=O)C(C)(C)C)ccc1Oc1ccnc(NC(=O)N(C)C)c1]

Example 62

A suspension of 2,2,2-trimethylacetamide (2.24 g, 22.1 mmol) in DCE (15 mL) was treated with oxalyl chloride (1.80 mL, 21.2 mmol), heated at 100° C. for 30 min, cooled to RT, added drop-wise to a solution of Example A14 (4.54 g, 15.8 mmol) and pyridine (1.80 mL, 22.3 mmol) in THF (75 mL), and stirred at RT for ~1 h. The reaction mixture was concentrated to dryness. The residue was partitioned into EtOAc and sat'd NaHCO₃. The aqueous layers was separated and back-extracted with EtOAc (3×). The combined organics were washed with H₂O, dried (Na₂SO₄) and concentrated to dryness to afford an orange solid. The solid was purified by silica gel chromatography (MeOH/EtOAc) to afford N-((5-((2-(3,3-dimethylureido)pyridin-4-yl)oxy)-6-methylpyridin-2-yl)carbamoyl)pivalamide (4.02 g, 61%) as a light cream-colored solid. ¹H NMR (400 MHz, DMSO-d₆): δ 11.14 (s, 1H), 10.39 (s, 1H), 8.87 (s, 1H), 8.09 (d, J=5.7 Hz, 1H), 7.90 (d, J=8.8 Hz, 1H), 7.60 (d, J=8.8 Hz, 1H), 7.30 (d, J=2.4 Hz, 1H), 6.55 (dd, J=5.7, 2.4 Hz, 1H), 2.87 (s, 6H), 2.23 (s, 3H), 1.21 (s, 9H); MS (ESI) m/z: 415.2 (M+H⁺).

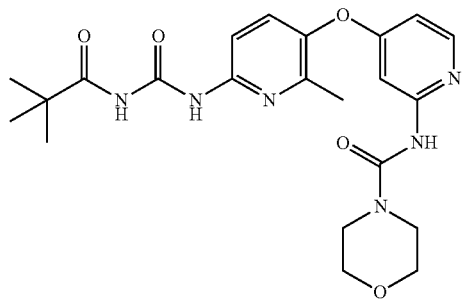 [SMILES: Cc1nc(NC(=O)NC(=O)C(C)(C)C)ccc1Oc1ccnc(NC(=O)N2CCOCC2)c1]

Example 63

A mixture of Example A3 (1.2 g, 4.52 mmol), t-butyl carbamate (1.058 g, 9.03 mmol), Cs₂CO₃ (2.94 g, 9.03 mmol) and DPPF (0.351 g, 0.632 mmol) in dioxane (25 mL) was sparged with Ar, treated with Pd₂(dba)₃ (0.290 g, 0.316 mmol), sparged again with Ar and heated at 100° C. for 3 days. The mixture was cooled to RT, diluted with EtOAc, the solids removed via filtration through diatomaceous earth and the filtrate concentrated to dryness and purified via silica gel chromatography (EtOAc/Hex) to afford tert-butyl (4-((2-methyl-6-nitropyridin-3-yl)oxy)pyridin-2-yl)carbamate (456 mg, 29%). MS (ESI) m/z: 347.2 (M+H⁺).

A mixture of tert-butyl (4-((2-methyl-6-nitropyridin-3-yl)oxy)pyridin-2-yl)carbamate (0.438 g, 1.265 mmol) and NH₄Cl (2.029 g, 37.9 mmol) in MeOH (10 mL) and THF (10 mL) was treated with zinc dust (0.827 g, 12.65 mmol) and stirred at RT overnight. The mixture was diluted with EtOAc, the solids removed via filtration through diatomaceous earth, washed with EtOAc and the filtrate concentrated to dryness to afford crude tert-butyl (4-((6-amino-2-methylpyridin-3-yl)oxy)pyridin-2-yl)carbamate (100% yield assumed) which was used without further purification. MS (ESI) m/z: 317.2 (M+H⁺).

A suspension of 2,2,2-trimethylacetamide (0.192 g, 1.897 mmol) in DCE (5 mL) was treated with oxalyl chloride (0.160 mL, 1.897 mmol), stirred at RT for 10 min, then heated at 80° C. for 1 h. The mixture was cooled to RT, added to a solution of tert-butyl (4-((6-amino-2-methylpyridin-3-yl)oxy)pyridin-2-yl)carbamate (0.400 g, 1.264 mmol) and pyridine (0.112 mL, 1.391 mmol) in THF (10 mL) and stirred at RT overnight. The mixture was concentrated to dryness and purified via silica gel chromatography (MeOH/DCM) to afford tert-butyl (4-((2-methyl-6-(3-pivaloylureido)pyridin-3-yl)oxy)pyridin-2-yl)carbamate (367 mg, 65%). MS (ESI) m/z: 444.3 (M+H⁺).

A mixture of tert-butyl (4-((2-methyl-6-(3-pivaloylureido)pyridin-3-yl)oxy)pyridin-2-yl)carbamate (0.370 g, 0.834 mmol in TFA (5 mL) was stirred at RT for 0.5 h and concentrated to dryness to afford N-((5-((2-aminopyridin-4-yl)oxy)-6-methylpyridin-2-yl)carbamoyl)pivalamide (280 mg, 98%). MS (ESI) m/z: 344.2 (M+H⁺).

A solution of N-((5-((2-aminopyridin-4-yl)oxy)-6-methylpyridin-2-yl)carbamoyl)pivalamide (0.280 g, 0.815 mmol) in pyridine (6 mL) was treated with isopropenyl chloroformate (0.100 mL, 0.913 mmol) and stirred at RT overnight. The mixture was treated with water and DCM, stirred for 0.5 h, the layers separated and the aqueous layer extracted with additional DCM (3×). The combined organics were dried over Na₂SO₄ and concentrated to dryness to afford prop-1-en-2-yl (4-((2-methyl-6-(3-pivaloylureido)pyridin-3-yl)oxy)pyridin-2-yl)carbamate (328 mg, 94%). MS (ESI) m/z: 428.2 (M+H⁺).

A mixture of prop-1-en-2-yl (4-((2-methyl-6-(3-pivaloylureido)pyridin-3-yl)oxy)pyridin-2-yl)carbamate (0.164 g, 0.384 mmol), morpholine (0.067 g, 0.767 mmol) and N-methylpyrrolidine (3.27 mg, 0.038 mmol) in dioxane (4 mL) was heated at 80° C. overnight. The mixture was cooled to RT, concentrated to dryness and purified twice via silica gel chromatography (MeOH/DCM, then MeOH/EtOAc). The material was treated with satd. NaHCO₃, extracted with DCM (4×) and the combined organics were dried over Na₂SO₄, concentrated to dryness and further purified via silica gel chromatography (MeOH/DCM) to afford N-(4-((2-methyl-6-(3-pivaloylureido)pyridin-3-yl)oxy)pyridin-2-yl)morpholine-4-carboxamide (21 mg, 12%). ¹H NMR (400 MHz, DMSO-d₆): δ 11.14 (s, 1H), 10.39 (s, 1H), 9.27 (s, 1H), 8.11 (d, J=5.7 Hz, 1H), 7.90 (d, J=8.8 Hz, 1H), 7.61 (d, J=8.8 Hz, 1H), 7.27 (d, J=2.3 Hz, 1H), 6.57 (dd, J=5.7, 2.4 Hz, 1H), 3.53 (m, 4H), 3.38 (m, 4H), 2.23 (s, 3H), 1.21 (s, 9H); MS (ESI) m/z: 457.2 (M+H⁺).

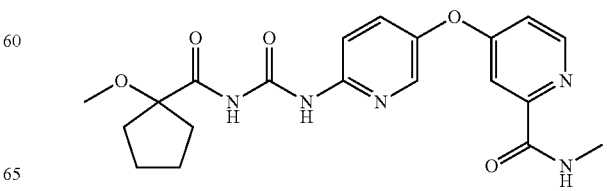

Example 64

A mixture of Example B9 (0.217 g, 0.573 mmol), Example A11 (0.07 g, 0.287 mmol), and 1-methylpyrrolidine (0.1 mL, 0.962 mmol) in dioxane (5 mL) was heated at 60° C. overnight. The mixture was cooled to RT, treated with satd. NaHCO$_3$, extracted with EtOAc (3×) and the combined organics were dried over Na$_2$SO$_4$, concentrated to dryness and purified via silica gel chromatography (MeOH/DCM). The material was further purified via reverse-phase chromatography (MeCN/H$_2$O with 0.1% TFA); combined fractions were treated with satd. NaHCO$_3$, extracted with EtOAc (3×) and the combined organics were washed with brine, dried over Na$_2$SO$_4$ and concentrated to dryness to afford 4-((6-(3-(1-methoxycyclopentanecarbonyl)ureido)pyridin-3-yl)oxy)-N-methylpicolinamide (40 mg, 34%). $^1$H NMR (400 MHz, DMSO-d$_6$): δ 10.86 (s, 1H), 10.45 (br s, 1H), 8.77 (q, J=4.8 Hz, 1H), 8.53 (d, J=5.6 Hz, 1H), 8.30 (d, J=2.9 Hz, 1H), 8.05 (br s, 1H), 7.79 (dd, J=9.0, 2.9 Hz, 1H), 7.41 (d, J=2.6 Hz, 1H), 7.19 (dd, J=5.6, 2.7 Hz, 1H), 3.16 (s, 3H), 2.78 (d, J=4.8 Hz, 3H), 1.93 (m, 4H), 1.66 (m, 4H); MS (ESI) m/z: 414.2 (M+H$^+$).

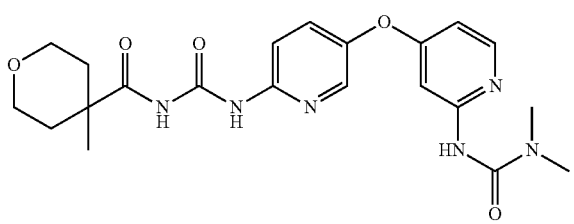 [SMILES: CN(C)C(=O)Nc1cc(Oc2ccc(NC(=O)NC(=O)C3(C)CCOCC3)nc2)ccn1]

Example 65

A mixture of Example B10 (98 mg, 0.686 mmol) in DCE (2 mL) was treated with oxalyl chloride (87 mg, 0.686 mmol), stirred at RT for 5 min, then heated at 80° C. for 45 min. The mixture was cooled to RT, added drop-wise to a solution of DIEA (254 mg, 1.967 mmol) and Example A9 (125 mg, 0.457 mmol) in dioxane (2 mL) and stirred at RT for 2 h. The mixture was treated with EtOAc, washed with satd. NaHCO$_3$, then brine, dried over Na$_2$SO$_4$, concentrated to dryness and purified via reverse-phase chromatography (MeCN/H$_2$O with 0.1% TFA). The organics were removed under reduced pressure and the aqueous residue was treated with satd. NaHCO$_3$, allowed to stand at RT and the resulting solid was collected via filtration and dried to afford N-((5-((2-(3,3-dimethylureido)pyridin-4-yl)oxy)pyridin-2-yl)carbamoyl)-4-methyltetrahydro-2H-pyran-4-carboxamide (74 mg, 36%). $^1$H NMR (400 MHz, DMSO-d$_6$): δ 11.36 (br s, 1H), 10.52 (br s, 1H), 8.88 (s, 1H), 8.20 (s, 1H), 8.14-8.08 (m, 2H), 7.68 (br d, J=7.2 Hz, 1H), 7.38 (s, 1H), 6.62-6.58 (m, 1H), 3.66-3.59 (m, 2H), 3.44 (t, J=11.2 Hz, 2H), 2.88 (s, 6H), 2.06 (d, J=13.4 Hz, 2H), 1.45 (br s, 2H), 1.23 (s, 3H); MS (ESI) m/z: 443.2 (M+H$^+$).

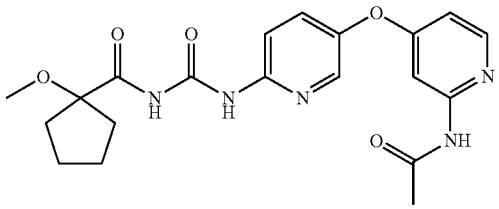 [SMILES: COC1(C(=O)NC(=O)Nc2ccc(Oc3ccnc(NC(C)=O)c3)cn2)CCCC1]

Example 66

A suspension of isobutyramide (3.00 g, 34.4 mmol) in DCE (30 mL) was treated with oxalyl chloride (4.40 g, 34.7 mmol) and stirred at RT for 1 hour and then at 90° C. for 1 h. The mixture was cooled to RT and added to a solution of Example A13 (5.80 g, 17.7 mmol) in DCM (100 mL) and the resultant mixture was stirred at RT overnight. The solvent was evaporated and the residue was purified by silica gel chromatography (MeOH/DCM). The enriched material was crystallized from MeCN to provide 4-methyl-N-(4-((6-(3-pivaloylureido)pyridin-3-yl)oxy)pyridin-2-yl)piperazine-1-carboxamideas a light yellow solid (2.95 g, 37%). $^1$H NMR (400 MHz, DMSO-d$_6$): δ 11.10 (s, 1H), 10.84 (s, 1H), 9.23 (s, 1H), 8.23 (d, J=2.9 Hz, 1H), 8.12 (d, J=5.7 Hz, 1H), 8.08 (d, J=9.0 Hz, 1H), 7.70 (dd, J=9.0, 2.9 Hz, 1H), 7.36 (d, J=2.3 Hz, 1H), 6.60 (dd, J=5.7, 2.4 Hz, 1H), 3.40 (t, J=4.8 Hz, 4H), 2.67 (m, 1H), 2.24 (t, J=4.8 Hz, 4H), 2.15 (s, 3H), 1.09 (d, J=6.8 Hz, 6H); MS (ESI) m/z: 442.2 (M+H$^+$).

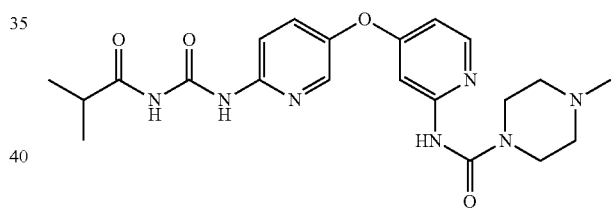

Example 67

A mixture of Example B9 (0.186 g, 0.819 mmol), Example A2 (0.1 g, 0.409 mmol) and N-methylpyrrolidine (10.46 mg, 0.123 mmol) in THF (4 mL) was heated at 55° C. for 4 h, cooled to RT, and stirred overnight. The mixture was concentrated to dryness and purified via reverse-phase chromatography (MeCN/H$_2$O with 0.1% TFA). Combined fractions were treated with satd. NaHCO$_3$, extracted with EtOAc (2×) and the combined organics were washed with brine, dried over Na$_2$SO$_4$ and concentrated to dryness to afford N-((5-((2-acetamidopyridin-4-yl)oxy)pyridin-2-yl)carbamoyl)-1-methoxycyclopentanecarboxamide (79 mg, 47%). $^1$H NMR (400 MHz, DMSO-d$_6$): δ 10.84 (s, 1H), 10.55 (s, 1H), 10.40 (br s, 1H), 8.24 (d, J=2.9 Hz, 1H), 8.18 (d, J=5.7 Hz, 1H), 8.04 (br s, 1H), 7.73 (dd, J=9.0, 2.9 Hz, 1H), 7.64 (d, J=2.4 Hz, 1H), 6.69 (dd, J=5.7, 2.4 Hz, 1H), 3.15 (s, 3H), 2.03 (s, 3H), 1.94-1.92 (m, 4H), 1.67-1.65 (m, 4H); MS (ESI) m/z: 414.2 (M+H$^+$).

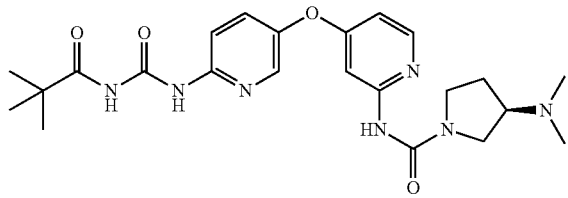 [SMILES: CN(C)[C@@H]1CCN(C(=O)Nc2cc(Oc3ccc(NC(=O)NC(=O)C(C)(C)C)nc3)ccn2)C1]

Example 68

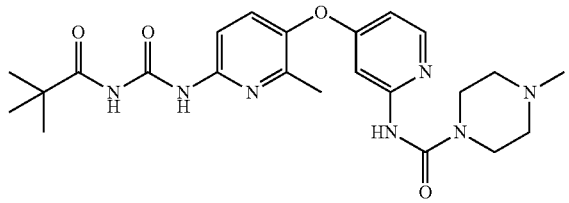 [SMILES: Cc1nc(NC(=O)NC(=O)C(C)(C)C)ccc1Oc1ccnc(NC(=O)N2CCN(C)CC2)c1]

Example 69

A solution of phenyl carbamate (2 g, 14.58 mmol) in dioxane (15 mL) was treated with (R)—N,N-dimethylpyrrolidin-3-amine (2.498 g, 21.88 mmol), stirred at RT for 3 h and concentrated to dryness. The residue was dissolved in Et₂O, treated with HCl (2M in Et₂O, 3 mL), stirred for 1 h and concentrated to dryness. The material was dissolved in EtOAc, treated slowly with Hex until solids formed, sonicated and the resulting solid collected via filtration to afford (R)-3-(dimethylamino)pyrrolidine-1-carboxamide hydrochloride (1.8 g, 79%). MS (ESI) m/z: 158.1 (M+H⁺).

A mixture of Example A1 (0.500 g, 1.987 mmol), (R)-3-(dimethylamino)pyrrolidine-1-carboxamide hydrochloride (0.770 g, 3.97 mmol) and Cs₂CO₃ (1.295 g, 3.97 mmol) and Xantphos (0.230 g, 0.397 mmol) in dioxane (10 mL) was sparged with Ar, treated with Pd₂(dba)₃ (0.182 g, 0.199 mmol), sparged again with Ar and heated at 100° C. overnight. The mixture was cooled to RT, treated with THF, the solids removed via filtration, washed with THF and the filtrate concentrated to dryness and purified via silica gel chromatography (MeOH/EtOAc) to afford (R)-3-(dimethylamino)-N-(4-((6-nitropyridin-3-yl)oxy)pyridin-2-yl)pyrrolidine-1-carboxamide (720 mg, 97%). MS (ESI) m/z: 373.1 (M+H⁺).

A solution of (R)-3-(dimethylamino)-N-(4-((6-nitropyridin-3-yl)oxy)pyridin-2-yl)pyrrolidine-1-carboxamide (0.720 g, 1.934 mmol) in MeOH (10 mL) and THF (10 mL) was treated with NH4Cl (3.10 g, 58.0 mmol) followed by zinc dust (1.264 g, 19.34 mmol) and the mixture stirred at RT for 0.5 h. The mixture was diluted with EtOAc, the solids removed via filtration and washed with EtOAc. The filtrate was re-filtered and concentrated to dryness to afford (R)—N-(4-((6-aminopyridin-3-yl)oxy)pyridin-2-yl)-3-(dimethylamino)pyrrolidine-1-carboxamide (600 mg, 91%). MS (ESI) m/z: 343.2 (M+H⁺).

A solution of 2,2,2-trimethylacetamide (0.248 g, 2.453 mmol) in DCE (5 mL) was treated with oxalyl chloride (0.197 mL, 2.331 mmol), heated at 100° C. for 1 h, cooled to RT, added drop-wise to a solution of (R)—N-(4-((6-aminopyridin-3-yl)oxy)pyridin-2-yl)-3-(dimethylamino)pyrrolidine-1-carboxamide (0.600 g, 1.752 mmol) and pyridine (0.198 mL, 2.453 mmol) in THF (10 mL) and stirred at RT overnight. The mixture was concentrated to dryness, treated with satd. NH₄Cl, extracted with EtOAc (4×) and the combined organics were washed with water, dried over Na₂SO₄ and concentrated to dryness. The residue was suspended in MeCN, sonicated and the resulting solid collected via filtration to afford (R)-3-(dimethylamino)-N-(4-((6-(3-pivaloylureido)pyridin-3-yl)oxy)pyridin-2-yl)pyrrolidine-1-carboxamide (280 mg, 34%). ¹H NMR (400 MHz, DMSO-d₆): δ 11.22 (s, 1H), 10.44 (br s, 1H), 8.78 (s, 1H), 8.23 (d, J=2.9 Hz, 1H), 8.11 (d, J=5.7 Hz, 1H), 8.08 (d, J=8.9 Hz, 1H), 7.71 (dd, J=9.0, 2.9 Hz, 1H), 7.46 (d, J=2.4 Hz, 1H), 6.61 (dd, J=5.7, 2.4 Hz, 1H), 3.62 (m, 1H), 3.52 (m, 1H), 3.27 (m, 1H), 3.08 (m, 1H), 2.65 (m, 1H), 2.15 (s, 6H), 2.08-1.95 (m, 1H), 1.65 (m, 1H), 1.21 (s, 9H); MS (ESI) m/z: 470.3 (M+H⁺).

A suspension of Example A3 (0.700 g, 2.64 mmol), Example C3 (0.300 g, 2.095 mmol), Cs₂CO₃ (1.717 g, 5.27 mmol) and X-Phos (0.050 g, 0.105 mmol) in dioxane (20 mL) was sparged with Ar, treated with Pd₂(dba)₃ (0.048 g, 0.053 mmol) and heated at 110° C. for 13 h. The mixture was cooled to RT, the solids removed via filtration, washed with THF and the filtrate concentrated to dryness and purified via silica gel chromatography (MeOH/DCM) to afford 4-methyl-N-(4-((2-methyl-6-nitropyridin-3-yl)oxy)pyridin-2-yl)piperazine-1-carboxamide (76 mg, 56%). ¹H NMR (400 MHz, DMSO-d₆): δ 9.37 (s, 1H), 8.22 (t, J=8.6 Hz, 2H), 7.81 (d, J=8.7 Hz, 1H), 7.48 (d, J=2.4 Hz, 1H), 6.71 (dd, J=5.7, 2.4 Hz, 1H), 3.41 (t, J=4.8 Hz, 4H), 2.47 (s, 3H), 2.25 (t, J=4.8 Hz, 4H), 2.15 (s, 3H); MS (ESI) m/z: 373.2 (M+H⁺).

A solution of 4-methyl-N-(4-((2-methyl-6-nitropyridin-3-yl)oxy)pyridin-2-yl)piperazine-1-carboxamide (0.400 g, 1.074 mmol) in MeOH (20 mL) was treated with NH₄Cl (2.00 g, 37.4 mmol) followed by zinc powder (1.00 g, 15.29 mmol) and the mixture stirred at RT overnight. The solids were removed via filtration, washed with DCM and the filtrate concentrated to dryness. The residue was treated with DCM and a few drops of MeOH, the solids again removed via filtration and the filtrate concentrated to dryness to afford N-(4-((6-amino-2-methylpyridin-3-yl)oxy)pyridin-2-yl)-4-methylpiperazine-1-carboxamide (290 mg, 79%). MS (ESI) m/z: 343.2 (M+H⁺).

A solution of trimethylacetylchloride (0.300 g, 2.488 mmol) in DCM (10 mL) was treated with silver cyanate (0.600 g, 4.00 mmol), stirred at RT for 1 h, treated with N-(4-((6-amino-2-methylpyridin-3-yl)oxy)pyridin-2-yl)-4-methylpiperazine-1-carboxamide (0.290 g, 0.847 mmol) and catalytic pyridine and stirred at RT for 1 week. The solids were removed via filtration, washed with DCM and THF and the filtrate concentrated to dryness and purified via silica gel chromatography (MeOH/DCM) to afford 4-methyl-N-(4-((2-methyl-6-(3-pivaloylureido)pyridin-3-yl)oxy)pyridin-2-yl)piperazine-1-carboxamide (280 mg, 68%). ¹H NMR (400 MHz, DMSO-d₆): δ 11.15 (s, 1H), 10.41 (s, 1H), 9.24 (s, 1H), 8.10 (d, J=5.7 Hz, 1H), 7.90 (br d, J=8.8 Hz, 1H), 7.61 (d, J=8.8 Hz, 1H), 7.28 (d, J=2.3 Hz, 1H), 6.55 (dd, J=5.7, 2.4 Hz, 1H), 3.39 (br s, 4H), 2.28-2.23 (m, 4H), 2.23 (s, 3H), 2.16 (s, 3H), 1.21 (s, 9H); MS (ESI) m/z: 470.3 (M+H⁺).

Example 70

A solution of Example B10 (0.053 g, 0.373 mmol) in DCE (1 mL) was treated with oxalyl chloride (0.033 mL, 0.373 mmol), stirred at RT for 0.5 h, then heated at 75° C. for 1 h. The mixture was cooled to RT, treated with a solution of Example A11 (0.070 g, 0.287 mmol) and TEA (0.12 mL) in THF (3 mL) and stirred at RT for 3 h. The mixture was treated with satd. NaHCO$_3$, extracted with EtOAc (2×) and the combined organics were dried over Na$_2$SO$_4$, concentrated to dryness and purified via silica gel chromatography (MeOH/DCM) to afford N-methyl-4-((6-(3-(4-methyltetrahydro-2H-pyran-4-carbonyl)ureido)pyridin-3-yl)oxy)picolinamide (71 mg, 58%). $^1$H NMR (400 MHz, DMSO-d$_6$): δ 11.24 (s, 1H), 10.57 (s, 1H), 8.80 (q, J=4.8 Hz, 1H), 8.53 (d, J=5.6 Hz, 1H), 8.32 (d, J=2.9 Hz, 1H), 8.12 (d, J=9.0 Hz, 1H), 7.80 (dd, J=9.0, 2.9 Hz, 1H), 7.41 (d, J=2.6 Hz, 1H), 7.20 (dd, J=5.6, 2.7 Hz, 1H), 3.65 (m, 2H), 3.45 (m, 2H), 2.78 (d, J=4.8 Hz, 3H), 2.05 (m, 2H), 1.50 (m, 2H), 1.27 (s, 3H); MS (ESI) m/z: 414.2 (M+H$^+$).

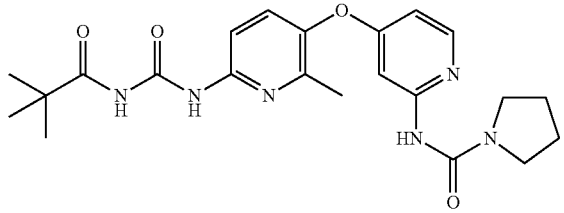 [SMILES: Cc1nc(NC(=O)NC(=O)C(C)(C)C)ccc1Oc1ccnc(NC(=O)N2CCCC2)c1]

Example 71

A solution of phenylcarbamate (2 g, 14.58 mmol) in dioxane (15 mL) was treated with pyrrolidine (4 mL, 47.9 mmol), stirred at RT overnight and concentrated to dryness. The residue was suspended in DCM, sonicated and the resulting solid collected via filtration to afford pyrrolidine-1-carboxamide (1.305 g, 78%). $^1$H NMR (400 MHz, DMSO-d$_6$): δ 5.61 (s, 2H), 3.15 (m, 4H), 1.75 (m, 4H); MS (ESI) m/z: 115.1 (M+H$^+$).

A mixture of Example A3 (0.500 g, 1.882 mmol), pyrrolidine-1-carboxamide (1.074 g, 9.41 mmol), Cs$_2$CO$_3$ (1.226 g, 3.76 mmol) and Xantphos (0.218 g, 0.376 mmol) in dioxane (100 mL) was sparged with Ar, treated with Pd2(dba)$_3$ (0.172 g, 0.188 mmol), sparged again with Ar and heated at 100° C. overnight. The mixture was cooled to RT, diluted with THF, the solids removed via filtration and the filtrate concentrated to dryness and purified via silica gel chromatography (MeOH/DCM) to afford N-(4-((2-methyl-6-nitropyridin-3-yl)oxy)pyridin-2-yl)pyrrolidine-1-carboxamide (648 mg, 100%). MS (ESI) m/z: 344.1 (M+H$^+$).

A mixture of N-(4-((2-methyl-6-nitropyridin-3-yl)oxy)pyridin-2-yl)pyrrolidine-1-carboxamide (0.720 g, 2.097 mmol) and NH$_4$Cl (3.37 g, 62.9 mmol) in MeOH (10 mL) and THF (10 mL) was treated with zinc dust (1.371 g, 20.97 mmol) and stirred at RT overnight. The mixture was diluted with EtOAc, the solids removed via filtration and the filtrate concentrated to dryness to afford N-(4-((6-amino-2-methylpyridin-3-yl)oxy)pyridin-2-yl)pyrrolidine-1-carboxamide (658 mg, 100%). MS (ESI) m/z: 314.2 (M+H$^+$).

A suspension of 2,2,2-trimethylacetamide (0.297 g, 2.94 mmol) in DCE (5 mL) was treated with oxalyl chloride (0.236 mL, 2.79 mmol), heated at 100° C. for 1 h, cooled to RT, added drop-wise to a solution of N-(4-(((6-amino-2-methylpyridin-3-yl)oxy)pyridin-2-yl)pyrrolidine-1-carboxamide (0.658 g, 2.100 mmol) and pyridine (0.237 mL, 2.94 mmol) in THF (10 mL) and stirred at RT for 2 h. The mixture was concentrated to dryness, treated with satd. NaHCO$_3$, extracted with EtOAc (4×) and the combined organics were dried over Na$_2$SO$_4$ and concentrated to dryness. The residue was treated with MeCN, sonicated and the resulting solid was removed via filtration. The filtrate was concentrated to dryness, suspended in MeCN, sonicated, allowed to stand for 3 h and the resulting solid collected via filtration to afford N-(4-((2-methyl-6-(3-pivaloylureido)pyridin-3-yl)oxy)pyridin-2-yl)pyrrolidine-1-carboxamide (161 mg, 17%). $^1$H NMR (400 MHz, DMSO-d$_6$): δ 11.16 (s, 1H), 10.41 (s, 1H), 8.70 (s, 1H), 8.09 (d, J=5.7 Hz, 1H), 7.90 (m, 1H), 7.61 (d, J=8.8 Hz, 1H), 7.38-7.37 (m, 1H), 6.55 (dd, J=5.7, 2.4 Hz, 1H), 3.31 (m, 4H), 2.23 (s, 3H), 1.78 (m, 4H), 1.21 (s, 9H); MS (ESI) m/z: 441.2 (M+H$^+$).

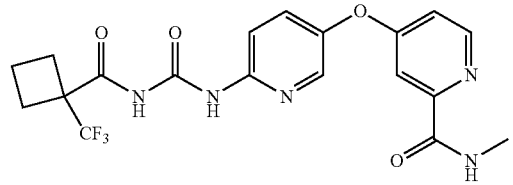 [SMILES: CNC(=O)c1cc(Oc2ccc(NC(=O)NC(=O)C3(C(F)(F)F)CCC3)nc2)ccn1]

Example 72

A solution of 1-trifluoromethyl-cyclobutane-1-carboxylic acid (0.413 g, 2.457 mmol) in DCM (8 mL) was treated with oxalyl chloride (0.179 mL, 2.047 mmol) and DMF (1 drop), stirred for at RT for 2 h, treated with silver cyanate (0.982 g, 6.55 mmol), stirred at RT for 1 h, treated with a solution of 4-((6-aminopyridin-3-yl)oxy)-N-methylpicolinamide (0.2 g, 0.819 mmol) and DIEA (0.858 mL, 4.91 mmol) in dioxane (8 mL) and stirred at RT overnight. The mixture was diluted with EtOAc, the solids removed via filtration through diatomaceous earth and washed with EtOAc. The filtrate was washed with satd. NaHCO$_3$, water, then brine and the combined aqueous washes were back-extracted with EtOAc. The combined organics were dried over Na$_2$SO$_4$, concentrated to dryness and purified by silica gel chromatography (EtOAc/DCM) to afford N-methyl-4-((6-(3-(1-(trifluoromethyl)cyclobutanecarbonyl)ureido)pyridin-3-yl)oxy)picolinamide (0.259 g, 72%). $^1$H NMR (400 MHz, DMSO-d$_6$): δ 11.16 (br s, 1H), 10.87 (s, 1H), 8.79 (d, J=5.1 Hz, 1H), 8.53 (d, J=5.6 Hz, 1H), 8.32 (d, J=2.9 Hz, 1H), 8.08 (d, J=9.1 Hz, 1H), 7.81 (dd, J=9.0, 2.9 Hz, 1H), 7.41 (d, J=2.6 Hz, 1H), 7.19 (dd, J=5.6, 2.7 Hz, 1H), 2.78 (d, J=4.8 Hz, 3H), 2.67 (t, J=10.5 Hz, 2H), 2.41 (m, 2H), 1.90-1.87 (m, 2H); MS (ESI) m/z: 438.2 (M+H$^+$).

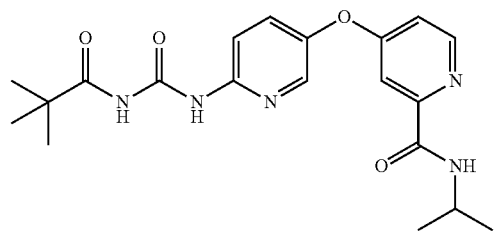 [SMILES: CC(C)NC(=O)c1cc(Oc2ccc(NC(=O)NC(=O)C(C)(C)C)nc2)ccn1]

Example 73

A 0° C. solution of isopropylamine (0.971 mL, 11.30 mmol) and DIEA (1.973 mL, 11.30 mmol) in MeOH (10 mL) and THF (5 mL) was treated with 4-chloropicolinoyl chloride hydrochloride (0.8 g, 3.77 mmol) in one portion, warmed to RT and stirred for 2 h. The mixture was diluted with EtOAc, washed with satd. NaHCO$_3$, then brine and the organic layer was dried over Na$_2$SO$_4$, concentrated to dryness and purified by silica gel chromatography (EtOAc/Hex) to afford 4-chloro-N-isopropylpicolinamide (0.67 g, 90%). $^1$H NMR (400 MHz, DMSO-d$_6$): δ 8.60 (d, J=5.3 Hz, 1H), 8.56 (d, J=8.4 Hz, 1H), 8.00 (d, J=2.2 Hz, 1H), 7.75 (dd, J=5.3, 2.1 Hz, 1H), 4.10-4.09 (m, 1H), 1.17 (d, J=6.6 Hz, 6H); MS (ESI) m/z: 199.1 (M+H$^+$).

A solution of 2-amino-5-hydroxypyridine (0.446 g, 4.05 mmol) in DMA (6.75 mL) was treated with potassium tert-butoxide (0.511 g, 4.55 mmol), stirred at RT for 1 h, treated with DMA (2 mL) and a solution of 4-chloro-N-isopropylpicolinamide (0.67 g, 3.37 mmol) in DMA (6.75 mL) and stirred at RT overnight under Ar. The mixture was diluted with EtOAc, washed with 1N NaOH, then brine and the organic layer was dried over Na2SO4, concentrated to dryness and purified by silica gel chromatography (MeOH/EtOAc) to afford 4-((6-aminopyridin-3-yl)oxy)-N-isopropylpicolinamide (0.523 g, 57%). $^1$H NMR (400 MHz, DMSO-d6): δ 8.46 (t, J=5.6 Hz, 2H), 7.82 (d, J=2.9 Hz, 1H), 7.33 (d, J=2.6 Hz, 1H), 7.30 (dd, J=8.9, 3.0 Hz, 1H), 7.12 (dd, J=5.6, 2.6 Hz, 1H), 6.53 (d, J=8.9 Hz, 1H), 6.08 (s, 2H), 4.05-4.04 (m, 1H), 1.14 (d, J=6.6 Hz, 6H); MS (ESI) m/z: 273.1 (M+H+).

A suspension of 2,2,2-trimethylacetamide (0.149 g, 1.469 mmol) in DCE (4 mL) was treated with oxalyl chloride (0.129 mL, 1.469 mmol), heated at 80° C. for 1 h, cooled to RT, added drop-wise to a solution of 4-((6-aminopyridin-3-yl)oxy)-N-isopropylpicolinamide (0.2 g, 0.734 mmol) and DIEA (0.641 mL, 3.67 mmol) in dioxane (4 mL) and stirred at RT overnight. The mixture was diluted with EtOAc, washed with satd. NaHCO$_3$, water, and brine, and the combined aqueous washes were back-extracted with EtOAc. The combined organics were dried over Na$_2$SO$_4$, concentrated to dryness and purified by silica gel chromatography (EtOAc/DCM) to afford N-isopropyl-4-((6-(3-pivaloylureido)pyridin-3-yl)oxy)picolinamide (0.241 g, 82%). $^1$H NMR (400 MHz, DMSO-d$_6$): δ 11.24 (s, 1H), 10.45 (s, 1H), 8.50-8.49 (m, 2H), 8.30 (d, J=2.9 Hz, 1H), 8.11 (d, J=9.0 Hz, 1H), 7.78 (dd, J=9.0, 2.9 Hz, 1H), 7.40 (d, J=2.6 Hz, 1H), 7.21 (dd, J=5.6, 2.7 Hz, 1H), 4.05-4.04 (m, 1H), 1.21 (s, 9H), 1.15 (d, J=6.5 Hz, 6H); MS (ESI) m/z: 400.2 (M+H$^+$).

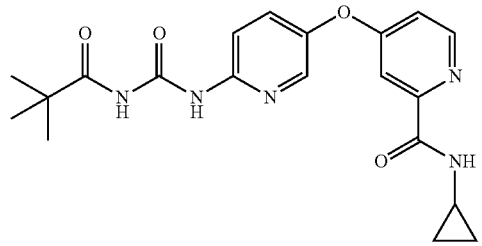 [SMILES: CC(C)(C)C(=O)NC(=O)Nc1ccc(Oc2ccnc(C(=O)NC3CC3)c2)cn1]

Example 74

A 0° C. solution of cyclopropylamine (0.645 g, 11.30 mmol) and DIEA (1.973 mL, 11.30 mmol) in THF (15 mL) was treated with 4-chloropicolinoyl chloride hydrochloride (0.8 g, 3.77 mmol) in one portion, stirred at RT for 2 h, diluted with EtOAc and washed with satd. NaHCO$_3$, then brine. The organic layer was dried over Na$_2$SO$_4$ and concentrated to dryness to afford 4-chloro-N-cyclopropylpicolinamide (0.86 g, 116%). $^1$H NMR (400 MHz, DMSO-d$_6$): δ 8.83 (d, J=5.0 Hz, 1H), 8.58 (d, J=5.3 Hz, 1H), 7.99 (d, J=2.1 Hz, 1H), 7.74 (dd, J=5.3, 2.2 Hz, 1H), 2.89-2.88 (m, 1H), 0.68-0.66 (m, 4H); MS (ESI) m/z: 197.1 (M+H$^+$).

A solution of 2-amino-5-hydroxypyridine (0.578 g, 5.25 mmol) in DMA (8.75 mL) was treated with potassium tert-butoxide (0.663 g, 5.90 mmol), stirred at RT for 1 h, treated with a solution of 4-chloro-N-cyclopropylpicolinamide (0.86 g, 4.37 mmol) in DMA (8.75 mL) and stirred at RT for 20 h. The mixture was diluted with EtOAc, washed with 1N NaOH, then brine and the organic layer was dried over Na$_2$SO$_4$, concentrated to dryness and purified by silica gel chromatography (MeOH/EtOAc) to afford 4-((6-aminopyridin-3-yl)oxy)-N-cyclopropylpicolinamide (0.674 g, 57%). $^1$H NMR (400 MHz, DMSO-d6): δ 8.72 (d, J=5.0 Hz, 1H), 8.44 (d, J=5.6 Hz, 1H), 7.82 (d, J=2.9 Hz, 1H), 7.31-7.30 (m, 2H), 7.11 (dd, J=5.6, 2.6 Hz, 1H), 6.53 (d, J=8.9 Hz, 1H), 6.08 (s, 2H), 2.85-2.84 (m, 1H), 0.65-0.62 (m, 4H); MS (ESI) m/z: 271.1 (M+H$^+$).

A suspension of 2,2,2-trimethylacetamide (0.150 g, 1.480 mmol) in DCE (4 mL) was treated with oxalyl chloride (0.130 mL, 1.480 mmol), heated at 80° C. for 1 h, cooled to RT, added drop-wise to a solution of 4-((6-aminopyridin-3-yl)oxy)-N-cyclopropylpicolinamide (0.2 g, 0.740 mmol) and DIEA (0.646 mL, 3.70 mmol) in dioxane (4 mL) and stirred at RT for 20 h. The mixture was diluted with EtOAc, washed with satd. NaHCO$_3$, water, then brine and the combined aqueous washes were back-extracted with EtOAc. The combined organics were dried over Na$_2$SO$_4$, concentrated to dryness and purified by silica gel chromatography (EtOAc/DCM) to afford N-cyclopropyl-4-((6-(3-pivaloylureido)pyridin-3-yl)oxy)picolinamide (0.196 g, 67%). $^1$H NMR (400 MHz, DMSO-d$_6$): δ 11.24 (s, 1H), 10.46 (s, 1H), 8.75 (d, J=5.1 Hz, 1H), 8.50 (d, J=5.6 Hz, 1H), 8.30 (d, J=2.9 Hz, 1H), 8.11 (d, J=9.0 Hz, 1H), 7.78 (dd, J=9.0, 2.9 Hz, 1H), 7.40 (d, J=2.6 Hz, 1H), 7.19 (dd, J=5.6, 2.6 Hz, 1H), 2.87-2.85 (m, 1H), 1.21 (s, 9H), 0.65 (d, J=8.0 Hz, 4H); MS (ESI) m/z: 398.2 (M+H$^+$).

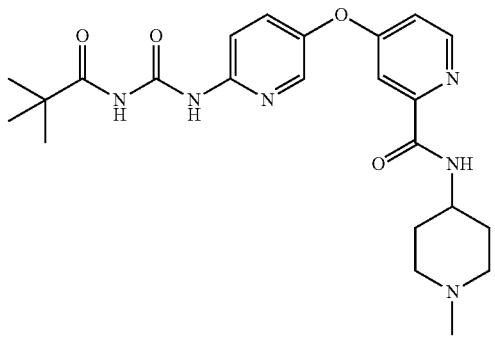 [SMILES: CN1CCC(NC(=O)c2cc(Oc3ccc(NC(=O)NC(=O)C(C)(C)C)nc3)ccn2)CC1]

Example 75

A 0° C. solution of 1-methyl-4-amino-piperidine (0.860 g, 7.53 mmol) and DIEA (2.63 mL, 15.06 mmol) in THF (15 mL) was treated with 4-chloropicolinoyl chloride hydrochloride (0.8 g, 3.77 mmol) in one portion, stirred at RT for 2 h, diluted with EtOAc and washed with satd. NaHCO$_3$, then brine. The organic layer was dried over Na$_2$SO$_4$ and concentrated to dryness to afford 4-chloro-N-(1-methylpiperidin-4-yl)picolinamide (1.07 g, 112%). ¹H NMR (400 MHz, DMSO-d₆): δ 8.61-8.60 (m, 2H), 8.00 (d, J=2.1 Hz, 1H), 7.75 (dd, J=5.3, 2.2 Hz, 1H), 3.74-3.72 (m, 1H), 2.71 (d, J=11.3 Hz, 2H), 2.13 (s, 3H), 1.93 (m, 2H), 1.69-1.67 (m, 4H); MS (ESI) m/z: 254.1 (M+H⁺).

A solution of 2-amino-5-hydroxypyridine (0.557 g, 5.06 mmol) in DMA (8.5 mL) was treated with potassium tert-butoxide (0.639 g, 5.69 mmol), stirred at RT for 1 h, treated with a solution of 4-chloro-N-(1-methylpiperidin-4-yl)picolinamide (1.07 g, 4.22 mmol) in DMA (8.5 mL) and stirred at RT for 20 h. The mixture was diluted with EtOAc, washed with 1N NaOH, then brine and the organic layer was dried over Na₂SO₄, concentrated to dryness and purified by silica gel chromatography (MeOH/DCM/NH₄OH) to afford 4-((6-aminopyridin-3-yl)oxy)-N-(1-methylpiperidin-4-yl)picolinamide (0.654 g, 47%). ¹H NMR (400 MHz, DMSO-d₆): δ 8.49-8.48 (m, 2H), 7.81 (d, J=2.9 Hz, 1H), 7.33 (d, J=2.6 Hz, 1H), 7.30 (dd, J=8.9, 3.0 Hz, 1H), 7.12 (dd, J=5.6, 2.6 Hz, 1H), 6.52 (d, J=8.9 Hz, 1H), 6.08 (s, 2H), 3.69 (d, J=9.9 Hz, 1H), 2.69 (d, J=11.1 Hz, 2H), 2.13 (s, 3H), 1.93 (t, J=11.2 Hz, 2H), 1.68-1.62 (m, 4H); MS (ESI) m/z: 328.2 (M+H⁺).

A suspension of 2,2,2-trimethylacetamide (0.124 g, 1.222 mmol) in DCE (4 mL) was treated with oxalyl chloride (0.107 mL, 1.222 mmol), heated at 80° C. for 1 h, cooled to RT, added to a solution of 4-((6-aminopyridin-3-yl)oxy)-N-(1-methylpiperidin-4-yl)picolinamide (0.2 g, 0.611 mmol) and DIEA (0.533 mL, 3.05 mmol) in dioxane (4 mL) and stirred at RT overnight. The mixture was diluted with EtOAc, washed with satd. NaHCO₃, then brine and the combined aqueous washes were back-extracted with EtOAc. The combined organics were dried over Na₂SO₄, concentrated to dryness and purified by silica gel chromatography (MeOH/DCM/TEA). The material was treated with MeCN, sonicated and the resulting solid collected via filtration to afford N-(1-methylpiperidin-4-yl)-4-((6-(3-pivaloylureido)pyridin-3-yl)oxy)picolinamide (186 mg, 67%). ¹H NMR (400 MHz, DMSO-d₆): δ 11.24 (s, 1H), 10.45 (s, 1H), 8.54-8.53 (m, 2H), 8.30 (d, J=2.9 Hz, 1H), 8.11 (d, J=9.0 Hz, 1H), 7.78 (dd, J=9.0, 2.9 Hz, 1H), 7.41 (d, J=2.6 Hz, 1H), 7.20 (dd, J=5.6, 2.6 Hz, 1H), 3.72-3.66 (m, 1H), 2.70 (d, J=11.0 Hz, 2H), 2.13 (s, 3H), 1.93 (t, J=11.1 Hz, 2H), 1.67-1.64 (m, 4H), 1.21 (s, 9H); MS (ESI) m/z: 455.2 (M+H⁺).

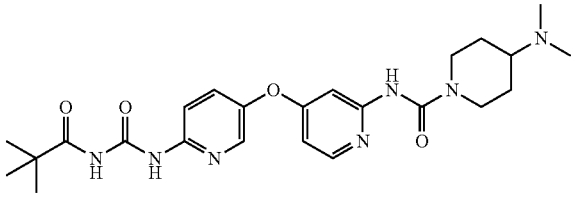 [SMILES: CN(C)C1CCN(C(=O)Nc2cc(Oc3ccc(NC(=O)NC(=O)C(C)(C)C)nc3)ccn2)CC1]

Example 76

A mixture of Example C2 (0.42 g, 1.02 mmol), 4-(dimethylamino)piperidine dihydrochloride (0.204 g, 1.02 mmol) and N-methylpyrrolidine (0.182 g, 2.13 mmol) in dioxane (5 mL) was heated at 80° C. overnight, cooled to RT, concentrated to dryness and purified via silica gel chromatography (MeOH/DCM). The resultant material was dissolved in MeCN/H₂O, frozen and lyophilized to afford 4-(dimethylamino)-N-(4-((6-(3-pivaloylureido)pyridin-3-yl)oxy)pyridin-2-yl)piperidine-1-carboxamide as a yellowish solid (64 mg, 13%). ¹H NMR (400 MHz, DMSO-d₆): δ 11.17 (s, 1H), 10.40 (s, 1H), 9.23 (s, 1H), 8.18 (d, J=2.9 Hz, 1H), 8.07 (d, J=5.7 Hz, 1H), 8.03 (d, J=9.0 Hz, 1H), 7.66 (dd, J=9.0, 2.9 Hz, 1H), 7.32 (d, J=2.4 Hz, 1H), 6.56 (dd, J=5.7, 2.4 Hz, 1H), 4.13-4.01 (m, 2H), 3.37-3.11 (br s, 1H), 2.74-2.62 (m, 2 H), 2.28 (s, 6H), 1.76-1.70 (m, 2H), 1.29-1.24 (m, 2H), 1.16 (s, 9H); MS (ESI) m/z: 484.3 (M+H⁺).

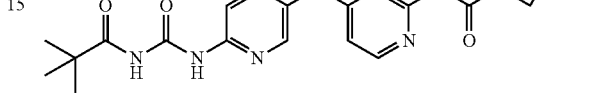

Example 77

A mixture of Example C2 (0.42 g, 1.02 mmol), N,N-dimethyl-3-azetidinamine dihydrochloride (0.176 g, 1.02 mmol) and N-methylpyrrolidine (0.182 g, 2.13 mmol) in dioxane (5 mL) was heated at 80° C. overnight, cooled to RT, concentrated to dryness and purified via silica gel chromatography (MeOH/DCM). The resultant material was dissolved in MeCN/H₂O, frozen and lyophilized to afford 3-(dimethylamino)-N-(4-((6-(3-pivaloylureido)pyridin-3-yl)oxy)pyridin-2-yl)azetidine-1-carboxamide as a yellowish-white solid (59 mg, 11%). ¹H NMR (400 MHz, DMSO-d₆): δ 11.22 (s, 1H), 10.45 (s, 1H), 9.51 (s, 1H), 8.23 (d, J=2.9 Hz, 1H), 8.13 (d, J=5.7 Hz, 1H), 8.08 (d, J=9.0 Hz, 1H), 7.72 (dd, J=9.0, 2.9 Hz, 1H), 7.46 (d, J=2.38 Hz, 1H), 6.63 (dd, J=5.7, 2.4 Hz, 1H), 4.17-4.03 (m, 4H), 3.95-3.82 (br s, 1H), 2.62 (s, 6H), 1.21 (s, 9H); MS (ESI) m/z: 456.2 (M+H⁺).

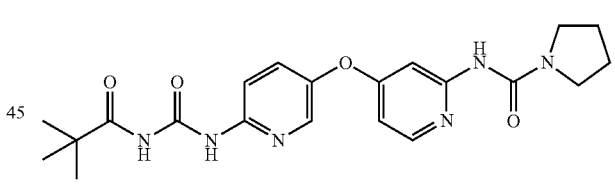

Example 78

A mixture of Example C2 (0.163 g, 0.394 mmol), pyrrolidine (0.028 g, 0.394 mmol) and N-methylpyrrolidine (0.017 g, 0.197 mmol) in dioxane (3 mL) was heated at 80° C. for 45 min, cooled to RT, and concentrated to dryness. The residue was suspended in MeCN and the mixture was sonicated for a few minutes. The light beige solid was collected by filtration, washed with MeCN and dried overnight at 80° C. to provide N-(4-((6-(3-pivaloylureido)pyridin-3-yl)oxy)pyridin-2-yl)pyrrolidine-1-carboxamide (0.118 g, 67%). ¹H NMR (400 MHz, DMSO-d₆): δ 11.22 (s, 1H), 10.44 (s, 1H), 8.72 (s, 1H), 8.23 (d, J=2.9 Hz, 1H), 8.13-8.04 (m, 2H), 7.71 (dd, J=9.0, 2.9 Hz, 1H), 7.47 (d, J=2.4 Hz, 1H), 6.60 (dd, J=5.7, 2.4 Hz, 1H), 3.39-3.30 (m, 4H), 1.84-1.71 (m, 4H), 1.21 (s, 9H); MS (ESI) m/z: 427.2 (M+H⁺).

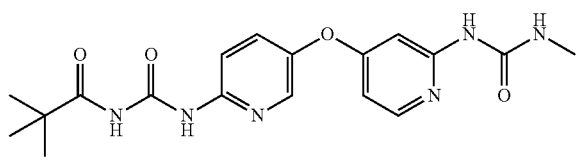 [SMILES: CNC(=O)Nc1cc(Oc2ccc(NC(=O)NC(=O)C(C)(C)C)nc2)ccn1]

Example 79

A mixture of Example C2 (0.163 g, 0.394 mmol), methylamine hydrochloride (0.053 g, 0.789 mmol) and N-methylpyrrolidine (0.070 g, 0.828 mmol) in dioxane (3 mL) was heated at 80° C. overnight, cooled to RT, and concentrated to dryness. The residue was suspended in MeCN and the mixture was sonicated for a few minutes. The light beige solid was collected by filtration and washed with MeCN. This solid was partitioned with DCM and water with stirring for 15 min. The aqueous layer was separated and extracted with DCM (2×). The combined organics were dried ($Na_2SO_4$) and concentrated to dryness. The residue was suspended in MeCN/water, frozen and lyophilized to afford N-((5-((2-(3-methylureido)pyridin-4-yl)oxy)pyridin-2-yl)carbamoyl)pivalamide as a white solid (0.199 g, 125%). $^1$H NMR (400 MHz, DMSO-$d_6$): δ 11.20 (s, 1H), 10.50 (s, 1H), 9.20 s, (1H), 8.22 (d, J=2.9 Hz, 1H), 8.09-8.03 (m, 2H), 7.97-7.87 (m, 1H), 7.73 (d, J=2.9 Hz, 1H), 7.00 (s, 1H), 6.55 (dd, J=5.8, 2.4 Hz, 1H), 2.64 (d, J=4.6 Hz, 3H), 1.21 (s, 9H); MS (ESI) m/z: 387.2 (M+H$^+$).

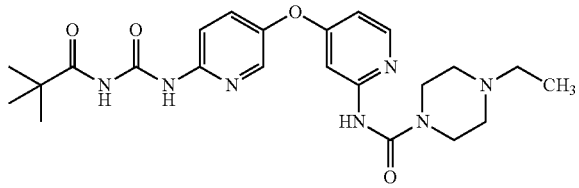 [SMILES: CCN1CCN(C(=O)Nc2cc(Oc3ccc(NC(=O)NC(=O)C(C)(C)C)nc3)ccn2)CC1]

Example 80

A mixture of Example C2 (0.203 g, 0.491 mmol), N-ethyl piperazine (0.1 mL, 0.79 mmol) and N-methylpyrrolidine (0.021 g, 0.25 mmol) in dioxane (5 mL) was heated at 80° C. for 3 h, cooled to RT, and concentrated to dryness. The residue was dissolved in DCM and stirred with sat'd $NaHCO_3$ for ~15 min. The aqueous layer was back-extracted with DCM (3×) and the organic phases combined, dried ($Na_2SO_4$) and concentrated to afford a light brown oil. The crude residue was purified via silica gel chromatography (MeOH/DCM) to afford a colorless oil, which was suspended in MeCN/$H_2O$, sonicated, frozen and lypholized overnight to afford 4-ethyl-N-(4-((6-(3-pivaloylureido)pyridin-3-yl)oxy)pyridin-2-yl)piperazine-1-carboxamide as a white solid (74 mg, 32%). $^1$H NMR (400 MHz, DMSO-$d_6$): δ 11.22 (s, 1H), 10.44 (s, 1H), 9.25 (s, 1H), 8.23 (d, J=2.9 Hz, 1H), 8.12 (d, J=5.7 Hz, 1H), 8.08 (d, J=9.0 Hz, 1H), 7.71 (dd, J=9.0, 2.9 Hz, 1H), 7.37 (d, J=2.4 Hz, 1H), 6.61 (dd, J=5.7, 2.4 Hz, 1H), 3.44-3.35 (m, 4H), 2.35-2.23 (m, 6H), 1.21 (s, 9H), 0.98 (t, J=7.2 Hz, 3H); MS (ESI) m/z: 470.3 (M+H$^+$).

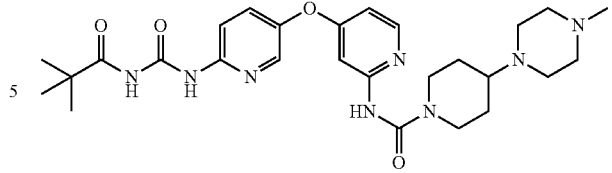

Example 81

A mixture of Example C2 (0.120 g, 0.29 mmol), 1-methyl-4-(piperidin-4-yl)piperazine (0.053 g, 0.290 mmol) and N-methylpyrrolidine (0.012 g, 0.15 mmol) in dioxane (5 mL) was heated at 80° C. for 2 days. The reaction mixture was concentrated to dryness. The residue was dissolved in DCM and stirred with sat'd $NaHCO_3$. The aqueous layer was back-extracted with DCM (3×) and the organic phases combined, dried ($Na_2SO_4$) and concentrated to afford a light brown oil. The crude residue was purified via silica gel chromatography (MeOH/DCM/$Et_3$N) to afford a light yellow oil, which was dissolved in MeCN/$H_2O$, frozen and lypholized overnight to afford 4-(4-methylpiperazin-1-yl)-N-(4-((6-(3-pivaloylureido)pyridin-3-yl)oxy)pyridin-2-yl)piperidine-1-carboxamide as a white solid (63 mg, 40%). $^1$H NMR (400 MHz, DMSO-$d_6$): δ 11.22 (s, 1H), 10.44 (s, 1H), 9.22 (s, 1H), 8.23 (d, J=2.9 Hz, 1H), 8.12-8.05 (m, 2H), 7.71 (dd, J=9.0, 2.9 Hz, 1H), 7.36 (d, J=2.4 Hz, 1H), 6.59 (dd, J=5.7, 2.4 Hz, 1H), 4.13-4.02 (m, 2H), 3.38-3.31 (m, 1H), 2.77-2.64 (m, 2H), 2.52-2.26 (m, 8H), 2.16 (s, 3H), 1.75-1.62 (m, 2H), 1.31-1.23 (m, 2H), 1.21 (s, 9H); MS (ESI) m/z: 539.4 (M+H$^+$).

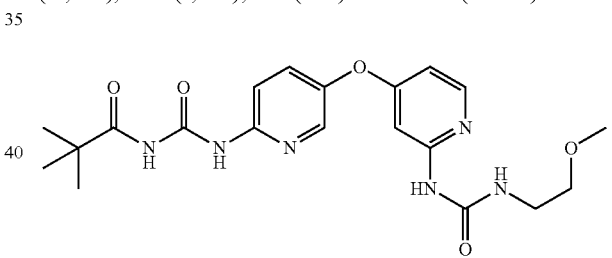

Example 82

A mixture of Example C2 (0.120 g, 0.290 mmol), 2-methoxyethylamine (0.1 mL, 1.15 mmol) and N-methylpyrrolidine (0.012 g, 0.145 mmol) in dioxane (5 mL) was heated at 80° C. overnight, cooled to RT, and concentrated to dryness. The residue was dissolved in DCM and stirred with sat'd $NaHCO_3$. The aqueous layer was back-extracted with DCM (3×) and the organic phases combined, dried ($Na_2SO_4$) and concentrated to afford a light brown oil. The crude residue was purified via silica gel chromatography (MeOH/DCM) to afford a white solid, which was dissolved in MeCN/$H_2O$, frozen and lypholized overnight to afford N-((5-((2-(3-(2-methoxyethyl)ureido)pyridin-4-yl)oxy)pyridin-2-yl)carbamoyl)pivalamide as a white solid (54 mg, 43%). $^1$H NMR (400 MHz, DMSO-$d_6$): δ 11.22 (s, 1H), 10.44 (s, 1H), 9.14 (s, 1H), 8.24 (d, J=2.9 Hz, 1H), 8.07-8.06 (m, 2H), 7.96 (s, 1H), 7.72 (dd, J=9.0, 2.9 Hz, 1H), 6.97 (d, J=2.3 Hz, 1H), 6.57 (dd, J=5.9, 2.4 Hz, 1H), 3.35-3.34 (m, 2H), 3.28-3.22 (m, 2H), 3.24 (s, 3H), 1.21 (s, 9H); MS (ESI) m/z: 431.2 (M+H$^+$).

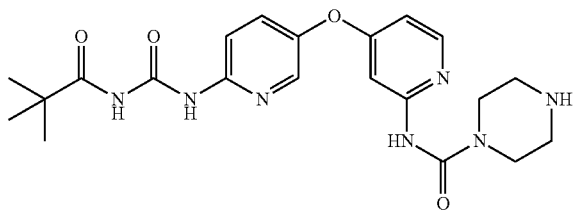 [SMILES: CC(C)(C)C(=O)NC(=O)Nc1ccc(Oc2ccnc(NC(=O)N3CCNCC3)c2)cn1]

Example 83

1-benzylpiperazine (17.63 g, 100 mmol) and phenyl carbamate (16.46 g, 120 mmol) were combined in DMSO (500 mL) and stirred overnight with heating at 60° C. The mixture was diluted with brine (1000 mL) and extracted with $CH_2Cl_2$ (4×250 mL). The combined organics were treated with 5% NaOH (250-275 mL) for 15 min. The organic layer was separated, dried ($Na_2SO_4$), filtered and concentrated to afford a pale yellow solid (27.8 g). The solid was then triturated for 90 min with stirring in MTBE (100 mL). The suspension was cooled well in ice. The solids were collected by filtration, rinsed with ice cold MTBE and dried to afford 4-benzylpiperazine-1-carboxamide (14.7 g, 67%) as a white solid. $^1$H NMR (400 MHz, DMSO-$d_6$): δ 7.33-7.05 (m, 5H), 5.91 (s, 2H), 3.45 (s, 2H), 3.24 (t, J=4.9 Hz, 4H), 2.26 (t, J=4.9 Hz, 4H); MS (ESI) m/z: 220.1 (M+H$^+$).

A suspension of Example A1 (0.5 g, 1.987 mmol), 4-benzylpiperazine-1-carboxamide (0.741 g, 3.38 mmol), cesium carbonate (0.971 g, 2.98 mmol) and X-Phos (0.047 g, 0.099 mmol) in dioxane (20 mL) was purged 5 min with Ar. To the reaction mixture was added Pd$_2$ dba$_3$ (0.055 g, 0.060 mmol) and it was then heated to 120° C. After 16 h, the reaction was cooled to RT, diluted with EtOAc (100 mL) and filtered through diatomaceous earth. The filter cake was washed with additional EtOAc and the combined filtrates concentrated to afford crude product. This was purified by silica gel chromatography (0-8% MeOH/DCM) to afford 4-benzyl-N-(4-((6-nitropyridin-3-yl)oxy)pyridin-2-yl)piperazine-1-carboxamide (0.574 g, 66%). 1H NMR (400 MHz, DMSO-d6): δ 9.41 (s, 1H), 8.56 (d, J=2.8 Hz, 1H), 8.40 (d, J=8.9 Hz, 1H), 8.23 (d, J=5.7 Hz, 1H), 7.94 (dd, J=8.9, 2.8 Hz, 1H), 7.55 (d, J=2.3 Hz, 1H), 7.30-7.29 (m, 5H), 6.79 (dd, J=5.7, 2.4 Hz, 1H), 3.47 (s, 2H), 3.43 (t, J=4.7 Hz, 4H), 2.32 (t, J=4.7 Hz, 4H); MS (ESI) m/z: 435.2 (M+H$^+$).

To a stirring solution of 4-benzyl-N-(4-((6-nitropyridin-3-yl)oxy)pyridin-2-yl)piperazine-1-carboxamide (0.574 g, 1.321 mmol) in MeOH/THF (1:1, 30 mL) at RT was sequentially added ammonium formate (0.833 g, 13.21 mmol) and zinc powder (0.864 g, 13.21 mmol). The resulting suspension was stirred briskly at RT. After 75 min, the reaction was filtered through diatomaceous earth, rinsing with THF. The combined filtrates were concentrated and purified by silica gel chromatography (0-10% MeOH/DCM) to afford N-(4-((6-aminopyridin-3-yl)oxy)pyridin-2-yl)-4-benzylpiperazine-1-carboxamide (0.355 g, 64%) as a brittle pink foam. 1H NMR (400 MHz, DMSO-d6): δ 9.13 (s, 1H), 8.05 (d, J=5.7 Hz, 1H), 7.75 (d, J=2.9 Hz, 1H), 7.30-7.29 (m, 5H), 7.24-7.23 (m, 2H), 6.52 (dd, J=5.7, 2.4 Hz, 1H), 6.49 (d, J=8.9 Hz, 1H), 5.99 (s, 2H), 3.46 (s, 2H), 3.40 (t, J=4.7 Hz, 4H), 2.31 (t, J=4.7 Hz, 4H); MS (ESI) m/z: 405.2 (M+H$^+$).

To a stirring suspension of trimethylacetamide (0.115 g, 1.141 mmol) in 1,2-dichloroethane (5 mL) at RT was added oxalyl chloride (0.100 mL, 1.141 mmol). The mixture was stirred 1 h at RT and then at 90° C. for 1 h. The mixture was cooled to RT and added slowly to a stirring solution of N-(4-((6-aminopyridin-3-yl)oxy)pyridin-2-yl)-4-benzylpiperazine-1-carboxamide (0.355 g, 0.878 mmol) in $CH_2Cl_2$ (15 mL). Solids precipitated and the suspension was stirred overnight at RT. DIEA (0.6 mL) was added and the resulting solution stirred 45 min. It was washed with $H_2O$ (2×), brine (1×), dried (MgSO$_4$), and evaporated. The crude product was purified by silica gel chromatography (0-6% MeOH/$CH_2Cl_2$) and then re-purified by silica gel chromatography (0-10% MeOH/EtOAc) to afford 4-benzyl-N-(4-((6-(3-pivaloylureido)pyridin-3-yl)oxy)pyridin-2-yl)piperazine-1-carboxamide (0.151 g, 32%) as an off-white brittle foam. $^1$H NMR (400 MHz, DMSO-$d_6$): δ 11.22 (s, 1H), 10.44 (s, 1H), 9.24 (s, 1H), 8.23 (d, J=2.9 Hz, 1H), 8.11 (d, J=5.7 Hz, 1H), 8.08 (d, J=9.1 Hz, 1H), 7.71 (dd, J=9.0, 2.9 Hz, 1H), 7.36 (d, J=2.4 Hz, 1H), 7.28-7.26 (m, 5H), 6.61 (dd, J=5.7, 2.4 Hz, 1H), 3.46 (s, 2H), 3.40 (m, 4H), 2.31 (t, J=4.7 Hz, 4H), 1.21 (s, 9H); MS (ESI) m/z: 532.3 (M+H$^+$).

4-Benzyl-N-(4-((6-(3-pivaloylureido)pyridin-3-yl)oxy) pyridin-2-yl)piperazine-1-carboxamide (0.151 g, 0.284 mmol), 10% Pd/C (50% $H_2O$, 0.121 g, 0.057 mmol) and ammonium formate (0.054 g, 0.852 mmol) were combined in MeOH (5 mL) and stirred with heating at 70° C. After 2 h, the reaction was cooled to RT and filtered through diatomaceous earth. The cake was washed well with MeOH and the combined filtrates were concentrated to afford crude product (0.11 g). This was purified by silica gel chromatography (10% MeOH/$CH_2Cl_2$; then 0-10% 7M $NH_3$ in MeOH/$CH_2Cl_2$) to afford N-(4-((6-(3-pivaloylureido)pyridin-3-yl)oxy)pyridin-2-yl)piperazine-1-carboxamide (66 mg; 53%) as a white solid. 1H NMR (400 MHz, DMSO-d6) δ 11.22 (s, 1H), 10.44 (s, 1H), 9.18 (s, 1H), 8.23 (d, J=2.9 Hz, 1H), 8.11 (d, J=5.7 Hz, 1H), 8.08 (d, J=9.0 Hz, 1H), 7.71 (dd, J=9.0, 2.9 Hz, 1H), 7.36 (d, J=2.4 Hz, 1H), 6.61 (dd, J=5.7, 2.4 Hz, 1H), 3.33-3.31 (m, 4H), 2.63 (t, J=4.9 Hz, 4H), 2.47 (m, 1H), 1.21 (s, 9H); MS (ESI) m/z: 442.2 (M+H$^+$).

The following assays demonstrate that certain compounds of Formula I inhibit kinase activity of c-FMS kinase, c-KIT kinase, or PDGFR kinase in enzymatic assays and also inhibit the activity of c-FMS kinase in M-NFS-60 and THP-1 cell lines. In vivo evaluations of certain compounds of Formula I also demonstrate inhibition of c-FMS in a pharmcodynamic model or also exhibit efficacy in a peritibial implant model, a U-251 or GL-261 glioma model, or in a MDA-MB-231 breast cancer xenograft model.

uFMS kinase (Seq. ID No. 1) Assay

Activity of unphosphorylated c-FMS kinase (uFMS, Seq. ID no. 1) was determined by following the production of ADP from the FMS kinase reaction with ATP and poly E4Y as substrates through coupling with the pyruvate kinase/lactate dehydrogenase system (e.g., Schindler et al. Science (2000) 289: 1938-1942). In this assay, the oxidation of NADH (thus the decrease at A340 nm) was continuously monitored spectrophometrically. The reaction mixture (100 μL) contained FMS (purchased from Millipore) (10 nM), polyE4Y (1 mg/mL), MgCl$_2$ (10 mM), pyruvate kinase (4 units), lactate dehydrogenase (0.7 units), phosphoenol pyruvate (1 mM), NADH (0.28 mM) and ATP (500 μM) in 90 mM Tris buffer containing 0.2% octyl-glucoside and 1% DMSO, pH 7.5. The inhibition reaction was started by mixing serial diluted test compound with the above reaction mixture. The absorption at 340 nm was monitored continuously for 4 hours at 30° C. on Synergy 2 plate reader. The reaction rate was calculated using the 3 to 4 h time frame. Percent inhibition was obtained by comparison of reaction rate with that of a control (i.e. in the absence of test compound). IC$_{50}$ values were calculated from a series of percent inhibition values determined at a range of inhibitor concentrations using software routines as implemented in the GraphPad Prism software package.

```
uFMS Kinase sequence (Y538-end) used for
screening
                                      (Seq. ID No. 1)
YKYKQKPKYQ VRWKIIESYE GNSYTFIDPT QLPYNEKWEF

PRNNLQFGKT LGAGAFGKVV EATAFGLGKE DAVLKVAVKM

LKSTAHADEK EALMSELKIM SHLGQHENIV NLLGACTHGG

PVLVITEYCC YGDLLNFLRR KAEAMLGPSL SPGQDPEGGV

DYKNIHLEKK YVRRDSGFSS QGVDTYVEMR PVSTSSNDSF

SEQDLDKEDG RPLELRDLLH FSSQVAQGMA FLASKNCIHR

DVAARNVLLT NGHVAKIGDF GLARDIMNDS NYIVKGNARL

PVKWMAPESI FDCVYTVQSD VWSYGILLWE IFSLGLNPYP

GILVNSKFYK LVKDGYQMAQ PAFAPKNIYS IMQACWALEP

THRPTFQQIC SFLQEQAQED RRERDYTNLP SSSRSGGSGS

SSSELEEESS SEHLTCCEQG DIAQPLLQPN NYQFC
``` uKit kinase (Seq. ID No. 2) assay

Activity of unphosphorylated c-KIT kinase (uKIT, Seq. ID no. 2) was determined by following the production of ADP from the KIT kinase reaction with ATP and poly E4Y as substrates through coupling with the pyruvate kinase/lactate dehydrogenase system (e.g., Schindler et al. Science (2000) 289: 1938-1942). In this assay, the oxidation of NADH (thus the decrease at A340 nm) was continuously monitored spectrophotometrically. The reaction mixture (100 μl) contained unphosphorylated KIT (12 nM), polyE4Y (1 mg/mL), MgCl$_2$ (10 mM), pyruvate kinase (4 units), lactate dehydrogenase (0.7 units), phosphoenol pyruvate (1 mM), and NADH (0.28 mM) and ATP (2000 μM) in 90 mM Tris buffer containing 0.2% octyl-glucoside and 1% DMSO, pH 7.5. The inhibition reaction was started by mixing serial diluted test compound with the above reaction mixture. The absorption at 340 nm was monitored continuously for 4 hours at 30° C. on Synergy 2 plate reader (BioTech). Reaction rates around 3 to 4 h time frame were used to calculate % inhibitions, from which IC$_{50}$ values were generated.

```
uKit with N-terminal GST fusion used for
screening
                                      (Seq ID No. 2)
LGYWKIKGLV QPTRLLLEYL EEKYEEHLYE RDEGDKWRNK

KFELGLEFPN LPYYIDGDVK LTQSMAIIRY IADKHNMLGG

CPKERAEISM LEGAVDIRYG VSRIAYSKDF ETLKVDFLSK

LPEMLKMFED RLCHKTYLNG DHVTHPDFML YDALDVVLYM

DPMCLDAFPK LVCFKKRIEA IPQIDKYLKS SKYIWPLQGW

QATFGGGDHP PKSDLVPRHN QTSLYKKAGS AAAVLEENLY

FQGTYKYLQK PMYEVQWKVV EEINGNNYVY IDPTQLPYDH

KWEFPRNRLS FGKTLGAGAF GKVVEATAYG LIKSDAAMTV

AVKMLKPSAH LTEREALMSE LKVLSYLGNH MNIVNLLGAC

TIGGPTLVIT EYCCYGDLLN FLRRKRDSFI CSKQEDHAEA

ALYKNLLHSK ESSCSDSTNE YMDMKPGVSY VVPTKADKRR
```

```
                    -continued
SVRIGSYIER DVTPAIMEDD ELALDLEDLL SFSYQVAKGM

AFLASKNCIH RDLAARNILL THGRITKICD FGLARDIKND

SNYVVKGNAR LPVKWMAPES IFNCVYTFESD VWSYGIFLWE

LFSLGSSPYP GMPVDSKFYK MIKEGFRMLS PEHAPAEMYD

IMKTCWDADP LKRPTFKQIV QLIEKQISES TNHIYSNLAN

CSPNRQKPVV DHSVRINSVG STASSSQPLL VHDDV
```

Unphosyhorylated PDGFRβ (uPDGFRβkinase (Seq. ID No. 3) assay

Activity of unphosphorylated PDGFRβ kinase (uPDGFRβ, Seq. ID No. 3) was determined by following the production of ADP from the kinase reaction with ATP and poly E4Y as substrates through coupling with the pyruvate kinase/lactate dehydrogenase system (e.g., Schindler et al. Science (2000) 289: 1938-1942). In this assay, the oxidation of NADH (thus the decrease at A340 nm) was continuously monitored spectrophometrically. The reaction mixture (100 μL) contained PDGFRβ (DeCode, 15.7 nM), polyE4Y (2.5 mg/mL), MgCl$_2$ (10 mM), pyruvate kinase (4 units), lactate dehydrogenase (0.7 units), phosphoenol pyruvate (1 mM) and NADH (0.28 mM) and ATP (500 μM) in a 90 mM Tris buffer containing 0.2% octyl-glucoside and 1% DMSO, at pH 7.5. The inhibition reaction was started by mixing serial diluted test compound with the above reaction mixture. The absorption at 340 nm was monitored continuously for 4 h at 30° C. on a Polarstar Optima or Synergy 2 plate reader. The reaction rate was calculated using the 1.5 to 2.5 h time frame. Percent inhibition was obtained by comparison of reaction rate with that of a control (i.e. with no test compound). IC$_{50}$ values were calculated from a series of percent inhibition values determined at a range of inhibitor concentrations using software routines as implemented in the GraphPad Prism software package.

```
uPDGFRβ Kinase Sequence (residues 557-1106)
used for screening
                                      (Seq ID No. 3)
QKKP RYEIRW KVIE SVSSDG HEYI YVDPMQ LPYDSTWELP

RDQLVLGRTL GSGAFGQVVE ATAHGLSHSQ ATMKVAVKML

KSTARSSEKQ ALMSELKIMS HLGPHLNVVN LLGACTKGGP

IYIITEYCRY GDLVDYLHRN KHTFLQHHSD KRRPPSAELY

SNALPVGLPL PSHVSLTGE SDGGYMDMSK DESVDYVPML

DMKGDVKYAD IESSNYMAPY DNYVPSAPER TCRAT LINES

PVLSYMDLVG FSYQVANGME FLASKNCVHR DLAARNVLIC

EGKLVKICDF GLARDIMRDS NYISKGSTFL PLKWMAPESI

FNSLYTTLSD VWSFGILLWE IFTLGGTPYP ELPMNEQFYN

AIKRGYRMAQ PAHASDEIYE IMQKCWEEKF EIRPPFSQLV

LLLERLLGEG YKKKYQQVDE EFLRSDHPAI LRSQARLPGF

HGLRSPLDTS SVLYTAVQPN EGDNDYIIPL PDPKPEVADE

GPLEGSPSLA SSTLNEVNTS STISCDSPLE PQDEPEPEPQ

LELQVEPEPE LEQLPDSGCP APRAEAEDSF
```

Using the enzymatic protocols described above, compounds of Formula I were shown to be inhibitors in assays measuring the kinase activity of uFMS kinase, uKIT kinase, or uPDGFRβ kinase, as indicated below in Table 1.

TABLE 1

Activity of Compounds of Formula Ia in Enyzmatic Assays of uFMS kinase, uKIT kinase, or uPDGFRβ kinase.

| Example | uFMS | uKIT | uPDGFRβ |
|---|---|---|---|
| 1 | +++ | ++ | NT |
| 2 | ++++ | ++ | ++++ |
| 3 | ++++ | + | + |
| 4 | ++++ | +++ | NT |
| 5 | +++ | ++ | ++ |
| 6 | +++ | + | +++ |
| 7 | +++ | + | ++ |
| 8 | ++++ | ++ | +++ |
| 9 | ++++ | + | + |
| 10 | +++ | + | ++ |
| 11 | ++++ | + | +++ |
| 12 | ++++ | + | ++ |
| 13 | ++++ | + | ++ |
| 14 | ++ | + | + |
| 15 | +++ | + | ++ |
| 16 | ++ | + | + |
| 17 | +++ | + | ++ |
| 18 | ++++ | ++ | ++ |
| 19 | +++ | ++ | ++ |
| 20 | +++ | + | + |
| 21 | ++++ | + | + |
| 22 | +++ | + | + |
| 23 | ++++ | + | ++ |
| 24 | +++ | ++ | ++ |
| 25 | +++ | + | ++ |
| 26 | ++++ | + | ++ |
| 27 | +++ | + | ++ |
| 28 | ++++ | ++ | NT |
| 29 | +++ | + | NT |
| 30 | ++++ | +++ | ++ |
| 31 | ++++ | ++ | ++ |
| 32 | +++ | + | +++ |
| 33 | +++ | + | ++ |
| 34 | ++++ | + | + |
| 35 | ++++ | ++ | ++++ |
| 36 | ++++ | ++ | +++ |
| 37 | ++++ | + | ++ |
| 38 | ++++ | ++ | +++ |
| 39 | +++ | + | + |
| 40 | +++ | + | NT |
| 41 | ++++ | ++ | +++ |
| 42 | ++++ | ++ | +++ |
| 43 | ++++ | ++ | ++ |
| 44 | ++++ | ++ | ++ |
| 45 | ++++ | ++ | ++ |
| 46 | ++++ | ++ | ++ |
| 47 | ++++ | + | +++ |
| 48 | ++++ | ++ | +++ |
| 49 | +++ | + | + |
| 50 | ++++ | +++ | +++ |
| 51 | ++++ | ++ | +++ |
| 52 | ++++ | +++ | ++ |
| 53 | +++ | + | + |
| 54 | +++ | + | + |
| 55 | +++ | + | + |
| 56 | +++ | + | ++ |
| 57 | ++ | + | + |
| 58 | +++ | + | + |
| 59 | ++++ | ++ | ++ |
| 60 | +++ | + | ++ |
| 61 | +++ | + | ++ |
| 62 | ++++ | + | + |
| 63 | ++++ | + | + |
| 64 | ++++ | ++ | + |
| 65 | ++++ | ++ | ++ |
| 66 | ++++ | + | ++ |
| 67 | +++ | ++ | +++ |
| 68 | ++++ | + | +++ |
| 69 | ++++ | + | + |
| 70 | ++ | + | + |
| 71 | ++++ | + | ++ |
| 72 | +++ | + | + |
| 73 | ++ | + | + |
| 74 | +++ | + | + |
| 75 | ++ | + | + |
| 76 | ++++ | + | ++ |
| 77 | ++++ | ++ | +++ |
| 78 | ++++ | +++ | +++ |
| 79 | ++++ | + | ++ |
| 80 | ++++ | + | ++ |
| 81 | ++++ | + | ++ |
| 82 | +++ | + | + |
| 83 | ++++ | + | ++ |

NT: Not Tested;
+: $IC_{50} > 1$ uM;
++: $0.1$ uM $< IC_{50} \leq 1$ uM;
+++: $0.01$ uM $< IC_{50} \leq 0.1$ uM;
++++: $IC_{50} \leq 0.01$ uM M-NFS-60 Cell Culture M-NFS-60 cells (catalog #CRL-1838) were obtained from the American Type Culture Collection (ATCC, Manassas, Va.). Briefly, cells were grown in suspension in RPMI 1640 medium supplemented with 10% characterized fetal bovine serum (Invitrogen, Carlsbad, Calif.), 0.05 mM 2-mercaptoethanol, and 20 ng/mL mouse recombinant macrophage colony stimulating factor (M-CSF) at 37° C., 5% $CO_2$, and 95% humidity. Cells were allowed to expand until reaching saturation at which point they were subcultured or harvested for assay use.

M-NFS-60 Cell Proliferation Assay

A serial dilution of test compound was dispensed into a 384-well black clear bottom plate (Corning, Corning, N.Y.). Two thousand five hundred cells were added per well in 50 µL complete growth medium. Plates were incubated for 67 h at 37° C., 5% $CO_2$, and 95% humidity. At the end of the incubation period 10 µL of a 440 µM solution of resazurin (Sigma, St. Louis, Mo.) in PBS was added to each well and incubated for an additional 5 h at 37° C., 5% $CO_2$, and 95% humidity. Plates were read on a Synergy2 reader (Biotek, Winooski, Vt.) using an excitation of 540 nM and an emission of 600 nM. $IC_{50}$ values were calculated from a series of percent inhibition values determined at a range of inhibitor concentrations using software routines as implemented in the GraphPad Prism software package.

THP-1 Cell Culture

THP-1 cells (catalog #TIB-202) were obtained from the ATCC. Briefly, cells were grown in RPMI 1640 supplemented with 10% characterized fetal bovine serum, 1% sodium pyruvate, 1% Penicillin-Streptomycin-Glutamine (PSG) and 55 uM 2-mercaptoethanol (Invitrogen, Carlsbad, Calif.) at 37 degrees Celsius, 5% $CO_2$, 95% humidity. Cells were allowed to expand until reaching 70-95% confluency at which point they were subcultured or harvested for assay use.

Phospho-FMS ELISA Assay

A serial dilution of test compound was diluted 1:100 in assay medium (RPMI 1640 supplemented with 10% characterized fetal bovine serum) in a 96 well black clear bottom plate (Corning, Corning, N.Y.). In a separate 96 well black clear bottom plate, one hundred and fifty thousand THP-1 cells were added per well in 100 µL in assay medium. Fifty microliters of diluted compound was then added to the cells. Plates were incubated for 4 hours at 37 degrees Celsius, 5% $CO_2$, 95% humidity. At the end of the incubation period, cells were stimulated with 50 µL of a 100 nM solution of recombinant human M-CSF (catalog #216-MC, R & D Systems, Minneapolis, Minn.) in assay medium and the plate was incubated for 5 minutes at 37 degrees Celsius, 5% $CO_2$, 95% humidity. Lysates were prepared and used to perform the phospho-FMS ELISA as described by the manufacturer (catalog #DYC3268, R & D Systems, Minneapolis, Minn.). GraphPad Prism was used to calculate $IC_{50}$ values obtained from data generated from the ELISA assay.

Osteoclast Tartrate-Resistant Acid Phosphatase Assay

A serial dilution of test compound was dispensed into a 384-well black clear bottom plate (Nalge Nunc International, Rochester, N.Y.). Compound was diluted by the addition of DMEM media supplemented with 10% characterized fetal bovine serum (Invitrogen, Carlsbad, Calif.). Diluted compound was transferred to a 384-well black clear bottom plate. Two-thousand five hundred osteoclast precursors (Lonza, Walkersville, Md.) were added per well in growth media containing Receptor Activator of Nuclear Factor Kappa-beta ligand (RANKL) and M-CSF (R&D Systems, Minneapolis, Minn.). Plates were incubated for 7-14 days at 37 degrees Celsius, 5% $CO_2$, and 95% humidity to allow differentiation of osteoclast precursors. At the end of the incubation period, 10 µL of supernatant from each well was transferred to a clear 384-well plate. Tartrate-resistant acid phosphatase activity in the supernatant samples was determined using an acid phosphatase assay kit (Sigma, St. Louis, Mo.). Absorbance was measured at 550 nm using a plate reader. Data was analyzed using Prism software (Graphpad, San Diego, Calif.) to calculate $IC_{50}$ values.

The compounds of formula I were demonstrated to be functional inhibitors in one or more of the cellular assays described above, as indicated in Table 2.

TABLE 2

Inhibitory effects of compounds of formula I versus M-NFS-60, THP-1 and Osteoclast Cells

| Example | M-NFS-60 cell proliferation | Osteoclast assay | pFMS inhibition in THP-1 cells |
|---|---|---|---|
| 1 | ++++ | ++++ | NT |
| 2 | +++ | ++++ | +++ |
| 3 | +++ | ++++ | ++++ |
| 4 | ++++ | ++++ | NT |
| 5 | +++ | ++++ | ++++ |
| 6 | ++ | +++ | NT |
| 7 | +++ | +++ | ++++ |
| 8 | ++++ | ++++ | ++++ |
| 9 | ++++ | ++++ | ++++ |
| 10 | +++ | +++ | NT |
| 11 | ++++ | ++++ | ++++ |
| 12 | ++++ | +++ | +++ |
| 13 | ++++ | +++ | ++++ |
| 14 | +++ | ++ | NT |
| 15 | +++ | +++ | NT |
| 16 | ++ | ++ | NT |
| 17 | +++ | +++ | +++ |
| 18 | ++++ | ++++ | NT |
| 19 | +++ | ++++ | +++ |
| 20 | ++++ | +++ | ++++ |
| 21 | +++ | ++++ | +++ |
| 22 | ++ | +++ | NT |
| 23 | ++++ | ++++ | ++++ |
| 24 | +++ | ++++ | ++++ |
| 25 | +++ | ++++ | ++++ |
| 26 | +++ | ++++ | ++++ |
| 27 | +++ | ++++ | +++ |
| 28 | +++ | ++++ | NT |
| 29 | +++ | +++ | NT |
| 30 | +++ | ++++ | ++++ |
| 31 | +++ | ++++ | ++++ |
| 32 | +++ | +++ | NT |
| 33 | ++ | +++ | +++ |
| 34 | +++ | +++ | +++ |
| 35 | ++++ | ++++ | NT |
| 36 | +++ | ++++ | +++ |
| 37 | +++ | +++ | ++++ |
| 38 | ++++ | +++ | ++++ |
| 39 | +++ | +++ | NT |
| 40 | ++ | +++ | NT |
| 41 | +++ | ++++ | +++ |
| 42 | ++++ | ++++ | ++++ |
| 43 | ++++ | ++++ | NT |
| 44 | ++++ | ++++ | NT |
| 45 | ++++ | ++++ | ++++ |
| 46 | ++++ | ++++ | ++++ |
| 47 | ++++ | ++++ | ++++ |
| 48 | ++++ | ++++ | ++++ |
| 49 | + | ++ | NT |
| 50 | ++++ | ++++ | NT |
| 51 | +++ | +++ | NT |
| 52 | ++++ | ++++ | NT |
| 53 | + | +++ | NT |
| 54 | ++ | ++ | NT |
| 55 | + | ++ | NT |
| 56 | + | ++ | NT |
| 57 | + | ++ | NT |
| 58 | +++ | +++ | ++++ |
| 59 | ++++ | ++++ | NT |
| 60 | ++ | +++ | NT |
| 61 | ++ | +++ | NT |
| 62 | ++++ | +++ | ++++ |
| 63 | +++ | ++++ | +++ |
| 64 | +++ | +++ | ++++ |
| 65 | +++ | ++++ | +++ |
| 66 | ++++ | ++++ | ++++ |
| 67 | ++++ | ++++ | ++++ |
| 68 | ++++ | ++++ | ++++ |
| 69 | ++++ | ++++ | ++++ |
| 70 | ++ | +++ | +++ |
| 71 | ++++ | ++++ | ++++ |
| 72 | ++ | +++ | NT |
| 73 | + | +++ | NT |
| 74 | ++ | +++ | NT |
| 75 | + | +++ | NT |
| 76 | +++ | ++++ | ++++ |
| 77 | ++++ | ++++ | +++ |
| 78 | ++++ | ++++ | NT |
| 79 | ++ | +++ | +++ |
| 80 | +++ | ++++ | ++++ |
| 81 | +++ | ++++ | ++++ |
| 82 | ++ | +++ | ++++ |
| 83 | +++ | ++++ | ++++ |

NT: Not Tested;
+: $IC_{50} > 1$ uM;
++: $0.1$ uM $< IC_{50} \leq 1$ uM;
+++: $0.01$ uM $< IC_{50} \leq 0.1$ uM;
++++: $IC_{50} \leq 0.01$ uM Measurements of In Vivo Activity Analysis of cFOS mRNA Production in a c-FMS Mouse Spleen Pharmacodynamic Model To examine the in vivo modulation of FMS activity by compounds of formula I, spleen samples from female DBA/1 mice were collected and analyzed for M-CSF stimulated production of cFOS mRNA. Briefly, six to seven week old female Taconic DBA/1BO J Bom Tac mice were treated with a single oral dose (by gavage) of either vehicle or compound. Plasma and spleen samples are collected from four mice at each timepoint 2, 4, 6, 8, 12, 18, and 24 hours after dosing. Fifteen minutes prior to euthanasia, all mice were injected IV with 1 µg (100 µL fixed volume) of M-CSF. M-CSF, Recombinant Mouse Macrophage Colony Stimulating Factor (36.4 kDa homodimer, ≥98% purity) was obtained from Gibco. All procedures carried out in this experiment were conducted in compliance with all the laws, regulations and guidelines of the National Institutes of Health (NIH). cFOS mRNA levels in spleen extracts were determined using a quantitative reverse transcriptase PCR kit from Life Technologies. Plasma levels of FMS inhibitors were determined by mass spectrometer analysis. The degree of FMS inhibition was correlative to the amount of decrease observed in cFOS mRNA levels in the spleen samples of treated animals compared to vehicle.

In this model, Examples 3, 8, 11, 21, 23, 26, 34, 45, 62 and 83 afforded ≥50% inhibition of cFOS mRNA levels out to 8 h post 30 mg/kg dose.

PC-3 Peritibial Implant Model of Cancer Bone Metastasis

To evaluate in vivo anti-cancer activity of compounds of formula I, the PC-3 M-luc peritibial injection model of bone invasiveness model was employed. Briefly, PC-3 M-luc cells were obtained from Xenogen Corporation (Caliper Life Sciences) and expanded using MEM media modified with L-Glutamine (Cell Gro® #10-045-CV) supplemented with 10% fetal bovine serum, 1% penicillin-streptomycin-glutamine, 1% non-essential amino acids, and 1% MEM vitamins in 5% $CO_2$ atmosphere at 37° C. Six to 7 week old male nude mice (Crl:NU-Foxn1nu) were obtained from Charles River Laboratories. Test mice were implanted peritibially on Day 0 with $1\times10^6$ cells/mouse (0.1 mL) using an insulin syringe with a fixed 28-gauge needle. The needle was inserted at the ankle between the tibia and fibula until the bevel of the needle reaches approximately half way between the knee and ankle Treatments began on Day 0. Animals were dosed by oral gavage twice daily for the study duration. All procedures carried out in this experiment were conducted in compliance with all the laws, regulations and guidelines of the National Institutes of Health (NIH). When the primary tumor reaches approximately 800 mg in size, ex-vivo micro-CT was performed on the tumor bearing fixed hind limb samples using a GE RS150 small animal micro-CT scanner using with the following settings:

X-ray tube voltage=70 k Vp
X-ray tube current=25 mA
Exposure time=20 ms
Number of frames=500
Angle increment between frames=0.4o
Number of averages per frame=2
Acquisition method=Parker Images were then reconstructed at high resolution (100 microns; isotropic). Isosurface volume renderings were used to delineate lesions in the hind limbs. A constant threshold was used to produce consistent representation of the isosurface between different anatomical sites and samples. Lesions in the right hind limb were scored with values of 0, 1, 2, 3, or 4 based on a qualitative assessment of lesion size as defined by:

0: Normal Bone
1: Minimal lesions. Some roughening of the isosurface. Small areas of apparent bone resorption.
2: Mild. More numerous lesions. Significant roughening of the isosurface. Full thickness lesions apparent.
3: Moderate. Full thickness lesions larger and more numerous.
4: Marked. Many, large, full thickness lesions. Significant distortion of remaining structure. Marked bone loss.

Example 45 was evaluated in this model an demonstrated positive benefit with a lesion score of 3 compared to a lesion score of 4 in vehicle-treated animals.

U251 Intra-Cerebro-Ventricular Implant in Mice

To evaluate in vivo anti-cancer activity compounds of formula I in combination with fractionated, localized head radiation, an orthotopic U251-luc (Luc) human glioma carcinoma model in female outbred nu/nu mice was employed. Briefly, U251 cells were obtained from the ATCC and altered to be luciferase expressing. They were grown in RPMI 1640 Media supplemented with 10% FBS and 1% PSG. The growth environment was maintained in an incubator with a 5% $CO_2$ atmosphere at 37° C. Female Harlan Nude mice (Hsd:AthymicNude-Fox1nu) 8-9 weeks old were used in this study. Test animals were implanted intracranially with U251-luc (Luc-mCherry) cells. Briefly, animals were injected subcutaneously with 5 mg/kg carprofen and anesthetized using 2% isoflurane in air. The animals were then secured in a stereotaxic frame (ASIinstruments, Inc.) and a hole drilled 2 mm right lateral, 1 mm anterior to the coronal suture. The cell suspension (stored on wet ice) was mixed thoroughly and drawn up into a 50 μL syringe. The syringe needle was centered over the burr hole and lowered 3 mm into the brain and retracted 1 mm to form a "reservoir" for the deposition of the cell suspension. 10 μL of the cell suspension ($1\times10^6$ cells/mouse) was then injected slowly into the brain tissue. Tumor progression was tracked with in vivo bioluminescence imaging performed using an IVIS 50 optical imaging system (Xenogen, Alameda, Calif.). Bioluminescence images were acquired at periodic intervals for tumor burden estimation. All procedures carried out in this experiment were conducted in compliance with all the laws, regulations and guidelines of the National Institutes of Health (NIH). Treatment began when the mean brain bioluminescence signal for all groups in the experiment is ~$1.3\times109$ photons/sec (typically 9 days post-implant). All mice received 2Gy of radiation each day for five consecutive days from a RadSource RS-2000 irradiator. Additionally, mice received test compound dosed by oral gavage or optionally with co-administered bevacizumab by tail vein injection. Bioluminescence images were acquired generally on days 8, 10, 14, 17, 21, 22, 24, 28 and 35 post-implant for tumor burden estimation. For each measurement, each mouse was injected subcutaneously with 150 mg/kg D-Luciferin (Promega) and imaged 10 minutes after the injection. Images were analyzed using Living Image (Xenogen, Alameda, Calif.) software. The BLI signal in the brain was calculated with a fixed area ROI to estimate the tumor burden. Average BLI signal for each group was compared to vehicle control to determine therapeutic benefit. Twenty-eight days after the first radiation treatment mice were euthanized, via over-exposure to carbon dioxide, for blood and brain collection. Whole blood was collected via terminal cardiac puncture and placed into EDTA Microtainer® tubes. Brains were excised and placed into 10% neutral buffered formalin.

Example 45, when dosed at 30 mg/kg twice daily, effected an 80% reduction in tumor re-growth 10 days post irradiation compared to vehicle treated control animals.

GL261 Intracranial Implant Model

To evaluate the in vivo anti-cancer activity of compounds of formula I, an intracranial implant of GL261-luc2 murine glioma is employed. Briefly GL261-luc2 cells are obtained from Caliper Life Sciences, Inc and expanded in Dulbecco's Modified Eagle Media (DMEM) which is supplemented with 10% FBS and 1% PSG. The growth environment is maintained in an incubator with a 5% $CO_2$ atmosphere at 37° C. Following expansion, cells are re-suspended using serum-free media to generate a concentration of $1\times10^8$ cells/mL. Six to seven week old female C57BL/6J-Tyrc-2J/J from Jackson Labs are implanted intracranially on Day 0 with GL261-luc2 cells. For aseptic surgical implantation, animals are injected subcutaneously with 5 mg/kg carprofen, anesthetized using 2% isoflurane in air. The animals are then secured in a stereotaxic frame (ASIinstruments, Inc.) and a hole is drilled 2 mm right lateral, 1 mm anterior to the coronal suture. The cell suspension (stored on wet ice) is mixed thoroughly and drawn up into a 50 µL syringe. The syringe needle is centered over the burr hole and lowered 3 mm into the brain and retracted 1 mm to form a "reservoir" for the deposition of the cell suspension. 10 µL of the cell suspension ($1\times10^6$ cells/mouse) is then injected slowly into the brain tissue. Tumor progression is tracked with in vivo bioluminescence imaging performed using an IVIS 50 optical imaging system (Xenogen, Alameda, Calif.). Bioluminescence images are acquired at periodic intervals for tumor burden estimation. The quantity of emitted light from the tumor after systemic injection of D-Luciferin is expected to correlate with tumor size. Each mouse is injected intraperitoneally (IP) with 150 mg/kg D-Luciferin and imaged in the prone position 10 minutes after the injection. Medium and small binning of the CCD chip is used, and the exposure time is adjusted (10 seconds to 1 minute) to obtain at least several hundred counts from the tumors and to avoid saturation of the CCD chip. Images are analyzed using Living Image (Xenogen, Alameda, Calif.) software. Each unique signal is circled manually and labeled by group and mouse number. Treatment begins by oral gavage of test compound when the mean brain bioluminescence signal for all groups in the experiment is $280\times10^6$ photons/sec. All procedures carried out in this experiment are conducted in compliance with all the laws, regulations and guidelines of the National Institutes of Health (NIH).

At the end of study all mice are euthanized via over-exposure to carbon dioxide for blood and brain collection. Whole blood is collected via terminal cardiac puncture and placed into EDTA Microtainer® tubes. Brains are excised and placed into 10% neutral buffered formalin.

MDA-MB-231 XenoGraft Study

To evaluate the in vivo anti-cancer activity compounds of formula I, a MDA-MB-231-luc-D3H2LN human breast carcinoma xenograft is employed. Briefly, MDA-MB-231-luc-D3H2LN cells are obtained from Xenogen and expanded in Minimal Essential Media (MEM) with EBSS which is modified with 1% L-glutamine and supplemented with 10% FBS, 1% PSG, 1% non-essential amino acids, and 1% sodium pyruvate. The growth environment is maintained in an incubator with a 5% $CO_2$ atmosphere at 37° C. Cells are harvested and re-suspended using 50% serum-free media and 50% Matrigel® to generate a stock concentration of $5\times10^6$ cells/mL.

Six to 7 week old female C.B-17/IcrHsd-PrkdcscidLystbg mice are injected with 200 µL of cell suspension subcutaneously, just below the right axilla. All procedures carried out in this experiment are conducted in compliance with all the laws, regulations and guidelines of the National Institutes of Health (NIH). Treatment begins when the mean tumor burden is approximately 150 mg. All mice are dosed with test compound by oral gavage. Body weights and tumor measurements are recorded three times weekly. Tumor burden (mg) is estimated from caliper measurements by the formula for the volume of a prolate ellipsoid assuming unit density as: Tumor burden (mg)=(L×W2)/2, where L and W are the respective orthogonal tumor length and width measurements (mm). The primary endpoints to evaluate efficacy is % T/C. % T/C is defined as the median tumor mass of a Treated Group divided by the median tumor mass of the Control Group×100. Ex vivo bioluminescence imaging is performed as animals exit the study, using an IVIS 50 optical imaging system (Xenogen, Alameda, Calif.). Animals are injected IP with 150 mg/kg D-Luciferin (Promega) and euthanized 10 minutes following the injection. The primary tumor is removed and snap frozen for future analysis and the mouse opened and imaged in the supine position. Large binning of the CCD chip is used, and the exposure time is adjusted (1 to 2 minutes) to obtain at least several hundred counts from the tumors and to avoid saturation of the CCD chip. Images are analyzed using Living Image (Xenogen, Alameda, Calif.) software. Each unique signal is circled manually and labeled by group and mouse number. Total BLI signal is correlative to tumor size and compared to vehicle control to determine treatment benefit.

EQUIVALENTS

Those skilled in the art will recognize, or be able to ascertain, using no more than routine experimentation, numerous equivalents to the specific embodiments described specifically in this disclosure. Such equivalents are intended to be encompassed in the scope of the following claims.

What is claimed is:

1. A compound of Formula I:

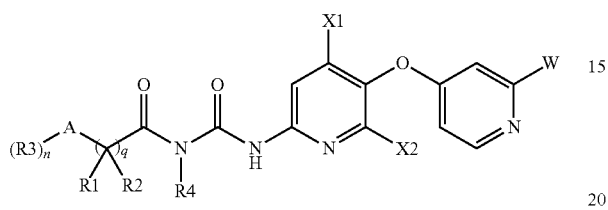

Formula I or a pharmaceutically acceptable salt, enantiomer, stereoisomer, or tautomer thereof, wherein A is selected from the group consisting of C1-C6 alkyl, deutero-C1-C6 alkyl wherein the alkyl chain is partially or completely deuterated, branched C3-C8alkyl, fluoroC1-C6alkyl wherein the alkyl is fully or partially fluorinated, and C3-C8carbocyclyl, and wherein each A moiety may be further substituted with one, two, or three R3 moieties;

W is —NHC(O)R5, —NHC(O)R6, —NHC(O)N(R7)R8 or —C(O)N(R7)R8;

X1 and X2 are individually and independently hydrogen, C1-C6 alkyl, fluoro-C1-C6 alkyl wherein the alkyl chain is partially or completely fluorinated;

each R1 and R2 is individually and independently H, C1-C6 alkyl, fluoroC1-C6alkyl wherein the alkyl is fully or partially fluorinated, hydroxyl, C1-C6 alkoxy, fluoroC1-C6alkoxy wherein the alkyl group is fully or partially fluorinated, or cyano;

each R3 is individually and independently H, halogen, C1-C6 alkyl, fluoro-C1-C6 alkyl wherein the alkyl chain is partially or completely fluorinated, branched C3-C8 alkyl, C3-C8 cycloalkyl, C1-C6 alkoxy, fluoro-C1-C6 alkoxy wherein the alkyl chain is partially or completely fluorinated, branched C3-C6 alkoxy, hydroxyl, or cyano;

each R4 is individually and independently hydrogen, C1-C6 alkyl, or branched C3-C8 alkyl;

each R5 is individually and independently hydrogen, C1-C6 alkyl, branched C3-C8 alkyl, C3-C8 cycloalkyl, —(CH$_2$)$_m$—CN, —(CH$_2$)$_m$—OR7, —(CH$_2$)$_m$—NR7(R8), or —(CH$_2$)$_m$—R6, wherein each alkylene of R5 may be further substituted with one or more C1-C6alkyl;

each R6 is independently and individually selected from the group consisting of

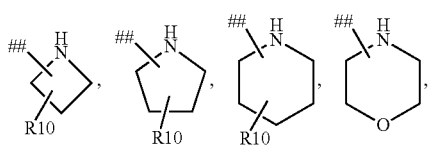

and wherein the symbol (##) is the point of attachment to respective R5 or W moieties containing a R6 moiety;

each R6 is optionally substituted with —(R9)$_p$;

each R7 and R8 is individually and independently H, C1-C6 alkyl, fluoro-C1-C6 alkyl wherein the alkyl chain is partially or completely fluorinated, branched C3-C8 alkyl, —(CH$_2$)$_m$—CN, —(CH$_2$)$_m$—OR7, —(CH$_2$)$_m$—NR7(R8), or —(CH$_2$)$_m$—R6, each R9 is individually and independently C1-C6 alkyl, —(CH$_2$)$_m$—CN, —(CH$_2$)$_m$—OR3, —(CH$_2$)$_m$—NR7(R8), or —(CH$_2$)$_m$—C(O)—R5, wherein each alkyl or alkylene is optionally substituted with one or two C1-C6 alkyl;

each R10 is H, 4-(C1-C4alkyl)-piperazin-1-yl, morpholinyl, piperidinyl, pyrrolidinyl or azetidinyl;

each m is individually and independently 0, 1, 2, or 3;

each n is individually and independently 0, 1, 2, or 3;

each p is 0, 1, 2, or 3; and each q is 0, 1, 2, or 3.

2. The compound of claim 1, wherein X1 and X2 are individually and independently hydrogen or C1-C6 alkyl.

3. The compound of claim 2, wherein the compound is a compound of Formula Ia,

Formula Ia or a pharmaceutically acceptable salt, enantiomer, stereoisomer, or tautomer thereof.

4. The compound of claim 3, wherein R3 is C1-C6alkyl, hydrogen or C1-C6alkoxy.

5. The compound of claim 4, wherein W is —NHC(O)R5, —NHC(O)R6 or —NHC(O)N(R7)R8.

6. The compound of claim 4, wherein W is —C(O)N(R7)R8.

7. The compound of claim 2, wherein the compound is a compound of Formula Ib:

Formula Ib

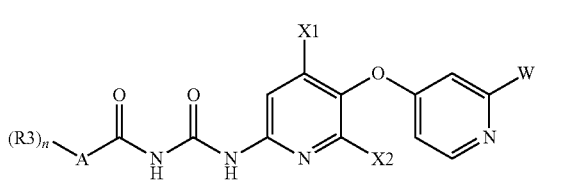

wherein A is C3-C8 carbocyclyl.

8. The compound of claim 7, wherein R3 is C1-C6alkyl, hydrogen, C1-C6alkoxy or fluoro-C1-C6 alkyl wherein the alkyl chain is partially or completely fluorinated.

9. The compound of claim 8, wherein W is —NHC(O)R5, —NHC(O)R6 or —NHC(O)N(R7)R8.

10. The compound of claim 8, wherein W is —C(O)N(R7)R8.

11. The compound of claim 1 selected from the group consisting of N-((5-((2-acetamidopyridin-4-yl)oxy)pyridin-2-yl)carbamoyl)cyclohexanecarboxamide, N-((5-((2-acetamidopyridin-4-yl)oxy)pyridin-2-yl)carbamoyl)cyclopentanecarboxamide, N-((5-((2-acetamidopyridin-4-yl)oxy)pyridin-2-yl)carbamoyl)pivalamide, N-((5-((2-acetamidopyridin-4-yl)oxy)pyridin-2-yl)carbamoyl)-2-cyclohexylacetamide, N-((5-((2-acetamidopyridin-4-yl)oxy)-6-methylpyridin-2-yl)carbamoyl)cyclopentanecarboxamide, N-((5-((2-acetamidopyridin-4-yl)oxy)-6-methylpyridin-2-yl)carbamoyl)pivalamide, N-((5-((2-acetamidopyridin-4-yl)oxy)-6-methylpyridin-2-yl)carbamoyl)isobutyramide, N-(4-((2-methyl-6-(3-pivaloylureido)pyridin-3-yl)oxy)pyridin-2-yl)cyclopropanecarboxamide, N-((6-methyl-5-((2-propionamidopyridin-4-yl)oxy)pyridin-2-yl)carbamoyl)pivalamide, N-((5-((2-isobutyramidopyridin-4-yl)oxy)-6-methylpyridin-2-yl)carbamoyl)pivalamide, N-((5-((2-acetamidopyridin-4-yl)oxy)pyridin-2-yl)carbamoyl)isobutyramide, N-((5-(2-acetamidopyridin-4-yl)oxy)pyridin-2-yl)carbamoyl)propionamide, N-((5-((2-isobutyramidopyridin-4-yl)oxy)pyridin-2-yl)carbamoyl)pivalamide, N-(4-((6-(3-pivaloylureido)pyridin-3-yl)oxy)pyridin-2-yl)cyclopropanecarboxamide, N-((5-((2-acetamidopyridin-4-yl)oxy)pyridin-2-yl)carbamoyl)-1-methylcyclopropanecarboxamide, N-((5-((2-acetamidopyridin-4-yl)oxy)-6-methylpyridin-2-yl)carbamoyl)-2-methoxy-2-methylpropanamide, 1-methyl-N-(4-((6-(3-pivaloylureido)pyridin-3-yl)oxy)pyridin-2-yl)piperidine-4-carboxamide, N-((5-((2-(3,3-dimethylureido)pyridin-4-yl)oxy)pyridin-2-yl)carbamoyl)pivalamide, N-((5-((2-propionamidopyridin-4-yl)oxy)pyridin-2-yl)carbamoyl)pivalamide, N-((5-((2-acetamidopyridin-4-yl)oxy)pyridin-2-yl)carbamoyl)-1-(trifluoromethyl)cyclobutanecarboxamide, N-((5-((2-acetamidopyridin-4-yl)oxy)pyridin-2-yl)carbamoyl)-2-methoxy-2-methylpropanamide, N-((5-((2-acetamidopyridin-4-yl)oxy)pyridin-2-yl)carbamoyl)-1-methoxycyclopropanecarboxamide, N-((5-((2-(cyclopropanecarboxamido)pyridin-4-yl)oxy)pyridin-2-yl)carbamoyl)-1-methylcyclopropanecarboxamide, N-(4-((6-(3-(2-methoxy-2-methylpropanoyl)ureido)pyridin-3-yl)oxy)pyridin-2-yl)cyclopropanecarboxamide, 1-methyl-N-(4-((6-(3-(1-methylcyclopropanecarbonyl)ureido)pyridin-3-yl)oxy)pyridin-2-yl)piperidine-4-carboxamide, N-methyl-4-((6-(3-pivaloylureido)pyridin-3-yl)oxy)picolinamide, 1-methyl-N-((5-((2-propionamidopyridin-4-yl)oxy)pyridin-2-yl)carbamoyl)cyclopropanecarboxamide, 2-methoxy-2-methyl-N-((5-((2-propionamidopyridin-4-yl)oxy)pyridin-2-yl)carbamoyl)propanamide, N-((5-((2-acetamidopyridin-4-yl)oxy)-4-methylpyridin-2-yl)carbamoyl)-2-methoxy-2-methylpropanamide, 1-methoxy-N-((5-((2-propionamidopyridin-4-yl)oxy)pyridin-2-yl)carbamoyl)cyclopropanecarboxamide, N-(4-((6-(3-(2-methoxy-2-methylpropanoyl)ureido)pyridin-3-yl)pyridin-2-yl)-1-methylpiperidine-4-carboxamide, N-((5-((2-(cyclopropanecarboxamido)pyridin-4-yl)oxy)pyridin-2-yl)carbamoyl)-1-methoxycyclopropanecarboxamide, N-((5-((2-acetamidopyridin-4-yl)oxy)-4-methylpyridin-2-yl)carbamoyl)pivalamide, N-((5-(2-acetamidopyridin-4-yl)oxy)-6-methylpyridin-2-yl)carbamoyl)-1-methylcyclobutanecarboxamide, N-((5-((2-acetamidopyridin-4-yl)oxy)pyridin-2-yl)carbamoyl)-1-methylcyclobutanecarboxamide, 4-methyl-N-(4-((6-(3-pivaloylureido)pyridin-3-yl)oxy)pyridin-2-yl)piperazine-1-carboxamide, N-(4-((6-(3-pivaloylureido)pyridin-3-yl)oxy)pyridin-2-yl)morpholine-4-carboxamide, (S)-3-(dimethylamino)-N-(4-((6-(3-pivaloylureido)pyridin-3-yl)oxy)pyridin-2-yl)pyrrolidine-1-carboxamide, N-(4-((6-(3-pivaloylureido)pyridin-3-yl)oxy)pyridin-2-yl)azetidine-1-carboxamide, N-(4-((6-(3-(1-methoxycyclopropanecarbonyl)ureido)pyridin-3-yl)oxy)pyridin-2-yl)-1-methylpiperidine-4-carboxamide, N-((5-((2-(3,3-dimethylureido)pyridin-4-yl)oxy)pyridin-2-yl)carbamoyl)-1-methylcyclopropanecarboxamide, 1-methyl-N-(4-((6-(3-pivaloylureido)pyridin-3-yl)oxy)pyridin-2-yl)-1H-pyrazole-4-carboxamide, N-((5-((2-(2-(pyrrolidin-1-yl)acetamido)pyridin-4-yl)oxy)pyridin-2-yl)carbamoyl)pivalamide, N-((5-((2-(2-(dimethylamino)acetamido)pyridin-4-yl)oxy)pyridin-2-yl)carbamoyl)pivalamide, 1-methyl-N-(4-((6-(3-pivaloylureido)pyridin-3-yl)oxy)pyridin-2-yl)pyrrolidine-3-carboxamide, N-((5-((2-(2-cyanoacetamido)pyridin-4-yl)oxy)pyridin-2-yl)carbamoyl)pivalamide, N-(4-((6-(3-isobutyrylureido)pyridin-3-yl)oxy)pyridin-2-yl)-1-methylpiperidine-4-carboxamide, 4-((6-(3-(2-methoxy-2-methylpropanoyl)ureido)pyridin-3-yl)oxy)-N-methylpicolinamide, 1-methyl-N-(4-((6-(3-pivaloylureido)pyridin-3-yl)oxy)pyridin-2-yl)-1H-imidazole-4-carboxamide, (1s,3s)-3-(dimethylamino)-N-(4-((6-(3-pivaloylureido)pyridin-3-yl)oxy)pyridin-2-yl)cyclobutanecarboxamide, (1r,3r)-3-(dimethylamino)-N-(4-((6-(3-pivaloylureido)pyridin-3-yl)oxy)pyridin-2-yl)cyclobutanecarboxamide, N-((5-((2-(3,3-dimethylureido)pyridin-4-yl)oxy)-6-methylpyridin-2-yl)carbamoyl)pivalamide, N-(4-((2-methyl-6-(3-pivaloylureido)pyridin-3-yl)oxy)pyridin-2-yl)morpholine-4-carboxamide, 4-((6-(3-(1-methoxycyclopentanecarbonyl)ureido)pyridin-3-yl)oxy)-N-methylpicolinamide, N-(4-((6-(3-isobutyrylureido)pyridin-3-yl)oxy)pyridin-2-yl)-4-methylpiperazine-1-carboxamide, N-((5-((2-acetamidopyridin-4-yl)oxy)pyridin-2-yl)carbamoyl)-1-methoxycyclopentanecarboxamide, (R)-3-(dimethylamino)-N-(4-((6-(3-pivaloylureido)pyridin-3-yl)oxy)pyridin-2-yl)pyrrolidine-1-carboxamide, 4-methyl-N-(4-((2-methyl-6-(3-pivaloylureido)pyridin-3-yl)oxy)pyridin-2-yl)piperazine-1-carboxamide, N-(4-((2-methyl-6-(3-pivaloylureido)pyridin-3-yl)oxy)pyridin-2-yl)pyrrolidine-1-carboxamide, N-methyl-4-((6-(3-(1-(trifluoromethyl)cyclobutanecarbonyl)ureido)pyridin-3-yl)oxy)picolinamide, N-isopropyl-4-((6-(3-pivaloylureido)pyridin-3-yl)oxy)picolinamide, N-cyclopropyl-4-((6-(3-pivaloylureido)pyridin-3-yl)oxy)picolinamide, N-(1-methylpiperidin-4-yl)-4-((6-(3-pivaloylureido)pyridin-3-yl)oxy)picolinamide, 4-(dimethylamino)-N-(4-((6-(3-pivaloylureido)pyridin-3-yl)oxy)pyridin-2-yl)piperidine-1-carboxamide, 3-(dimethylamino)-N-(4-((6-(3-pivaloylureido)pyridin-3-yl)oxy)pyridin-2-yl)azetidine-1- carboxamide, N-(4-((6-(3-pivaloylureido)pyridin-3-yl)oxy)pyridin-2-yl)pyrrolidine-1-carboxamide, N-((5-((2-(3-methylureido)pyridin-4-yl)oxy)pyridin-2-yl)carbamoyl)pivalamide, 4-ethyl-N-(4-((6-(3-pivaloylureido)pyridin-3-yl)oxy)pyridin-2-yl)piperazine-1-carboxamide, 4-(4-methylpiperazin-1-yl)-N-(4-((6-(3-pivaloylureido)pyridin-3-yl)oxy)pyridin-2-yl)piperidine-1-carboxamide, N-((5-((2-(3-(2-methoxyethyl)ureido)pyridin-4-yl)oxy)pyridin-2-yl)carbamoyl)pivalamide, and N-(4-((6-(3-pivaloylureido)pyridin-3-yl)oxy)pyridin-2-yl)piperazine-1-carboxamide.

12. A pharmaceutical composition, comprising a compound of claim 11 and a pharmaceutically acceptable carrier.

13. The compound of claim 1 selected from N-((5-((2-acetamidopyridin-4-yl)oxy)pyridin-2-yl)carbamoyl)pivalamide, N-((5-((2-acetamidopyridin-4-yl)oxy)pyridin-2-yl)carbamoyl)-2-methoxy-2-methylpropanamide, N-((5-((2-(3,3-dimethylureido)pyridin-4-yl)oxy)pyridin-2-yl)carbamoyl)pivalamide, N-((5-((2-(3,3-dimethylureido)pyridin-4-yl)oxy)-6-methylpyridin-2-yl)carbamoyl)pivalamide, N-((5-((2-acetamidopyridin-4-yl)oxy)-6-methylpyridin-2-yl)carbamoyl)pivalamide, or N-(4-((2-methyl-6-(3-pivaloylureido)pyridin-3-yl)oxy)pyridin-2-yl)cyclopropanecarboxamide.

14. A pharmaceutical composition, comprising a compound of claim 13 and a pharmaceutically acceptable carrier.

15. The compound of claim 1 selected from 4-methyl-N-(4-((6-(3-pivaloylureido)pyridin-3-yl)oxy)pyridin-2-yl)piperazine-1-carboxamide, 4-ethyl-N-(4-((6-(3-pivaloylureido)pyridin-3-yl)oxy)pyridin-2-yl)piperazine-1-carboxamide, N-(4-((6-(3-pivaloylureido)pyridin-3-yl)oxy)pyridin-2-yl)piperazine-1-carboxamide, 4-methyl-N-(4-((2-methyl-6-(3-pivaloylureido)pyridin-3-yl)oxy)pyridin-2-yl)piperazine-1-carboxamide, 1-methyl-N-(4-((6-(3-pivaloylureido)pyridin-3-yl)oxy)pyridin-2-yl)piperidine-4-carboxamide, (S)-3-(dimethylamino)-N-(4-((6-(3-pivaloylureido)pyridin-3-yl)oxy)pyridin-2-yl)pyrrolidine-1-carboxamide, (R)-3-(dimethylamino)-N-(4-((6-(3-pivaloylureido)pyridin-3-yl)oxy)pyridin-2-yl)pyrrolidine-1-carboxamide, 3-(dimethylamino)-N-(4-((6-(3-pivaloylureido)pyridin-3-yl)oxy)pyridin-2-yl)azetidine-1-carboxamide, 4-(dimethylamino)-N-(4-((6-(3-pivaloylureido)pyridin-3-yl)oxy)pyridin-2-yl)piperidine-1-carboxamide, N-(4-((6-(3-isobutyrylureido)pyridin-3-yl)oxy)pyridin-2-yl)-4-methylpiperazine-1-carboxamide, N-(4-((2-methyl-6-(3-pivaloylureido)pyridin-3-yl)oxy)pyridin-2-yl)morpholine-4-carboxamide, or N-(4-((6-(3-pivaloylureido)pyridin-3-yl)oxy)pyridin-2-yl)morpholine-4-carboxamide.

16. A pharmaceutical composition, comprising a compound of claim 15 and a pharmaceutically acceptable carrier.

17. The compound of claim 1 selected from N-methyl-4-((6-(3-pivaloylureido)pyridin-3-yl)oxy)picolinamide, 4-((6-(3-(2-methoxy-2-methylpropanoyl)ureido)pyridin-3-yl)oxy)-N-methylpicolinamide, or N-methyl-4-((6-(3-(1-(trifluoromethyl)cyclobutanecarbonyl)ureido)pyridin-3-yl)oxy)picolinamide.

18. A pharmaceutical composition, comprising a compound of claim 17 and a pharmaceutically acceptable carrier.

19. The compound of claim 1 wherein the compound is 4-methyl-N-(4-((6-(3-pivaloylureido)pyridin-3-yl)oxy)pyridin-2-yl)piperazine-1-carboxamide.

20. A pharmaceutical composition, comprising the compound of claim 19 and a pharmaceutically acceptable carrier.

21. The compound of claim 1, wherein the compound is 4-ethyl-N-(4-((6-(3-pivaloylureido)pyridin-3-yl)oxy)pyridin-2-yl)piperazine-1-carboxamide.

22. A pharmaceutical composition, comprising the compound of claim 21 and a pharmaceutically acceptable carrier.

23. The compound of claim 1, wherein the compound is N-(4-((6-(3-pivaloylureido)pyridin-3-yl)oxy)pyridin-2-yl)piperazine-1-carboxamide.

24. A pharmaceutical composition, comprising the compound of claim 23 and a pharmaceutically acceptable carrier.

25. The compound of claim 1, wherein the compound is N-methyl-4-46-(3-pivaloylureido)pyridin-3-yl)oxy)picolinamide.

26. A pharmaceutical composition, comprising the compound of claim 25 and a pharmaceutically acceptable carrier.

27. The compound of claim 1, wherein the compound is 4-((6-(3-(2-methoxy-2-methylpropanoyl)ureido)pyridin-3-yl)oxy)-N-methylpicolinamide.

28. A pharmaceutical composition, comprising the compound of claim 27 and a pharmaceutically acceptable carrier.

29. The compound of claim 1, wherein the compound is 4-methyl-N-(4-((2-methyl-6-(3-pivaloylureido)pyridin-3-yl)oxy)pyridin-2-yl)piperazine-1-carboxamide.

30. A pharmaceutical composition, comprising the compound of claim 29 and a pharmaceutically acceptable carrier.

31. The compound of claim 1, wherein the compound is N-((5-((2-(3,3-dimethylureido)pyridin-4-yl)oxy)-6-methylpyridin-2-yl)carbamoyl)pivalamide.

32. A pharmaceutical composition, comprising the compound of claim 31 and a pharmaceutically acceptable carrier.

33. The compound of claim 1, wherein the compound is compound N-((5-((2-(3,3-dimethylureido)pyridin-4-yl)oxy)pyridin-2-yl)carbamoyl)pivalamide.

34. A pharmaceutical composition, comprising the compound of claim 33 and a pharmaceutically acceptable carrier.

35. A pharmaceutical composition, comprising a compound of claim 1 and a pharmaceutically acceptable carrier.

36. The composition of claim 35, further comprising an additive selected from adjuvants, excipients, diluents, or stabilizers.

37. A method of treating cancer, gastrointestinal stromal tumors, hyperproliferative diseases, metabolic diseases, neurodegenerative diseases, solid tumors, melanomas, glioblastomas, ovarian cancer, pancreatic cancer, prostate cancer, lung cancers, breast cancers, renal cancers, hepatic cancers, osteosarcomas, multiple myelomas, cervical carcinomas, metastasis of primary tumor sites, cancers that are metastatic to bone, papillary thyroid carcinoma, non-small cell lung cancer, colonic cancers, rheumatoid arthritis, osteoarthritis, multiple sclerosis, autoimmune nephritis, lupus, Crohn's disease, asthma, chronic obstructive pulmonary disease, osteoporosis, mastocytosis, or mast cell leukemia, the method comprising administering to a patient in need thereof an effective amount of a compound of any of claim 1.

38. A method of treating glioblastomas, breast cancers, pancreatic cancers, metastasis of primary tumor sites, or cancers that are metastatic to bone, the method comprising administering to a patient in need thereof an effective amount of a compound of claim 1.

39. The method of claim 37, wherein the compound is administered orally, parenterally, by inhalation, or subcutaneously.

40. The method of claim 38, wherein the compound is administered orally, parenterally, by inhalation, or subcutaneously.

* * * * *